United States Patent
Cruse et al.

(10) Patent No.: US 11,268,096 B2
(45) Date of Patent: Mar. 8, 2022

(54) COMPOUNDS FOR MODULATING FC-EPSILON-RI-BETA EXPRESSION AND USES THEREOF

(71) Applicants: North Carolina State University, Raleigh, NC (US); The United States of America, as represented by the Secretary, Department of Health and Human Services, Bethesda, MD (US)

(72) Inventors: Glenn P. Cruse, Apex, NC (US); Dean D. Metcalfe, Bethesda, MD (US)

(73) Assignees: North Carolina State University, Raleigh, NC (US); The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 16/052,130

(22) Filed: Aug. 1, 2018

(65) Prior Publication Data
US 2019/0062756 A1 Feb. 28, 2019

Related U.S. Application Data

(63) Continuation of application No. PCT/US2017/016042, filed on Feb. 1, 2017.

(60) Provisional application No. 62/289,447, filed on Feb. 1, 2016.

(51) Int. Cl.
| | | |
|---|---|---|
| C07H 21/04 | (2006.01) | |
| C12N 15/113 | (2010.01) | |
| C12N 15/11 | (2006.01) | |
| A61K 31/7088 | (2006.01) | |
| A61P 29/00 | (2006.01) | |

(52) U.S. Cl.
CPC ...... *C12N 15/1138* (2013.01); *A61K 31/7088* (2013.01); *A61P 29/00* (2018.01); *C12N 15/11* (2013.01); *C12N 2310/11* (2013.01)

(58) Field of Classification Search
None
See application file for complete search history.

(56) References Cited

U.S. PATENT DOCUMENTS

| | | |
|---|---|---|
| 5,989,849 A | 11/1999 | Gewirtz et al. |
| 6,806,084 B1 | 10/2004 | Debs et al. |
| 7,973,015 B2 | 7/2011 | Van Ommen et al. |
| 8,236,557 B2 | 8/2012 | Dongsheng et al. |
| 8,268,962 B2 | 9/2012 | Heemskerk et al. |
| 8,304,398 B2 | 11/2012 | Hoen et al. |
| 8,361,979 B2 | 1/2013 | Aartsma-Rus et al. |
| 8,569,256 B2 | 10/2013 | Heyes et al. |
| 8,765,703 B2 | 7/2014 | Vickers et al. |
| 8,802,645 B2 | 8/2014 | Van Ommen et al. |
| 8,946,183 B2 | 2/2015 | Baker et al. |
| 9,080,170 B2 | 7/2015 | Garcia et al. |
| 9,238,042 B2 | 1/2016 | Schnell et al. |
| 9,598,703 B2 | 3/2017 | Garcia et al. |
| 9,738,891 B2 | 8/2017 | Leumann et al. |
| 9,862,945 B2 | 1/2018 | Flanigan et al. |
| 10,030,894 B2 | 7/2018 | Azuma et al. |
| 10,188,633 B2 | 1/2019 | Nelson et al. |
| 10,590,420 B2 | 3/2020 | Barkats et al. |
| 2011/0039334 A1 | 2/2011 | Bennett et al. |
| 2012/0029059 A1 | 2/2012 | Wilton et al. |
| 2013/0253033 A1 | 9/2013 | Wilton et al. |
| 2015/0238627 A1 | 8/2015 | Leger et al. |
| 2015/0361428 A1 | 12/2015 | Bestwick et al. |
| 2015/0376615 A1 | 12/2015 | Wilton et al. |
| 2019/0317099 A1* | 10/2019 | Halbert ................ C12N 15/115 |
| 2021/0363531 A1 | 11/2021 | Cruse |

FOREIGN PATENT DOCUMENTS

| | | |
|---|---|---|
| EP | 3844278 | 7/2021 |
| WO | WO01/74903 | 10/2001 |
| WO | WO2005/080410 | 9/2005 |
| WO | WO2005/085443 | 9/2005 |
| WO | WO 2019/200383 A1 | 10/2019 |
| WO | WO 2020/046985 | 3/2020 |
| WO | WO 2021/092562 A1 | 5/2021 |

OTHER PUBLICATIONS

Van Deutekom et al (Hum. Mol. Gen. 10(15):1547-1554, 2001).*
Aartsma-Rus et al (Neuromuscular Disorders 12: S71-S77, 2002).*
Arechavala-Gomeza et al (Hum. Gene Ther. Sep. 2007;18(9):798-810).*
Aartsma-Rus et al (Mol. Ther. 17(3): 548-553, 2009).*
Bulfone-Paus and Rahri, Front. Immunol. 2015; 6:394.
Cruse et al., Functional KCa3.1 K+ channels are required for human lung mast cell migration, Thorax 61:880-85 (2006).
Galli and Tsai, Nature Medicine. May 4, 2012;18(5):693-704.
International Preliminary Report on Patentability corresponding to International Patent Application No. PCT/US2017/016042 dated Aug. 7, 2018.
International Search Report corresponding to International Patent Application No. PCT/US2017/016042 dated Apr. 25, 2017.
Maeyama, K., et al., J. Biol. Chem. 261:2583-92 (1986).
Written Opinion of the International Searching Authority corresponding to International Patent Application No. PCT/US2017/016042 dated Aug. 10, 2017.
Cruse et al. (2011) Functional KCa3.1 K+ channels are required for human fibrocyte migration. J. Allergy and Clin. Immun. 128:1303-09.

(Continued)

*Primary Examiner* — Kimberly Chong
(74) *Attorney, Agent, or Firm* — Jenkins, Wilson, Taylor & Hunt, P.A.

(57) ABSTRACT

Methods for treating diseases and conditions mediated by the high affinity IgE receptor (FcεRI). Antisense oligomers for modulating splicing of mRNA encoding the FcεRIβ protein, thereby down-regulating cell-surface expression of FcεRI, and uses of the antisense oligomers for inhibiting mast cell degranulation, cytokine release, migration, and proliferation.

20 Claims, 15 Drawing Sheets

Specification includes a Sequence Listing.

(56) References Cited

OTHER PUBLICATIONS

International Search Report corresponding to International Patent Application No. PCT/US2019/048400 dated Dec. 12, 2019.
Ma et al., "The c-KIT mutation causing human mastocytosis is resistant to STI571 and other KIT kinase inhibitors; kinases with enzymatic site mutations show different inhibitor sensitivity profiles than wild-type kinases and those with regulatory-type mutations," Blood, vol. 99 (5), pp. 1741-1744 (2002).
Genbank® Accession No. NM_000139.4 (Aug. 19, 2010).
Genbank® Accession No. NM_013516.2 (Feb. 1, 2013).
Tkaczyk et al. (2003) The phospholipase C gamma 1-dependent pathway of Fc epsilon RI-mediated mast cell activation is regulated independently of phosphatidylinositol 3-kinase. J. Biol. Chem. 278:48474-84.
Written Opinion of the International Searching Authority corresponding to International Patent Application No. PCT/US2019/048400 dated Nov. 21, 2019.
Cruse et al., "Exon skipping of FcεERIβ eliminates expression of the high-affinity IgE receptor in mast cells with therapeutic potential for allergy," Proc Natl Acad Scie USA p. 14115-14120 (2016).
Liang et al., "Structural Organization of the Human MS4A Gene Cluster on Chromosome 11q12," Immunogenetics, vol. 53, pp. 357-368 (2001).
Notice of Publication corresponding to International application No. PCT/US2020/059682 dated May 14, 2021.
International Preliminary Report on Patentability corresponding to International Patent Application No. PCT/US2019/048400 dated Mar. 2, 2021.
International Search Report and Written Opinion of the International Searching Authority corresponding to International Patent Application No. PCT/US2020/59682 dated Mar. 29, 2021.
Alber et al., "Structure-function relationships in the mast cell high affinity receptor for IgE. Role of the cytoplasmic domains and of the beta subunit." J. Biol. Chern., vol. 266, p. 22613-22620 (1991).
Alshahrani et al., "CEACAM2 negatively regulates hemi (ITAM-bearing) GPVI and CLEC-2 pathways and thrombus growth in vitro and in vivo." Blood, vol. 124, pp. 2431-2441 (2014).
Antonescu et al. (2005) "Acquired Resistance to Imatinib in Gastrointestinal Stromal Tumor Occurs Through Secondary Gene Mutation." Clin Cancer Res 11(11): 4182-4190.
Arock et al. (2015) "KIT mutation analysis in mast cell neoplasms: recommendations of the European Competence Network on Mastocytosis." Leukemia 29(6): 1223-1232.
Asai et al. (2001) "Regulation of Mast Cell Survival by IgE." Immunity 14(6): 791-800.
Besmer et al. "A new acute transforming feline retrovirus and relationship of its oncogene v-kit with the protein kinase gene family." (1986) Nature 320(6061): 415-421.
Bieber et al., "Human epidermal Langerhans cells express the high affinity receptor for immunoglobulin E (Fc epsilon RI)." The Journal of Experimental Medicine, vol. 175, pp. 1285-1290 (1992).
Bubien et al., "Transfection of the CD20 cell surface molecule into ectopic cell types generates a Ca2+ conductance found constitutively in B lymphocytes." J. Cell Biol., vol. 121, pp. 1121-1132 (1993).
Chan et al. (2013) "Distinct signalling pathways for mutated KIT(V560G) and KIT(D816V) in mastocytosis." Clin Exp Dermatol 38(5): 538-544.
Cheung et al., "Cutting edge: CD49d+ neutrophils induce FcεRI expression on lung dendritic cells in a mouse model of postviral asthma." The Journal of Immunology, vol. 185, pp. 4983-4987 (2010).
Cruse et al. (2013) "A truncated splice-variant of the FcεRI receptor subunit is critical for microtubule formation and degranulation in mast cells." Immunity 38(5): 906-917.
Cruse et al. (2014) "Functional deregulation of kit: link to mast cell proliferative diseases and other neoplasms." Immunol Allergy Clin North Am 34(2): 219-237.
Cruse et al., "Mast cells in airway diseases and interstitial lung disease." European Journal of Pharmacology, vol. 778, pp. 125-138 (2016).
Cruse et al., "The CD20 homologue MS4A4 directs trafficking of KIT toward clathrin-independent endocytosis pathways and thus regulates receptor signaling and recycling." Mol Biol Cell, vol. 26, pp. 1711-1727 (2015).
Dalerba et al., "Single-cell dissection of transcriptional heterogeneity in human colon tumors." Nat Biotechnol, vol. 29, pp. 1120-1127 (2011).
De Angelis et al., "Chimeric snRNA molecules carrying antisense sequences against the splice junctions of exon 51 of the dystrophin pre-mRNA induce exon skipping and restoration of a dystrophin synthesis in Delta 48-50 DMD cells." Proc Natl Acad Sci USA, vol. 99, pp. 9456-9461 (2002).
Dehlink et al., "Relationships between levels of serum IgE, cell-bound IgE, and IgE-receptors on peripheral blood cells in a pediatric population." PLoS One, vol. 5, Article ID e12204 (2010).
Dent et al., "Chimeric adeno-associated virus/antisense U1 small nuclear RNA effectively rescues dystrophin synthesis and muscle function by local treatment of mdx mice." Hum Gene Ther, vol. 17, pp. 565-574 (2006).
Disterer et al. (2013) "Exon Skipping of Hepatic APOB Pre-mRNA With Splice-switching Oligonucleotides Reduces LDL Cholesterol In Vivo." Mol Ther 21(3): 602-609.
Dombrowicz et al., "Allergy-associated FcR is a molecular amplifier of IgE-and IgG-mediated in vivo responses." Immunity, vol. 8, pp. 517-529 (1998).
Dombrowicz et al., "Anaphylaxis mediated through a humanized high affinity IgE receptor." J Immunol, vol. 157, pp. 1645-1651 (1996).
Donnadieu et al., "A second amplifier function for the allergy-associated FcεRI- subunit." Immunity, vol. 12, pp. 515-523 (2000).
Dowling (2016) "Eteplirsen therapy for Duchenne muscular dystrophy: skipping to the front of the line." Nat Rev Neurol 12(12): 675-676.
Furumoto et al., "The FcepsilonRIbeta immunoreceptor tyrosine-based activation motif exerts inhibitory control on MAPK and IkappaB kinase phosphorylation and mast cell cytokine production." J Biol Chern, vol. 279, p. 49177-49187 (2004).
Galli et al. (1995) "Regulation of Mouse and Human Mast Cell Development, Survival and Function by Stem Cell Factor, the Ligand for the c-kit Receptor." Int Arch Allergy Immunol 107(1-3): 51-53.
Gallogly et al. (2017) "Midostaurin: a novel therapeutic agent for patients with FLT3-mutated acute myeloid leukemia and systemic mastocytosis." Ther Adv Hematol 8(9): 245-261.
Gleixner et al. (2006) "PKC412 inhibits in vitro growth of neoplastic human mast cells expressing the D816V-mutated variant of KIT: comparison with AMN107, imatinib, and cladribine (2CdA) and evaluation of cooperative drug effects." Blood 107(2): 752-759.
Gleixner et al. (2007) "Synergistic growth-inhibitory effects of two tyrosine kinase inhibitors, dasatinib and PKC412, on neoplastic mast cells expressing the D816V-mutated oncogenic variant of KIT." Haematologica 92(11): 1451-1459.
Godfrey et al. (2017) "Delivery is key: lessons learnt from developing splice-switching antisense therapies." EMBO Mol Med 9(5): 545-557.
Gotlib et al. (2016) "Efficacy and Safety of Midostaurin in Advanced Systemic Mastocytosis." N Engl J Med 374(26): 2530-2541.
Gould et al., "IgE in allergy and asthma today." Nature Reviews Immunology, vol. 8, pp. 205-217 (2008).
Goyenvalle et al., "Rescue of dystrophic muscle through U7 snRNA - mediated exon skipping." Science, vol. 306, pp. 1796-1799 (2004).
Greer et al., "A Family of non-GPCR Chemosensors Defines an Alternative Logic for Mammalian Olfaction." Cell, vol. 165, pp. 1734-1748 (2016).
Greer et al., "Serum IgE clearance is facilitated by human FcεRI internalization." The Journal of Clinical Investigation, vol. 124, pp. 1187-1198 (2014).
Haapaniemi et al. (2018) "CRISPR-Cas9 genome editing induces a p53-mediated DNA damage response." Nat Med 24(7):927-930.

(56) References Cited

OTHER PUBLICATIONS

Hazzan et al. (2017) "Apoptotic resistance of human skin mast cells is mediated by Mcl-1." Cell Death Discov 3: Article No. 17048.
Heinrich et al. (2006) "Molecular Correlates of Imatinib Resistance in Gastrointestinal Stromal Tumors." J Clin Oncol 24(29): 4764-4774.
Hollingworth et al., "Common variants at ABCA7, MS4A6A/MS4A4E, EPHA1, CD33 and CD2AP are associated with Alzheimer's disease." Nat Genet, vol. 43, pp. 429-435 (2011).
Iemura et al. (1994) "The c-kit ligand, stem cell factor, promotes mast cell survival by suppressing apoptosis." Am J Pathol 144(2): 321-328.
Ihry et al. (2018) "p53 inhibits CRISPR-Cas9 engineering in human pluripotent stem cells." Nat Med 24(7):939-946.
Ito et al. (2014) "Gastrointestinal stromal tumors with exon 8 c-kit gene mutation might occur at extragastric sites and have metastasis-prone nature." Int J Clin Exp Pathol 7(11): 8024-8031.
Jensen et al. (2008) "Pharmacological targeting of the KIT growth factor receptor: a therapeutic consideration for mast cell disorders." Br J Pharmacol 154(8): 1572-1582.
Juliano (2016) "The delivery of therapeutic oligonucleotides." Nucleic Acids Res 44(14): 6518-6548.
Kimura et al., "Downstream signaling molecules bind to different phosphorylated immunoreceptor tyrosine-based activation motif (ITAM) peptides of the high affinity IgE receptor." J Biol Chem, vol. 271, p. 27962-27968(1996).
Kinet, "The high-affinity IgE receptor (FceRI): from physiology to pathology." Annual Review of Immunology, vol. 17, pp. 931-972 (1999).
Kirshenbaum et al. (2003) "Characterization of novel stem cell factor responsive human mast cell lines LAD 1 and 2 established from a patient with mast cell sarcoma/leukemia; activation following aggregation of FcepsilonRI or FcgammaRI." Leuk Res 27(8): 677-682.
Koslowski et al., "MS4A12 is a colon-selective store-operated calcium channel promoting malignant cell processes." Cancer Res, vol. 68, pp. 3458-3466 (2008).
Kraft et al., "New developments in Fcepsilon]RI regulation, function and inhibition." Nature Reviews Immunology, vol. 7, pp. 365-378 (2007).
Kraft et al., "The role of the FceRI B-chain in allergic diseases." International Archives of Allergy and Immunology, vol. 135, pp. 62-72 (2004).
Kuster et al., "The gene and cDNA for the human high affinity immunoglobulin E receptor beta chain and expression of the complete human receptor." Journal of Biological Chemistry, vol. 267, p. 12782-12787 (1992).
Liang et al., "Identification of a CD20-, FcepsilonRIbeta-, and HTm4-related gene family: sixteen new MS4A family members expressed in human and mouse." Genomics, vol. 72, pp. 119-127 (2001).
Longley et al. (1999) "Activating and dominant inactivating c-KIT catalytic domain mutations in distinct clinical forms of human mastocytosis." Proc Natl Acad Sci U S A 96(4): 1609-1614.
Manne et al., "Distinct pathways regulate Syk protein activation downstream of immune tyrosine activation motif (ITAM) and hemITAM receptors in platelets." J Biol Chem, vol. 290, p. 11557-11568 (2015).
Maurer et al., "Expression of functional high affinity immunoglobulin E receptors (Fc epsilon RI) on monocytes of atopic individuals." The Journal of Experimental Medicine, vol. 179, pp. 745-750 (1994).
Maurer et al., "Peripheral blood dendritic cells express Fc epsilon RI as a complex composed of Fc epsilon RI alpha-and Fc epsilon RI gamma-chains and can use this receptor for IgE-mediated allergen presentation." The Journal of Immunology, vol. 157, pp. 607-616 (1996).
McClorey & Banerjee (2018) "Cell-Penetrating Peptides to Enhance Delivery of Oligonucleotide-Based Therapeutics." Biomedicines 6(2): 10.3390/biomedicines6020051.

Mekori et al. (1993) "IL-3-dependent murine mast cells undergo apoptosis on removal of IL-3. Prevention of apoptosis by c-kit ligand." J Immunol 151(7): 3775-3784.
Michel et al., "Identification of the novel differentiation marker MS4A8B and its murine homolog MS4A8A in colonic epithelial cells lost during neoplastic transformation in human colon." Cell Death Dis, vol. 4, Article ID e469 (2013).
Miettinen et al. (2002) "Pathology and diagnostic criteria of gastrointestinal stromal tumors (GISTs): a review." Eur J Cancer 38 Suppl 5: S39-51.
Naj et al., "Common variants at MS4A4/MS4A6E, CD2AP, CD33 and EPHA1 are associated with late-onset Alzheimer's disease." Nat Genet, vol. 43, pp. 436-441 (2011).
Obata et al. (2014) "Oncogenic Kit signals on endolysosomes and endoplasmic reticulum are essential for neoplastic mast cell proliferation." Nat Commun 5: Article No. 5715.
On et al., "Molecular dissection of the FcR signaling amplifier." Journal of Biological Chemistry, vol. 279, p. 45782-45790 (2004).
Osborne et al., "The inositol 5'-phosphatase SHIP binds to immunoreceptor signaling motifs and responds to high affinity IgE receptor aggregation." J Biol Chem, vol. 271, p. 29271-29278 (1996).
Pardanani et al. (2003) "Imatinib for systemic mast-cell disease." Lancet 362(9383): 535-536.
Parravicini et al., "Fyn kinase initiates complementary signals required for IgE-dependent mast cell degranulation." Nat Immunol, vol. 3, pp. 741-748 (2002).
Pittoni et al. (2011) "Tumor-intrinsic and -extrinsic roles of c-Kit: mast cells as the primary off-target of tyrosine kinase inhibitors." Oncogene 30(7): 757-769.
Platzer et al., "Dendritic cell-bound IgE functions to restrain allergic inflammation at mucosal sites." Mucosal Immunology, vol. 8, pp. 516-532 (2015).
Reber et al. (2018) "CRISPR-Trap: a clean approach for the generation of gene knockouts and gene replacements in human cells." Mol Biol Cell 29(2): 75-83.
Sandford et al., "Localisation of atopy and beta subunit of high-affinity IgE receptor (Fc epsilon RI) on chromosome 11q." Lancet, vol. 341, pp. 332-334 (1993).
Singleton et al., "The first transmembrane region of the 3-chain stabilizes the tetrameric FceRI complex." Molecular immunology, vol. 46, pp. 2333-2339 (2009).
Stafford et al., "A 2.8 Mb YAC contig in 11 q12-q13 localizes candidate genes for atopy: Fc epsilon RI beta and CD20." Hum Mol Genet, vol. 3, pp. 779-785 (1994).
Syed (2016) "Eteplirsen: First Global Approval." Drugs 76(17): 1699-1704.
Tamborini et al. (2006) "Functional analyses and molecular modeling of two c-Kit mutations responsible for imatinib secondary resistance in GIST patients." Oncogene 25(45): 6140-6146.
Taniguchi et al. (1999) "Effect of c-kit mutation on prognosis of gastrointestinal stromal tumors." Cancer Res 59(17): 4297-4300.
Miller et al. (2 015) "Mast Cells, Mastocytosis, and Related Disorders." N Engl J Med 373(19): 1885-1886.
Tsai M et al. (1991) "Induction of mast cell proliferation, maturation, and heparin synthesis by the rat c-kit ligand, stem cell factor." Proc Natl Acad Sci U S A 88(14): 6382-6386.
Valent et al. (2017) "Advances in the Classification and Treatment of Mastocytosis: Current Status and Outlook toward the Future." Cancer Res 77(6): 1261-1270.
Vasudev et al., "Expression of high-affinity IgE receptor on human peripheral blood dendritic cells in children." PLoS One, vol. 7, Article ID e32556 (2012).
Virk et al., "Mast cells and their activation in lung disease." Transl Res, vol. 174, pp. 60-76 (2016).
Wan et al. (2009) "Modification of HER2 pre-mRNA alternative splicing and its effects on breast cancer cells." Int J Cancer 124(4): 772-777.
Wiley & Burke (2001) "Regulation of Receptor Tyrosine Kinase Signaling by Endocytic Trafficking." Traffic 2(1): 12-18.
Wu et al. (2012) "Silencing of c-kit with small interference RNA attenuates inflammation in a murine model of allergic asthma." Int J Mol Med 30(1):63-68.

(56) References Cited

OTHER PUBLICATIONS

Yanagida et al. (1995) "Effects of T-helper 2-type cytokines, interleukin-3 (IL-3), IL-4, IL-5, and IL-6 on the survival of cultured human mast cells." Blood 86(10): 3705-3714.
Yang et al. (2015) "Silencing c-Kit expression in human DCs suppresses Th2, Th17 response ." but enhances Th1 response Am J Transl Res 7(9):1499-1509.
Ye et al., "MS4A8B promotes cell proliferation in prostate cancer." Prostate, vol. 74, pp. 911-922 (2014).

\* cited by examiner

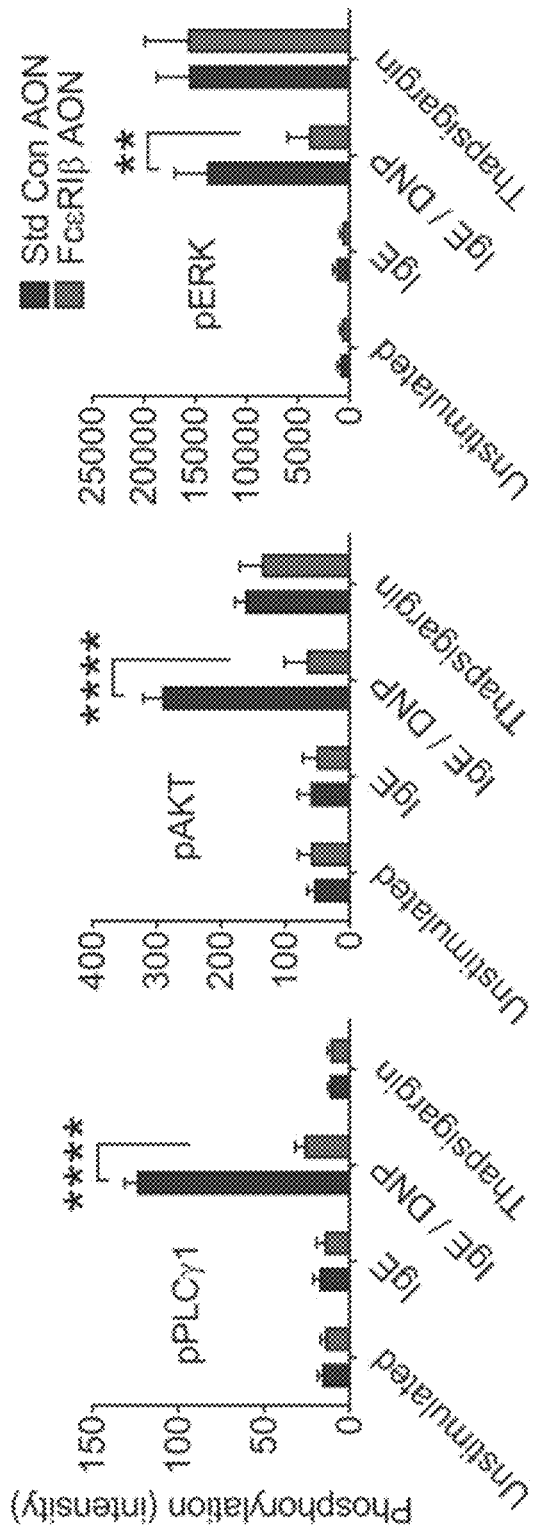
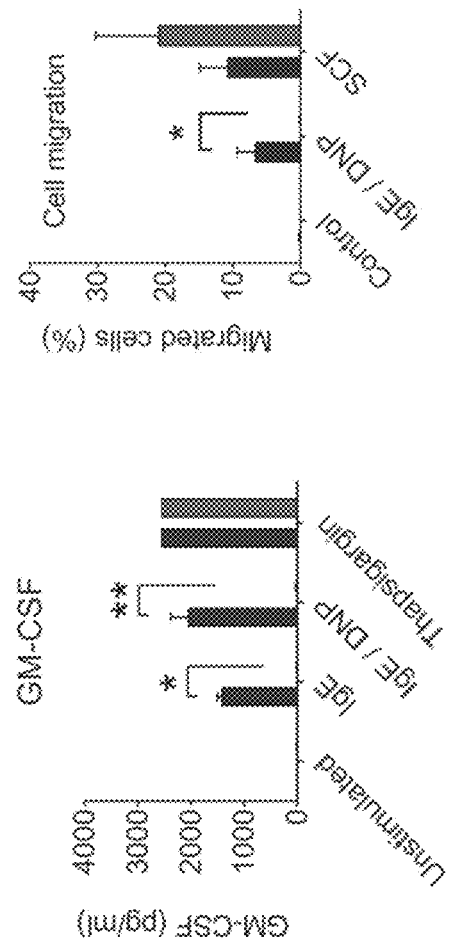
Figure 5B
Figure 5C
Figure 5D
Figure 5E
Figure 5F

SEQUENCE LISTING

<160> NUMBER OF SEQ ID NOS: 1015

<210> SEQ ID NO 1
<211> LENGTH: 3658
<212> TYPE: DNA
<213> ORGANISM: Homo sapiens

<400> SEQUENCE: 1

| | | | | | |
|---|---|---|---|---|---:|
| aacccatttc | aactgcctat | tcagagcatg | cagtaagagg | aaatccacca | agtctcaata | 60 |
| taataatatt | ctttattcct | ggacagctcg | gttaatgaaa | aaatggacac | agaaagtaat | 120 |
| aggagagcaa | atcttgctct | cccacaggag | ccttccagtg | tgcctgcatt | tgaagtcttg | 180 |
| gaaatatctc | cccaggaagt | atcttcaggc | agactattga | agtcggcctc | atccccacca | 240 |
| ctgcatacat | ggctgacagt | tttgaaaaaa | gagcaggagt | tcctggggt | aacacaaatt | 300 |
| ctgactgcta | tgatatgcct | ttgttttgga | acagttgtct | gctctgtact | tgatatttca | 360 |
| cacattgagg | gagacatttt | ttcatcattt | aaagcaggtt | atccattctg | ggagccata | 420 |
| ttttttcta | tttctggaat | gttgtcaatt | atatctgaaa | ggagaaatgc | aacatatctg | 480 |
| gtgagaggaa | gcctgggagc | aaacactgcc | agcagcatag | ctgggggaac | gggaattacc | 540 |
| atcctgatca | tcaacctgaa | gaagagcttg | gcctatatcc | acatccacag | ttgccagaaa | 600 |
| tttttgaga | ccaagtgctt | tatggcttcc | ttttccactg | aaattgtagt | gatgatgctg | 660 |
| tttctcacca | ttctgggact | tggtagtgct | gtgtcactca | caatctgtgg | agctggggaa | 720 |
| gaactcaaag | gaaacaaggt | tccagaggat | cgtgtttatg | aagaattaaa | catatattca | 780 |
| gctacttaca | gtgagttgga | agacccaggg | gaaatgtctc | ctcccattga | tttataagaa | 840 |
| tcacgtgtcc | agaacactct | gattcacagc | caaggatcca | gaaggccaag | gtcttgttaa | 900 |
| ggggctactg | gaaaaatttc | tattctctcc | acagcctgct | ggttttacat | tagatttatt | 960 |
| cgcctgataa | gaatattttg | tttctgctgc | ttctgtccac | cttaatattc | tccttctatt | 1020 |
| tgtagatatg | atagactcct | attttcttg | ttttatatta | tgaccacaca | catctctgct | 1080 |
| ggaaagtcaa | catgtagtaa | gcaagattta | actgtttgat | tataactgtg | caaatacaga | 1140 |
| aaaaagaag | gctggctgaa | agttgagtta | aactttgaca | gtttgataat | atttggttct | 1200 |
| tagggttttt | tttttttttt | agcattctta | atagttacag | ttgggcatga | tttgtaccat | 1260 |
| ccacccatac | ccacacagtc | acagtcacac | acacatatgt | attacttaca | ctatatataa | 1320 |
| cttcctatgc | aaatatttta | ccaccagtca | ataatacatt | tttgccaaga | catgaagttt | 1380 |
| tataaagatc | tgtataattg | cctgaatcac | cagcacattc | actgacatga | tattatttgc | 1440 |
| agattgacaa | gtaggaagtg | gggaatttta | ttaagttact | cgttgtctgg | ggaggtaaat | 1500 |
| aggttaaaaa | cagggaaatt | ataagtgcag | agattaacat | ttcacaaatg | tttagtgaaa | 1560 |
| catttgtgaa | aaaagaagac | taaattaaga | cctgagctga | aataaagtga | gtggaaatgg | 1620 |
| aaataatggt | tatatctaaa | acatgtagaa | aaagagtaac | tggtagattt | tgttaacaaa | 1680 |
| ttaaagaata | aagttagaca | agcaactggt | tgactaatac | attaagcgtt | tgagtctaag | 1740 |
| atgaaaggag | aacactggtt | atgttgatag | aatgataaaa | agggtcgggc | gcggaggctc | 1800 |
| acgcctgtaa | tcccagccct | ttgggaggcc | gaggtgggca | gatcacgaag | tcagtagttt | 1860 |
| gagaccagcc | tggccaacat | agtgaaaccc | cgtctctact | aaaatacaa | aaaaaaatt | 1920 |
| agctgggtgt | ggtggcagtc | acctgtagtc | ccagctactt | gggaggctga | ggcaggagaa | 1980 |
| tcgcttcaac | ctgggaggcg | gaggttgcag | tgagccgaga | tcgcaccagt | gcactccagc | 2040 |
| cttggtgaca | atgggagact | ccatctcaaa | aaaaaaaaa | aaaaaaaaa | agataaaaag | 2100 |

-continued

```
tcagaaatct gaaaagtgga ggaagagtac aaatagacct aaattaagct cattttttagg    2160 ctttgatttt ggggagacaa agggaaatgc agccatagag ggcctgatga catccaatac    2220
agagttctgg taaagataaa atttgataca ggtttggtgt cattataaga gaaatcatta    2280
ttaaatgaag caagttaaca ctctaagaga attattttga gatagaagtg aagctaagct    2340
aaacttcaca tgcctataat tggagggaaa aactaaggat aaaatctagc ctagaagata    2400
caataattag tcataaacat gcattgtgaa actgtagaga gcaggtagcc caaaatagag    2460
aaagattaga taaagagaaa ataagtatcc atcagagaca gtatctctag gcttgggcaa    2520
gagaaaagtc cacagtgata agcaactcca cctaaggcat gaatatgcgg cagagaaaac    2580
agcaatagtg aatgaatgca aaggtgctg agaaattcca cacatgagta ttgtgatgag    2640
taaatgaata aaacatttgc aaagaccttt agagaaagag aatgggagca tatgtgagaa    2700
ataagatagt tgattatgaa tagaaggtag tgaagaaaag caagctaaga aaaaattctg    2760
tttataaaag aaggaaaaga tagtttatgt ttttagccta agtataagag tcctacagat    2820
ggactgaaaa aaatcagtct gagagtatta gtcacaatta atgaaataat tacatttttat    2880 gtattgagga tgccaagatt aaaaggtgac aggtagatgt taatttccct agattgtgaa    2940
agtgatcacg acaatcacac aacaaataat taagtgactt ggtatgcttt atttaattgt    3000
agggcctgag gttttccatt ctcattttc taaaatacaa ttttgtttct ccaaatttga    3060
cagcagaata aaaaccctac cctttcactg tgtatcatgc taagctgcat ctctactctt    3120
gatcatctgt aggtattaat cacatcactt ccatggcatg gatgttcaca tacagactct    3180
taaccctggt ttaccaggac ctctaggagt ggatccaatc tatatctta cagttgtata    3240 gtatatgata tctctttat ttcactcaat ttatattttc atcattgact acatatttct    3300
tatacacaac acacaattta tgaatttttt ctcaagatca ttctgagagt tgccccaccc    3360
tacctgcctt ttatagtatg cccacctcag gcagacacag agcacaatgc tggggttctc    3420
ttcacactat cactgcccca aattgtcttt ctaaatttca acttcaatgt catcttctcc    3480
atgaagacca ctgaatgaac acctttcat ccagccttaa tttcttgctc cataactact    3540
ctatcccacg atgcagtatt gtatcattaa ttattagtgt gcttgtgacc tccttatgta    3600
ttctcaatta cctgtatttg tgcaataaat tggaataatg taacttgaaa aaaaaaa      3658
```

<210> SEQ ID NO 2
<211> LENGTH: 244
<212> TYPE: PRT
<213> ORGANISM: Homo sapiens

<400> SEQUENCE: 2

```
Met Asp Thr Glu Ser Asn Arg Arg Ala Asn Leu Ala Leu Pro Gln Glu
1               5                   10                  15

Pro Ser Ser Val Pro Ala Phe Glu Val Leu Glu Ile Ser Pro Gln Glu
            20                  25                  30

Val Ser Ser Gly Arg Leu Leu Lys Ser Ala Ser Pro Pro Leu His
        35                  40                  45

Thr Trp Leu Thr Val Leu Lys Lys Glu Gln Glu Phe Leu Gly Val Thr
    50                  55                  60

Gln Ile Leu Thr Ala Met Ile Cys Leu Cys Phe Gly Thr Val Val Cys
65                  70                  75                  80

Ser Val Leu Asp Ile Ser His Ile Glu Gly Asp Ile Phe Ser Ser Phe
                85                  90                  95
```

| | | | | | | | | | | | | |
|---|---|---|---|---|---|---|---|---|---|---|---|---|
|Lys|Ala|Gly|Tyr|Pro|Phe|Trp|Gly|Ala|Ile|Phe|Ser|Ile|Ser|Gly|
| | | |100| | | |105| | | |110| | | |

Lys Ala Gly Tyr Pro Phe Trp Gly Ala Ile Phe Ser Ile Ser Gly
            100                 105                 110

Met Leu Ser Ile Ile Ser Glu Arg Arg Asn Ala Thr Tyr Leu Val Arg
            115                 120                 125

Gly Ser Leu Gly Ala Asn Thr Ala Ser Ser Ile Ala Gly Gly Thr Gly
        130                 135                 140

Ile Thr Ile Leu Ile Ile Asn Leu Lys Lys Ser Leu Ala Tyr Ile His
145                 150                 155                 160

Ile His Ser Cys Gln Lys Phe Phe Glu Thr Lys Cys Phe Met Ala Ser
                165                 170                 175

Phe Ser Thr Glu Ile Val Val Met Met Leu Phe Leu Thr Ile Leu Gly
            180                 185                 190

Leu Gly Ser Ala Val Ser Leu Thr Ile Cys Gly Ala Gly Glu Glu Leu
            195                 200                 205

Lys Gly Asn Lys Val Pro Glu Asp Arg Val Tyr Glu Glu Leu Asn Ile
        210                 215                 220

Tyr Ser Ala Thr Tyr Ser Glu Leu Glu Asp Pro Gly Glu Met Ser Pro
225                 230                 235                 240

Pro Ile Asp Leu

<210> SEQ ID NO 3
<211> LENGTH: 2759
<212> TYPE: DNA
<213> ORGANISM: Mus musculus

<400> SEQUENCE: 3

```
ggtattcaga gccaacccat cttaactgcc catccagagc acaccgcatt tctgtgtaac      60
agtatctttc attcctggat agcccaatta atgaaaaaat ggacacagaa aataggagca     120
gagcagatct tgctctccca aatccacaag aatcctccag tgcacctgac attgaactct     180
tggaagcatc tcctgccaaa gcagcccac caaagcagac atggcggaca ttttgaaga      240
aagagttgga gttcctggga gcaacacaaa ttctggttgg tttgatatgc ctttgttttg     300
gaacaattgt ctgctccgta ctctatgttt cagactttga tgaagaagtg cttttacttt     360
ataaactagg ctatccattc tggggtgcag tgctgtttgt tttgtctgga tttttgtcaa     420
ttatctccga agaaaaaaac acattgtatc tggtgagagg cagcctggga gcaaacattg     480
tcagtagcat cgctgcaggg acgggatcg ccatgctgat cctcaatctg accataact      540
tcgcttatat gaacaactgc aagaatgtaa ccgaagacga cggctgcttt gtggcttctt     600
tcaccacaga actggtgttg atgatgctgt ttctcaccat cctggccttt tgcagtgctg     660
tgttgttcac tatctatagg attggacaag agttagaaag taaaaaggtc ccagatgatc     720
gtctttatga agaattaaat gtgtattcac caatttacag tgagttggaa gacaaagggg     780
aaacatcttc tccagttgat tcataagaat caggggacca ggacaatctg attcaagtat     840
aatcttgaaa gttgatcttt ttacaaaatt ctcgcaaaat ttctgtttgt tccacattct     900
gtcagttttt caattggatt gttctgcaga tgccactctt ttagttatgc tgtatctgat     960
cttctaaata tctcccttt tgcggatatc attcactcca attttcttgt tttgtgtcac    1020
aatttcacat acatctttc tggaaagtca tcaaggaata agttggcttt attgtatgtc    1080
tactttcatg aacaaaagga agatatggaa gaattaccct gagaatttaa ctaaccttag    1140
ataatcaggt aatatttggc tcttagttca ttttagaatt ctcaacagct atagttatat    1200
gtgatatata tccaccatat caagccttct gtatgtattt taacatgata tacacttttc    1260
```

```
tgtgtagata tatttccacc ctcaataata atggggttat tttagagaca taaagctttg    1320
tgaaaagacg acatcatctg gttgatgagt acattcacct gcacaggtat cgctcagtgg    1380
tttgccaatt ggtgagtagt aggcaataga gaacattatc aaaccattca gtctagtgag    1440
atggataggt acattcaggg atactgtgag tatcctttag taagacacat gggaagaatg    1500
aagaataaac tgatgaagac ttgagctaga aggtagtcaa tgggaatgac aagaaatgat    1560
tgtgtataac acatgtacgt aaatatctac caaaagttgg tagagattgg catgtttgcc    1620
tagaatctca gcacaaggcc agcctctgtt acatagtgag ttagaggcca gcctggctat    1680
atgatatcct acatcaaagg accaaaggag aaattggttc aagttgttaa taccttaaag    1740
gatagttaaa caaacagcag tttgatatat tcagtgtttg attctttaat aaaactaaat    1800
gaataacatt gagggggagg gaagcagtaa tgtagaagtc tggatggtgg aagagtagta    1860
gagacaactt aaaactcagt tttagacttt tgttctgaga tgggtataag agtgatcatt    1920
aaataaggag ggaagacacc aggagaatta ttttgagata gaactaaggc agtcaaactc    1980
cacatgccta cacttagaag gggaaagtaa ggatcaaaag tagaaaccct aacaagtcag    2040
gtaagcatat tacagaacat taaccagcag atgcctatag tggggaaaag ttagacaaag    2100
cgaaaataat tacccaccag agaccgtgca tgtaggcttg ggaaagacaa gagaaaatag    2160
caactccaaa tgaatgctaa ctctgaagag ggtgtgggca gaggaccaga acatttgcaa    2220
aggtgcccag agagcagacc atgaatagaa ggtagtgagg aaaaacaaac aaacaaacaa    2280
acaaacaccc ccaaaacagc tgagaaaatg attttgttgc tcctattaag attttttaaaa    2340 gaaacaaaaa gagatgttga aaaatctgtt tgctgggatc agttggtgtg ttctccatgt    2400
gtccaaggga caggtaactt ttctaaatct tcatgtaagg ctcgcctcat ttacatccgt    2460
ctctccacac agccatatcc tcaattcaca gttactctat cacggtagta aactgtgcgt    2520
gtgatctcct tatgtatctt caggcagtgt ttatccagta aatcagagtt atttaacttg    2580
atatttgtat tagcaaatga agttgaaaga atatgaggga agtcttgagg aagaaaatcg    2640
atggtggata tgatcatatt tcactgtaca catttgtaaa gttctcagaa ataaagaaaa    2700 ctcatttttaa aaagaaccat gtacattaaa acaattgatt aaatggtgcc aaggacaaa    2759
```

<210> SEQ ID NO 4
<211> LENGTH: 235
<212> TYPE: PRT
<213> ORGANISM: Mus musculus

<400> SEQUENCE: 4

Met Asp Thr Glu Asn Arg Ser Arg Ala Asp Leu Ala Leu Pro Asn Pro
1               5                   10                  15

Gln Glu Ser Ser Ala Pro Asp Ile Glu Leu Leu Glu Ala Ser Pro
            20                  25                  30

Ala Lys Ala Ala Pro Pro Lys Gln Thr Trp Arg Thr Phe Leu Lys Lys
        35                  40                  45

Glu Leu Glu Phe Leu Gly Ala Thr Gln Ile Leu Val Gly Leu Ile Cys
    50                  55                  60

Leu Cys Phe Gly Thr Ile Val Cys Ser Val Leu Tyr Val Ser Asp Phe
65                  70                  75                  80

Asp Glu Glu Val Leu Leu Leu Tyr Lys Leu Gly Tyr Pro Phe Trp Gly
                85                  90                  95

Ala Val Leu Phe Val Leu Ser Gly Phe Leu Ser Ile Ile Ser Glu Arg
            100                 105                 110

Lys Asn Thr Leu Tyr Leu Val Arg Gly Ser Leu Gly Ala Asn Ile Val
            115                 120                 125

Ser Ser Ile Ala Ala Gly Thr Gly Ile Ala Met Leu Ile Leu Asn Leu
        130                 135                 140

Thr Asn Asn Phe Ala Tyr Met Asn Asn Cys Lys Asn Val Thr Glu Asp
145                 150                 155                 160

Asp Gly Cys Phe Val Ala Ser Phe Thr Thr Glu Leu Val Leu Met Met
                165                 170                 175

Leu Phe Leu Thr Ile Leu Ala Phe Cys Ser Ala Val Leu Phe Thr Ile
            180                 185                 190

Tyr Arg Ile Gly Gln Glu Leu Glu Ser Lys Lys Val Pro Asp Asp Arg
        195                 200                 205

Leu Tyr Glu Glu Leu Asn Val Tyr Ser Pro Ile Tyr Ser Glu Leu Glu
    210                 215                 220

Asp Lys Gly Glu Thr Ser Ser Pro Val Asp Ser
225                 230                 235

<210> SEQ ID NO 5
<211> LENGTH: 514
<212> TYPE: DNA
<213> ORGANISM: Homo sapiens

<400> SEQUENCE: 5
gtgagtgagc ctcctccaac tttgactaga gtaagggttg ggtctagaaa agaatattga      60
gttgcatcaa ctgttttccc acttggattc atgagaggtg ttaggtcctt taaaaaacat    120
ggtagataaa gagttgacac taactgggtc cttttgggaa gagagaagca tttcctcata    180
aagactttaa attgctagga cgagaatggc caacaggagt gaaggattca taatctttat    240
ctttacttag atgtaaagaa caattactga tgttcaacat gactacgtac ataaaggcgc    300
atggagaaaa gtattggcct tccatgcatt aggtagtgct tgtatcaatt cttatagtgg    360
ctagggtatc ctggaaaatc ttacgtgtgg atcatttctc aggacagtct aggacactaa    420
cgcagtttct catgtttggc ttctattatt aaaaaatgat acaatctcgg gaaaattttt    480
ttgattttca tgaaattcat gtgttttcct atag                                514

<210> SEQ ID NO 6
<211> LENGTH: 135
<212> TYPE: DNA
<213> ORGANISM: Homo sapiens

<400> SEQUENCE: 6
gtaacacaaa ttctgactgc tatgatatgc ctttgttttg aacagttgt ctgctctgta      60 cttgatattt cacacattga gggagacatt ttttcatcat ttaaagcagg ttatccattc    120
tggggagcca tattt                                                     135

<210> SEQ ID NO 7
<211> LENGTH: 2321
<212> TYPE: DNA
<213> ORGANISM: Homo sapiens

<400> SEQUENCE: 7
gtgagtatat atctataatt gtttctgaaa taacactgaa cataggtttt tctctttctc      60
agatctaacc agttgtttat tcccagtatt aacatgatat ttataattct taattataaa    120
ttatatgtga gcatatataa catagatatg ctcattaaca acaacaaaag attcttttta    180
caattaacgg tgggttaaac atttagccca cagttttatc ccatgagaaa cctgaatcta    240

| | |
|---|---|
| atacaagtta aatgacttgc ctaagggcca cttgactaat agtaattgaa cctaaacttt | 300 |
| cagaatccaa ctccaggaac atacttctag cactattcat caataaagtt atatgataaa | 360 |
| tacatacaac tttatctgtc aactaaaaat aacaacaaag gctgggcatg gtggctcaca | 420 |
| cccgtaatcc cagcactttg ggaggctgag gcaggtggat cacctgaggt caggagtttg | 480 |
| agaccagcct gaccaacatg gtgaaacctc atctctacta aatataaaaa attagctgag | 540 |
| tgtgatagtg catgcctgta atcccagcta cttaagaggc tgaggcagga ggcttgtttg | 600 |
| aacctggaag gcagaggttg cagtgagctg agattgtgcc attgcactcc agcctgggca | 660 |
| ataagagcga aactctgtct caaaataata ataataataa tagaaaataa agttgtcttc | 720 |
| atgaaaaatg aggaaagaga ttgctggggt gagaaacatt aagatcaaag gcatatggt | 780 |
| gaccttctat gccctagaaa ctcttttagg tatttctcc tggtatctct tttactcatc | 840 |
| gttctatctg gaaaatagg tggatgagtg agataataag gtatataact ttttaaaggt | 900 |
| ctaattgaca tataataaat tgcaagtatt tcagatgtac aatttgctaa ccttgacaca | 960 |
| catagacaca catgaaaaca tcaccacatt aatacaatgt atgtatccat catttccaaa | 1020 |
| agcttccctg tgtatctttg taactctttc ttcctccctc cactccttgt cctctcgttc | 1080 |
| ccaagaaaac attgatctgc tttctgtgaa tataaattaa cttacatttt ttagagcttt | 1140 |
| atataagtat gttctcttta ctgtttgtct tccttcgctg cacagttatt ttgagattct | 1200 |
| tcaagttttt tctttatatc gatacttcat tcacaagaat atattttaat tctagactat | 1260 |
| gtcacattga ctttgtagtc tgctaaatcc ttagtgctca gatgacttgt tcaggactct | 1320 |
| ccttgaacct gtacctctgt tataattgaa acttgtctct actgtctttt tatttcaaac | 1380 |
| acagcttatg aggtgtctct caacccatca aactcacaat ctgagtcttt aggagattgc | 1440 |
| tttgaatttg tgctattgac ttatatttat atcaaatatg taaatgtttg gtaaaaatat | 1500 |
| catcatgtac attttcataa ttactctata ttcacatgat atatgtcaga ctctggaaat | 1560 |
| atgcatgcca cagacacgtg tttcttgcct aaagggctg atggaagacg cacatacaaa | 1620 |
| tagacgattg caatagaatg agagtggtgg tctaatcgat tcatgccctg atgttgctgg | 1680 |
| acgttgctac tccaagagta acccctgcat tgtcagggtt agcatctcct ggaagcctca | 1740 |
| tgtaaatgaa gaatttcatg ctccatccag gacctaatga ataagaatct gcattttagc | 1800 |
| aagaccctca tatgattcat atacactttt tttttttttt tttagatgga gtctcactct | 1860 |
| tgtcgcccag gctggagtgc aatggcatga tcttggctca ctgcaacctc tgcctcccgg | 1920 |
| gttcaagtga ttctcctgtc tcagcctccc tagtagctgg gactacaggt gcatgccaca | 1980 |
| gtggctggct aatttttgta tttttagtag agacagggtt tcaccatttt ggtcaggctg | 2040 |
| gtcttgaact catgacctcc ggtgattccc ccgcctcggc ttcccaaagt gctgggatta | 2100 |
| cagacatgag ccaccacacc cagccttatt cgtatacaca tttaattctg agaagcactc | 2160 |
| tatagaaaat aagaataaga aaatattggg ctcacaggtg acattaataa gtaactttat | 2220 |
| cgagtacccc aaatgttacc tatgtttgga agatggggtt aaaaaggaca cattgaaaac | 2280 |
| aagaaactca ttgtggcttt ttttttcctcc ttttttgaaca g | 2321 |

<210> SEQ ID NO 8
<211> LENGTH: 505
<212> TYPE: DNA
<213> ORGANISM: Mus musculus

<400> SEQUENCE: 8

```
gtgagtgcct ggcctttatt ctcaactcaa aatgcaggct ggctctagga cagagtattt      60
agttatatta acattttctc tcatgggctg atggtgtcct atagcattct tgataggcga     120
ggaattgacg gtattatttg cacactctgg gaagagaaaa gcattttctt ataaagacat     180
taagttgcta ggtcatgaat ggaaaacagg aatgaaggat acaaaatgtc tcctgttagt     240
tagatagaaa gaacaattat gcatgcctga cataagtatg caaataaagc tgtgtgtgac     300
atgtattgat aatgtatgcg ttagagtctg ctagtcatgg ctcaggatat atagtgaata     360
gaagacagtg gacaaatctc acaaatgggt caatccaagg aaagcctatg ataccaaaca     420
gattttgcat attcagtctt acagagaaat tggtacaatt ttgagaaaat agatcctaac     480
tttataaaat tcatgttttc cacag                                           505

<210> SEQ ID NO 9
<211> LENGTH: 135
<212> TYPE: DNA
<213> ORGANISM: Mus musculus

<400> SEQUENCE: 9
gcaacacaaa ttctggttgg tttgatatgc ctttgttttg gaacaattgt ctgctccgta      60
ctctatgttt cagactttga tgaagaagtg cttttacttt ataaactagg ctatccattc     120
tggggtgcag tgctg                                                      135

<210> SEQ ID NO 10
<211> LENGTH: 2369
<212> TYPE: DNA
<213> ORGANISM: Mus musculus

<400> SEQUENCE: 10
gtgagaacat atctgtaatt gtttctgaaa taatgctaag cagagatttt cttttaatca      60
aagctaatta attttctttt aatcaagtgc ttatctctag catttcaata atatctacag     120
ttcttcattt atatatacat agcatctcta aatgtagttt ccaaagcact ttccacatat     180
actcattaac aagagcaaaa gattcttatc acagttaact gtggtttata aaccattaac     240
atactttcat tgactgaaaa acttgacact ctatgaaact gtaaagaat aaatacataa      300 atatttaaaa gttaaatgac tgaagactta tattcaagaa atacccctta acactaccta     360
gtaataaaac tacctggtat atgtacttac atatatttta tccattaata aaaaataaga    420
ttgaagagtg gccttagtag ttaaggatgc ttgctgctct tccacaggac ctgagttcag     480
ttcttagtac catgtcatgt gcatatggct gccagtgact cttgctcaag gagataagaa     540
ccttcttctg gccttcttgg gccttcatac agattagcat atatacacac agacatatac     600
acacactagc acatatatgt ttttaaaaat ctaaaacaat acaatagtgt aaaaagttat     660
ctttaagaat ggagggggaaa gacatatttc agatgagaac aaagttaaca acattggatg    720
aacacaattc cttttaaaaa ttctactgtc tagaaagcaa atgactgaat gagattacaa     780
ggtcatatag ccttgtatct gtgtagtaca catacaataa atagcatatt ctgcatatag     840
aaggtgtaag atttgagaaa atttgactca tatatatgta catatatata tacatatata     900
tgtatatata aaatattagc ttatatctca acctcattat tacaagccta tccatgattt     960
tgtaagttac attcatttcc ctacaactct tcctgtccca ctctgctacc agacttctca    1020
tcttgaagca atcactataa ttgaaaatta gttttcaatt tttacagctt gtaggaaaa    1080 gaactgtatg ctacaatgtt ttatatgcct acctttcttc attcatatca tcattgtgta    1140 ttatctttt atcaatagtt aagttataaa aatgtattca aatctaagga aaccattgca    1200
```

```
ttggtttgat atgctgctat gtagttcttc gatctcctgg tcatatggcc aagaatcatc    1260
ttgaccattt accacatttt ccttgaaatt tctttccatt tttcaaagat ttcattttaa    1320
aaatttattc atttattctc tctctctctg tatgtgtatg tatgtctctg tctctgtctc    1380
tgtctctgtc tctgtctctg tctctctctc tctctctccc tctctctctc tctctctcgt    1440
gtgtgtgtgt gtgtgtgtgt gtgtgtgtgt gtgtgtgtgt atgtaccagt gccatagctc    1500
acgtagaggt cagatgtcag agaacaactg taagatgtca ggtctttttt tgctactttg    1560
tgagatcaaa aaattgaact tgggttctgt tacaagcact tctacccact ggggcatctc    1620
atagactcaa gctcctgact ctttaagtgt ctaggaacac aaatctcaat ttcttagaag    1680
gtagtctgat tttgaagctt caagttttac ttttttactag atatttgcaa atgtatattt    1740
tcatagttaa ctatatgacc atgtgctgca tatcagactc catagctaca caaggctggc    1800
ctgaagaagc tgacagtgta agtcaggaca tatgaactaa gcattacaat aaatgagacc    1860
actgttacag ttatacagca gatatcacta gcccttgcta tctgcccagt aggtatcaaa    1920
gtcaacctta tagaggagcc atgtaaacaa aaaaaaaaa aaaaaacaaa caaacaaaaa    1980
aaaaaaacga agagcctcgg gtcatctaag acctaatgag taggagccta tgtgcttctt    2040
ttgcttcttt ttctctttct tacagtgtag ctcaggcttt cctcatccgt acaaccttcc    2100
tgcctcagac tcctgagagc tgggattgca ggcatgtgcc accacacagc ttggaacttg    2160
tattttatca ggagtttcac atggtctgta taaggaattg gctttgagaa atattttaca    2220
ggagataata aataatggtc tcatgggaga tttttagtgga tagccttcta gaacatctaa    2280
aactcatttt tatattttga ggataggcga aaaagtacac cagagagcag aaactcactt    2340
tggtctctcc cctgtttcct tttggacag                                      2369

<210> SEQ ID NO 11
<211> LENGTH: 185
<212> TYPE: DNA
<213> ORGANISM: Homo Sapiens

<400> SEQUENCE: 11
atgaaattca tgtgttttc tataggtaac acaaattctg actgctatga tatgcctttg     60
ttttggaaca gttgtctgct ctgtacttga tatttcacac attgagggag acattttttc    120
atcatttaaa gcaggttatc cattctgggg agccatattt gtgagtatat atctataatt    180
gtttc                                                                185

<210> SEQ ID NO 12
<211> LENGTH: 50
<212> TYPE: DNA
<213> ORGANISM: Homo Sapiens

<400> SEQUENCE: 12
atgaaattca tgtgttttc tataggtaac acaaattctg actgctatga                50

<210> SEQ ID NO 13
<211> LENGTH: 50
<212> TYPE: DNA
<213> ORGANISM: Homo Sapiens

<400> SEQUENCE: 13
ttatccattc tggggagcca tatttgtgag tatatatcta taattgtttc                50

<210> SEQ ID NO 14
```

```
<211> LENGTH: 23
<212> TYPE: DNA
<213> ORGANISM: Homo Sapiens

<400> SEQUENCE: 14
agtacagagc agacaactgt tca                                           23

<210> SEQ ID NO 15
<211> LENGTH: 49
<212> TYPE: DNA
<213> ORGANISM: Mus musculus

<400> SEQUENCE: 15
tttataaaat tcatgttttc cacaggcaac acaaattctg gttggtttg               49

<210> SEQ ID NO 16
<211> LENGTH: 50
<212> TYPE: DNA
<213> ORGANISM: Mus musculus

<400> SEQUENCE: 16
ctatccattc tggggtgcag tgctggtgag aacatatctg taattgtttc              50

<210> SEQ ID NO 17
<211> LENGTH: 16
<212> TYPE: DNA
<213> ORGANISM: Mus musculus

<400> SEQUENCE: 17
gtacagagca gacaac                                                   16

<210> SEQ ID NO 18
<211> LENGTH: 22
<212> TYPE: DNA
<213> ORGANISM: Mus musculus

<400> SEQUENCE: 18
atggacacag aaaataggag ca                                            22

<210> SEQ ID NO 19
<211> LENGTH: 23
<212> TYPE: DNA
<213> ORGANISM: Mus musculus

<400> SEQUENCE: 19
tgaatcaact ggagaagatg ttt                                           23

<210> SEQ ID NO 20
<211> LENGTH: 23
<212> TYPE: DNA
<213> ORGANISM: Homo Sapiens

<400> SEQUENCE: 20
atggacacag aaagtaatag gag                                           23

<210> SEQ ID NO 21
<211> LENGTH: 22
<212> TYPE: DNA
<213> ORGANISM: Mus musculus

<400> SEQUENCE: 21
ttataaatca atgggaggag ac                                            22
```

```
<210> SEQ ID NO 22
<211> LENGTH: 25
<212> TYPE: DNA
<213> ORGANISM: Mus musculus

<400> SEQUENCE: 22
gtgttgcctg tggaaaacat gaatt                                          25

<210> SEQ ID NO 23
<211> LENGTH: 23
<212> TYPE: DNA
<213> ORGANISM: Homo Sapiens

<400> SEQUENCE: 23
agtacagagc agacaactgt tca                                            23

<210> SEQ ID NO 24
<211> LENGTH: 35
<212> TYPE: DNA
<213> ORGANISM: Homo Sapiens

<400> SEQUENCE: 24
tcatagcagt cagaatttgt gttacctata gaaaa                               35

<210> SEQ ID NO 25
<211> LENGTH: 35
<212> TYPE: DNA
<213> ORGANISM: Homo Sapiens

<400> SEQUENCE: 25
catagcagtc agaatttgtg ttacctatag aaaaa                               35

<210> SEQ ID NO 26
<211> LENGTH: 35
<212> TYPE: DNA
<213> ORGANISM: Homo Sapiens

<400> SEQUENCE: 26
atagcagtca gaatttgtgt tacctataga aaaac                               35

<210> SEQ ID NO 27
<211> LENGTH: 35
<212> TYPE: DNA
<213> ORGANISM: Homo Sapiens

<400> SEQUENCE: 27
tagcagtcag aatttgtgtt acctatagaa aaaca                               35

<210> SEQ ID NO 28
<211> LENGTH: 35
<212> TYPE: DNA
<213> ORGANISM: Homo Sapiens

<400> SEQUENCE: 28
agcagtcaga atttgtgtta cctatagaaa aacac                               35

<210> SEQ ID NO 29
<211> LENGTH: 35
<212> TYPE: DNA
<213> ORGANISM: Homo Sapiens

<400> SEQUENCE: 29
gcagtcagaa tttgtgttac ctatagaaaa acaca                               35
```

<210> SEQ ID NO 30
<211> LENGTH: 35
<212> TYPE: DNA
<213> ORGANISM: Homo Sapiens

<400> SEQUENCE: 30
cagtcagaat tgtgttacc tatagaaaaa cacat                           35

<210> SEQ ID NO 31
<211> LENGTH: 35
<212> TYPE: DNA
<213> ORGANISM: Homo Sapiens

<400> SEQUENCE: 31
agtcagaatt tgtgttacct atagaaaaac acatg                          35

<210> SEQ ID NO 32
<211> LENGTH: 35
<212> TYPE: DNA
<213> ORGANISM: Homo Sapiens

<400> SEQUENCE: 32
gtcagaattt gtgttaccta tagaaaaaca catga                          35

<210> SEQ ID NO 33
<211> LENGTH: 35
<212> TYPE: DNA
<213> ORGANISM: Homo Sapiens

<400> SEQUENCE: 33
tcagaatttg tgttacctat agaaaaacac atgaa                          35

<210> SEQ ID NO 34
<211> LENGTH: 35
<212> TYPE: DNA
<213> ORGANISM: Homo Sapiens

<400> SEQUENCE: 34
cagaatttgt gttacctata gaaaaacaca tgaat                          35

<210> SEQ ID NO 35
<211> LENGTH: 35
<212> TYPE: DNA
<213> ORGANISM: Homo Sapiens

<400> SEQUENCE: 35
agaatttgtg ttacctatag aaaaacacat gaatt                          35

<210> SEQ ID NO 36
<211> LENGTH: 35
<212> TYPE: DNA
<213> ORGANISM: Homo Sapiens

<400> SEQUENCE: 36
gaatttgtgt tacctataga aaaacacatg aattt                          35

<210> SEQ ID NO 37
<211> LENGTH: 35
<212> TYPE: DNA
<213> ORGANISM: Homo Sapiens

<400> SEQUENCE: 37
aatttgtgtt acctatagaa aaacacatga atttc                          35

```
<210> SEQ ID NO 38
<211> LENGTH: 35
<212> TYPE: DNA
<213> ORGANISM: Homo Sapiens

<400> SEQUENCE: 38
atttgtgtta cctatagaaa aacacatgaa tttca                              35

<210> SEQ ID NO 39
<211> LENGTH: 35
<212> TYPE: DNA
<213> ORGANISM: Homo Sapiens

<400> SEQUENCE: 39
tttgtgttac ctatagaaaa acacatgaat tcat                               35

<210> SEQ ID NO 40
<211> LENGTH: 34
<212> TYPE: DNA
<213> ORGANISM: Homo Sapiens

<400> SEQUENCE: 40
tcatagcagt cagaatttgt gttacctata gaaa                               34

<210> SEQ ID NO 41
<211> LENGTH: 34
<212> TYPE: DNA
<213> ORGANISM: Homo Sapiens

<400> SEQUENCE: 41
catagcagtc agaatttgtg ttacctatag aaaa                               34

<210> SEQ ID NO 42
<211> LENGTH: 34
<212> TYPE: DNA
<213> ORGANISM: Homo Sapiens

<400> SEQUENCE: 42
atagcagtca gaatttgtgt tacctataga aaaa                               34

<210> SEQ ID NO 43
<211> LENGTH: 34
<212> TYPE: DNA
<213> ORGANISM: Homo Sapiens

<400> SEQUENCE: 43
tagcagtcag aatttgtgtt acctatagaa aaac                               34

<210> SEQ ID NO 44
<211> LENGTH: 34
<212> TYPE: DNA
<213> ORGANISM: Homo Sapiens

<400> SEQUENCE: 44
agcagtcaga atttgtgtta cctatagaaa aaca                               34

<210> SEQ ID NO 45
<211> LENGTH: 34
<212> TYPE: DNA
<213> ORGANISM: Homo Sapiens

<400> SEQUENCE: 45
```
gcagtcagaa tttgtgttac ctatagaaaa acac                                34

<210> SEQ ID NO 46
<211> LENGTH: 34
<212> TYPE: DNA
<213> ORGANISM: Homo Sapiens

<400> SEQUENCE: 46
cagtcagaat tgtgttacc tatagaaaaa caca                                 34

<210> SEQ ID NO 47
<211> LENGTH: 34
<212> TYPE: DNA
<213> ORGANISM: Homo Sapiens

<400> SEQUENCE: 47
agtcagaatt tgtgttacct atagaaaaac acat                                34

<210> SEQ ID NO 48
<211> LENGTH: 34
<212> TYPE: DNA
<213> ORGANISM: Homo Sapiens

<400> SEQUENCE: 48
gtcagaattt gtgttaccta tagaaaaaca catg                                34

<210> SEQ ID NO 49
<211> LENGTH: 34
<212> TYPE: DNA
<213> ORGANISM: Homo Sapiens

<400> SEQUENCE: 49
tcagaatttg tgttacctat agaaaaacac atga                                34

<210> SEQ ID NO 50
<211> LENGTH: 34
<212> TYPE: DNA
<213> ORGANISM: Homo Sapiens

<400> SEQUENCE: 50
cagaatttgt gttacctata gaaaaacaca tgaa                                34

<210> SEQ ID NO 51
<211> LENGTH: 34
<212> TYPE: DNA
<213> ORGANISM: Homo Sapiens

<400> SEQUENCE: 51
agaatttgtg ttacctatag aaaaacacat gaat                                34

<210> SEQ ID NO 52
<211> LENGTH: 34
<212> TYPE: DNA
<213> ORGANISM: Homo Sapiens

<400> SEQUENCE: 52
gaatttgtgt tacctataga aaacacatg aatt                                 34

<210> SEQ ID NO 53
<211> LENGTH: 34
<212> TYPE: DNA
<213> ORGANISM: Homo Sapiens

<400> SEQUENCE: 53

```
aatttgtgtt acctatagaa aaacacatga attt                                    34

<210> SEQ ID NO 54
<211> LENGTH: 34
<212> TYPE: DNA
<213> ORGANISM: Homo Sapiens

<400> SEQUENCE: 54
atttgtgtta cctatagaaa aacacatgaa tttc                                    34

<210> SEQ ID NO 55
<211> LENGTH: 34
<212> TYPE: DNA
<213> ORGANISM: Homo Sapiens

<400> SEQUENCE: 55
tttgtgttac ctatagaaaa acacatgaat tca                                     34

<210> SEQ ID NO 56
<211> LENGTH: 34
<212> TYPE: DNA
<213> ORGANISM: Homo Sapiens

<400> SEQUENCE: 56
ttgtgttacc tatagaaaaa cacatgaatt tcat                                    34

<210> SEQ ID NO 57
<211> LENGTH: 33
<212> TYPE: DNA
<213> ORGANISM: Homo Sapiens

<400> SEQUENCE: 57
tcatagcagt cagaatttgt gttacctata gaa                                     33

<210> SEQ ID NO 58
<211> LENGTH: 33
<212> TYPE: DNA
<213> ORGANISM: Homo Sapiens

<400> SEQUENCE: 58
catagcagtc agaatttgtg ttacctatag aaa                                     33

<210> SEQ ID NO 59
<211> LENGTH: 33
<212> TYPE: DNA
<213> ORGANISM: Homo Sapiens

<400> SEQUENCE: 59
atagcagtca gaatttgtgt tacctataga aaa                                     33

<210> SEQ ID NO 60
<211> LENGTH: 33
<212> TYPE: DNA
<213> ORGANISM: Homo Sapiens

<400> SEQUENCE: 60
tagcagtcag aatttgtgtt acctatagaa aaa                                     33

<210> SEQ ID NO 61
<211> LENGTH: 33
<212> TYPE: DNA
<213> ORGANISM: Homo Sapiens
```

<400> SEQUENCE: 61
agcagtcaga atttgtgtta cctatagaaa aac                33

<210> SEQ ID NO 62
<211> LENGTH: 33
<212> TYPE: DNA
<213> ORGANISM: Homo Sapiens

<400> SEQUENCE: 62
gcagtcagaa tttgtgttac ctatagaaaa aca                33

<210> SEQ ID NO 63
<211> LENGTH: 33
<212> TYPE: DNA
<213> ORGANISM: Homo Sapiens

<400> SEQUENCE: 63
cagtcagaat tgtgttacc tatagaaaaa cac                33

<210> SEQ ID NO 64
<211> LENGTH: 33
<212> TYPE: DNA
<213> ORGANISM: Homo Sapiens

<400> SEQUENCE: 64
agtcagaatt tgtgttacct atagaaaaac aca                33

<210> SEQ ID NO 65
<211> LENGTH: 33
<212> TYPE: DNA
<213> ORGANISM: Homo Sapiens

<400> SEQUENCE: 65
gtcagaattt gtgttaccta tagaaaaaca cat                33

<210> SEQ ID NO 66
<211> LENGTH: 33
<212> TYPE: DNA
<213> ORGANISM: Homo Sapiens

<400> SEQUENCE: 66
tcagaatttg tgttacctat agaaaaacac atg                33

<210> SEQ ID NO 67
<211> LENGTH: 33
<212> TYPE: DNA
<213> ORGANISM: Homo Sapiens

<400> SEQUENCE: 67
cagaatttgt gttacctata gaaaaacaca tga                33

<210> SEQ ID NO 68
<211> LENGTH: 33
<212> TYPE: DNA
<213> ORGANISM: Homo Sapiens

<400> SEQUENCE: 68
agaatttgtg ttacctatag aaaaacacat gaa                33

<210> SEQ ID NO 69
<211> LENGTH: 33
<212> TYPE: DNA

<400> SEQUENCE: 69
gaatttgtgt tacctataga aaaacacatg aat					33

<210> SEQ ID NO 70
<211> LENGTH: 33
<212> TYPE: DNA
<213> ORGANISM: Homo Sapiens

<400> SEQUENCE: 70
aatttgtgtt acctatagaa aaacacatga att					33

<210> SEQ ID NO 71
<211> LENGTH: 33
<212> TYPE: DNA
<213> ORGANISM: Homo Sapiens

<400> SEQUENCE: 71
atttgtgtta cctatagaaa aacacatgaa ttt					33

<210> SEQ ID NO 72
<211> LENGTH: 33
<212> TYPE: DNA
<213> ORGANISM: Homo Sapiens

<400> SEQUENCE: 72
tttgtgttac ctatagaaaa acacatgaat ttc					33

<210> SEQ ID NO 73
<211> LENGTH: 33
<212> TYPE: DNA
<213> ORGANISM: Homo Sapiens

<400> SEQUENCE: 73
ttgtgttacc tatagaaaaa cacatgaatt tca					33

<210> SEQ ID NO 74
<211> LENGTH: 33
<212> TYPE: DNA
<213> ORGANISM: Homo Sapiens

<400> SEQUENCE: 74
tgtgttacct atagaaaaac acatgaattt cat					33

<210> SEQ ID NO 75
<211> LENGTH: 32
<212> TYPE: DNA
<213> ORGANISM: Homo Sapiens

<400> SEQUENCE: 75
tcatagcagt cagaatttgt gttacctata ga					32

<210> SEQ ID NO 76
<211> LENGTH: 32
<212> TYPE: DNA
<213> ORGANISM: Homo Sapiens

<400> SEQUENCE: 76
catagcagtc agaatttgtg ttacctatag aa					32

<210> SEQ ID NO 77
<211> LENGTH: 32
<212> TYPE: DNA

```
<213> ORGANISM: Homo Sapiens

<400> SEQUENCE: 77
atagcagtca gaatttgtgt tacctataga aa                              32

<210> SEQ ID NO 78
<211> LENGTH: 32
<212> TYPE: DNA
<213> ORGANISM: Homo Sapiens

<400> SEQUENCE: 78
tagcagtcag aatttgtgtt acctatagaa aa                              32

<210> SEQ ID NO 79
<211> LENGTH: 32
<212> TYPE: DNA
<213> ORGANISM: Homo Sapiens

<400> SEQUENCE: 79
agcagtcaga atttgtgtta cctatagaaa aa                              32

<210> SEQ ID NO 80
<211> LENGTH: 32
<212> TYPE: DNA
<213> ORGANISM: Homo Sapiens

<400> SEQUENCE: 80
gcagtcagaa tttgtgttac ctatagaaaa ac                              32

<210> SEQ ID NO 81
<211> LENGTH: 32
<212> TYPE: DNA
<213> ORGANISM: Homo Sapiens

<400> SEQUENCE: 81
cagtcagaat tgtgttacc tatagaaaaa ca                               32

<210> SEQ ID NO 82
<211> LENGTH: 32
<212> TYPE: DNA
<213> ORGANISM: Homo Sapiens

<400> SEQUENCE: 82
agtcagaatt tgtgttacct atagaaaaac ac                              32

<210> SEQ ID NO 83
<211> LENGTH: 32
<212> TYPE: DNA
<213> ORGANISM: Homo Sapiens

<400> SEQUENCE: 83
gtcagaattt gtgttaccta tagaaaaaca ca                              32

<210> SEQ ID NO 84
<211> LENGTH: 32
<212> TYPE: DNA
<213> ORGANISM: Homo Sapiens

<400> SEQUENCE: 84
tcagaatttg tgttacctat agaaaaacac at                              32

<210> SEQ ID NO 85
<211> LENGTH: 32
```

<212> TYPE: DNA
<213> ORGANISM: Homo Sapiens

<400> SEQUENCE: 85
cagaatttgt gttacctata gaaaaacaca tg                                    32

<210> SEQ ID NO 86
<211> LENGTH: 32
<212> TYPE: DNA
<213> ORGANISM: Homo Sapiens

<400> SEQUENCE: 86
agaatttgtg ttacctatag aaaaacacat ga                                    32

<210> SEQ ID NO 87
<211> LENGTH: 32
<212> TYPE: DNA
<213> ORGANISM: Homo Sapiens

<400> SEQUENCE: 87
gaatttgtgt tacctataga aaaacacatg aa                                    32

<210> SEQ ID NO 88
<211> LENGTH: 32
<212> TYPE: DNA
<213> ORGANISM: Homo Sapiens

<400> SEQUENCE: 88
aatttgtgtt acctatagaa aaacacatga at                                    32

<210> SEQ ID NO 89
<211> LENGTH: 32
<212> TYPE: DNA
<213> ORGANISM: Homo Sapiens

<400> SEQUENCE: 89
atttgtgtta cctatagaaa aacacatgaa tt                                    32

<210> SEQ ID NO 90
<211> LENGTH: 32
<212> TYPE: DNA
<213> ORGANISM: Homo Sapiens

<400> SEQUENCE: 90
tttgtgttac ctatagaaaa acacatgaat tt                                    32

<210> SEQ ID NO 91
<211> LENGTH: 32
<212> TYPE: DNA
<213> ORGANISM: Homo Sapiens

<400> SEQUENCE: 91
ttgtgttacc tatagaaaaa cacatgaatt tc                                    32

<210> SEQ ID NO 92
<211> LENGTH: 32
<212> TYPE: DNA
<213> ORGANISM: Homo Sapiens

<400> SEQUENCE: 92
tgtgttacct atagaaaaac acatgaattt ca                                    32

<210> SEQ ID NO 93

```
<211> LENGTH: 32
<212> TYPE: DNA
<213> ORGANISM: Homo Sapiens

<400> SEQUENCE: 93
gtgttaccta tagaaaaaca catgaatttc at                              32

<210> SEQ ID NO 94
<211> LENGTH: 31
<212> TYPE: DNA
<213> ORGANISM: Homo Sapiens

<400> SEQUENCE: 94
tcatagcagt cagaatttgt gttacctata g                               31

<210> SEQ ID NO 95
<211> LENGTH: 31
<212> TYPE: DNA
<213> ORGANISM: Homo Sapiens

<400> SEQUENCE: 95
catagcagtc agaatttgtg ttacctatag a                               31

<210> SEQ ID NO 96
<211> LENGTH: 31
<212> TYPE: DNA
<213> ORGANISM: Homo Sapiens

<400> SEQUENCE: 96
atagcagtca gaatttgtgt tacctataga a                               31

<210> SEQ ID NO 97
<211> LENGTH: 31
<212> TYPE: DNA
<213> ORGANISM: Homo Sapiens

<400> SEQUENCE: 97
tagcagtcag aatttgtgtt acctatagaa a                               31

<210> SEQ ID NO 98
<211> LENGTH: 31
<212> TYPE: DNA
<213> ORGANISM: Homo Sapiens

<400> SEQUENCE: 98
agcagtcaga atttgtgtta cctatagaaa a                               31

<210> SEQ ID NO 99
<211> LENGTH: 31
<212> TYPE: DNA
<213> ORGANISM: Homo Sapiens

<400> SEQUENCE: 99
gcagtcagaa tttgtgttac ctatagaaaa a                               31

<210> SEQ ID NO 100
<211> LENGTH: 31
<212> TYPE: DNA
<213> ORGANISM: Homo Sapiens

<400> SEQUENCE: 100
cagtcagaat ttgtgttacc tatagaaaaa c                               31
```

```
<210> SEQ ID NO 101
<211> LENGTH: 31
<212> TYPE: DNA
<213> ORGANISM: Homo Sapiens

<400> SEQUENCE: 101
agtcagaatt tgtgttacct atagaaaaac a                              31

<210> SEQ ID NO 102
<211> LENGTH: 31
<212> TYPE: DNA
<213> ORGANISM: Homo Sapiens

<400> SEQUENCE: 102
gtcagaattt gtgttaccta tagaaaaaca c                              31

<210> SEQ ID NO 103
<211> LENGTH: 31
<212> TYPE: DNA
<213> ORGANISM: Homo Sapiens

<400> SEQUENCE: 103
tcagaatttg tgttacctat agaaaaacac a                              31

<210> SEQ ID NO 104
<211> LENGTH: 31
<212> TYPE: DNA
<213> ORGANISM: Homo Sapiens

<400> SEQUENCE: 104
cagaatttgt gttacctata gaaaaacaca t                              31

<210> SEQ ID NO 105
<211> LENGTH: 31
<212> TYPE: DNA
<213> ORGANISM: Homo Sapiens

<400> SEQUENCE: 105
agaatttgtg ttacctatag aaaaacacat g                              31

<210> SEQ ID NO 106
<211> LENGTH: 31
<212> TYPE: DNA
<213> ORGANISM: Homo Sapiens

<400> SEQUENCE: 106
gaatttgtgt tacctataga aaaacacatg a                              31

<210> SEQ ID NO 107
<211> LENGTH: 31
<212> TYPE: DNA
<213> ORGANISM: Homo Sapiens

<400> SEQUENCE: 107
aatttgtgtt acctatagaa aaacacatga a                              31

<210> SEQ ID NO 108
<211> LENGTH: 31
<212> TYPE: DNA
<213> ORGANISM: Homo Sapiens

<400> SEQUENCE: 108
atttgtgtta cctatagaaa aacacatgaa t                              31
```

```
<210> SEQ ID NO 109
<211> LENGTH: 31
<212> TYPE: DNA
<213> ORGANISM: Homo Sapiens

<400> SEQUENCE: 109
tttgtgttac ctatagaaaa acacatgaat t                           31

<210> SEQ ID NO 110
<211> LENGTH: 31
<212> TYPE: DNA
<213> ORGANISM: Homo Sapiens

<400> SEQUENCE: 110
ttgtgttacc tatagaaaaa cacatgaatt t                           31

<210> SEQ ID NO 111
<211> LENGTH: 31
<212> TYPE: DNA
<213> ORGANISM: Homo Sapiens

<400> SEQUENCE: 111
tgtgttacct atagaaaaac acatgaattt c                           31

<210> SEQ ID NO 112
<211> LENGTH: 31
<212> TYPE: DNA
<213> ORGANISM: Homo Sapiens

<400> SEQUENCE: 112
gtgttaccta tagaaaaaca catgaatttc a                           31

<210> SEQ ID NO 113
<211> LENGTH: 31
<212> TYPE: DNA
<213> ORGANISM: Homo Sapiens

<400> SEQUENCE: 113
tgttacctat agaaaaacac atgaatttca t                           31

<210> SEQ ID NO 114
<211> LENGTH: 30
<212> TYPE: DNA
<213> ORGANISM: Homo Sapiens

<400> SEQUENCE: 114
tcatagcagt cagaatttgt gttacctata                             30

<210> SEQ ID NO 115
<211> LENGTH: 30
<212> TYPE: DNA
<213> ORGANISM: Homo Sapiens

<400> SEQUENCE: 115
catagcagtc agaatttgtg ttacctatag                             30

<210> SEQ ID NO 116
<211> LENGTH: 30
<212> TYPE: DNA
<213> ORGANISM: Homo Sapiens

<400> SEQUENCE: 116
atagcagtca gaatttgtgt tacctataga                             30
```

<210> SEQ ID NO 117
<211> LENGTH: 30
<212> TYPE: DNA
<213> ORGANISM: Homo Sapiens

<400> SEQUENCE: 117
tagcagtcag aatttgtgtt acctatagaa                                           30

<210> SEQ ID NO 118
<211> LENGTH: 30
<212> TYPE: DNA
<213> ORGANISM: Homo Sapiens

<400> SEQUENCE: 118
agcagtcaga atttgtgtta cctatagaaa                                           30

<210> SEQ ID NO 119
<211> LENGTH: 30
<212> TYPE: DNA
<213> ORGANISM: Homo Sapiens

<400> SEQUENCE: 119
gcagtcagaa tttgtgttac ctatagaaaa                                           30

<210> SEQ ID NO 120
<211> LENGTH: 30
<212> TYPE: DNA
<213> ORGANISM: Homo Sapiens

<400> SEQUENCE: 120
cagtcagaat tgtgttacc tatagaaaaa                                            30

<210> SEQ ID NO 121
<211> LENGTH: 30
<212> TYPE: DNA
<213> ORGANISM: Homo Sapiens

<400> SEQUENCE: 121
agtcagaatt tgtgttacct atagaaaaac                                           30

<210> SEQ ID NO 122
<211> LENGTH: 30
<212> TYPE: DNA
<213> ORGANISM: Homo Sapiens

<400> SEQUENCE: 122
gtcagaattt gtgttaccta tagaaaaaca                                           30

<210> SEQ ID NO 123
<211> LENGTH: 30
<212> TYPE: DNA
<213> ORGANISM: Homo Sapiens

<400> SEQUENCE: 123
tcagaatttg tgttacctat agaaaaacac                                           30

<210> SEQ ID NO 124
<211> LENGTH: 30
<212> TYPE: DNA
<213> ORGANISM: Homo Sapiens

<400> SEQUENCE: 124
cagaatttgt gttacctata gaaaaacaca                                          30

<210> SEQ ID NO 125
<211> LENGTH: 30
<212> TYPE: DNA
<213> ORGANISM: Homo Sapiens

<400> SEQUENCE: 125
agaatttgtg ttacctatag aaaaacacat                                          30

<210> SEQ ID NO 126
<211> LENGTH: 30
<212> TYPE: DNA
<213> ORGANISM: Homo Sapiens

<400> SEQUENCE: 126
gaatttgtgt tacctataga aaaacacatg                                          30

<210> SEQ ID NO 127
<211> LENGTH: 30
<212> TYPE: DNA
<213> ORGANISM: Homo Sapiens

<400> SEQUENCE: 127
aatttgtgtt acctatagaa aaacacatga                                          30

<210> SEQ ID NO 128
<211> LENGTH: 30
<212> TYPE: DNA
<213> ORGANISM: Homo Sapiens

<400> SEQUENCE: 128
atttgtgtta cctatagaaa aacacatgaa                                          30

<210> SEQ ID NO 129
<211> LENGTH: 30
<212> TYPE: DNA
<213> ORGANISM: Homo Sapiens

<400> SEQUENCE: 129
tttgtgttac ctatagaaaa acacatgaat                                          30

<210> SEQ ID NO 130
<211> LENGTH: 30
<212> TYPE: DNA
<213> ORGANISM: Homo Sapiens

<400> SEQUENCE: 130
ttgtgttacc tatagaaaaa cacatgaatt                                          30

<210> SEQ ID NO 131
<211> LENGTH: 30
<212> TYPE: DNA
<213> ORGANISM: Homo Sapiens

<400> SEQUENCE: 131
tgtgttacct atagaaaaac acatgaattt                                          30

<210> SEQ ID NO 132
<211> LENGTH: 30
<212> TYPE: DNA
<213> ORGANISM: Homo Sapiens

<400> SEQUENCE: 132
gtgttaccta tagaaaaaca catgaatttc                                    30

<210> SEQ ID NO 133
<211> LENGTH: 30
<212> TYPE: DNA
<213> ORGANISM: Homo Sapiens

<400> SEQUENCE: 133
tgttacctat agaaaaacac atgaatttca                                    30

<210> SEQ ID NO 134
<211> LENGTH: 30
<212> TYPE: DNA
<213> ORGANISM: Homo Sapiens

<400> SEQUENCE: 134
gttacctata gaaaaacaca tgaatttcat                                    30

<210> SEQ ID NO 135
<211> LENGTH: 29
<212> TYPE: DNA
<213> ORGANISM: Homo Sapiens

<400> SEQUENCE: 135
tcatagcagt cagaatttgt gttacctat                                     29

<210> SEQ ID NO 136
<211> LENGTH: 29
<212> TYPE: DNA
<213> ORGANISM: Homo Sapiens

<400> SEQUENCE: 136
catagcagtc agaatttgtg ttacctata                                     29

<210> SEQ ID NO 137
<211> LENGTH: 29
<212> TYPE: DNA
<213> ORGANISM: Homo Sapiens

<400> SEQUENCE: 137
atagcagtca gaatttgtgt tacctatag                                     29

<210> SEQ ID NO 138
<211> LENGTH: 29
<212> TYPE: DNA
<213> ORGANISM: Homo Sapiens

<400> SEQUENCE: 138
tagcagtcag aatttgtgtt acctataga                                     29

<210> SEQ ID NO 139
<211> LENGTH: 29
<212> TYPE: DNA
<213> ORGANISM: Homo Sapiens

<400> SEQUENCE: 139
agcagtcaga atttgtgtta cctatagaa                                     29

<210> SEQ ID NO 140
<211> LENGTH: 29
<212> TYPE: DNA
<213> ORGANISM: Homo Sapiens

<400> SEQUENCE: 140
gcagtcagaa tttgtgttac ctatagaaa                                29

<210> SEQ ID NO 141
<211> LENGTH: 29
<212> TYPE: DNA
<213> ORGANISM: Homo Sapiens

<400> SEQUENCE: 141
cagtcagaat ttgtgttacc tatagaaaa                                29

<210> SEQ ID NO 142
<211> LENGTH: 29
<212> TYPE: DNA
<213> ORGANISM: Homo Sapiens

<400> SEQUENCE: 142
agtcagaatt tgtgttacct atagaaaaa                                29

<210> SEQ ID NO 143
<211> LENGTH: 29
<212> TYPE: DNA
<213> ORGANISM: Homo Sapiens

<400> SEQUENCE: 143
gtcagaattt gtgttaccta tagaaaaac                                29

<210> SEQ ID NO 144
<211> LENGTH: 29
<212> TYPE: DNA
<213> ORGANISM: Homo Sapiens

<400> SEQUENCE: 144
tcagaatttg tgttacctat agaaaaaca                                29

<210> SEQ ID NO 145
<211> LENGTH: 29
<212> TYPE: DNA
<213> ORGANISM: Homo Sapiens

<400> SEQUENCE: 145
cagaatttgt gttacctata gaaaaacac                                29

<210> SEQ ID NO 146
<211> LENGTH: 29
<212> TYPE: DNA
<213> ORGANISM: Homo Sapiens

<400> SEQUENCE: 146
agaatttgtg ttacctatag aaaaacaca                                29

<210> SEQ ID NO 147
<211> LENGTH: 29
<212> TYPE: DNA
<213> ORGANISM: Homo Sapiens

<400> SEQUENCE: 147
gaatttgtgt tacctataga aaaacacat                                29

<210> SEQ ID NO 148
<211> LENGTH: 29
<212> TYPE: DNA
<213> ORGANISM: Homo Sapiens

<400> SEQUENCE: 148
aatttgtgtt acctatagaa aaacacatg                                29

<210> SEQ ID NO 149
<211> LENGTH: 29
<212> TYPE: DNA
<213> ORGANISM: Homo Sapiens

<400> SEQUENCE: 149
atttgtgtta cctatagaaa aacacatga                                29

<210> SEQ ID NO 150
<211> LENGTH: 29
<212> TYPE: DNA
<213> ORGANISM: Homo Sapiens

<400> SEQUENCE: 150
tttgtgttac ctatagaaaa acacatgaa                                29

<210> SEQ ID NO 151
<211> LENGTH: 29
<212> TYPE: DNA
<213> ORGANISM: Homo Sapiens

<400> SEQUENCE: 151
ttgtgttacc tatagaaaaa cacatgaat                                29

<210> SEQ ID NO 152
<211> LENGTH: 29
<212> TYPE: DNA
<213> ORGANISM: Homo Sapiens

<400> SEQUENCE: 152
tgtgttacct atagaaaaac acatgaatt                                29

<210> SEQ ID NO 153
<211> LENGTH: 29
<212> TYPE: DNA
<213> ORGANISM: Homo Sapiens

<400> SEQUENCE: 153
gtgttaccta tagaaaaaca catgaattt                                29

<210> SEQ ID NO 154
<211> LENGTH: 29
<212> TYPE: DNA
<213> ORGANISM: Homo Sapiens

<400> SEQUENCE: 154
tgttacctat agaaaaacac atgaatttc                                29

<210> SEQ ID NO 155
<211> LENGTH: 29
<212> TYPE: DNA
<213> ORGANISM: Homo Sapiens

<400> SEQUENCE: 155
gttacctata gaaaaacaca tgaatttca                                29

<210> SEQ ID NO 156
<211> LENGTH: 29
<212> TYPE: DNA

```
<213> ORGANISM: Homo Sapiens

<400> SEQUENCE: 156
ttacctatag aaaaacacat gaatttcat                                           29

<210> SEQ ID NO 157
<211> LENGTH: 28
<212> TYPE: DNA
<213> ORGANISM: Homo Sapiens

<400> SEQUENCE: 157
tcatagcagt cagaatttgt gttaccta                                            28

<210> SEQ ID NO 158
<211> LENGTH: 28
<212> TYPE: DNA
<213> ORGANISM: Homo Sapiens

<400> SEQUENCE: 158
catagcagtc agaatttgtg ttacctat                                            28

<210> SEQ ID NO 159
<211> LENGTH: 28
<212> TYPE: DNA
<213> ORGANISM: Homo Sapiens

<400> SEQUENCE: 159
atagcagtca gaatttgtgt tacctata                                            28

<210> SEQ ID NO 160
<211> LENGTH: 28
<212> TYPE: DNA
<213> ORGANISM: Homo Sapiens

<400> SEQUENCE: 160
tagcagtcag aatttgtgtt acctatag                                            28

<210> SEQ ID NO 161
<211> LENGTH: 28
<212> TYPE: DNA
<213> ORGANISM: Homo Sapiens

<400> SEQUENCE: 161
agcagtcaga atttgtgtta cctataga                                            28

<210> SEQ ID NO 162
<211> LENGTH: 28
<212> TYPE: DNA
<213> ORGANISM: Homo Sapiens

<400> SEQUENCE: 162
gcagtcagaa tttgtgttac ctatagaa                                            28

<210> SEQ ID NO 163
<211> LENGTH: 28
<212> TYPE: DNA
<213> ORGANISM: Homo Sapiens

<400> SEQUENCE: 163
cagtcagaat ttgtgttacc tatagaaa                                            28

<210> SEQ ID NO 164
<211> LENGTH: 28
```

<212> TYPE: DNA
<213> ORGANISM: Homo Sapiens

<400> SEQUENCE: 164
agtcagaatt tgtgttacct atagaaaa                                         28

<210> SEQ ID NO 165
<211> LENGTH: 28
<212> TYPE: DNA
<213> ORGANISM: Homo Sapiens

<400> SEQUENCE: 165
gtcagaattt gtgttaccta tagaaaaa                                         28

<210> SEQ ID NO 166
<211> LENGTH: 28
<212> TYPE: DNA
<213> ORGANISM: Homo Sapiens

<400> SEQUENCE: 166
tcagaatttg tgttacctat agaaaaac                                         28

<210> SEQ ID NO 167
<211> LENGTH: 28
<212> TYPE: DNA
<213> ORGANISM: Homo Sapiens

<400> SEQUENCE: 167
cagaatttgt gttacctata gaaaaaca                                         28

<210> SEQ ID NO 168
<211> LENGTH: 28
<212> TYPE: DNA
<213> ORGANISM: Homo Sapiens

<400> SEQUENCE: 168
agaatttgtg ttacctatag aaaaacac                                         28

<210> SEQ ID NO 169
<211> LENGTH: 28
<212> TYPE: DNA
<213> ORGANISM: Homo Sapiens

<400> SEQUENCE: 169
gaatttgtgt tacctataga aaaacaca                                         28

<210> SEQ ID NO 170
<211> LENGTH: 28
<212> TYPE: DNA
<213> ORGANISM: Homo Sapiens

<400> SEQUENCE: 170
aatttgtgtt acctatagaa aaacacat                                         28

<210> SEQ ID NO 171
<211> LENGTH: 28
<212> TYPE: DNA
<213> ORGANISM: Homo Sapiens

<400> SEQUENCE: 171
atttgtgtta cctatagaaa aacacatg                                         28

<210> SEQ ID NO 172

```
<211> LENGTH: 28
<212> TYPE: DNA
<213> ORGANISM: Homo Sapiens

<400> SEQUENCE: 172
tttgtgttac ctatagaaaa acacatga                                       28

<210> SEQ ID NO 173
<211> LENGTH: 28
<212> TYPE: DNA
<213> ORGANISM: Homo Sapiens

<400> SEQUENCE: 173
ttgtgttacc tatagaaaaa cacatgaa                                       28

<210> SEQ ID NO 174
<211> LENGTH: 28
<212> TYPE: DNA
<213> ORGANISM: Homo Sapiens

<400> SEQUENCE: 174
tgtgttacct atagaaaaac acatgaat                                       28

<210> SEQ ID NO 175
<211> LENGTH: 28
<212> TYPE: DNA
<213> ORGANISM: Homo Sapiens

<400> SEQUENCE: 175
gtgttaccta tagaaaaaca catgaatt                                       28

<210> SEQ ID NO 176
<211> LENGTH: 28
<212> TYPE: DNA
<213> ORGANISM: Homo Sapiens

<400> SEQUENCE: 176
tgttacctat agaaaaacac atgaattt                                       28

<210> SEQ ID NO 177
<211> LENGTH: 28
<212> TYPE: DNA
<213> ORGANISM: Homo Sapiens

<400> SEQUENCE: 177
gttacctata gaaaaacaca tgaatttc                                       28

<210> SEQ ID NO 178
<211> LENGTH: 28
<212> TYPE: DNA
<213> ORGANISM: Homo Sapiens

<400> SEQUENCE: 178
ttacctatag aaaaacacat gaatttca                                       28

<210> SEQ ID NO 179
<211> LENGTH: 28
<212> TYPE: DNA
<213> ORGANISM: Homo Sapiens

<400> SEQUENCE: 179
tacctataga aaaacacatg aatttcat                                       28
```

```
<210> SEQ ID NO 180
<211> LENGTH: 27
<212> TYPE: DNA
<213> ORGANISM: Homo Sapiens

<400> SEQUENCE: 180
tcatagcagt cagaatttgt gttacct                                        27

<210> SEQ ID NO 181
<211> LENGTH: 27
<212> TYPE: DNA
<213> ORGANISM: Homo Sapiens

<400> SEQUENCE: 181
catagcagtc agaatttgtg ttaccta                                        27

<210> SEQ ID NO 182
<211> LENGTH: 27
<212> TYPE: DNA
<213> ORGANISM: Homo Sapiens

<400> SEQUENCE: 182
atagcagtca gaatttgtgt tacctat                                        27

<210> SEQ ID NO 183
<211> LENGTH: 27
<212> TYPE: DNA
<213> ORGANISM: Homo Sapiens

<400> SEQUENCE: 183
tagcagtcag aatttgtgtt acctata                                        27

<210> SEQ ID NO 184
<211> LENGTH: 27
<212> TYPE: DNA
<213> ORGANISM: Homo Sapiens

<400> SEQUENCE: 184
agcagtcaga atttgtgtta cctatag                                        27

<210> SEQ ID NO 185
<211> LENGTH: 27
<212> TYPE: DNA
<213> ORGANISM: Homo Sapiens

<400> SEQUENCE: 185
gcagtcagaa tttgtgttac ctataga                                        27

<210> SEQ ID NO 186
<211> LENGTH: 27
<212> TYPE: DNA
<213> ORGANISM: Homo Sapiens

<400> SEQUENCE: 186
cagtcagaat ttgtgttacc tatagaa                                        27

<210> SEQ ID NO 187
<211> LENGTH: 27
<212> TYPE: DNA
<213> ORGANISM: Homo Sapiens

<400> SEQUENCE: 187
agtcagaatt tgtgttacct atagaaa                                        27
```

-continued

<210> SEQ ID NO 188
<211> LENGTH: 27
<212> TYPE: DNA
<213> ORGANISM: Homo Sapiens

<400> SEQUENCE: 188
gtcagaattt gtgttaccta tagaaaa                                27

<210> SEQ ID NO 189
<211> LENGTH: 27
<212> TYPE: DNA
<213> ORGANISM: Homo Sapiens

<400> SEQUENCE: 189
tcagaatttg tgttacctat agaaaaa                                27

<210> SEQ ID NO 190
<211> LENGTH: 27
<212> TYPE: DNA
<213> ORGANISM: Homo Sapiens

<400> SEQUENCE: 190
cagaatttgt gttacctata gaaaaac                                27

<210> SEQ ID NO 191
<211> LENGTH: 27
<212> TYPE: DNA
<213> ORGANISM: Homo Sapiens

<400> SEQUENCE: 191
agaatttgtg ttacctatag aaaaaca                                27

<210> SEQ ID NO 192
<211> LENGTH: 27
<212> TYPE: DNA
<213> ORGANISM: Homo Sapiens

<400> SEQUENCE: 192
gaatttgtgt tacctataga aaaacac                                27

<210> SEQ ID NO 193
<211> LENGTH: 27
<212> TYPE: DNA
<213> ORGANISM: Homo Sapiens

<400> SEQUENCE: 193
aatttgtgtt acctatagaa aaacaca                                27

<210> SEQ ID NO 194
<211> LENGTH: 27
<212> TYPE: DNA
<213> ORGANISM: Homo Sapiens

<400> SEQUENCE: 194
atttgtgtta cctatagaaa aacacat                                27

<210> SEQ ID NO 195
<211> LENGTH: 27
<212> TYPE: DNA
<213> ORGANISM: Homo Sapiens

<400> SEQUENCE: 195
tttgtgttac ctatagaaaa acacatg                                27

<210> SEQ ID NO 196
<211> LENGTH: 27
<212> TYPE: DNA
<213> ORGANISM: Homo Sapiens

<400> SEQUENCE: 196
ttgtgttacc tatagaaaaa cacatga                                              27

<210> SEQ ID NO 197
<211> LENGTH: 27
<212> TYPE: DNA
<213> ORGANISM: Homo Sapiens

<400> SEQUENCE: 197
tgtgttacct atagaaaaac acatgaa                                              27

<210> SEQ ID NO 198
<211> LENGTH: 27
<212> TYPE: DNA
<213> ORGANISM: Homo Sapiens

<400> SEQUENCE: 198
gtgttaccta tagaaaaaca catgaat                                              27

<210> SEQ ID NO 199
<211> LENGTH: 27
<212> TYPE: DNA
<213> ORGANISM: Homo Sapiens

<400> SEQUENCE: 199
tgttacctat agaaaaacac atgaatt                                              27

<210> SEQ ID NO 200
<211> LENGTH: 27
<212> TYPE: DNA
<213> ORGANISM: Homo Sapiens

<400> SEQUENCE: 200
gttacctata gaaaaacaca tgaattt                                              27

<210> SEQ ID NO 201
<211> LENGTH: 27
<212> TYPE: DNA
<213> ORGANISM: Homo Sapiens

<400> SEQUENCE: 201
ttacctatag aaaacacat gaatttc                                               27

<210> SEQ ID NO 202
<211> LENGTH: 27
<212> TYPE: DNA
<213> ORGANISM: Homo Sapiens

<400> SEQUENCE: 202
tacctataga aaacacatg aatttca                                               27

<210> SEQ ID NO 203
<211> LENGTH: 27
<212> TYPE: DNA
<213> ORGANISM: Homo Sapiens

<400> SEQUENCE: 203
acctatagaa aaacacatga atttcat                                              27

<210> SEQ ID NO 204
<211> LENGTH: 26
<212> TYPE: DNA
<213> ORGANISM: Homo Sapiens

<400> SEQUENCE: 204
tcatagcagt cagaatttgt gttacc                                               26

<210> SEQ ID NO 205
<211> LENGTH: 26
<212> TYPE: DNA
<213> ORGANISM: Homo Sapiens

<400> SEQUENCE: 205
catagcagtc agaatttgtg ttacct                                               26

<210> SEQ ID NO 206
<211> LENGTH: 26
<212> TYPE: DNA
<213> ORGANISM: Homo Sapiens

<400> SEQUENCE: 206
atagcagtca gaatttgtgt taccta                                               26

<210> SEQ ID NO 207
<211> LENGTH: 26
<212> TYPE: DNA
<213> ORGANISM: Homo Sapiens

<400> SEQUENCE: 207
tagcagtcag aatttgtgtt acctat                                               26

<210> SEQ ID NO 208
<211> LENGTH: 26
<212> TYPE: DNA
<213> ORGANISM: Homo Sapiens

<400> SEQUENCE: 208
agcagtcaga atttgtgtta cctata                                               26

<210> SEQ ID NO 209
<211> LENGTH: 26
<212> TYPE: DNA
<213> ORGANISM: Homo Sapiens

<400> SEQUENCE: 209
gcagtcagaa tttgtgttac ctatag                                               26

<210> SEQ ID NO 210
<211> LENGTH: 26
<212> TYPE: DNA
<213> ORGANISM: Homo Sapiens

<400> SEQUENCE: 210
cagtcagaat ttgtgttacc tataga                                               26

<210> SEQ ID NO 211
<211> LENGTH: 26
<212> TYPE: DNA
<213> ORGANISM: Homo Sapiens

<400> SEQUENCE: 211
agtcagaatt tgtgttacct atagaa								26

<210> SEQ ID NO 212
<211> LENGTH: 26
<212> TYPE: DNA
<213> ORGANISM: Homo Sapiens

<400> SEQUENCE: 212
gtcagaattt gtgttaccta tagaaa								26

<210> SEQ ID NO 213
<211> LENGTH: 26
<212> TYPE: DNA
<213> ORGANISM: Homo Sapiens

<400> SEQUENCE: 213
tcagaatttg tgttacctat agaaaa								26

<210> SEQ ID NO 214
<211> LENGTH: 26
<212> TYPE: DNA
<213> ORGANISM: Homo Sapiens

<400> SEQUENCE: 214
cagaatttgt gttacctata gaaaaa								26

<210> SEQ ID NO 215
<211> LENGTH: 26
<212> TYPE: DNA
<213> ORGANISM: Homo Sapiens

<400> SEQUENCE: 215
agaatttgtg ttacctatag aaaaac								26

<210> SEQ ID NO 216
<211> LENGTH: 26
<212> TYPE: DNA
<213> ORGANISM: Homo Sapiens

<400> SEQUENCE: 216
gaatttgtgt tacctataga aaaaca								26

<210> SEQ ID NO 217
<211> LENGTH: 26
<212> TYPE: DNA
<213> ORGANISM: Homo Sapiens

<400> SEQUENCE: 217
aatttgtgtt acctatagaa aaacac								26

<210> SEQ ID NO 218
<211> LENGTH: 26
<212> TYPE: DNA
<213> ORGANISM: Homo Sapiens

<400> SEQUENCE: 218
atttgtgtta cctatagaaa aacaca								26

<210> SEQ ID NO 219
<211> LENGTH: 26
<212> TYPE: DNA
<213> ORGANISM: Homo Sapiens

<400> SEQUENCE: 219
tttgtgttac ctatagaaaa acacat                                           26

<210> SEQ ID NO 220
<211> LENGTH: 26
<212> TYPE: DNA
<213> ORGANISM: Homo Sapiens

<400> SEQUENCE: 220
ttgtgttacc tatagaaaaa cacatg                                           26

<210> SEQ ID NO 221
<211> LENGTH: 26
<212> TYPE: DNA
<213> ORGANISM: Homo Sapiens

<400> SEQUENCE: 221
tgtgttacct atagaaaaac acatga                                           26

<210> SEQ ID NO 222
<211> LENGTH: 26
<212> TYPE: DNA
<213> ORGANISM: Homo Sapiens

<400> SEQUENCE: 222
gtgttaccta tagaaaaaca catgaa                                           26

<210> SEQ ID NO 223
<211> LENGTH: 26
<212> TYPE: DNA
<213> ORGANISM: Homo Sapiens

<400> SEQUENCE: 223
tgttacctat agaaaaacac atgaat                                           26

<210> SEQ ID NO 224
<211> LENGTH: 26
<212> TYPE: DNA
<213> ORGANISM: Homo Sapiens

<400> SEQUENCE: 224
gttacctata gaaaaacaca tgaatt                                           26

<210> SEQ ID NO 225
<211> LENGTH: 26
<212> TYPE: DNA
<213> ORGANISM: Homo Sapiens

<400> SEQUENCE: 225
ttacctatag aaaaacacat gaattt                                           26

<210> SEQ ID NO 226
<211> LENGTH: 26
<212> TYPE: DNA
<213> ORGANISM: Homo Sapiens

<400> SEQUENCE: 226
tacctataga aaaacacatg aatttc                                           26

<210> SEQ ID NO 227
<211> LENGTH: 26
<212> TYPE: DNA
<213> ORGANISM: Homo Sapiens

```
<400> SEQUENCE: 227
acctatagaa aaacacatga atttca                                          26

<210> SEQ ID NO 228
<211> LENGTH: 26
<212> TYPE: DNA
<213> ORGANISM: Homo Sapiens

<400> SEQUENCE: 228
cctatagaaa aacacatgaa tttcat                                          26

<210> SEQ ID NO 229
<211> LENGTH: 25
<212> TYPE: DNA
<213> ORGANISM: Homo Sapiens

<400> SEQUENCE: 229
tcatagcagt cagaatttgt gttac                                           25

<210> SEQ ID NO 230
<211> LENGTH: 25
<212> TYPE: DNA
<213> ORGANISM: Homo Sapiens

<400> SEQUENCE: 230
catagcagtc agaatttgtg ttacc                                           25

<210> SEQ ID NO 231
<211> LENGTH: 25
<212> TYPE: DNA
<213> ORGANISM: Homo Sapiens

<400> SEQUENCE: 231
atagcagtca gaatttgtgt tacct                                           25

<210> SEQ ID NO 232
<211> LENGTH: 25
<212> TYPE: DNA
<213> ORGANISM: Homo Sapiens

<400> SEQUENCE: 232
tagcagtcag aatttgtgtt accta                                           25

<210> SEQ ID NO 233
<211> LENGTH: 25
<212> TYPE: DNA
<213> ORGANISM: Homo Sapiens

<400> SEQUENCE: 233
agcagtcaga atttgtgtta cctat                                           25

<210> SEQ ID NO 234
<211> LENGTH: 25
<212> TYPE: DNA
<213> ORGANISM: Homo Sapiens

<400> SEQUENCE: 234
gcagtcagaa tttgtgttac ctata                                           25

<210> SEQ ID NO 235
<211> LENGTH: 25
<212> TYPE: DNA
```

<213> ORGANISM: Homo Sapiens

<400> SEQUENCE: 235
cagtcagaat ttgtgttacc tatag                                  25

<210> SEQ ID NO 236
<211> LENGTH: 25
<212> TYPE: DNA
<213> ORGANISM: Homo Sapiens

<400> SEQUENCE: 236
agtcagaatt tgtgttacct ataga                                  25

<210> SEQ ID NO 237
<211> LENGTH: 25
<212> TYPE: DNA
<213> ORGANISM: Homo Sapiens

<400> SEQUENCE: 237
gtcagaattt gtgttaccta tagaa                                  25

<210> SEQ ID NO 238
<211> LENGTH: 25
<212> TYPE: DNA
<213> ORGANISM: Homo Sapiens

<400> SEQUENCE: 238
tcagaatttg tgttacctat agaaa                                  25

<210> SEQ ID NO 239
<211> LENGTH: 25
<212> TYPE: DNA
<213> ORGANISM: Homo Sapiens

<400> SEQUENCE: 239
cagaatttgt gttacctata gaaaa                                  25

<210> SEQ ID NO 240
<211> LENGTH: 25
<212> TYPE: DNA
<213> ORGANISM: Homo Sapiens

<400> SEQUENCE: 240
agaatttgtg ttacctatag aaaaa                                  25

<210> SEQ ID NO 241
<211> LENGTH: 25
<212> TYPE: DNA
<213> ORGANISM: Homo Sapiens

<400> SEQUENCE: 241
gaatttgtgt tacctataga aaaac                                  25

<210> SEQ ID NO 242
<211> LENGTH: 25
<212> TYPE: DNA
<213> ORGANISM: Homo Sapiens

<400> SEQUENCE: 242
aatttgtgtt acctatagaa aaaca                                  25

<210> SEQ ID NO 243
<211> LENGTH: 25

<212> TYPE: DNA
<213> ORGANISM: Homo Sapiens

<400> SEQUENCE: 243
atttgtgtta cctatagaaa aacac                                              25

<210> SEQ ID NO 244
<211> LENGTH: 25
<212> TYPE: DNA
<213> ORGANISM: Homo Sapiens

<400> SEQUENCE: 244
tttgtgttac ctatagaaaa acaca                                              25

<210> SEQ ID NO 245
<211> LENGTH: 25
<212> TYPE: DNA
<213> ORGANISM: Homo Sapiens

<400> SEQUENCE: 245
ttgtgttacc tatagaaaaa cacat                                              25

<210> SEQ ID NO 246
<211> LENGTH: 25
<212> TYPE: DNA
<213> ORGANISM: Homo Sapiens

<400> SEQUENCE: 246
tgtgttacct atagaaaaac acatg                                              25

<210> SEQ ID NO 247
<211> LENGTH: 25
<212> TYPE: DNA
<213> ORGANISM: Homo Sapiens

<400> SEQUENCE: 247
gtgttaccta tagaaaaaca catga                                              25

<210> SEQ ID NO 248
<211> LENGTH: 25
<212> TYPE: DNA
<213> ORGANISM: Homo Sapiens

<400> SEQUENCE: 248
tgttacctat agaaaaacac atgaa                                              25

<210> SEQ ID NO 249
<211> LENGTH: 25
<212> TYPE: DNA
<213> ORGANISM: Homo Sapiens

<400> SEQUENCE: 249
gttacctata gaaaaacaca tgaat                                              25

<210> SEQ ID NO 250
<211> LENGTH: 25
<212> TYPE: DNA
<213> ORGANISM: Homo Sapiens

<400> SEQUENCE: 250
ttacctatag aaaaacacat gaatt                                              25

<210> SEQ ID NO 251

<211> LENGTH: 25
<212> TYPE: DNA
<213> ORGANISM: Homo Sapiens

<400> SEQUENCE: 251
tacctataga aaaacacatg aattt								25

<210> SEQ ID NO 252
<211> LENGTH: 25
<212> TYPE: DNA
<213> ORGANISM: Homo Sapiens

<400> SEQUENCE: 252
acctatagaa aaacacatga atttc								25

<210> SEQ ID NO 253
<211> LENGTH: 25
<212> TYPE: DNA
<213> ORGANISM: Homo Sapiens

<400> SEQUENCE: 253
cctatagaaa aacacatgaa tttca								25

<210> SEQ ID NO 254
<211> LENGTH: 25
<212> TYPE: DNA
<213> ORGANISM: Homo Sapiens

<400> SEQUENCE: 254
ctatagaaaa acacatgaat ttcat								25

<210> SEQ ID NO 255
<211> LENGTH: 24
<212> TYPE: DNA
<213> ORGANISM: Homo Sapiens

<400> SEQUENCE: 255
catagcagtc agaatttgtg ttac								24

<210> SEQ ID NO 256
<211> LENGTH: 24
<212> TYPE: DNA
<213> ORGANISM: Homo Sapiens

<400> SEQUENCE: 256
atagcagtca gaatttgtgt tacc								24

<210> SEQ ID NO 257
<211> LENGTH: 24
<212> TYPE: DNA
<213> ORGANISM: Homo Sapiens

<400> SEQUENCE: 257
tagcagtcag aatttgtgtt acct								24

<210> SEQ ID NO 258
<211> LENGTH: 24
<212> TYPE: DNA
<213> ORGANISM: Homo Sapiens

<400> SEQUENCE: 258
agcagtcaga atttgtgtta ccta								24

```
<210> SEQ ID NO 259
<211> LENGTH: 24
<212> TYPE: DNA
<213> ORGANISM: Homo Sapiens

<400> SEQUENCE: 259
gcagtcagaa tttgtgttac ctat                                          24

<210> SEQ ID NO 260
<211> LENGTH: 24
<212> TYPE: DNA
<213> ORGANISM: Homo Sapiens

<400> SEQUENCE: 260
cagtcagaat ttgtgttacc tata                                          24

<210> SEQ ID NO 261
<211> LENGTH: 24
<212> TYPE: DNA
<213> ORGANISM: Homo Sapiens

<400> SEQUENCE: 261
agtcagaatt tgtgttacct atag                                          24

<210> SEQ ID NO 262
<211> LENGTH: 24
<212> TYPE: DNA
<213> ORGANISM: Homo Sapiens

<400> SEQUENCE: 262
gtcagaattt gtgttaccta taga                                          24

<210> SEQ ID NO 263
<211> LENGTH: 24
<212> TYPE: DNA
<213> ORGANISM: Homo Sapiens

<400> SEQUENCE: 263
tcagaatttg tgttacctat agaa                                          24

<210> SEQ ID NO 264
<211> LENGTH: 24
<212> TYPE: DNA
<213> ORGANISM: Homo Sapiens

<400> SEQUENCE: 264
cagaatttgt gttacctata gaaa                                          24

<210> SEQ ID NO 265
<211> LENGTH: 24
<212> TYPE: DNA
<213> ORGANISM: Homo Sapiens

<400> SEQUENCE: 265
agaatttgtg ttacctatag aaaa                                          24

<210> SEQ ID NO 266
<211> LENGTH: 24
<212> TYPE: DNA
<213> ORGANISM: Homo Sapiens

<400> SEQUENCE: 266
gaatttgtgt tacctataga aaaa                                          24
```

```
<210> SEQ ID NO 267
<211> LENGTH: 24
<212> TYPE: DNA
<213> ORGANISM: Homo Sapiens

<400> SEQUENCE: 267
aatttgtgtt acctatagaa aaac                                              24

<210> SEQ ID NO 268
<211> LENGTH: 24
<212> TYPE: DNA
<213> ORGANISM: Homo Sapiens

<400> SEQUENCE: 268
atttgtgtta cctatagaaa aaca                                              24

<210> SEQ ID NO 269
<211> LENGTH: 24
<212> TYPE: DNA
<213> ORGANISM: Homo Sapiens

<400> SEQUENCE: 269
tttgtgttac ctatagaaaa acac                                              24

<210> SEQ ID NO 270
<211> LENGTH: 24
<212> TYPE: DNA
<213> ORGANISM: Homo Sapiens

<400> SEQUENCE: 270
ttgtgttacc tatagaaaaa caca                                              24

<210> SEQ ID NO 271
<211> LENGTH: 24
<212> TYPE: DNA
<213> ORGANISM: Homo Sapiens

<400> SEQUENCE: 271
tgtgttacct atagaaaaac acat                                              24

<210> SEQ ID NO 272
<211> LENGTH: 24
<212> TYPE: DNA
<213> ORGANISM: Homo Sapiens

<400> SEQUENCE: 272
gtgttaccta tagaaaaaca catg                                              24

<210> SEQ ID NO 273
<211> LENGTH: 24
<212> TYPE: DNA
<213> ORGANISM: Homo Sapiens

<400> SEQUENCE: 273
tgttacctat agaaaaacac atga                                              24

<210> SEQ ID NO 274
<211> LENGTH: 24
<212> TYPE: DNA
<213> ORGANISM: Homo Sapiens

<400> SEQUENCE: 274
gttacctata gaaaaacaca tgaa                                              24
```

```
<210> SEQ ID NO 275
<211> LENGTH: 24
<212> TYPE: DNA
<213> ORGANISM: Homo Sapiens

<400> SEQUENCE: 275
ttacctatag aaaaacacat gaat                                            24

<210> SEQ ID NO 276
<211> LENGTH: 24
<212> TYPE: DNA
<213> ORGANISM: Homo Sapiens

<400> SEQUENCE: 276
tacctataga aaaacacatg aatt                                            24

<210> SEQ ID NO 277
<211> LENGTH: 24
<212> TYPE: DNA
<213> ORGANISM: Homo Sapiens

<400> SEQUENCE: 277
acctatagaa aaacacatga attt                                            24

<210> SEQ ID NO 278
<211> LENGTH: 24
<212> TYPE: DNA
<213> ORGANISM: Homo Sapiens

<400> SEQUENCE: 278
cctatagaaa aacacatgaa tttc                                            24

<210> SEQ ID NO 279
<211> LENGTH: 24
<212> TYPE: DNA
<213> ORGANISM: Homo Sapiens

<400> SEQUENCE: 279
ctatagaaaa acacatgaat ttca                                            24

<210> SEQ ID NO 280
<211> LENGTH: 23
<212> TYPE: DNA
<213> ORGANISM: Homo Sapiens

<400> SEQUENCE: 280
atagcagtca gaatttgtgt tac                                             23

<210> SEQ ID NO 281
<211> LENGTH: 23
<212> TYPE: DNA
<213> ORGANISM: Homo Sapiens

<400> SEQUENCE: 281
tagcagtcag aatttgtgtt acc                                             23

<210> SEQ ID NO 282
<211> LENGTH: 23
<212> TYPE: DNA
<213> ORGANISM: Homo Sapiens

<400> SEQUENCE: 282
```
agcagtcaga atttgtgtta cct                                                  23

<210> SEQ ID NO 283
<211> LENGTH: 23
<212> TYPE: DNA
<213> ORGANISM: Homo Sapiens

<400> SEQUENCE: 283
gcagtcagaa tttgtgttac cta                                                  23

<210> SEQ ID NO 284
<211> LENGTH: 23
<212> TYPE: DNA
<213> ORGANISM: Homo Sapiens

<400> SEQUENCE: 284
cagtcagaat ttgtgttacc tat                                                  23

<210> SEQ ID NO 285
<211> LENGTH: 23
<212> TYPE: DNA
<213> ORGANISM: Homo Sapiens

<400> SEQUENCE: 285
agtcagaatt tgtgttacct ata                                                  23

<210> SEQ ID NO 286
<211> LENGTH: 23
<212> TYPE: DNA
<213> ORGANISM: Homo Sapiens

<400> SEQUENCE: 286
gtcagaattt gtgttaccta tag                                                  23

<210> SEQ ID NO 287
<211> LENGTH: 23
<212> TYPE: DNA
<213> ORGANISM: Homo Sapiens

<400> SEQUENCE: 287
tcagaatttg tgttacctat aga                                                  23

<210> SEQ ID NO 288
<211> LENGTH: 23
<212> TYPE: DNA
<213> ORGANISM: Homo Sapiens

<400> SEQUENCE: 288
cagaatttgt gttacctata gaa                                                  23

<210> SEQ ID NO 289
<211> LENGTH: 23
<212> TYPE: DNA
<213> ORGANISM: Homo Sapiens

<400> SEQUENCE: 289
agaatttgtg ttacctatag aaa                                                  23

<210> SEQ ID NO 290
<211> LENGTH: 23
<212> TYPE: DNA
<213> ORGANISM: Homo Sapiens

<400> SEQUENCE: 290

```
gaatttgtgt tacctataga aaa                                           23

<210> SEQ ID NO 291
<211> LENGTH: 23
<212> TYPE: DNA
<213> ORGANISM: Homo Sapiens

<400> SEQUENCE: 291
aatttgtgtt acctatagaa aaa                                           23

<210> SEQ ID NO 292
<211> LENGTH: 23
<212> TYPE: DNA
<213> ORGANISM: Homo Sapiens

<400> SEQUENCE: 292
atttgtgtta cctatagaaa aac                                           23

<210> SEQ ID NO 293
<211> LENGTH: 23
<212> TYPE: DNA
<213> ORGANISM: Homo Sapiens

<400> SEQUENCE: 293
tttgtgttac ctatagaaaa aca                                           23

<210> SEQ ID NO 294
<211> LENGTH: 23
<212> TYPE: DNA
<213> ORGANISM: Homo Sapiens

<400> SEQUENCE: 294
ttgtgttacc tatagaaaaa cac                                           23

<210> SEQ ID NO 295
<211> LENGTH: 23
<212> TYPE: DNA
<213> ORGANISM: Homo Sapiens

<400> SEQUENCE: 295
tgtgttacct atagaaaaac aca                                           23

<210> SEQ ID NO 296
<211> LENGTH: 23
<212> TYPE: DNA
<213> ORGANISM: Homo Sapiens

<400> SEQUENCE: 296
gtgttaccta tagaaaaaca cat                                           23

<210> SEQ ID NO 297
<211> LENGTH: 23
<212> TYPE: DNA
<213> ORGANISM: Homo Sapiens

<400> SEQUENCE: 297
tgttacctat agaaaaacac atg                                           23

<210> SEQ ID NO 298
<211> LENGTH: 23
<212> TYPE: DNA
<213> ORGANISM: Homo Sapiens
```

```
<400> SEQUENCE: 298
gttacctata gaaaaacaca tga                                              23

<210> SEQ ID NO 299
<211> LENGTH: 23
<212> TYPE: DNA
<213> ORGANISM: Homo Sapiens

<400> SEQUENCE: 299
ttacctatag aaaaacacat gaa                                              23

<210> SEQ ID NO 300
<211> LENGTH: 23
<212> TYPE: DNA
<213> ORGANISM: Homo Sapiens

<400> SEQUENCE: 300
tacctataga aaaacacatg aat                                              23

<210> SEQ ID NO 301
<211> LENGTH: 23
<212> TYPE: DNA
<213> ORGANISM: Homo Sapiens

<400> SEQUENCE: 301
acctatagaa aaacacatga att                                              23

<210> SEQ ID NO 302
<211> LENGTH: 23
<212> TYPE: DNA
<213> ORGANISM: Homo Sapiens

<400> SEQUENCE: 302
cctatagaaa aacacatgaa ttt                                              23

<210> SEQ ID NO 303
<211> LENGTH: 23
<212> TYPE: DNA
<213> ORGANISM: Homo Sapiens

<400> SEQUENCE: 303
ctatagaaaa acacatgaat ttc                                              23

<210> SEQ ID NO 304
<211> LENGTH: 22
<212> TYPE: DNA
<213> ORGANISM: Homo Sapiens

<400> SEQUENCE: 304
tagcagtcag aatttgtgtt ac                                               22

<210> SEQ ID NO 305
<211> LENGTH: 22
<212> TYPE: DNA
<213> ORGANISM: Homo Sapiens

<400> SEQUENCE: 305
agcagtcaga atttgtgtta cc                                               22

<210> SEQ ID NO 306
<211> LENGTH: 22
<212> TYPE: DNA
<213> ORGANISM: Homo Sapiens
```

```
<400> SEQUENCE: 306
gcagtcagaa tttgtgttac ct                                              22

<210> SEQ ID NO 307
<211> LENGTH: 22
<212> TYPE: DNA
<213> ORGANISM: Homo Sapiens

<400> SEQUENCE: 307
cagtcagaat ttgtgttacc ta                                              22

<210> SEQ ID NO 308
<211> LENGTH: 22
<212> TYPE: DNA
<213> ORGANISM: Homo Sapiens

<400> SEQUENCE: 308
agtcagaatt tgtgttacct at                                              22

<210> SEQ ID NO 309
<211> LENGTH: 22
<212> TYPE: DNA
<213> ORGANISM: Homo Sapiens

<400> SEQUENCE: 309
gtcagaattt gtgttaccta ta                                              22

<210> SEQ ID NO 310
<211> LENGTH: 22
<212> TYPE: DNA
<213> ORGANISM: Homo Sapiens

<400> SEQUENCE: 310
tcagaatttg tgttacctat ag                                              22

<210> SEQ ID NO 311
<211> LENGTH: 22
<212> TYPE: DNA
<213> ORGANISM: Homo Sapiens

<400> SEQUENCE: 311
cagaatttgt gttacctata ga                                              22

<210> SEQ ID NO 312
<211> LENGTH: 22
<212> TYPE: DNA
<213> ORGANISM: Homo Sapiens

<400> SEQUENCE: 312
agaatttgtg ttacctatag aa                                              22

<210> SEQ ID NO 313
<211> LENGTH: 22
<212> TYPE: DNA
<213> ORGANISM: Homo Sapiens

<400> SEQUENCE: 313
gaatttgtgt tacctataga aa                                              22

<210> SEQ ID NO 314
<211> LENGTH: 22
<212> TYPE: DNA
```

<213> ORGANISM: Homo Sapiens

<400> SEQUENCE: 314
aatttgtgtt acctatagaa aa                                              22

<210> SEQ ID NO 315
<211> LENGTH: 22
<212> TYPE: DNA
<213> ORGANISM: Homo Sapiens

<400> SEQUENCE: 315
atttgtgtta cctatagaaa aa                                              22

<210> SEQ ID NO 316
<211> LENGTH: 22
<212> TYPE: DNA
<213> ORGANISM: Homo Sapiens

<400> SEQUENCE: 316
tttgtgttac ctatagaaaa ac                                              22

<210> SEQ ID NO 317
<211> LENGTH: 22
<212> TYPE: DNA
<213> ORGANISM: Homo Sapiens

<400> SEQUENCE: 317
ttgtgttacc tatagaaaaa ca                                              22

<210> SEQ ID NO 318
<211> LENGTH: 22
<212> TYPE: DNA
<213> ORGANISM: Homo Sapiens

<400> SEQUENCE: 318
tgtgttacct atagaaaaac ac                                              22

<210> SEQ ID NO 319
<211> LENGTH: 22
<212> TYPE: DNA
<213> ORGANISM: Homo Sapiens

<400> SEQUENCE: 319
gtgttaccta tagaaaaaca ca                                              22

<210> SEQ ID NO 320
<211> LENGTH: 22
<212> TYPE: DNA
<213> ORGANISM: Homo Sapiens

<400> SEQUENCE: 320
tgttacctat agaaaaacac at                                              22

<210> SEQ ID NO 321
<211> LENGTH: 22
<212> TYPE: DNA
<213> ORGANISM: Homo Sapiens

<400> SEQUENCE: 321
gttacctata gaaaaacaca tg                                              22

<210> SEQ ID NO 322
<211> LENGTH: 22

```
<212> TYPE: DNA
<213> ORGANISM: Homo Sapiens

<400> SEQUENCE: 322
ttacctatag aaaaacacat ga                                              22

<210> SEQ ID NO 323
<211> LENGTH: 22
<212> TYPE: DNA
<213> ORGANISM: Homo Sapiens

<400> SEQUENCE: 323
tacctataga aaaacacatg aa                                              22

<210> SEQ ID NO 324
<211> LENGTH: 22
<212> TYPE: DNA
<213> ORGANISM: Homo Sapiens

<400> SEQUENCE: 324
acctatagaa aaacacatga at                                              22

<210> SEQ ID NO 325
<211> LENGTH: 22
<212> TYPE: DNA
<213> ORGANISM: Homo Sapiens

<400> SEQUENCE: 325
cctatagaaa aacacatgaa tt                                              22

<210> SEQ ID NO 326
<211> LENGTH: 22
<212> TYPE: DNA
<213> ORGANISM: Homo Sapiens

<400> SEQUENCE: 326
ctatagaaaa acacatgaat tt                                              22

<210> SEQ ID NO 327
<211> LENGTH: 21
<212> TYPE: DNA
<213> ORGANISM: Homo Sapiens

<400> SEQUENCE: 327
agcagtcaga atttgtgtta c                                               21

<210> SEQ ID NO 328
<211> LENGTH: 21
<212> TYPE: DNA
<213> ORGANISM: Homo Sapiens

<400> SEQUENCE: 328
gcagtcagaa tttgtgttac c                                               21

<210> SEQ ID NO 329
<211> LENGTH: 21
<212> TYPE: DNA
<213> ORGANISM: Homo Sapiens

<400> SEQUENCE: 329
cagtcagaat ttgtgttacc t                                               21

<210> SEQ ID NO 330
```

```
<211> LENGTH: 21
<212> TYPE: DNA
<213> ORGANISM: Homo Sapiens

<400> SEQUENCE: 330
agtcagaatt tgtgttacct a                                              21

<210> SEQ ID NO 331
<211> LENGTH: 21
<212> TYPE: DNA
<213> ORGANISM: Homo Sapiens

<400> SEQUENCE: 331
gtcagaattt gtgttaccta t                                              21

<210> SEQ ID NO 332
<211> LENGTH: 21
<212> TYPE: DNA
<213> ORGANISM: Homo Sapiens

<400> SEQUENCE: 332
tcagaatttg tgttacctat a                                              21

<210> SEQ ID NO 333
<211> LENGTH: 21
<212> TYPE: DNA
<213> ORGANISM: Homo Sapiens

<400> SEQUENCE: 333
cagaatttgt gttacctata g                                              21

<210> SEQ ID NO 334
<211> LENGTH: 21
<212> TYPE: DNA
<213> ORGANISM: Homo Sapiens

<400> SEQUENCE: 334
agaatttgtg ttacctatag a                                              21

<210> SEQ ID NO 335
<211> LENGTH: 21
<212> TYPE: DNA
<213> ORGANISM: Homo Sapiens

<400> SEQUENCE: 335
gaatttgtgt tacctataga a                                              21

<210> SEQ ID NO 336
<211> LENGTH: 21
<212> TYPE: DNA
<213> ORGANISM: Homo Sapiens

<400> SEQUENCE: 336
aatttgtgtt acctatagaa a                                              21

<210> SEQ ID NO 337
<211> LENGTH: 21
<212> TYPE: DNA
<213> ORGANISM: Homo Sapiens

<400> SEQUENCE: 337
atttgtgtta cctatagaaa a                                              21
```

```
<210> SEQ ID NO 338
<211> LENGTH: 21
<212> TYPE: DNA
<213> ORGANISM: Homo Sapiens

<400> SEQUENCE: 338
tttgtgttac ctatagaaaa a                                            21

<210> SEQ ID NO 339
<211> LENGTH: 21
<212> TYPE: DNA
<213> ORGANISM: Homo Sapiens

<400> SEQUENCE: 339
ttgtgttacc tatagaaaaa c                                            21

<210> SEQ ID NO 340
<211> LENGTH: 21
<212> TYPE: DNA
<213> ORGANISM: Homo Sapiens

<400> SEQUENCE: 340
tgtgttacct atagaaaaac a                                            21

<210> SEQ ID NO 341
<211> LENGTH: 21
<212> TYPE: DNA
<213> ORGANISM: Homo Sapiens

<400> SEQUENCE: 341
gtgttaccta tagaaaaaca c                                            21

<210> SEQ ID NO 342
<211> LENGTH: 21
<212> TYPE: DNA
<213> ORGANISM: Homo Sapiens

<400> SEQUENCE: 342
tgttacctat agaaaaacac a                                            21

<210> SEQ ID NO 343
<211> LENGTH: 21
<212> TYPE: DNA
<213> ORGANISM: Homo Sapiens

<400> SEQUENCE: 343
gttacctata gaaaaacaca t                                            21

<210> SEQ ID NO 344
<211> LENGTH: 21
<212> TYPE: DNA
<213> ORGANISM: Homo Sapiens

<400> SEQUENCE: 344
ttacctatag aaaaacacat g                                            21

<210> SEQ ID NO 345
<211> LENGTH: 21
<212> TYPE: DNA
<213> ORGANISM: Homo Sapiens

<400> SEQUENCE: 345
tacctataga aaacacatg a                                             21
```

```
<210> SEQ ID NO 346
<211> LENGTH: 21
<212> TYPE: DNA
<213> ORGANISM: Homo Sapiens

<400> SEQUENCE: 346
acctatagaa aaacacatga a                                              21

<210> SEQ ID NO 347
<211> LENGTH: 21
<212> TYPE: DNA
<213> ORGANISM: Homo Sapiens

<400> SEQUENCE: 347
cctatagaaa aacacatgaa t                                              21

<210> SEQ ID NO 348
<211> LENGTH: 21
<212> TYPE: DNA
<213> ORGANISM: Homo Sapiens

<400> SEQUENCE: 348
ctatagaaaa acacatgaat t                                              21

<210> SEQ ID NO 349
<211> LENGTH: 20
<212> TYPE: DNA
<213> ORGANISM: Homo Sapiens

<400> SEQUENCE: 349
gcagtcagaa tttgtgttac                                                20

<210> SEQ ID NO 350
<211> LENGTH: 20
<212> TYPE: DNA
<213> ORGANISM: Homo Sapiens

<400> SEQUENCE: 350
cagtcagaat ttgtgttacc                                                20

<210> SEQ ID NO 351
<211> LENGTH: 20
<212> TYPE: DNA
<213> ORGANISM: Homo Sapiens

<400> SEQUENCE: 351
agtcagaatt tgtgttacct                                                20

<210> SEQ ID NO 352
<211> LENGTH: 20
<212> TYPE: DNA
<213> ORGANISM: Homo Sapiens

<400> SEQUENCE: 352
gtcagaattt gtgttaccta                                                20

<210> SEQ ID NO 353
<211> LENGTH: 20
<212> TYPE: DNA
<213> ORGANISM: Homo Sapiens

<400> SEQUENCE: 353
tcagaatttg tgttacctat                                                20
```

<210> SEQ ID NO 354
<211> LENGTH: 20
<212> TYPE: DNA
<213> ORGANISM: Homo Sapiens

<400> SEQUENCE: 354
cagaatttgt gttacctata                                      20

<210> SEQ ID NO 355
<211> LENGTH: 20
<212> TYPE: DNA
<213> ORGANISM: Homo Sapiens

<400> SEQUENCE: 355
agaatttgtg ttacctatag                                      20

<210> SEQ ID NO 356
<211> LENGTH: 20
<212> TYPE: DNA
<213> ORGANISM: Homo Sapiens

<400> SEQUENCE: 356
gaatttgtgt tacctataga                                      20

<210> SEQ ID NO 357
<211> LENGTH: 20
<212> TYPE: DNA
<213> ORGANISM: Homo Sapiens

<400> SEQUENCE: 357
aatttgtgtt acctatagaa                                      20

<210> SEQ ID NO 358
<211> LENGTH: 20
<212> TYPE: DNA
<213> ORGANISM: Homo Sapiens

<400> SEQUENCE: 358
atttgtgtta cctatagaaa                                      20

<210> SEQ ID NO 359
<211> LENGTH: 20
<212> TYPE: DNA
<213> ORGANISM: Homo Sapiens

<400> SEQUENCE: 359
tttgtgttac ctatagaaaa                                      20

<210> SEQ ID NO 360
<211> LENGTH: 20
<212> TYPE: DNA
<213> ORGANISM: Homo Sapiens

<400> SEQUENCE: 360
ttgtgttacc tatagaaaaa                                      20

<210> SEQ ID NO 361
<211> LENGTH: 20
<212> TYPE: DNA
<213> ORGANISM: Homo Sapiens

<400> SEQUENCE: 361

```
tgtgttacct atagaaaaac                                              20

<210> SEQ ID NO 362
<211> LENGTH: 20
<212> TYPE: DNA
<213> ORGANISM: Homo Sapiens

<400> SEQUENCE: 362
gtgttaccta tagaaaaaca                                              20

<210> SEQ ID NO 363
<211> LENGTH: 20
<212> TYPE: DNA
<213> ORGANISM: Homo Sapiens

<400> SEQUENCE: 363
tgttacctat agaaaaacac                                              20

<210> SEQ ID NO 364
<211> LENGTH: 20
<212> TYPE: DNA
<213> ORGANISM: Homo Sapiens

<400> SEQUENCE: 364
gttacctata gaaaaacaca                                              20

<210> SEQ ID NO 365
<211> LENGTH: 20
<212> TYPE: DNA
<213> ORGANISM: Homo Sapiens

<400> SEQUENCE: 365
ttacctatag aaaaacacat                                              20

<210> SEQ ID NO 366
<211> LENGTH: 20
<212> TYPE: DNA
<213> ORGANISM: Homo Sapiens

<400> SEQUENCE: 366
tacctataga aaaacacatg                                              20

<210> SEQ ID NO 367
<211> LENGTH: 20
<212> TYPE: DNA
<213> ORGANISM: Homo Sapiens

<400> SEQUENCE: 367 acctataga aaaacacatga                                              20

<210> SEQ ID NO 368
<211> LENGTH: 20
<212> TYPE: DNA
<213> ORGANISM: Homo Sapiens

<400> SEQUENCE: 368
cctatagaaa aacacatgaa                                              20

<210> SEQ ID NO 369
<211> LENGTH: 20
<212> TYPE: DNA
<213> ORGANISM: Homo Sapiens

<400> SEQUENCE: 369
```

| | |
|---|---|
| ctatagaaaa acacatgaat | 20 |

<210> SEQ ID NO 370
<211> LENGTH: 19
<212> TYPE: DNA
<213> ORGANISM: Homo Sapiens

<400> SEQUENCE: 370

| | |
|---|---|
| cagtcagaat ttgtgttac | 19 |

<210> SEQ ID NO 371
<211> LENGTH: 19
<212> TYPE: DNA
<213> ORGANISM: Homo Sapiens

<400> SEQUENCE: 371

| | |
|---|---|
| agtcagaatt tgtgttacc | 19 |

<210> SEQ ID NO 372
<211> LENGTH: 19
<212> TYPE: DNA
<213> ORGANISM: Homo Sapiens

<400> SEQUENCE: 372

| | |
|---|---|
| gtcagaattt gtgttacct | 19 |

<210> SEQ ID NO 373
<211> LENGTH: 19
<212> TYPE: DNA
<213> ORGANISM: Homo Sapiens

<400> SEQUENCE: 373

| | |
|---|---|
| tcagaatttg tgttaccta | 19 |

<210> SEQ ID NO 374
<211> LENGTH: 19
<212> TYPE: DNA
<213> ORGANISM: Homo Sapiens

<400> SEQUENCE: 374

| | |
|---|---|
| cagaatttgt gttacctat | 19 |

<210> SEQ ID NO 375
<211> LENGTH: 19
<212> TYPE: DNA
<213> ORGANISM: Homo Sapiens

<400> SEQUENCE: 375

| | |
|---|---|
| agaatttgtg ttacctata | 19 |

<210> SEQ ID NO 376
<211> LENGTH: 19
<212> TYPE: DNA
<213> ORGANISM: Homo Sapiens

<400> SEQUENCE: 376

| | |
|---|---|
| gaatttgtgt tacctatag | 19 |

<210> SEQ ID NO 377
<211> LENGTH: 19
<212> TYPE: DNA
<213> ORGANISM: Homo Sapiens

```
<400> SEQUENCE: 377
aatttgtgtt acctataga                                                    19

<210> SEQ ID NO 378
<211> LENGTH: 19
<212> TYPE: DNA
<213> ORGANISM: Homo Sapiens

<400> SEQUENCE: 378
atttgtgtta cctatagaa                                                    19

<210> SEQ ID NO 379
<211> LENGTH: 19
<212> TYPE: DNA
<213> ORGANISM: Homo Sapiens

<400> SEQUENCE: 379
tttgtgttac ctatagaaa                                                    19

<210> SEQ ID NO 380
<211> LENGTH: 19
<212> TYPE: DNA
<213> ORGANISM: Homo Sapiens

<400> SEQUENCE: 380
ttgtgttacc tatagaaaa                                                    19

<210> SEQ ID NO 381
<211> LENGTH: 19
<212> TYPE: DNA
<213> ORGANISM: Homo Sapiens

<400> SEQUENCE: 381
tgtgttacct atagaaaaa                                                    19

<210> SEQ ID NO 382
<211> LENGTH: 19
<212> TYPE: DNA
<213> ORGANISM: Homo Sapiens

<400> SEQUENCE: 382
gtgttaccta tagaaaaac                                                    19

<210> SEQ ID NO 383
<211> LENGTH: 19
<212> TYPE: DNA
<213> ORGANISM: Homo Sapiens

<400> SEQUENCE: 383
tgttacctat agaaaaaca                                                    19

<210> SEQ ID NO 384
<211> LENGTH: 19
<212> TYPE: DNA
<213> ORGANISM: Homo Sapiens

<400> SEQUENCE: 384
gttacctata gaaaaacac                                                    19

<210> SEQ ID NO 385
<211> LENGTH: 19
<212> TYPE: DNA
<213> ORGANISM: Homo Sapiens
```

```
<400> SEQUENCE: 385
ttacctatag aaaaacaca                                                    19

<210> SEQ ID NO 386
<211> LENGTH: 19
<212> TYPE: DNA
<213> ORGANISM: Homo Sapiens

<400> SEQUENCE: 386
tacctataga aaaacacat                                                    19

<210> SEQ ID NO 387
<211> LENGTH: 19
<212> TYPE: DNA
<213> ORGANISM: Homo Sapiens

<400> SEQUENCE: 387
acctatagaa aaacacatg                                                    19

<210> SEQ ID NO 388
<211> LENGTH: 19
<212> TYPE: DNA
<213> ORGANISM: Homo Sapiens

<400> SEQUENCE: 388
cctatagaaa aacacatga                                                    19

<210> SEQ ID NO 389
<211> LENGTH: 19
<212> TYPE: DNA
<213> ORGANISM: Homo Sapiens

<400> SEQUENCE: 389
ctatagaaaa acacatgaa                                                    19

<210> SEQ ID NO 390
<211> LENGTH: 18
<212> TYPE: DNA
<213> ORGANISM: Homo Sapiens

<400> SEQUENCE: 390
agtcagaatt tgtgttac                                                     18

<210> SEQ ID NO 391
<211> LENGTH: 18
<212> TYPE: DNA
<213> ORGANISM: Homo Sapiens

<400> SEQUENCE: 391
gtcagaattt gtgttacc                                                     18

<210> SEQ ID NO 392
<211> LENGTH: 18
<212> TYPE: DNA
<213> ORGANISM: Homo Sapiens

<400> SEQUENCE: 392
tcagaatttg tgttacct                                                     18

<210> SEQ ID NO 393
<211> LENGTH: 18
<212> TYPE: DNA
```

<213> ORGANISM: Homo Sapiens

<400> SEQUENCE: 393
cagaatttgt gttaccta        18

<210> SEQ ID NO 394
<211> LENGTH: 18
<212> TYPE: DNA
<213> ORGANISM: Homo Sapiens

<400> SEQUENCE: 394
agaatttgtg ttacctat        18

<210> SEQ ID NO 395
<211> LENGTH: 18
<212> TYPE: DNA
<213> ORGANISM: Homo Sapiens

<400> SEQUENCE: 395
gaatttgtgt tacctata        18

<210> SEQ ID NO 396
<211> LENGTH: 18
<212> TYPE: DNA
<213> ORGANISM: Homo Sapiens

<400> SEQUENCE: 396
aatttgtgtt acctatag        18

<210> SEQ ID NO 397
<211> LENGTH: 18
<212> TYPE: DNA
<213> ORGANISM: Homo Sapiens

<400> SEQUENCE: 397
atttgtgtta cctataga        18

<210> SEQ ID NO 398
<211> LENGTH: 18
<212> TYPE: DNA
<213> ORGANISM: Homo Sapiens

<400> SEQUENCE: 398
tttgtgttac ctatagaa        18

<210> SEQ ID NO 399
<211> LENGTH: 18
<212> TYPE: DNA
<213> ORGANISM: Homo Sapiens

<400> SEQUENCE: 399
ttgtgttacc tatagaaa        18

<210> SEQ ID NO 400
<211> LENGTH: 18
<212> TYPE: DNA
<213> ORGANISM: Homo Sapiens

<400> SEQUENCE: 400
tgtgttacct atagaaaa        18

<210> SEQ ID NO 401
<211> LENGTH: 18

```
<212> TYPE: DNA
<213> ORGANISM: Homo Sapiens

<400> SEQUENCE: 401
gtgttaccta tagaaaaa                                                  18

<210> SEQ ID NO 402
<211> LENGTH: 18
<212> TYPE: DNA
<213> ORGANISM: Homo Sapiens

<400> SEQUENCE: 402
tgttacctat agaaaaac                                                  18

<210> SEQ ID NO 403
<211> LENGTH: 18
<212> TYPE: DNA
<213> ORGANISM: Homo Sapiens

<400> SEQUENCE: 403
gttacctata gaaaaaca                                                  18

<210> SEQ ID NO 404
<211> LENGTH: 18
<212> TYPE: DNA
<213> ORGANISM: Homo Sapiens

<400> SEQUENCE: 404
ttacctatag aaaacac                                                   18

<210> SEQ ID NO 405
<211> LENGTH: 18
<212> TYPE: DNA
<213> ORGANISM: Homo Sapiens

<400> SEQUENCE: 405
tacctataga aaacaca                                                   18

<210> SEQ ID NO 406
<211> LENGTH: 18
<212> TYPE: DNA
<213> ORGANISM: Homo Sapiens

<400> SEQUENCE: 406
acctatagaa aaacacat                                                  18

<210> SEQ ID NO 407
<211> LENGTH: 18
<212> TYPE: DNA
<213> ORGANISM: Homo Sapiens

<400> SEQUENCE: 407
cctatagaaa aacacatg                                                  18

<210> SEQ ID NO 408
<211> LENGTH: 18
<212> TYPE: DNA
<213> ORGANISM: Homo Sapiens

<400> SEQUENCE: 408
ctatagaaaa acacatga                                                  18

<210> SEQ ID NO 409
```

```
<211> LENGTH: 17
<212> TYPE: DNA
<213> ORGANISM: Homo Sapiens

<400> SEQUENCE: 409
gtcagaattt gtgttac                                                      17

<210> SEQ ID NO 410
<211> LENGTH: 17
<212> TYPE: DNA
<213> ORGANISM: Homo Sapiens

<400> SEQUENCE: 410
tcagaatttg tgttacc                                                      17

<210> SEQ ID NO 411
<211> LENGTH: 17
<212> TYPE: DNA
<213> ORGANISM: Homo Sapiens

<400> SEQUENCE: 411
cagaatttgt gttacct                                                      17

<210> SEQ ID NO 412
<211> LENGTH: 17
<212> TYPE: DNA
<213> ORGANISM: Homo Sapiens

<400> SEQUENCE: 412
agaatttgtg ttaccta                                                      17

<210> SEQ ID NO 413
<211> LENGTH: 17
<212> TYPE: DNA
<213> ORGANISM: Homo Sapiens

<400> SEQUENCE: 413
gaatttgtgt tacctat                                                      17

<210> SEQ ID NO 414
<211> LENGTH: 17
<212> TYPE: DNA
<213> ORGANISM: Homo Sapiens

<400> SEQUENCE: 414
aatttgtgtt acctata                                                      17

<210> SEQ ID NO 415
<211> LENGTH: 17
<212> TYPE: DNA
<213> ORGANISM: Homo Sapiens

<400> SEQUENCE: 415
atttgtgtta cctatag                                                      17

<210> SEQ ID NO 416
<211> LENGTH: 17
<212> TYPE: DNA
<213> ORGANISM: Homo Sapiens

<400> SEQUENCE: 416
tttgtgttac ctataga                                                      17
```

```
<210> SEQ ID NO 417
<211> LENGTH: 17
<212> TYPE: DNA
<213> ORGANISM: Homo Sapiens

<400> SEQUENCE: 417
ttgtgttacc tatagaa                                                    17

<210> SEQ ID NO 418
<211> LENGTH: 17
<212> TYPE: DNA
<213> ORGANISM: Homo Sapiens

<400> SEQUENCE: 418
tgtgttacct atagaaa                                                    17

<210> SEQ ID NO 419
<211> LENGTH: 17
<212> TYPE: DNA
<213> ORGANISM: Homo Sapiens

<400> SEQUENCE: 419
gtgttaccta tagaaaa                                                    17

<210> SEQ ID NO 420
<211> LENGTH: 17
<212> TYPE: DNA
<213> ORGANISM: Homo Sapiens

<400> SEQUENCE: 420
tgttacctat agaaaaa                                                    17

<210> SEQ ID NO 421
<211> LENGTH: 17
<212> TYPE: DNA
<213> ORGANISM: Homo Sapiens

<400> SEQUENCE: 421
gttacctata gaaaaac                                                    17

<210> SEQ ID NO 422
<211> LENGTH: 17
<212> TYPE: DNA
<213> ORGANISM: Homo Sapiens

<400> SEQUENCE: 422
ttacctatag aaaaaca                                                    17

<210> SEQ ID NO 423
<211> LENGTH: 17
<212> TYPE: DNA
<213> ORGANISM: Homo Sapiens

<400> SEQUENCE: 423
tacctataga aaaacac                                                    17

<210> SEQ ID NO 424
<211> LENGTH: 17
<212> TYPE: DNA
<213> ORGANISM: Homo Sapiens

<400> SEQUENCE: 424
acctatagaa aaacaca                                                    17
```

```
<210> SEQ ID NO 425
<211> LENGTH: 17
<212> TYPE: DNA
<213> ORGANISM: Homo Sapiens

<400> SEQUENCE: 425
cctatagaaa aacacat                                                  17

<210> SEQ ID NO 426
<211> LENGTH: 17
<212> TYPE: DNA
<213> ORGANISM: Homo Sapiens

<400> SEQUENCE: 426
ctatagaaaa acacatg                                                  17

<210> SEQ ID NO 427
<211> LENGTH: 16
<212> TYPE: DNA
<213> ORGANISM: Homo Sapiens

<400> SEQUENCE: 427
tcagaatttg tgttac                                                   16

<210> SEQ ID NO 428
<211> LENGTH: 16
<212> TYPE: DNA
<213> ORGANISM: Homo Sapiens

<400> SEQUENCE: 428
cagaatttgt gttacc                                                   16

<210> SEQ ID NO 429
<211> LENGTH: 16
<212> TYPE: DNA
<213> ORGANISM: Homo Sapiens

<400> SEQUENCE: 429
agaatttgtg ttacct                                                   16

<210> SEQ ID NO 430
<211> LENGTH: 16
<212> TYPE: DNA
<213> ORGANISM: Homo Sapiens

<400> SEQUENCE: 430
gaatttgtgt taccta                                                   16

<210> SEQ ID NO 431
<211> LENGTH: 16
<212> TYPE: DNA
<213> ORGANISM: Homo Sapiens

<400> SEQUENCE: 431
aatttgtgtt acctat                                                   16

<210> SEQ ID NO 432
<211> LENGTH: 16
<212> TYPE: DNA
<213> ORGANISM: Homo Sapiens

<400> SEQUENCE: 432
atttgtgtta cctata                                                   16
```

<210> SEQ ID NO 433
<211> LENGTH: 16
<212> TYPE: DNA
<213> ORGANISM: Homo Sapiens

<400> SEQUENCE: 433
tttgtgttac ctatag                                                     16

<210> SEQ ID NO 434
<211> LENGTH: 16
<212> TYPE: DNA
<213> ORGANISM: Homo Sapiens

<400> SEQUENCE: 434
ttgtgttacc tataga                                                     16

<210> SEQ ID NO 435
<211> LENGTH: 16
<212> TYPE: DNA
<213> ORGANISM: Homo Sapiens

<400> SEQUENCE: 435
tgtgttacct atagaa                                                     16

<210> SEQ ID NO 436
<211> LENGTH: 16
<212> TYPE: DNA
<213> ORGANISM: Homo Sapiens

<400> SEQUENCE: 436
gtgttaccta tagaaa                                                     16

<210> SEQ ID NO 437
<211> LENGTH: 16
<212> TYPE: DNA
<213> ORGANISM: Homo Sapiens

<400> SEQUENCE: 437
tgttacctat agaaaa                                                     16

<210> SEQ ID NO 438
<211> LENGTH: 16
<212> TYPE: DNA
<213> ORGANISM: Homo Sapiens

<400> SEQUENCE: 438
gttacctata gaaaaa                                                     16

<210> SEQ ID NO 439
<211> LENGTH: 16
<212> TYPE: DNA
<213> ORGANISM: Homo Sapiens

<400> SEQUENCE: 439
ttacctatag aaaaac                                                     16

<210> SEQ ID NO 440
<211> LENGTH: 16
<212> TYPE: DNA
<213> ORGANISM: Homo Sapiens

<400> SEQUENCE: 440
tacctataga aaaaca                                                16

<210> SEQ ID NO 441
<211> LENGTH: 16
<212> TYPE: DNA
<213> ORGANISM: Homo Sapiens

<400> SEQUENCE: 441
acctatagaa aaacac                                                16

<210> SEQ ID NO 442
<211> LENGTH: 16
<212> TYPE: DNA
<213> ORGANISM: Homo Sapiens

<400> SEQUENCE: 442
cctatagaaa aacaca                                                16

<210> SEQ ID NO 443
<211> LENGTH: 16
<212> TYPE: DNA
<213> ORGANISM: Homo Sapiens

<400> SEQUENCE: 443
ctatagaaaa acacat                                                16

<210> SEQ ID NO 444
<211> LENGTH: 15
<212> TYPE: DNA
<213> ORGANISM: Homo Sapiens

<400> SEQUENCE: 444
cagaatttgt gttac                                                 15

<210> SEQ ID NO 445
<211> LENGTH: 15
<212> TYPE: DNA
<213> ORGANISM: Homo Sapiens

<400> SEQUENCE: 445
agaatttgtg ttacc                                                 15

<210> SEQ ID NO 446
<211> LENGTH: 15
<212> TYPE: DNA
<213> ORGANISM: Homo Sapiens

<400> SEQUENCE: 446
gaatttgtgt tacct                                                 15

<210> SEQ ID NO 447
<211> LENGTH: 15
<212> TYPE: DNA
<213> ORGANISM: Homo Sapiens

<400> SEQUENCE: 447
aatttgtgtt accta                                                 15

<210> SEQ ID NO 448
<211> LENGTH: 15
<212> TYPE: DNA
<213> ORGANISM: Homo Sapiens

<400> SEQUENCE: 448
atttgtgtta cctat                                                    15

<210> SEQ ID NO 449
<211> LENGTH: 15
<212> TYPE: DNA
<213> ORGANISM: Homo Sapiens

<400> SEQUENCE: 449
tttgtgttac ctata                                                    15

<210> SEQ ID NO 450
<211> LENGTH: 15
<212> TYPE: DNA
<213> ORGANISM: Homo Sapiens

<400> SEQUENCE: 450
ttgtgttacc tatag                                                    15

<210> SEQ ID NO 451
<211> LENGTH: 15
<212> TYPE: DNA
<213> ORGANISM: Homo Sapiens

<400> SEQUENCE: 451
tgtgttacct ataga                                                    15

<210> SEQ ID NO 452
<211> LENGTH: 15
<212> TYPE: DNA
<213> ORGANISM: Homo Sapiens

<400> SEQUENCE: 452
gtgttaccta tagaa                                                    15

<210> SEQ ID NO 453
<211> LENGTH: 15
<212> TYPE: DNA
<213> ORGANISM: Homo Sapiens

<400> SEQUENCE: 453
tgttacctat agaaa                                                    15

<210> SEQ ID NO 454
<211> LENGTH: 15
<212> TYPE: DNA
<213> ORGANISM: Homo Sapiens

<400> SEQUENCE: 454
gttacctata gaaaa                                                    15

<210> SEQ ID NO 455
<211> LENGTH: 15
<212> TYPE: DNA
<213> ORGANISM: Homo Sapiens

<400> SEQUENCE: 455
ttacctatag aaaaa                                                    15

<210> SEQ ID NO 456
<211> LENGTH: 15
<212> TYPE: DNA
<213> ORGANISM: Homo Sapiens

```
<400> SEQUENCE: 456
tacctataga aaaac                                                    15

<210> SEQ ID NO 457
<211> LENGTH: 15
<212> TYPE: DNA
<213> ORGANISM: Homo Sapiens

<400> SEQUENCE: 457
acctatagaa aaaca                                                    15

<210> SEQ ID NO 458
<211> LENGTH: 15
<212> TYPE: DNA
<213> ORGANISM: Homo Sapiens

<400> SEQUENCE: 458
cctatagaaa aacac                                                    15

<210> SEQ ID NO 459
<211> LENGTH: 15
<212> TYPE: DNA
<213> ORGANISM: Homo Sapiens

<400> SEQUENCE: 459
ctatagaaaa acaca                                                    15

<210> SEQ ID NO 460
<211> LENGTH: 35
<212> TYPE: DNA
<213> ORGANISM: Homo Sapiens

<400> SEQUENCE: 460
gaaacaatta tagatatata ctcacaaata tggct                              35

<210> SEQ ID NO 461
<211> LENGTH: 35
<212> TYPE: DNA
<213> ORGANISM: Homo Sapiens

<400> SEQUENCE: 461
aaacaattat agatatatac tcacaaatat ggctc                              35

<210> SEQ ID NO 462
<211> LENGTH: 35
<212> TYPE: DNA
<213> ORGANISM: Homo Sapiens

<400> SEQUENCE: 462
aacaattata gatatatact cacaaatatg gctcc                              35

<210> SEQ ID NO 463
<211> LENGTH: 35
<212> TYPE: DNA
<213> ORGANISM: Homo Sapiens

<400> SEQUENCE: 463
acaattatag atatatactc acaaatatgg ctccc                              35

<210> SEQ ID NO 464
<211> LENGTH: 35
<212> TYPE: DNA
<213> ORGANISM: Homo Sapiens
```

<400> SEQUENCE: 464
caattataga tatatactca caaatatggc tcccc                                    35

<210> SEQ ID NO 465
<211> LENGTH: 35
<212> TYPE: DNA
<213> ORGANISM: Homo Sapiens

<400> SEQUENCE: 465
aattatagat atatactcac aaatatggct cccca                                    35

<210> SEQ ID NO 466
<211> LENGTH: 35
<212> TYPE: DNA
<213> ORGANISM: Homo Sapiens

<400> SEQUENCE: 466
attatagata tatactcaca aatatggctc cccag                                    35

<210> SEQ ID NO 467
<211> LENGTH: 35
<212> TYPE: DNA
<213> ORGANISM: Homo Sapiens

<400> SEQUENCE: 467
ttatagatat atactcacaa atatggctcc ccaga                                    35

<210> SEQ ID NO 468
<211> LENGTH: 35
<212> TYPE: DNA
<213> ORGANISM: Homo Sapiens

<400> SEQUENCE: 468
tatagatata tactcacaaa tatggctccc cagaa                                    35

<210> SEQ ID NO 469
<211> LENGTH: 35
<212> TYPE: DNA
<213> ORGANISM: Homo Sapiens

<400> SEQUENCE: 469
atagatatat actcacaaat atggctcccc agaat                                    35

<210> SEQ ID NO 470
<211> LENGTH: 35
<212> TYPE: DNA
<213> ORGANISM: Homo Sapiens

<400> SEQUENCE: 470
tagatatata ctcacaaata tggctcccca gaatg                                    35

<210> SEQ ID NO 471
<211> LENGTH: 35
<212> TYPE: DNA
<213> ORGANISM: Homo Sapiens

<400> SEQUENCE: 471
agatatatac tcacaaatat ggctccccag aatgg                                    35

<210> SEQ ID NO 472
<211> LENGTH: 35
<212> TYPE: DNA

<213> ORGANISM: Homo Sapiens

<400> SEQUENCE: 472
gatatatact cacaaatatg gctccccaga atgga        35

<210> SEQ ID NO 473
<211> LENGTH: 35
<212> TYPE: DNA
<213> ORGANISM: Homo Sapiens

<400> SEQUENCE: 473
atatatactc acaaatatgg ctccccagaa tggat        35

<210> SEQ ID NO 474
<211> LENGTH: 35
<212> TYPE: DNA
<213> ORGANISM: Homo Sapiens

<400> SEQUENCE: 474
tatatactca caaatatggc tccccagaat ggata        35

<210> SEQ ID NO 475
<211> LENGTH: 35
<212> TYPE: DNA
<213> ORGANISM: Homo Sapiens

<400> SEQUENCE: 475
atatactcac aaatatggct ccccagaatg gataa        35

<210> SEQ ID NO 476
<211> LENGTH: 34
<212> TYPE: DNA
<213> ORGANISM: Homo Sapiens

<400> SEQUENCE: 476
gaaacaatta tagatatata ctcacaaata tggc        34

<210> SEQ ID NO 477
<211> LENGTH: 34
<212> TYPE: DNA
<213> ORGANISM: Homo Sapiens

<400> SEQUENCE: 477
aaacaattat agatatatac tcacaaatat ggct        34

<210> SEQ ID NO 478
<211> LENGTH: 34
<212> TYPE: DNA
<213> ORGANISM: Homo Sapiens

<400> SEQUENCE: 478
aacaattata gatatatact cacaaatatg gctc        34

<210> SEQ ID NO 479
<211> LENGTH: 34
<212> TYPE: DNA
<213> ORGANISM: Homo Sapiens

<400> SEQUENCE: 479
acaattatag atatatactc acaaatatgg ctcc        34

<210> SEQ ID NO 480
<211> LENGTH: 34

```
<212> TYPE: DNA
<213> ORGANISM: Homo Sapiens

<400> SEQUENCE: 480
caattataga tatatactca caaatatggc tccc                               34

<210> SEQ ID NO 481
<211> LENGTH: 34
<212> TYPE: DNA
<213> ORGANISM: Homo Sapiens

<400> SEQUENCE: 481
aattatagat atatactcac aaatatggct cccc                               34

<210> SEQ ID NO 482
<211> LENGTH: 34
<212> TYPE: DNA
<213> ORGANISM: Homo Sapiens

<400> SEQUENCE: 482
attatagata tatactcaca aatatggctc ccca                               34

<210> SEQ ID NO 483
<211> LENGTH: 34
<212> TYPE: DNA
<213> ORGANISM: Homo Sapiens

<400> SEQUENCE: 483
ttatagatat atactcacaa atatggctcc ccag                               34

<210> SEQ ID NO 484
<211> LENGTH: 34
<212> TYPE: DNA
<213> ORGANISM: Homo Sapiens

<400> SEQUENCE: 484
tatagatata tactcacaaa tatggctccc caga                               34

<210> SEQ ID NO 485
<211> LENGTH: 34
<212> TYPE: DNA
<213> ORGANISM: Homo Sapiens

<400> SEQUENCE: 485
atagatatat actcacaaat atggctcccc agaa                               34

<210> SEQ ID NO 486
<211> LENGTH: 34
<212> TYPE: DNA
<213> ORGANISM: Homo Sapiens

<400> SEQUENCE: 486
tagatatata ctcacaaata tggctcccca gaat                               34

<210> SEQ ID NO 487
<211> LENGTH: 34
<212> TYPE: DNA
<213> ORGANISM: Homo Sapiens

<400> SEQUENCE: 487
agatatatac tcacaaatat ggctccccag aatg                               34

<210> SEQ ID NO 488
```

```
<211> LENGTH: 34
<212> TYPE: DNA
<213> ORGANISM: Homo Sapiens

<400> SEQUENCE: 488
gatatatact cacaaatatg gctccccaga atgg                              34

<210> SEQ ID NO 489
<211> LENGTH: 34
<212> TYPE: DNA
<213> ORGANISM: Homo Sapiens

<400> SEQUENCE: 489
atatatactc acaaatatgg ctccccagaa tgga                              34

<210> SEQ ID NO 490
<211> LENGTH: 34
<212> TYPE: DNA
<213> ORGANISM: Homo Sapiens

<400> SEQUENCE: 490
tatatactca caaatatggc tccccagaat ggat                              34

<210> SEQ ID NO 491
<211> LENGTH: 34
<212> TYPE: DNA
<213> ORGANISM: Homo Sapiens

<400> SEQUENCE: 491
atatactcac aaatatggct ccccagaatg gata                              34

<210> SEQ ID NO 492
<211> LENGTH: 34
<212> TYPE: DNA
<213> ORGANISM: Homo Sapiens

<400> SEQUENCE: 492
tatactcaca aatatggctc cccagaatgg ataa                              34

<210> SEQ ID NO 493
<211> LENGTH: 33
<212> TYPE: DNA
<213> ORGANISM: Homo Sapiens

<400> SEQUENCE: 493
gaaacaatta tagatatata ctcacaaata tgg                               33

<210> SEQ ID NO 494
<211> LENGTH: 33
<212> TYPE: DNA
<213> ORGANISM: Homo Sapiens

<400> SEQUENCE: 494
aaacaattat agatatatac tcacaaatat ggc                               33

<210> SEQ ID NO 495
<211> LENGTH: 33
<212> TYPE: DNA
<213> ORGANISM: Homo Sapiens

<400> SEQUENCE: 495
aacaattata gatatatact cacaaatatg gct                               33
```

```
<210> SEQ ID NO 496
<211> LENGTH: 33
<212> TYPE: DNA
<213> ORGANISM: Homo Sapiens

<400> SEQUENCE: 496
acaattatag atatatactc acaaatatgg ctc                                    33

<210> SEQ ID NO 497
<211> LENGTH: 33
<212> TYPE: DNA
<213> ORGANISM: Homo Sapiens

<400> SEQUENCE: 497
caattataga tatatactca caaatatggc tcc                                    33

<210> SEQ ID NO 498
<211> LENGTH: 33
<212> TYPE: DNA
<213> ORGANISM: Homo Sapiens

<400> SEQUENCE: 498
aattatagat atatactcac aaatatggct ccc                                    33

<210> SEQ ID NO 499
<211> LENGTH: 33
<212> TYPE: DNA
<213> ORGANISM: Homo Sapiens

<400> SEQUENCE: 499
attatagata tatactcaca aatatggctc ccc                                    33

<210> SEQ ID NO 500
<211> LENGTH: 33
<212> TYPE: DNA
<213> ORGANISM: Homo Sapiens

<400> SEQUENCE: 500
ttatagatat atactcacaa atatggctcc cca                                    33

<210> SEQ ID NO 501
<211> LENGTH: 33
<212> TYPE: DNA
<213> ORGANISM: Homo Sapiens

<400> SEQUENCE: 501
tatagatata tactcacaaa tatggctccc cag                                    33

<210> SEQ ID NO 502
<211> LENGTH: 33
<212> TYPE: DNA
<213> ORGANISM: Homo Sapiens

<400> SEQUENCE: 502
atagatatat actcacaaat atggctcccc aga                                    33

<210> SEQ ID NO 503
<211> LENGTH: 33
<212> TYPE: DNA
<213> ORGANISM: Homo Sapiens

<400> SEQUENCE: 503
tagatatata ctcacaaata tggctcccca gaa                                    33
```

<210> SEQ ID NO 504
<211> LENGTH: 33
<212> TYPE: DNA
<213> ORGANISM: Homo Sapiens

<400> SEQUENCE: 504
agatatatac tcacaaatat ggctccccag aat                         33

<210> SEQ ID NO 505
<211> LENGTH: 33
<212> TYPE: DNA
<213> ORGANISM: Homo Sapiens

<400> SEQUENCE: 505
gatatatact cacaaatatg gctccccaga atg                         33

<210> SEQ ID NO 506
<211> LENGTH: 33
<212> TYPE: DNA
<213> ORGANISM: Homo Sapiens

<400> SEQUENCE: 506
atatatactc acaaatatgg ctccccagaa tgg                         33

<210> SEQ ID NO 507
<211> LENGTH: 33
<212> TYPE: DNA
<213> ORGANISM: Homo Sapiens

<400> SEQUENCE: 507
tatatactca caaatatggc tccccagaat gga                         33

<210> SEQ ID NO 508
<211> LENGTH: 33
<212> TYPE: DNA
<213> ORGANISM: Homo Sapiens

<400> SEQUENCE: 508
atatactcac aaatatggct ccccagaatg gat                         33

<210> SEQ ID NO 509
<211> LENGTH: 33
<212> TYPE: DNA
<213> ORGANISM: Homo Sapiens

<400> SEQUENCE: 509
tatactcaca aatatggctc cccagaatgg ata                         33

<210> SEQ ID NO 510
<211> LENGTH: 33
<212> TYPE: DNA
<213> ORGANISM: Homo Sapiens

<400> SEQUENCE: 510
atactcacaa atatggctcc ccagaatgga taa                         33

<210> SEQ ID NO 511
<211> LENGTH: 32
<212> TYPE: DNA
<213> ORGANISM: Homo Sapiens

<400> SEQUENCE: 511
gaaacaatta tagatatata ctcacaaata tg                          32

```
<210> SEQ ID NO 512
<211> LENGTH: 32
<212> TYPE: DNA
<213> ORGANISM: Homo Sapiens

<400> SEQUENCE: 512
aaacaattat agatatatac tcacaaatat gg                              32

<210> SEQ ID NO 513
<211> LENGTH: 32
<212> TYPE: DNA
<213> ORGANISM: Homo Sapiens

<400> SEQUENCE: 513
aacaattata gatatatact cacaaatatg gc                              32

<210> SEQ ID NO 514
<211> LENGTH: 32
<212> TYPE: DNA
<213> ORGANISM: Homo Sapiens

<400> SEQUENCE: 514
acaattatag atatatactc acaaatatgg ct                              32

<210> SEQ ID NO 515
<211> LENGTH: 32
<212> TYPE: DNA
<213> ORGANISM: Homo Sapiens

<400> SEQUENCE: 515
caattataga tatatactca caaatatggc tc                              32

<210> SEQ ID NO 516
<211> LENGTH: 32
<212> TYPE: DNA
<213> ORGANISM: Homo Sapiens

<400> SEQUENCE: 516
aattatagat atatactcac aaatatggct cc                              32

<210> SEQ ID NO 517
<211> LENGTH: 32
<212> TYPE: DNA
<213> ORGANISM: Homo Sapiens

<400> SEQUENCE: 517
attatagata tatactcaca aatatggctc cc                              32

<210> SEQ ID NO 518
<211> LENGTH: 32
<212> TYPE: DNA
<213> ORGANISM: Homo Sapiens

<400> SEQUENCE: 518
ttatagatat atactcacaa atatggctcc cc                              32

<210> SEQ ID NO 519
<211> LENGTH: 32
<212> TYPE: DNA
<213> ORGANISM: Homo Sapiens

<400> SEQUENCE: 519
```

```
tatagatata tactcacaaa tatggctccc ca                                32

<210> SEQ ID NO 520
<211> LENGTH: 32
<212> TYPE: DNA
<213> ORGANISM: Homo Sapiens

<400> SEQUENCE: 520
atagatatat actcacaaat atggctcccc ag                                32

<210> SEQ ID NO 521
<211> LENGTH: 32
<212> TYPE: DNA
<213> ORGANISM: Homo Sapiens

<400> SEQUENCE: 521
tagatatata ctcacaaata tggctcccca ga                                32

<210> SEQ ID NO 522
<211> LENGTH: 32
<212> TYPE: DNA
<213> ORGANISM: Homo Sapiens

<400> SEQUENCE: 522
agatatatac tcacaaatat ggctccccag aa                                32

<210> SEQ ID NO 523
<211> LENGTH: 32
<212> TYPE: DNA
<213> ORGANISM: Homo Sapiens

<400> SEQUENCE: 523
gatatatact cacaaatatg gctccccaga at                                32

<210> SEQ ID NO 524
<211> LENGTH: 32
<212> TYPE: DNA
<213> ORGANISM: Homo Sapiens

<400> SEQUENCE: 524
atatatactc acaaatatgg ctccccagaa tg                                32

<210> SEQ ID NO 525
<211> LENGTH: 32
<212> TYPE: DNA
<213> ORGANISM: Homo Sapiens

<400> SEQUENCE: 525
tatatactca caaatatggc tccccagaat gg                                32

<210> SEQ ID NO 526
<211> LENGTH: 32
<212> TYPE: DNA
<213> ORGANISM: Homo Sapiens

<400> SEQUENCE: 526
atatactcac aaatatggct ccccagaatg ga                                32

<210> SEQ ID NO 527
<211> LENGTH: 32
<212> TYPE: DNA
<213> ORGANISM: Homo Sapiens

<400> SEQUENCE: 527
```

-continued tatactcaca aatatggctc cccagaatgg at                    32

<210> SEQ ID NO 528
<211> LENGTH: 32
<212> TYPE: DNA
<213> ORGANISM: Homo Sapiens

<400> SEQUENCE: 528
atactcacaa atatggctcc ccagaatgga ta                    32

<210> SEQ ID NO 529
<211> LENGTH: 32
<212> TYPE: DNA
<213> ORGANISM: Homo Sapiens

<400> SEQUENCE: 529
tactcacaaa tatggctccc cagaatggat aa                    32

<210> SEQ ID NO 530
<211> LENGTH: 31
<212> TYPE: DNA
<213> ORGANISM: Homo Sapiens

<400> SEQUENCE: 530
gaaacaatta tagatatata ctcacaaata t                     31

<210> SEQ ID NO 531
<211> LENGTH: 31
<212> TYPE: DNA
<213> ORGANISM: Homo Sapiens

<400> SEQUENCE: 531
aaacaattat agatatatac tcacaaatat g                     31

<210> SEQ ID NO 532
<211> LENGTH: 31
<212> TYPE: DNA
<213> ORGANISM: Homo Sapiens

<400> SEQUENCE: 532
aacaattata gatatatact cacaaatatg g                     31

<210> SEQ ID NO 533
<211> LENGTH: 31
<212> TYPE: DNA
<213> ORGANISM: Homo Sapiens

<400> SEQUENCE: 533
acaattatag atatatactc acaaatatgg c                     31

<210> SEQ ID NO 534
<211> LENGTH: 31
<212> TYPE: DNA
<213> ORGANISM: Homo Sapiens

<400> SEQUENCE: 534
caattataga tatatactca caaatatggc t                     31

<210> SEQ ID NO 535
<211> LENGTH: 31
<212> TYPE: DNA
<213> ORGANISM: Homo Sapiens

```
<400> SEQUENCE: 535
aattatagat atatactcac aaatatggct c                                31

<210> SEQ ID NO 536
<211> LENGTH: 31
<212> TYPE: DNA
<213> ORGANISM: Homo Sapiens

<400> SEQUENCE: 536
attatagata tactcacaaa atatggctc c                                 31

<210> SEQ ID NO 537
<211> LENGTH: 31
<212> TYPE: DNA
<213> ORGANISM: Homo Sapiens

<400> SEQUENCE: 537
ttatagatat actcacaaa atatggctcc c                                 31

<210> SEQ ID NO 538
<211> LENGTH: 31
<212> TYPE: DNA
<213> ORGANISM: Homo Sapiens

<400> SEQUENCE: 538
tatagatata tactcacaaa tatggctccc c                                31

<210> SEQ ID NO 539
<211> LENGTH: 31
<212> TYPE: DNA
<213> ORGANISM: Homo Sapiens

<400> SEQUENCE: 539
atagatatat actcacaaat atggctcccc a                                31

<210> SEQ ID NO 540
<211> LENGTH: 31
<212> TYPE: DNA
<213> ORGANISM: Homo Sapiens

<400> SEQUENCE: 540
tagatatata ctcacaaata tggctcccca g                                31

<210> SEQ ID NO 541
<211> LENGTH: 31
<212> TYPE: DNA
<213> ORGANISM: Homo Sapiens

<400> SEQUENCE: 541
agatatatac tcacaaatat ggctccccag a                                31

<210> SEQ ID NO 542
<211> LENGTH: 31
<212> TYPE: DNA
<213> ORGANISM: Homo Sapiens

<400> SEQUENCE: 542
gatatatact cacaaatatg gctccccaga a                                31

<210> SEQ ID NO 543
<211> LENGTH: 31
<212> TYPE: DNA
<213> ORGANISM: Homo Sapiens
```

```
<400> SEQUENCE: 543
atatatactc acaaatatgg ctccccagaa t                                31

<210> SEQ ID NO 544
<211> LENGTH: 31
<212> TYPE: DNA
<213> ORGANISM: Homo Sapiens

<400> SEQUENCE: 544
tatatactca caaatatggc tccccagaat g                                31

<210> SEQ ID NO 545
<211> LENGTH: 31
<212> TYPE: DNA
<213> ORGANISM: Homo Sapiens

<400> SEQUENCE: 545
atatactcac aaatatggct ccccagaatg g                                31

<210> SEQ ID NO 546
<211> LENGTH: 31
<212> TYPE: DNA
<213> ORGANISM: Homo Sapiens

<400> SEQUENCE: 546
tatactcaca aatatggctc cccagaatgg a                                31

<210> SEQ ID NO 547
<211> LENGTH: 31
<212> TYPE: DNA
<213> ORGANISM: Homo Sapiens

<400> SEQUENCE: 547
atactcacaa atatggctcc ccagaatgga t                                31

<210> SEQ ID NO 548
<211> LENGTH: 31
<212> TYPE: DNA
<213> ORGANISM: Homo Sapiens

<400> SEQUENCE: 548
tactcacaaa tatggctccc cagaatggat a                                31

<210> SEQ ID NO 549
<211> LENGTH: 31
<212> TYPE: DNA
<213> ORGANISM: Homo Sapiens

<400> SEQUENCE: 549
actcacaaat atggctcccc agaatggata a                                31

<210> SEQ ID NO 550
<211> LENGTH: 30
<212> TYPE: DNA
<213> ORGANISM: Homo Sapiens

<400> SEQUENCE: 550
gaaacaatta tagatatata ctcacaaata                                  30

<210> SEQ ID NO 551
<211> LENGTH: 30
<212> TYPE: DNA
```

```
<213> ORGANISM: Homo Sapiens

<400> SEQUENCE: 551
aaacaattat agatatatac tcacaaatat                                30

<210> SEQ ID NO 552
<211> LENGTH: 30
<212> TYPE: DNA
<213> ORGANISM: Homo Sapiens

<400> SEQUENCE: 552
aacaattata gatatatact cacaaatatg                                30

<210> SEQ ID NO 553
<211> LENGTH: 30
<212> TYPE: DNA
<213> ORGANISM: Homo Sapiens

<400> SEQUENCE: 553
acaattatag atatatactc acaaatatgg                                30

<210> SEQ ID NO 554
<211> LENGTH: 30
<212> TYPE: DNA
<213> ORGANISM: Homo Sapiens

<400> SEQUENCE: 554
caattataga tatatactca caaatatggc                                30

<210> SEQ ID NO 555
<211> LENGTH: 30
<212> TYPE: DNA
<213> ORGANISM: Homo Sapiens

<400> SEQUENCE: 555
aattatagat atatactcac aaatatggct                                30

<210> SEQ ID NO 556
<211> LENGTH: 30
<212> TYPE: DNA
<213> ORGANISM: Homo Sapiens

<400> SEQUENCE: 556
attatagata tatactcaca aatatggctc                                30

<210> SEQ ID NO 557
<211> LENGTH: 30
<212> TYPE: DNA
<213> ORGANISM: Homo Sapiens

<400> SEQUENCE: 557
ttatagatat atactcacaa atatggctcc                                30

<210> SEQ ID NO 558
<211> LENGTH: 30
<212> TYPE: DNA
<213> ORGANISM: Homo Sapiens

<400> SEQUENCE: 558
tatagatata tactcacaaa tatggctccc                                30

<210> SEQ ID NO 559
<211> LENGTH: 30
```

<212> TYPE: DNA
<213> ORGANISM: Homo Sapiens

<400> SEQUENCE: 559
atagatatat actcacaaat atggctcccc                                      30

<210> SEQ ID NO 560
<211> LENGTH: 30
<212> TYPE: DNA
<213> ORGANISM: Homo Sapiens

<400> SEQUENCE: 560
tagatatata ctcacaaata tggctcccca                                      30

<210> SEQ ID NO 561
<211> LENGTH: 30
<212> TYPE: DNA
<213> ORGANISM: Homo Sapiens

<400> SEQUENCE: 561
agatatatac tcacaaatat ggctccccag                                      30

<210> SEQ ID NO 562
<211> LENGTH: 30
<212> TYPE: DNA
<213> ORGANISM: Homo Sapiens

<400> SEQUENCE: 562
gatatatact cacaaatatg gctccccaga                                      30

<210> SEQ ID NO 563
<211> LENGTH: 30
<212> TYPE: DNA
<213> ORGANISM: Homo Sapiens

<400> SEQUENCE: 563
atatatactc acaaatatgg ctccccagaa                                      30

<210> SEQ ID NO 564
<211> LENGTH: 30
<212> TYPE: DNA
<213> ORGANISM: Homo Sapiens

<400> SEQUENCE: 564
tatatactca caaatatggc tccccagaat                                      30

<210> SEQ ID NO 565
<211> LENGTH: 30
<212> TYPE: DNA
<213> ORGANISM: Homo Sapiens

<400> SEQUENCE: 565
atatactcac aaatatggct ccccagaatg                                      30

<210> SEQ ID NO 566
<211> LENGTH: 30
<212> TYPE: DNA
<213> ORGANISM: Homo Sapiens

<400> SEQUENCE: 566
tatactcaca aatatggctc cccagaatgg                                      30

<210> SEQ ID NO 567

```
<211> LENGTH: 30
<212> TYPE: DNA
<213> ORGANISM: Homo Sapiens

<400> SEQUENCE: 567
atactcacaa atatggctcc ccagaatgga                                            30

<210> SEQ ID NO 568
<211> LENGTH: 30
<212> TYPE: DNA
<213> ORGANISM: Homo Sapiens

<400> SEQUENCE: 568
tactcacaaa tatggctccc cagaatggat                                            30

<210> SEQ ID NO 569
<211> LENGTH: 30
<212> TYPE: DNA
<213> ORGANISM: Homo Sapiens

<400> SEQUENCE: 569
actcacaaat atggctcccc agaatggata                                            30

<210> SEQ ID NO 570
<211> LENGTH: 30
<212> TYPE: DNA
<213> ORGANISM: Homo Sapiens

<400> SEQUENCE: 570
ctcacaaata tggctcccca gaatggataa                                            30

<210> SEQ ID NO 571
<211> LENGTH: 29
<212> TYPE: DNA
<213> ORGANISM: Homo Sapiens

<400> SEQUENCE: 571
gaaacaatta tagatatata ctcacaaat                                             29

<210> SEQ ID NO 572
<211> LENGTH: 29
<212> TYPE: DNA
<213> ORGANISM: Homo Sapiens

<400> SEQUENCE: 572
aaacaattat agatatatac tcacaaata                                             29

<210> SEQ ID NO 573
<211> LENGTH: 29
<212> TYPE: DNA
<213> ORGANISM: Homo Sapiens

<400> SEQUENCE: 573
aacaattata gatatatact cacaaatat                                             29

<210> SEQ ID NO 574
<211> LENGTH: 29
<212> TYPE: DNA
<213> ORGANISM: Homo Sapiens

<400> SEQUENCE: 574
acaattatag atatatactc acaaatatg                                             29
```

```
<210> SEQ ID NO 575
<211> LENGTH: 29
<212> TYPE: DNA
<213> ORGANISM: Homo Sapiens

<400> SEQUENCE: 575
caattataga tatatactca caaatatgg                                    29

<210> SEQ ID NO 576
<211> LENGTH: 29
<212> TYPE: DNA
<213> ORGANISM: Homo Sapiens

<400> SEQUENCE: 576
aattatagat atatactcac aaatatggc                                    29

<210> SEQ ID NO 577
<211> LENGTH: 29
<212> TYPE: DNA
<213> ORGANISM: Homo Sapiens

<400> SEQUENCE: 577
attatagata tatactcaca aatatggct                                    29

<210> SEQ ID NO 578
<211> LENGTH: 29
<212> TYPE: DNA
<213> ORGANISM: Homo Sapiens

<400> SEQUENCE: 578
ttatagatat atactcacaa atatggctc                                    29

<210> SEQ ID NO 579
<211> LENGTH: 29
<212> TYPE: DNA
<213> ORGANISM: Homo Sapiens

<400> SEQUENCE: 579
tatagatata tactcacaaa tatggctcc                                    29

<210> SEQ ID NO 580
<211> LENGTH: 29
<212> TYPE: DNA
<213> ORGANISM: Homo Sapiens

<400> SEQUENCE: 580
atagatatat actcacaaat atggctccc                                    29

<210> SEQ ID NO 581
<211> LENGTH: 29
<212> TYPE: DNA
<213> ORGANISM: Homo Sapiens

<400> SEQUENCE: 581
tagatatata ctcacaaata tggctcccc                                    29

<210> SEQ ID NO 582
<211> LENGTH: 29
<212> TYPE: DNA
<213> ORGANISM: Homo Sapiens

<400> SEQUENCE: 582
agatatatac tcacaaatat ggctcccca                                    29
```

<210> SEQ ID NO 583
<211> LENGTH: 29
<212> TYPE: DNA
<213> ORGANISM: Homo Sapiens

<400> SEQUENCE: 583
gatatatact cacaaatatg gctccccag                                29

<210> SEQ ID NO 584
<211> LENGTH: 29
<212> TYPE: DNA
<213> ORGANISM: Homo Sapiens

<400> SEQUENCE: 584
atatatactc acaaatatgg ctccccaga                                29

<210> SEQ ID NO 585
<211> LENGTH: 29
<212> TYPE: DNA
<213> ORGANISM: Homo Sapiens

<400> SEQUENCE: 585
tatatactca caaatatggc tccccagaa                                29

<210> SEQ ID NO 586
<211> LENGTH: 29
<212> TYPE: DNA
<213> ORGANISM: Homo Sapiens

<400> SEQUENCE: 586
atatactcac aaatatggct ccccagaat                                29

<210> SEQ ID NO 587
<211> LENGTH: 29
<212> TYPE: DNA
<213> ORGANISM: Homo Sapiens

<400> SEQUENCE: 587
tatactcaca aatatggctc cccagaatg                                29

<210> SEQ ID NO 588
<211> LENGTH: 29
<212> TYPE: DNA
<213> ORGANISM: Homo Sapiens

<400> SEQUENCE: 588
atactcacaa atatggctcc ccagaatgg                                29

<210> SEQ ID NO 589
<211> LENGTH: 29
<212> TYPE: DNA
<213> ORGANISM: Homo Sapiens

<400> SEQUENCE: 589
tactcacaaa tatggctccc cagaatgga                                29

<210> SEQ ID NO 590
<211> LENGTH: 29
<212> TYPE: DNA
<213> ORGANISM: Homo Sapiens

<400> SEQUENCE: 590
actcacaaat atggctcccc agaatggat                                29

<210> SEQ ID NO 591
<211> LENGTH: 29
<212> TYPE: DNA
<213> ORGANISM: Homo Sapiens

<400> SEQUENCE: 591
ctcacaaata tggctcccca gaatggata                                    29

<210> SEQ ID NO 592
<211> LENGTH: 29
<212> TYPE: DNA
<213> ORGANISM: Homo Sapiens

<400> SEQUENCE: 592
tcacaaatat ggctccccag aatggataa                                    29

<210> SEQ ID NO 593
<211> LENGTH: 28
<212> TYPE: DNA
<213> ORGANISM: Homo Sapiens

<400> SEQUENCE: 593
gaaacaatta tagatatata ctcacaaa                                     28

<210> SEQ ID NO 594
<211> LENGTH: 28
<212> TYPE: DNA
<213> ORGANISM: Homo Sapiens

<400> SEQUENCE: 594
aaacaattat agatatatac tcacaaat                                     28

<210> SEQ ID NO 595
<211> LENGTH: 28
<212> TYPE: DNA
<213> ORGANISM: Homo Sapiens

<400> SEQUENCE: 595
aacaattata gatatatact cacaaata                                     28

<210> SEQ ID NO 596
<211> LENGTH: 28
<212> TYPE: DNA
<213> ORGANISM: Homo Sapiens

<400> SEQUENCE: 596
acaattatag atatatactc acaaatat                                     28

<210> SEQ ID NO 597
<211> LENGTH: 28
<212> TYPE: DNA
<213> ORGANISM: Homo Sapiens

<400> SEQUENCE: 597
caattataga tatatactca caaatatg                                     28

<210> SEQ ID NO 598
<211> LENGTH: 28
<212> TYPE: DNA
<213> ORGANISM: Homo Sapiens

<400> SEQUENCE: 598

```
aattatagat atatactcac aaatatgg                                28

<210> SEQ ID NO 599
<211> LENGTH: 28
<212> TYPE: DNA
<213> ORGANISM: Homo Sapiens

<400> SEQUENCE: 599
attatagata tatactcaca aatatggc                                28

<210> SEQ ID NO 600
<211> LENGTH: 28
<212> TYPE: DNA
<213> ORGANISM: Homo Sapiens

<400> SEQUENCE: 600
ttatagatat atactcacaa atatggct                                28

<210> SEQ ID NO 601
<211> LENGTH: 28
<212> TYPE: DNA
<213> ORGANISM: Homo Sapiens

<400> SEQUENCE: 601
tatagatata tactcacaaa tatggctc                                28

<210> SEQ ID NO 602
<211> LENGTH: 28
<212> TYPE: DNA
<213> ORGANISM: Homo Sapiens

<400> SEQUENCE: 602
atagatatat actcacaaat atggctcc                                28

<210> SEQ ID NO 603
<211> LENGTH: 28
<212> TYPE: DNA
<213> ORGANISM: Homo Sapiens

<400> SEQUENCE: 603
tagatatata ctcacaaata tggctccc                                28

<210> SEQ ID NO 604
<211> LENGTH: 28
<212> TYPE: DNA
<213> ORGANISM: Homo Sapiens

<400> SEQUENCE: 604
agatatatac tcacaaatat ggctcccc                                28

<210> SEQ ID NO 605
<211> LENGTH: 28
<212> TYPE: DNA
<213> ORGANISM: Homo Sapiens

<400> SEQUENCE: 605
gatatatact cacaaatatg gctcccca                                28

<210> SEQ ID NO 606
<211> LENGTH: 28
<212> TYPE: DNA
<213> ORGANISM: Homo Sapiens

<400> SEQUENCE: 606
```

```
atatatactc acaaatatgg ctccccag                                            28

<210> SEQ ID NO 607
<211> LENGTH: 28
<212> TYPE: DNA
<213> ORGANISM: Homo Sapiens

<400> SEQUENCE: 607
tatatactca caaatatggc tccccaga                                            28

<210> SEQ ID NO 608
<211> LENGTH: 28
<212> TYPE: DNA
<213> ORGANISM: Homo Sapiens

<400> SEQUENCE: 608
atatactcac aaatatggct ccccagaa                                            28

<210> SEQ ID NO 609
<211> LENGTH: 28
<212> TYPE: DNA
<213> ORGANISM: Homo Sapiens

<400> SEQUENCE: 609
tatactcaca aatatggctc cccagaat                                            28

<210> SEQ ID NO 610
<211> LENGTH: 28
<212> TYPE: DNA
<213> ORGANISM: Homo Sapiens

<400> SEQUENCE: 610
atactcacaa atatggctcc ccagaatg                                            28

<210> SEQ ID NO 611
<211> LENGTH: 28
<212> TYPE: DNA
<213> ORGANISM: Homo Sapiens

<400> SEQUENCE: 611
tactcacaaa tatggctccc cagaatgg                                            28

<210> SEQ ID NO 612
<211> LENGTH: 28
<212> TYPE: DNA
<213> ORGANISM: Homo Sapiens

<400> SEQUENCE: 612
actcacaaat atggctcccc agaatgga                                            28

<210> SEQ ID NO 613
<211> LENGTH: 28
<212> TYPE: DNA
<213> ORGANISM: Homo Sapiens

<400> SEQUENCE: 613
ctcacaaata tggctcccca gaatggat                                            28

<210> SEQ ID NO 614
<211> LENGTH: 28
<212> TYPE: DNA
<213> ORGANISM: Homo Sapiens
```

```
<400> SEQUENCE: 614
tcacaaatat ggctccccag aatggata                                    28

<210> SEQ ID NO 615
<211> LENGTH: 28
<212> TYPE: DNA
<213> ORGANISM: Homo Sapiens

<400> SEQUENCE: 615
cacaaatatg gctccccaga atggataa                                    28

<210> SEQ ID NO 616
<211> LENGTH: 27
<212> TYPE: DNA
<213> ORGANISM: Homo Sapiens

<400> SEQUENCE: 616
gaaacaatta tagatatata ctcacaa                                     27

<210> SEQ ID NO 617
<211> LENGTH: 27
<212> TYPE: DNA
<213> ORGANISM: Homo Sapiens

<400> SEQUENCE: 617
aaacaattat agatatatac tcacaaa                                     27

<210> SEQ ID NO 618
<211> LENGTH: 27
<212> TYPE: DNA
<213> ORGANISM: Homo Sapiens

<400> SEQUENCE: 618
aacaattata gatatatact cacaaat                                     27

<210> SEQ ID NO 619
<211> LENGTH: 27
<212> TYPE: DNA
<213> ORGANISM: Homo Sapiens

<400> SEQUENCE: 619
acaattatag atatactc acaaata                                       27

<210> SEQ ID NO 620
<211> LENGTH: 27
<212> TYPE: DNA
<213> ORGANISM: Homo Sapiens

<400> SEQUENCE: 620
caattataga tatatactca caaatat                                     27

<210> SEQ ID NO 621
<211> LENGTH: 27
<212> TYPE: DNA
<213> ORGANISM: Homo Sapiens

<400> SEQUENCE: 621
aattatagat atatactcac aaatatg                                     27

<210> SEQ ID NO 622
<211> LENGTH: 27
<212> TYPE: DNA
<213> ORGANISM: Homo Sapiens
```

```
<400> SEQUENCE: 622
attatagata tatactcaca aatatgg                                          27

<210> SEQ ID NO 623
<211> LENGTH: 27
<212> TYPE: DNA
<213> ORGANISM: Homo Sapiens

<400> SEQUENCE: 623
ttatagatat atactcacaa atatggc                                          27

<210> SEQ ID NO 624
<211> LENGTH: 27
<212> TYPE: DNA
<213> ORGANISM: Homo Sapiens

<400> SEQUENCE: 624
tatagatata tactcacaaa tatggct                                          27

<210> SEQ ID NO 625
<211> LENGTH: 27
<212> TYPE: DNA
<213> ORGANISM: Homo Sapiens

<400> SEQUENCE: 625
atagatatat actcacaaat atggctc                                          27

<210> SEQ ID NO 626
<211> LENGTH: 27
<212> TYPE: DNA
<213> ORGANISM: Homo Sapiens

<400> SEQUENCE: 626
tagatatata ctcacaaata tggctcc                                          27

<210> SEQ ID NO 627
<211> LENGTH: 27
<212> TYPE: DNA
<213> ORGANISM: Homo Sapiens

<400> SEQUENCE: 627
agatatatac tcacaaatat ggctccc                                          27

<210> SEQ ID NO 628
<211> LENGTH: 27
<212> TYPE: DNA
<213> ORGANISM: Homo Sapiens

<400> SEQUENCE: 628
gatatatact cacaaatatg gctcccc                                          27

<210> SEQ ID NO 629
<211> LENGTH: 27
<212> TYPE: DNA
<213> ORGANISM: Homo Sapiens

<400> SEQUENCE: 629
atatatactc acaaatatgg ctcccca                                          27

<210> SEQ ID NO 630
<211> LENGTH: 27
<212> TYPE: DNA
```

```
<213> ORGANISM: Homo Sapiens

<400> SEQUENCE: 630
tatatactca caaatatggc tccccag                                              27

<210> SEQ ID NO 631
<211> LENGTH: 27
<212> TYPE: DNA
<213> ORGANISM: Homo Sapiens

<400> SEQUENCE: 631
atatactcac aaatatggct ccccaga                                              27

<210> SEQ ID NO 632
<211> LENGTH: 27
<212> TYPE: DNA
<213> ORGANISM: Homo Sapiens

<400> SEQUENCE: 632
tatactcaca aatatggctc cccagaa                                              27

<210> SEQ ID NO 633
<211> LENGTH: 27
<212> TYPE: DNA
<213> ORGANISM: Homo Sapiens

<400> SEQUENCE: 633
atactcacaa atatggctcc ccagaat                                              27

<210> SEQ ID NO 634
<211> LENGTH: 27
<212> TYPE: DNA
<213> ORGANISM: Homo Sapiens

<400> SEQUENCE: 634
tactcacaaa tatggctccc cagaatg                                              27

<210> SEQ ID NO 635
<211> LENGTH: 27
<212> TYPE: DNA
<213> ORGANISM: Homo Sapiens

<400> SEQUENCE: 635
actcacaaat atggctcccc agaatgg                                              27

<210> SEQ ID NO 636
<211> LENGTH: 27
<212> TYPE: DNA
<213> ORGANISM: Homo Sapiens

<400> SEQUENCE: 636
ctcacaaata tggctcccca gaatgga                                              27

<210> SEQ ID NO 637
<211> LENGTH: 27
<212> TYPE: DNA
<213> ORGANISM: Homo Sapiens

<400> SEQUENCE: 637
tcacaaatat ggctccccag aatggat                                              27

<210> SEQ ID NO 638
<211> LENGTH: 27
```

<212> TYPE: DNA
<213> ORGANISM: Homo Sapiens

<400> SEQUENCE: 638
cacaaatatg gctccccaga atggata                                              27

<210> SEQ ID NO 639
<211> LENGTH: 27
<212> TYPE: DNA
<213> ORGANISM: Homo Sapiens

<400> SEQUENCE: 639
acaaatatgg ctccccagaa tggataa                                              27

<210> SEQ ID NO 640
<211> LENGTH: 26
<212> TYPE: DNA
<213> ORGANISM: Homo Sapiens

<400> SEQUENCE: 640
gaaacaatta tagatatata ctcaca                                               26

<210> SEQ ID NO 641
<211> LENGTH: 26
<212> TYPE: DNA
<213> ORGANISM: Homo Sapiens

<400> SEQUENCE: 641
aaacaattat agatatatac tcacaa                                               26

<210> SEQ ID NO 642
<211> LENGTH: 26
<212> TYPE: DNA
<213> ORGANISM: Homo Sapiens

<400> SEQUENCE: 642
aacaattata gatatatact cacaaa                                               26

<210> SEQ ID NO 643
<211> LENGTH: 26
<212> TYPE: DNA
<213> ORGANISM: Homo Sapiens

<400> SEQUENCE: 643
acaattatag atatactc acaaat                                                 26

<210> SEQ ID NO 644
<211> LENGTH: 26
<212> TYPE: DNA
<213> ORGANISM: Homo Sapiens

<400> SEQUENCE: 644
caattataga tatactca caaata                                                 26

<210> SEQ ID NO 645
<211> LENGTH: 26
<212> TYPE: DNA
<213> ORGANISM: Homo Sapiens

<400> SEQUENCE: 645
aattatagat atactcac aaatat                                                 26

<210> SEQ ID NO 646

```
<211> LENGTH: 26
<212> TYPE: DNA
<213> ORGANISM: Homo Sapiens

<400> SEQUENCE: 646
attatagata tatactcaca aatatg                                              26

<210> SEQ ID NO 647
<211> LENGTH: 26
<212> TYPE: DNA
<213> ORGANISM: Homo Sapiens

<400> SEQUENCE: 647
ttatagatat atactcacaa atatgg                                              26

<210> SEQ ID NO 648
<211> LENGTH: 26
<212> TYPE: DNA
<213> ORGANISM: Homo Sapiens

<400> SEQUENCE: 648
tatagatata tactcacaaa tatggc                                              26

<210> SEQ ID NO 649
<211> LENGTH: 26
<212> TYPE: DNA
<213> ORGANISM: Homo Sapiens

<400> SEQUENCE: 649
atagatatat actcacaaat atggct                                              26

<210> SEQ ID NO 650
<211> LENGTH: 26
<212> TYPE: DNA
<213> ORGANISM: Homo Sapiens

<400> SEQUENCE: 650
tagatatata ctcacaaata tggctc                                              26

<210> SEQ ID NO 651
<211> LENGTH: 26
<212> TYPE: DNA
<213> ORGANISM: Homo Sapiens

<400> SEQUENCE: 651
agatatatac tcacaaatat ggctcc                                              26

<210> SEQ ID NO 652
<211> LENGTH: 26
<212> TYPE: DNA
<213> ORGANISM: Homo Sapiens

<400> SEQUENCE: 652
gatatatact cacaaatatg gctccc                                              26

<210> SEQ ID NO 653
<211> LENGTH: 26
<212> TYPE: DNA
<213> ORGANISM: Homo Sapiens

<400> SEQUENCE: 653
atatatactc acaaatatgg ctcccc                                              26
```

```
<210> SEQ ID NO 654
<211> LENGTH: 26
<212> TYPE: DNA
<213> ORGANISM: Homo Sapiens

<400> SEQUENCE: 654
tatatactca caaatatggc tcccca                                          26

<210> SEQ ID NO 655
<211> LENGTH: 26
<212> TYPE: DNA
<213> ORGANISM: Homo Sapiens

<400> SEQUENCE: 655
atatactcac aaatatggct ccccag                                          26

<210> SEQ ID NO 656
<211> LENGTH: 26
<212> TYPE: DNA
<213> ORGANISM: Homo Sapiens

<400> SEQUENCE: 656
tatactcaca aatatggctc cccaga                                          26

<210> SEQ ID NO 657
<211> LENGTH: 26
<212> TYPE: DNA
<213> ORGANISM: Homo Sapiens

<400> SEQUENCE: 657
atactcacaa atatggctcc ccagaa                                          26

<210> SEQ ID NO 658
<211> LENGTH: 26
<212> TYPE: DNA
<213> ORGANISM: Homo Sapiens

<400> SEQUENCE: 658
tactcacaaa tatggctccc cagaat                                          26

<210> SEQ ID NO 659
<211> LENGTH: 26
<212> TYPE: DNA
<213> ORGANISM: Homo Sapiens

<400> SEQUENCE: 659
actcacaaat atggctcccc agaatg                                          26

<210> SEQ ID NO 660
<211> LENGTH: 26
<212> TYPE: DNA
<213> ORGANISM: Homo Sapiens

<400> SEQUENCE: 660
ctcacaaata tggctcccca gaatgg                                          26

<210> SEQ ID NO 661
<211> LENGTH: 26
<212> TYPE: DNA
<213> ORGANISM: Homo Sapiens

<400> SEQUENCE: 661
tcacaaatat ggctccccag aatgga                                          26
```

<210> SEQ ID NO 662
<211> LENGTH: 26
<212> TYPE: DNA
<213> ORGANISM: Homo Sapiens

<400> SEQUENCE: 662
cacaaatatg gctccccaga atggat                                          26

<210> SEQ ID NO 663
<211> LENGTH: 26
<212> TYPE: DNA
<213> ORGANISM: Homo Sapiens

<400> SEQUENCE: 663
acaaatatgg ctccccagaa tggata                                          26

<210> SEQ ID NO 664
<211> LENGTH: 26
<212> TYPE: DNA
<213> ORGANISM: Homo Sapiens

<400> SEQUENCE: 664
caaatatggc tccccagaat ggataa                                          26

<210> SEQ ID NO 665
<211> LENGTH: 25
<212> TYPE: DNA
<213> ORGANISM: Homo Sapiens

<400> SEQUENCE: 665
gaaacaatta tagatatata ctcac                                           25

<210> SEQ ID NO 666
<211> LENGTH: 25
<212> TYPE: DNA
<213> ORGANISM: Homo Sapiens

<400> SEQUENCE: 666
aaacaattat agatatatac tcaca                                           25

<210> SEQ ID NO 667
<211> LENGTH: 25
<212> TYPE: DNA
<213> ORGANISM: Homo Sapiens

<400> SEQUENCE: 667
aacaattata gatatatact cacaa                                           25

<210> SEQ ID NO 668
<211> LENGTH: 25
<212> TYPE: DNA
<213> ORGANISM: Homo Sapiens

<400> SEQUENCE: 668
acaattatag atatatactc acaaa                                           25

<210> SEQ ID NO 669
<211> LENGTH: 25
<212> TYPE: DNA
<213> ORGANISM: Homo Sapiens

<400> SEQUENCE: 669
caattataga tatatactca caaat                                           25

<210> SEQ ID NO 670
<211> LENGTH: 25
<212> TYPE: DNA
<213> ORGANISM: Homo Sapiens

<400> SEQUENCE: 670
aattatagat atatactcac aaata                                  25

<210> SEQ ID NO 671
<211> LENGTH: 25
<212> TYPE: DNA
<213> ORGANISM: Homo Sapiens

<400> SEQUENCE: 671
attatagata tatactcaca aatat                                  25

<210> SEQ ID NO 672
<211> LENGTH: 25
<212> TYPE: DNA
<213> ORGANISM: Homo Sapiens

<400> SEQUENCE: 672
ttatagatat atactcacaa atatg                                  25

<210> SEQ ID NO 673
<211> LENGTH: 25
<212> TYPE: DNA
<213> ORGANISM: Homo Sapiens

<400> SEQUENCE: 673
tatagatata tactcacaaa tatgg                                  25

<210> SEQ ID NO 674
<211> LENGTH: 25
<212> TYPE: DNA
<213> ORGANISM: Homo Sapiens

<400> SEQUENCE: 674
atagatatat actcacaaat atggc                                  25

<210> SEQ ID NO 675
<211> LENGTH: 25
<212> TYPE: DNA
<213> ORGANISM: Homo Sapiens

<400> SEQUENCE: 675
tagatatata ctcacaaata tggct                                  25

<210> SEQ ID NO 676
<211> LENGTH: 25
<212> TYPE: DNA
<213> ORGANISM: Homo Sapiens

<400> SEQUENCE: 676
agatatatac tcacaaatat ggctc                                  25

<210> SEQ ID NO 677
<211> LENGTH: 25
<212> TYPE: DNA
<213> ORGANISM: Homo Sapiens

<400> SEQUENCE: 677

```
gatatatact cacaaatatg gctcc                                              25

<210> SEQ ID NO 678
<211> LENGTH: 25
<212> TYPE: DNA
<213> ORGANISM: Homo Sapiens

<400> SEQUENCE: 678
atatatactc acaaatatgg ctccc                                              25

<210> SEQ ID NO 679
<211> LENGTH: 25
<212> TYPE: DNA
<213> ORGANISM: Homo Sapiens

<400> SEQUENCE: 679
tatatactca caaatatggc tcccc                                              25

<210> SEQ ID NO 680
<211> LENGTH: 25
<212> TYPE: DNA
<213> ORGANISM: Homo Sapiens

<400> SEQUENCE: 680
atatactcac aaatatggct cccca                                              25

<210> SEQ ID NO 681
<211> LENGTH: 25
<212> TYPE: DNA
<213> ORGANISM: Homo Sapiens

<400> SEQUENCE: 681
tatactcaca aatatggctc cccag                                              25

<210> SEQ ID NO 682
<211> LENGTH: 25
<212> TYPE: DNA
<213> ORGANISM: Homo Sapiens

<400> SEQUENCE: 682
atactcacaa atatggctcc ccaga                                              25

<210> SEQ ID NO 683
<211> LENGTH: 25
<212> TYPE: DNA
<213> ORGANISM: Homo Sapiens

<400> SEQUENCE: 683
tactcacaaa tatggctccc cagaa                                              25

<210> SEQ ID NO 684
<211> LENGTH: 25
<212> TYPE: DNA
<213> ORGANISM: Homo Sapiens

<400> SEQUENCE: 684
actcacaaat atggctcccc agaat                                              25

<210> SEQ ID NO 685
<211> LENGTH: 25
<212> TYPE: DNA
<213> ORGANISM: Homo Sapiens

<400> SEQUENCE: 685
```

```
ctcacaaata tggctcccca gaatg                                              25

<210> SEQ ID NO 686
<211> LENGTH: 25
<212> TYPE: DNA
<213> ORGANISM: Homo Sapiens

<400> SEQUENCE: 686
tcacaaatat ggctccccag aatgg                                              25

<210> SEQ ID NO 687
<211> LENGTH: 25
<212> TYPE: DNA
<213> ORGANISM: Homo Sapiens

<400> SEQUENCE: 687
cacaaatatg gctccccaga atgga                                              25

<210> SEQ ID NO 688
<211> LENGTH: 25
<212> TYPE: DNA
<213> ORGANISM: Homo Sapiens

<400> SEQUENCE: 688
acaaatatgg ctccccagaa tggat                                              25

<210> SEQ ID NO 689
<211> LENGTH: 25
<212> TYPE: DNA
<213> ORGANISM: Homo Sapiens

<400> SEQUENCE: 689
caaatatggc tccccagaat ggata                                              25

<210> SEQ ID NO 690
<211> LENGTH: 25
<212> TYPE: DNA
<213> ORGANISM: Homo Sapiens

<400> SEQUENCE: 690
aaatatggct ccccagaatg gataa                                              25

<210> SEQ ID NO 691
<211> LENGTH: 24
<212> TYPE: DNA
<213> ORGANISM: Homo Sapiens

<400> SEQUENCE: 691
aaacaattat agatatatac tcac                                               24

<210> SEQ ID NO 692
<211> LENGTH: 24
<212> TYPE: DNA
<213> ORGANISM: Homo Sapiens

<400> SEQUENCE: 692
aacaattata gatatatact caca                                               24

<210> SEQ ID NO 693
<211> LENGTH: 24
<212> TYPE: DNA
<213> ORGANISM: Homo Sapiens
```

```
<400> SEQUENCE: 693
acaattatag atatatactc acaa                                          24

<210> SEQ ID NO 694
<211> LENGTH: 24
<212> TYPE: DNA
<213> ORGANISM: Homo Sapiens

<400> SEQUENCE: 694
caattataga tatatactca caaa                                          24

<210> SEQ ID NO 695
<211> LENGTH: 24
<212> TYPE: DNA
<213> ORGANISM: Homo Sapiens

<400> SEQUENCE: 695
aattatagat atatactcac aaat                                          24

<210> SEQ ID NO 696
<211> LENGTH: 24
<212> TYPE: DNA
<213> ORGANISM: Homo Sapiens

<400> SEQUENCE: 696
attatagata tatactcaca aata                                          24

<210> SEQ ID NO 697
<211> LENGTH: 24
<212> TYPE: DNA
<213> ORGANISM: Homo Sapiens

<400> SEQUENCE: 697
ttatagatat atactcacaa atat                                          24

<210> SEQ ID NO 698
<211> LENGTH: 24
<212> TYPE: DNA
<213> ORGANISM: Homo Sapiens

<400> SEQUENCE: 698
tatagatata tactcacaaa tatg                                          24

<210> SEQ ID NO 699
<211> LENGTH: 24
<212> TYPE: DNA
<213> ORGANISM: Homo Sapiens

<400> SEQUENCE: 699
atagatatat actcacaaat atgg                                          24

<210> SEQ ID NO 700
<211> LENGTH: 24
<212> TYPE: DNA
<213> ORGANISM: Homo Sapiens

<400> SEQUENCE: 700
tagatatata ctcacaaata tggc                                          24

<210> SEQ ID NO 701
<211> LENGTH: 24
<212> TYPE: DNA
<213> ORGANISM: Homo Sapiens
```

```
<400> SEQUENCE: 701
agatatatac tcacaaatat ggct                                          24

<210> SEQ ID NO 702
<211> LENGTH: 24
<212> TYPE: DNA
<213> ORGANISM: Homo Sapiens

<400> SEQUENCE: 702
gatatatact cacaaatatg gctc                                          24

<210> SEQ ID NO 703
<211> LENGTH: 24
<212> TYPE: DNA
<213> ORGANISM: Homo Sapiens

<400> SEQUENCE: 703
atatatactc acaaatatgg ctcc                                          24

<210> SEQ ID NO 704
<211> LENGTH: 24
<212> TYPE: DNA
<213> ORGANISM: Homo Sapiens

<400> SEQUENCE: 704
tatatactca caaatatggc tccc                                          24

<210> SEQ ID NO 705
<211> LENGTH: 24
<212> TYPE: DNA
<213> ORGANISM: Homo Sapiens

<400> SEQUENCE: 705
atatactcac aaatatggct cccc                                          24

<210> SEQ ID NO 706
<211> LENGTH: 24
<212> TYPE: DNA
<213> ORGANISM: Homo Sapiens

<400> SEQUENCE: 706
tatactcaca aatatggctc ccca                                          24

<210> SEQ ID NO 707
<211> LENGTH: 24
<212> TYPE: DNA
<213> ORGANISM: Homo Sapiens

<400> SEQUENCE: 707
atactcacaa atatggctcc ccag                                          24

<210> SEQ ID NO 708
<211> LENGTH: 24
<212> TYPE: DNA
<213> ORGANISM: Homo Sapiens

<400> SEQUENCE: 708
tactcacaaa tatggctccc caga                                          24

<210> SEQ ID NO 709
<211> LENGTH: 24
<212> TYPE: DNA
```

```
<213> ORGANISM: Homo Sapiens

<400> SEQUENCE: 709
actcacaaat atggctcccc agaa                                        24

<210> SEQ ID NO 710
<211> LENGTH: 24
<212> TYPE: DNA
<213> ORGANISM: Homo Sapiens

<400> SEQUENCE: 710
ctcacaaata tggctcccca gaat                                        24

<210> SEQ ID NO 711
<211> LENGTH: 24
<212> TYPE: DNA
<213> ORGANISM: Homo Sapiens

<400> SEQUENCE: 711
tcacaaatat ggctccccag aatg                                        24

<210> SEQ ID NO 712
<211> LENGTH: 24
<212> TYPE: DNA
<213> ORGANISM: Homo Sapiens

<400> SEQUENCE: 712
cacaaatatg gctccccaga atgg                                        24

<210> SEQ ID NO 713
<211> LENGTH: 24
<212> TYPE: DNA
<213> ORGANISM: Homo Sapiens

<400> SEQUENCE: 713
acaaatatgg ctccccagaa tgga                                        24

<210> SEQ ID NO 714
<211> LENGTH: 24
<212> TYPE: DNA
<213> ORGANISM: Homo Sapiens

<400> SEQUENCE: 714
caaatatggc tccccagaat ggat                                        24

<210> SEQ ID NO 715
<211> LENGTH: 24
<212> TYPE: DNA
<213> ORGANISM: Homo Sapiens

<400> SEQUENCE: 715
aaatatggct ccccagaatg gata                                        24

<210> SEQ ID NO 716
<211> LENGTH: 23
<212> TYPE: DNA
<213> ORGANISM: Homo Sapiens

<400> SEQUENCE: 716
aacaattata gatatatact cac                                         23

<210> SEQ ID NO 717
<211> LENGTH: 23
```

```
<212> TYPE: DNA
<213> ORGANISM: Homo Sapiens

<400> SEQUENCE: 717
acaattatag atatatactc aca                                           23

<210> SEQ ID NO 718
<211> LENGTH: 23
<212> TYPE: DNA
<213> ORGANISM: Homo Sapiens

<400> SEQUENCE: 718
caattataga tatatactca caa                                           23

<210> SEQ ID NO 719
<211> LENGTH: 23
<212> TYPE: DNA
<213> ORGANISM: Homo Sapiens

<400> SEQUENCE: 719
aattatagat atatactcac aaa                                           23

<210> SEQ ID NO 720
<211> LENGTH: 23
<212> TYPE: DNA
<213> ORGANISM: Homo Sapiens

<400> SEQUENCE: 720
attatagata tatactcaca aat                                           23

<210> SEQ ID NO 721
<211> LENGTH: 23
<212> TYPE: DNA
<213> ORGANISM: Homo Sapiens

<400> SEQUENCE: 721
ttatagatat atactcacaa ata                                           23

<210> SEQ ID NO 722
<211> LENGTH: 23
<212> TYPE: DNA
<213> ORGANISM: Homo Sapiens

<400> SEQUENCE: 722
tatagatata tactcacaaa tat                                           23

<210> SEQ ID NO 723
<211> LENGTH: 23
<212> TYPE: DNA
<213> ORGANISM: Homo Sapiens

<400> SEQUENCE: 723
atagatatat actcacaaat atg                                           23

<210> SEQ ID NO 724
<211> LENGTH: 23
<212> TYPE: DNA
<213> ORGANISM: Homo Sapiens

<400> SEQUENCE: 724
tagatatata ctcacaaata tgg                                           23

<210> SEQ ID NO 725
```

```
<211> LENGTH: 23
<212> TYPE: DNA
<213> ORGANISM: Homo Sapiens

<400> SEQUENCE: 725
agatatatac tcacaaatat ggc                                              23

<210> SEQ ID NO 726
<211> LENGTH: 23
<212> TYPE: DNA
<213> ORGANISM: Homo Sapiens

<400> SEQUENCE: 726
gatatatact cacaaatatg gct                                              23

<210> SEQ ID NO 727
<211> LENGTH: 23
<212> TYPE: DNA
<213> ORGANISM: Homo Sapiens

<400> SEQUENCE: 727
atatatactc acaaatatgg ctc                                              23

<210> SEQ ID NO 728
<211> LENGTH: 23
<212> TYPE: DNA
<213> ORGANISM: Homo Sapiens

<400> SEQUENCE: 728
tatatactca caaatatggc tcc                                              23

<210> SEQ ID NO 729
<211> LENGTH: 23
<212> TYPE: DNA
<213> ORGANISM: Homo Sapiens

<400> SEQUENCE: 729
atatactcac aaatatggct ccc                                              23

<210> SEQ ID NO 730
<211> LENGTH: 23
<212> TYPE: DNA
<213> ORGANISM: Homo Sapiens

<400> SEQUENCE: 730
tatactcaca aatatggctc ccc                                              23

<210> SEQ ID NO 731
<211> LENGTH: 23
<212> TYPE: DNA
<213> ORGANISM: Homo Sapiens

<400> SEQUENCE: 731
atactcacaa atatggctcc cca                                              23

<210> SEQ ID NO 732
<211> LENGTH: 23
<212> TYPE: DNA
<213> ORGANISM: Homo Sapiens

<400> SEQUENCE: 732
tactcacaaa tatggctccc cag                                              23
```

```
<210> SEQ ID NO 733
<211> LENGTH: 23
<212> TYPE: DNA
<213> ORGANISM: Homo Sapiens

<400> SEQUENCE: 733
actcacaaat atggctcccc aga                                            23

<210> SEQ ID NO 734
<211> LENGTH: 23
<212> TYPE: DNA
<213> ORGANISM: Homo Sapiens

<400> SEQUENCE: 734
ctcacaaata tggctcccca gaa                                            23

<210> SEQ ID NO 735
<211> LENGTH: 23
<212> TYPE: DNA
<213> ORGANISM: Homo Sapiens

<400> SEQUENCE: 735
tcacaaatat ggctccccag aat                                            23

<210> SEQ ID NO 736
<211> LENGTH: 23
<212> TYPE: DNA
<213> ORGANISM: Homo Sapiens

<400> SEQUENCE: 736
cacaaatatg gctccccaga atg                                            23

<210> SEQ ID NO 737
<211> LENGTH: 23
<212> TYPE: DNA
<213> ORGANISM: Homo Sapiens

<400> SEQUENCE: 737
acaaatatgg ctccccagaa tgg                                            23

<210> SEQ ID NO 738
<211> LENGTH: 23
<212> TYPE: DNA
<213> ORGANISM: Homo Sapiens

<400> SEQUENCE: 738
caaatatggc tccccagaat gga                                            23

<210> SEQ ID NO 739
<211> LENGTH: 23
<212> TYPE: DNA
<213> ORGANISM: Homo Sapiens

<400> SEQUENCE: 739
aaatatggct ccccagaatg gat                                            23

<210> SEQ ID NO 740
<211> LENGTH: 22
<212> TYPE: DNA
<213> ORGANISM: Homo Sapiens

<400> SEQUENCE: 740
acaattatag atatatactc ac                                             22
```

```
<210> SEQ ID NO 741
<211> LENGTH: 22
<212> TYPE: DNA
<213> ORGANISM: Homo Sapiens

<400> SEQUENCE: 741
caattataga tatatactca ca                                              22

<210> SEQ ID NO 742
<211> LENGTH: 22
<212> TYPE: DNA
<213> ORGANISM: Homo Sapiens

<400> SEQUENCE: 742
aattatagat atatactcac aa                                              22

<210> SEQ ID NO 743
<211> LENGTH: 22
<212> TYPE: DNA
<213> ORGANISM: Homo Sapiens

<400> SEQUENCE: 743
attatagata tatactcaca aa                                              22

<210> SEQ ID NO 744
<211> LENGTH: 22
<212> TYPE: DNA
<213> ORGANISM: Homo Sapiens

<400> SEQUENCE: 744
ttatagatat atactcacaa at                                              22

<210> SEQ ID NO 745
<211> LENGTH: 22
<212> TYPE: DNA
<213> ORGANISM: Homo Sapiens

<400> SEQUENCE: 745
tatagatata tactcacaaa ta                                              22

<210> SEQ ID NO 746
<211> LENGTH: 22
<212> TYPE: DNA
<213> ORGANISM: Homo Sapiens

<400> SEQUENCE: 746
atagatatat actcacaaat at                                              22

<210> SEQ ID NO 747
<211> LENGTH: 22
<212> TYPE: DNA
<213> ORGANISM: Homo Sapiens

<400> SEQUENCE: 747
tagatatata ctcacaaata tg                                              22

<210> SEQ ID NO 748
<211> LENGTH: 22
<212> TYPE: DNA
<213> ORGANISM: Homo Sapiens

<400> SEQUENCE: 748
agatatatac tcacaaatat gg                                              22
```

```
<210> SEQ ID NO 749
<211> LENGTH: 22
<212> TYPE: DNA
<213> ORGANISM: Homo Sapiens

<400> SEQUENCE: 749
gatatatact cacaaatatg gc                                          22

<210> SEQ ID NO 750
<211> LENGTH: 22
<212> TYPE: DNA
<213> ORGANISM: Homo Sapiens

<400> SEQUENCE: 750
atatatactc acaaatatgg ct                                          22

<210> SEQ ID NO 751
<211> LENGTH: 22
<212> TYPE: DNA
<213> ORGANISM: Homo Sapiens

<400> SEQUENCE: 751
tatatactca caaatatggc tc                                          22

<210> SEQ ID NO 752
<211> LENGTH: 22
<212> TYPE: DNA
<213> ORGANISM: Homo Sapiens

<400> SEQUENCE: 752
atatactcac aaatatggct cc                                          22

<210> SEQ ID NO 753
<211> LENGTH: 22
<212> TYPE: DNA
<213> ORGANISM: Homo Sapiens

<400> SEQUENCE: 753
tatactcaca aatatggctc cc                                          22

<210> SEQ ID NO 754
<211> LENGTH: 22
<212> TYPE: DNA
<213> ORGANISM: Homo Sapiens

<400> SEQUENCE: 754
atactcacaa atatggctcc cc                                          22

<210> SEQ ID NO 755
<211> LENGTH: 22
<212> TYPE: DNA
<213> ORGANISM: Homo Sapiens

<400> SEQUENCE: 755
tactcacaaa tatggctccc ca                                          22

<210> SEQ ID NO 756
<211> LENGTH: 22
<212> TYPE: DNA
<213> ORGANISM: Homo Sapiens

<400> SEQUENCE: 756
```
actcacaaat atggctcccc ag                        22

<210> SEQ ID NO 757
<211> LENGTH: 22
<212> TYPE: DNA
<213> ORGANISM: Homo Sapiens

<400> SEQUENCE: 757
ctcacaaata tggctcccca ga                        22

<210> SEQ ID NO 758
<211> LENGTH: 22
<212> TYPE: DNA
<213> ORGANISM: Homo Sapiens

<400> SEQUENCE: 758
tcacaaatat ggctccccag aa                        22

<210> SEQ ID NO 759
<211> LENGTH: 22
<212> TYPE: DNA
<213> ORGANISM: Homo Sapiens

<400> SEQUENCE: 759
cacaaatatg gctccccaga at                        22

<210> SEQ ID NO 760
<211> LENGTH: 22
<212> TYPE: DNA
<213> ORGANISM: Homo Sapiens

<400> SEQUENCE: 760
acaaatatgg ctccccagaa tg                        22

<210> SEQ ID NO 761
<211> LENGTH: 22
<212> TYPE: DNA
<213> ORGANISM: Homo Sapiens

<400> SEQUENCE: 761
caaatatggc tccccagaat gg                        22

<210> SEQ ID NO 762
<211> LENGTH: 22
<212> TYPE: DNA
<213> ORGANISM: Homo Sapiens

<400> SEQUENCE: 762
aaatatggct ccccagaatg ga                        22

<210> SEQ ID NO 763
<211> LENGTH: 21
<212> TYPE: DNA
<213> ORGANISM: Homo Sapiens

<400> SEQUENCE: 763
caattataga tatatactca c                         21

<210> SEQ ID NO 764
<211> LENGTH: 21
<212> TYPE: DNA
<213> ORGANISM: Homo Sapiens

<400> SEQUENCE: 764
aattatagat atatactcac a    21

<210> SEQ ID NO 765
<211> LENGTH: 21
<212> TYPE: DNA
<213> ORGANISM: Homo Sapiens

<400> SEQUENCE: 765
attatagata tatactcaca a    21

<210> SEQ ID NO 766
<211> LENGTH: 21
<212> TYPE: DNA
<213> ORGANISM: Homo Sapiens

<400> SEQUENCE: 766
ttatagatat atactcacaa a    21

<210> SEQ ID NO 767
<211> LENGTH: 21
<212> TYPE: DNA
<213> ORGANISM: Homo Sapiens

<400> SEQUENCE: 767
tatagatata tactcacaaa t    21

<210> SEQ ID NO 768
<211> LENGTH: 21
<212> TYPE: DNA
<213> ORGANISM: Homo Sapiens

<400> SEQUENCE: 768
atagatatat actcacaaat a    21

<210> SEQ ID NO 769
<211> LENGTH: 21
<212> TYPE: DNA
<213> ORGANISM: Homo Sapiens

<400> SEQUENCE: 769
tagatatata ctcacaaata t    21

<210> SEQ ID NO 770
<211> LENGTH: 21
<212> TYPE: DNA
<213> ORGANISM: Homo Sapiens

<400> SEQUENCE: 770
agatatatac tcacaaatat g    21

<210> SEQ ID NO 771
<211> LENGTH: 21
<212> TYPE: DNA
<213> ORGANISM: Homo Sapiens

<400> SEQUENCE: 771
gatatatact cacaaatatg g    21

<210> SEQ ID NO 772
<211> LENGTH: 21
<212> TYPE: DNA
<213> ORGANISM: Homo Sapiens

<400> SEQUENCE: 772
atatatactc acaaatatgg c                                              21

<210> SEQ ID NO 773
<211> LENGTH: 21
<212> TYPE: DNA
<213> ORGANISM: Homo Sapiens

<400> SEQUENCE: 773
tatatactca caaatatggc t                                              21

<210> SEQ ID NO 774
<211> LENGTH: 21
<212> TYPE: DNA
<213> ORGANISM: Homo Sapiens

<400> SEQUENCE: 774
atatactcac aaatatggct c                                              21

<210> SEQ ID NO 775
<211> LENGTH: 21
<212> TYPE: DNA
<213> ORGANISM: Homo Sapiens

<400> SEQUENCE: 775
tatactcaca aatatggctc c                                              21

<210> SEQ ID NO 776
<211> LENGTH: 21
<212> TYPE: DNA
<213> ORGANISM: Homo Sapiens

<400> SEQUENCE: 776
atactcacaa atatggctcc c                                              21

<210> SEQ ID NO 777
<211> LENGTH: 21
<212> TYPE: DNA
<213> ORGANISM: Homo Sapiens

<400> SEQUENCE: 777
tactcacaaa tatggctccc c                                              21

<210> SEQ ID NO 778
<211> LENGTH: 21
<212> TYPE: DNA
<213> ORGANISM: Homo Sapiens

<400> SEQUENCE: 778
actcacaaat atggctcccc a                                              21

<210> SEQ ID NO 779
<211> LENGTH: 21
<212> TYPE: DNA
<213> ORGANISM: Homo Sapiens

<400> SEQUENCE: 779
ctcacaaata tggctcccca g                                              21

<210> SEQ ID NO 780
<211> LENGTH: 21
<212> TYPE: DNA
<213> ORGANISM: Homo Sapiens

<400> SEQUENCE: 780
tcacaaatat ggctccccag a                                              21

<210> SEQ ID NO 781
<211> LENGTH: 21
<212> TYPE: DNA
<213> ORGANISM: Homo Sapiens

<400> SEQUENCE: 781
cacaaatatg gctccccaga a                                              21

<210> SEQ ID NO 782
<211> LENGTH: 21
<212> TYPE: DNA
<213> ORGANISM: Homo Sapiens

<400> SEQUENCE: 782
acaaatatgg ctccccagaa t                                              21

<210> SEQ ID NO 783
<211> LENGTH: 21
<212> TYPE: DNA
<213> ORGANISM: Homo Sapiens

<400> SEQUENCE: 783
caaatatggc tccccagaat g                                              21

<210> SEQ ID NO 784
<211> LENGTH: 21
<212> TYPE: DNA
<213> ORGANISM: Homo Sapiens

<400> SEQUENCE: 784
aaatatggct ccccagaatg g                                              21

<210> SEQ ID NO 785
<211> LENGTH: 20
<212> TYPE: DNA
<213> ORGANISM: Homo Sapiens

<400> SEQUENCE: 785
aattatagat atatactcac                                                20

<210> SEQ ID NO 786
<211> LENGTH: 20
<212> TYPE: DNA
<213> ORGANISM: Homo Sapiens

<400> SEQUENCE: 786
attatagata tactctcaca                                                20

<210> SEQ ID NO 787
<211> LENGTH: 20
<212> TYPE: DNA
<213> ORGANISM: Homo Sapiens

<400> SEQUENCE: 787
ttatagatat atactcacaa                                                20

<210> SEQ ID NO 788
<211> LENGTH: 20
<212> TYPE: DNA

```
<213> ORGANISM: Homo Sapiens

<400> SEQUENCE: 788
tatagatata tactcacaaa                                              20

<210> SEQ ID NO 789
<211> LENGTH: 20
<212> TYPE: DNA
<213> ORGANISM: Homo Sapiens

<400> SEQUENCE: 789
atagatatat actcacaaat                                              20

<210> SEQ ID NO 790
<211> LENGTH: 20
<212> TYPE: DNA
<213> ORGANISM: Homo Sapiens

<400> SEQUENCE: 790
tagatatata ctcacaaata                                              20

<210> SEQ ID NO 791
<211> LENGTH: 20
<212> TYPE: DNA
<213> ORGANISM: Homo Sapiens

<400> SEQUENCE: 791
agatatatac tcacaaatat                                              20

<210> SEQ ID NO 792
<211> LENGTH: 20
<212> TYPE: DNA
<213> ORGANISM: Homo Sapiens

<400> SEQUENCE: 792
gatatatact cacaaatatg                                              20

<210> SEQ ID NO 793
<211> LENGTH: 20
<212> TYPE: DNA
<213> ORGANISM: Homo Sapiens

<400> SEQUENCE: 793
atatatactc acaaatatgg                                              20

<210> SEQ ID NO 794
<211> LENGTH: 20
<212> TYPE: DNA
<213> ORGANISM: Homo Sapiens

<400> SEQUENCE: 794
tatatactca caaatatggc                                              20

<210> SEQ ID NO 795
<211> LENGTH: 20
<212> TYPE: DNA
<213> ORGANISM: Homo Sapiens

<400> SEQUENCE: 795
atatactcac aaatatggct                                              20

<210> SEQ ID NO 796
<211> LENGTH: 20
```

-continued

<212> TYPE: DNA
<213> ORGANISM: Homo Sapiens

<400> SEQUENCE: 796
tatactcaca aatatggctc                                               20

<210> SEQ ID NO 797
<211> LENGTH: 20
<212> TYPE: DNA
<213> ORGANISM: Homo Sapiens

<400> SEQUENCE: 797
atactcacaa atatggctcc                                               20

<210> SEQ ID NO 798
<211> LENGTH: 20
<212> TYPE: DNA
<213> ORGANISM: Homo Sapiens

<400> SEQUENCE: 798
tactcacaaa tatggctccc                                               20

<210> SEQ ID NO 799
<211> LENGTH: 20
<212> TYPE: DNA
<213> ORGANISM: Homo Sapiens

<400> SEQUENCE: 799
actcacaaat atggctcccc                                               20

<210> SEQ ID NO 800
<211> LENGTH: 20
<212> TYPE: DNA
<213> ORGANISM: Homo Sapiens

<400> SEQUENCE: 800
ctcacaaata tggctcccca                                               20

<210> SEQ ID NO 801
<211> LENGTH: 20
<212> TYPE: DNA
<213> ORGANISM: Homo Sapiens

<400> SEQUENCE: 801
tcacaaatat ggctccccag                                               20

<210> SEQ ID NO 802
<211> LENGTH: 20
<212> TYPE: DNA
<213> ORGANISM: Homo Sapiens

<400> SEQUENCE: 802
cacaaatatg gctccccaga                                               20

<210> SEQ ID NO 803
<211> LENGTH: 20
<212> TYPE: DNA
<213> ORGANISM: Homo Sapiens

<400> SEQUENCE: 803
acaaatatgg ctccccagaa                                               20

<210> SEQ ID NO 804

```
<211> LENGTH: 20
<212> TYPE: DNA
<213> ORGANISM: Homo Sapiens

<400> SEQUENCE: 804
caaatatggc tccccagaat                                              20

<210> SEQ ID NO 805
<211> LENGTH: 20
<212> TYPE: DNA
<213> ORGANISM: Homo Sapiens

<400> SEQUENCE: 805
aaatatggct ccccagaatg                                              20

<210> SEQ ID NO 806
<211> LENGTH: 19
<212> TYPE: DNA
<213> ORGANISM: Homo Sapiens

<400> SEQUENCE: 806
attatagata tatactcac                                               19

<210> SEQ ID NO 807
<211> LENGTH: 19
<212> TYPE: DNA
<213> ORGANISM: Homo Sapiens

<400> SEQUENCE: 807
ttatagatat atactcaca                                               19

<210> SEQ ID NO 808
<211> LENGTH: 19
<212> TYPE: DNA
<213> ORGANISM: Homo Sapiens

<400> SEQUENCE: 808
tatagatata tactcacaa                                               19

<210> SEQ ID NO 809
<211> LENGTH: 19
<212> TYPE: DNA
<213> ORGANISM: Homo Sapiens

<400> SEQUENCE: 809
atagatatat actcacaaa                                               19

<210> SEQ ID NO 810
<211> LENGTH: 19
<212> TYPE: DNA
<213> ORGANISM: Homo Sapiens

<400> SEQUENCE: 810
tagatatata ctcacaaat                                               19

<210> SEQ ID NO 811
<211> LENGTH: 19
<212> TYPE: DNA
<213> ORGANISM: Homo Sapiens

<400> SEQUENCE: 811
agatatatac tcacaaata                                               19
```

```
<210> SEQ ID NO 812
<211> LENGTH: 19
<212> TYPE: DNA
<213> ORGANISM: Homo Sapiens

<400> SEQUENCE: 812
gatatatact cacaaatat                                                19

<210> SEQ ID NO 813
<211> LENGTH: 19
<212> TYPE: DNA
<213> ORGANISM: Homo Sapiens

<400> SEQUENCE: 813
atatatactc acaaatatg                                                19

<210> SEQ ID NO 814
<211> LENGTH: 19
<212> TYPE: DNA
<213> ORGANISM: Homo Sapiens

<400> SEQUENCE: 814
tatatactca caaatatgg                                                19

<210> SEQ ID NO 815
<211> LENGTH: 19
<212> TYPE: DNA
<213> ORGANISM: Homo Sapiens

<400> SEQUENCE: 815
atatactcac aaatatggc                                                19

<210> SEQ ID NO 816
<211> LENGTH: 19
<212> TYPE: DNA
<213> ORGANISM: Homo Sapiens

<400> SEQUENCE: 816
tatactcaca aatatggct                                                19

<210> SEQ ID NO 817
<211> LENGTH: 19
<212> TYPE: DNA
<213> ORGANISM: Homo Sapiens

<400> SEQUENCE: 817
atactcacaa atatggctc                                                19

<210> SEQ ID NO 818
<211> LENGTH: 19
<212> TYPE: DNA
<213> ORGANISM: Homo Sapiens

<400> SEQUENCE: 818
tactcacaaa tatggctcc                                                19

<210> SEQ ID NO 819
<211> LENGTH: 19
<212> TYPE: DNA
<213> ORGANISM: Homo Sapiens

<400> SEQUENCE: 819
actcacaaat atggctccc                                                19
```

```
<210> SEQ ID NO 820
<211> LENGTH: 19
<212> TYPE: DNA
<213> ORGANISM: Homo Sapiens

<400> SEQUENCE: 820
ctcacaaata tggctcccc                                                  19

<210> SEQ ID NO 821
<211> LENGTH: 19
<212> TYPE: DNA
<213> ORGANISM: Homo Sapiens

<400> SEQUENCE: 821
tcacaaatat ggctcccca                                                  19

<210> SEQ ID NO 822
<211> LENGTH: 19
<212> TYPE: DNA
<213> ORGANISM: Homo Sapiens

<400> SEQUENCE: 822
cacaaatatg gctccccag                                                  19

<210> SEQ ID NO 823
<211> LENGTH: 19
<212> TYPE: DNA
<213> ORGANISM: Homo Sapiens

<400> SEQUENCE: 823
acaaatatgg ctccccaga                                                  19

<210> SEQ ID NO 824
<211> LENGTH: 19
<212> TYPE: DNA
<213> ORGANISM: Homo Sapiens

<400> SEQUENCE: 824
caaatatggc tccccagaa                                                  19

<210> SEQ ID NO 825
<211> LENGTH: 19
<212> TYPE: DNA
<213> ORGANISM: Homo Sapiens

<400> SEQUENCE: 825
aaatatggct ccccagaat                                                  19

<210> SEQ ID NO 826
<211> LENGTH: 18
<212> TYPE: DNA
<213> ORGANISM: Homo Sapiens

<400> SEQUENCE: 826
ttatagatat atactcac                                                   18

<210> SEQ ID NO 827
<211> LENGTH: 18
<212> TYPE: DNA
<213> ORGANISM: Homo Sapiens

<400> SEQUENCE: 827
tatagatata tactcaca                                                   18
```

```
<210> SEQ ID NO 828
<211> LENGTH: 18
<212> TYPE: DNA
<213> ORGANISM: Homo Sapiens

<400> SEQUENCE: 828
atagatatat actcacaa                                                 18

<210> SEQ ID NO 829
<211> LENGTH: 18
<212> TYPE: DNA
<213> ORGANISM: Homo Sapiens

<400> SEQUENCE: 829
tagatatata ctcacaaa                                                 18

<210> SEQ ID NO 830
<211> LENGTH: 18
<212> TYPE: DNA
<213> ORGANISM: Homo Sapiens

<400> SEQUENCE: 830
agatatatac tcacaaat                                                 18

<210> SEQ ID NO 831
<211> LENGTH: 18
<212> TYPE: DNA
<213> ORGANISM: Homo Sapiens

<400> SEQUENCE: 831
gatatatact cacaaata                                                 18

<210> SEQ ID NO 832
<211> LENGTH: 18
<212> TYPE: DNA
<213> ORGANISM: Homo Sapiens

<400> SEQUENCE: 832
atatatactc acaaatat                                                 18

<210> SEQ ID NO 833
<211> LENGTH: 18
<212> TYPE: DNA
<213> ORGANISM: Homo Sapiens

<400> SEQUENCE: 833
tatatactca caaatatg                                                 18

<210> SEQ ID NO 834
<211> LENGTH: 18
<212> TYPE: DNA
<213> ORGANISM: Homo Sapiens

<400> SEQUENCE: 834
atatactcac aaatatgg                                                 18

<210> SEQ ID NO 835
<211> LENGTH: 18
<212> TYPE: DNA
<213> ORGANISM: Homo Sapiens

<400> SEQUENCE: 835
```
tatactcaca aatatggc                                          18

<210> SEQ ID NO 836
<211> LENGTH: 18
<212> TYPE: DNA
<213> ORGANISM: Homo Sapiens

<400> SEQUENCE: 836
atactcacaa atatggct                                          18

<210> SEQ ID NO 837
<211> LENGTH: 18
<212> TYPE: DNA
<213> ORGANISM: Homo Sapiens

<400> SEQUENCE: 837
tactcacaaa tatggctc                                          18

<210> SEQ ID NO 838
<211> LENGTH: 18
<212> TYPE: DNA
<213> ORGANISM: Homo Sapiens

<400> SEQUENCE: 838
actcacaaat atggctcc                                          18

<210> SEQ ID NO 839
<211> LENGTH: 18
<212> TYPE: DNA
<213> ORGANISM: Homo Sapiens

<400> SEQUENCE: 839
ctcacaaata tggctccc                                          18

<210> SEQ ID NO 840
<211> LENGTH: 18
<212> TYPE: DNA
<213> ORGANISM: Homo Sapiens

<400> SEQUENCE: 840
tcacaaatat ggctcccc                                          18

<210> SEQ ID NO 841
<211> LENGTH: 18
<212> TYPE: DNA
<213> ORGANISM: Homo Sapiens

<400> SEQUENCE: 841
cacaaatatg gctcccca                                          18

<210> SEQ ID NO 842
<211> LENGTH: 18
<212> TYPE: DNA
<213> ORGANISM: Homo Sapiens

<400> SEQUENCE: 842
acaaatatgg ctccccag                                          18

<210> SEQ ID NO 843
<211> LENGTH: 18
<212> TYPE: DNA
<213> ORGANISM: Homo Sapiens

<400> SEQUENCE: 843

```
caaatatggc tcccaga                                              18

<210> SEQ ID NO 844
<211> LENGTH: 18
<212> TYPE: DNA
<213> ORGANISM: Homo Sapiens

<400> SEQUENCE: 844
aaatatggct ccccagaa                                             18

<210> SEQ ID NO 845
<211> LENGTH: 17
<212> TYPE: DNA
<213> ORGANISM: Homo Sapiens

<400> SEQUENCE: 845
tatagatata tactcac                                              17

<210> SEQ ID NO 846
<211> LENGTH: 17
<212> TYPE: DNA
<213> ORGANISM: Homo Sapiens

<400> SEQUENCE: 846
atagatatat actcaca                                              17

<210> SEQ ID NO 847
<211> LENGTH: 17
<212> TYPE: DNA
<213> ORGANISM: Homo Sapiens

<400> SEQUENCE: 847
tagatatata ctcacaa                                              17

<210> SEQ ID NO 848
<211> LENGTH: 17
<212> TYPE: DNA
<213> ORGANISM: Homo Sapiens

<400> SEQUENCE: 848
agatatatac tcacaaa                                              17

<210> SEQ ID NO 849
<211> LENGTH: 17
<212> TYPE: DNA
<213> ORGANISM: Homo Sapiens

<400> SEQUENCE: 849
gatatatact cacaaat                                              17

<210> SEQ ID NO 850
<211> LENGTH: 17
<212> TYPE: DNA
<213> ORGANISM: Homo Sapiens

<400> SEQUENCE: 850
atatatactc acaaata                                              17

<210> SEQ ID NO 851
<211> LENGTH: 17
<212> TYPE: DNA
<213> ORGANISM: Homo Sapiens
```

```
<400> SEQUENCE: 851
tatatactca caaatat                                                17

<210> SEQ ID NO 852
<211> LENGTH: 17
<212> TYPE: DNA
<213> ORGANISM: Homo Sapiens

<400> SEQUENCE: 852
atatactcac aaatatg                                                17

<210> SEQ ID NO 853
<211> LENGTH: 17
<212> TYPE: DNA
<213> ORGANISM: Homo Sapiens

<400> SEQUENCE: 853
tatactcaca aatatgg                                                17

<210> SEQ ID NO 854
<211> LENGTH: 17
<212> TYPE: DNA
<213> ORGANISM: Homo Sapiens

<400> SEQUENCE: 854
atactcacaa atatggc                                                17

<210> SEQ ID NO 855
<211> LENGTH: 17
<212> TYPE: DNA
<213> ORGANISM: Homo Sapiens

<400> SEQUENCE: 855
tactcacaaa tatggct                                                17

<210> SEQ ID NO 856
<211> LENGTH: 17
<212> TYPE: DNA
<213> ORGANISM: Homo Sapiens

<400> SEQUENCE: 856
actcacaaat atggctc                                                17

<210> SEQ ID NO 857
<211> LENGTH: 17
<212> TYPE: DNA
<213> ORGANISM: Homo Sapiens

<400> SEQUENCE: 857
ctcacaaata tggctcc                                                17

<210> SEQ ID NO 858
<211> LENGTH: 17
<212> TYPE: DNA
<213> ORGANISM: Homo Sapiens

<400> SEQUENCE: 858
tcacaaatat ggctccc                                                17

<210> SEQ ID NO 859
<211> LENGTH: 17
<212> TYPE: DNA
<213> ORGANISM: Homo Sapiens
```

```
<400> SEQUENCE: 859
cacaaatatg gctcccc                                                  17

<210> SEQ ID NO 860
<211> LENGTH: 17
<212> TYPE: DNA
<213> ORGANISM: Homo Sapiens

<400> SEQUENCE: 860
acaaatatgg ctcccca                                                  17

<210> SEQ ID NO 861
<211> LENGTH: 17
<212> TYPE: DNA
<213> ORGANISM: Homo Sapiens

<400> SEQUENCE: 861
caaatatggc tccccag                                                  17

<210> SEQ ID NO 862
<211> LENGTH: 17
<212> TYPE: DNA
<213> ORGANISM: Homo Sapiens

<400> SEQUENCE: 862
aaatatggct ccccaga                                                  17

<210> SEQ ID NO 863
<211> LENGTH: 16
<212> TYPE: DNA
<213> ORGANISM: Homo Sapiens

<400> SEQUENCE: 863
atagatatat actcac                                                   16

<210> SEQ ID NO 864
<211> LENGTH: 16
<212> TYPE: DNA
<213> ORGANISM: Homo Sapiens

<400> SEQUENCE: 864
tagatatata ctcaca                                                   16

<210> SEQ ID NO 865
<211> LENGTH: 16
<212> TYPE: DNA
<213> ORGANISM: Homo Sapiens

<400> SEQUENCE: 865
agatatatac tcacaa                                                   16

<210> SEQ ID NO 866
<211> LENGTH: 16
<212> TYPE: DNA
<213> ORGANISM: Homo Sapiens

<400> SEQUENCE: 866
gatatatact cacaaa                                                   16

<210> SEQ ID NO 867
<211> LENGTH: 16
<212> TYPE: DNA
```

```
<213> ORGANISM: Homo Sapiens

<400> SEQUENCE: 867
atatatactc acaaat                                                     16

<210> SEQ ID NO 868
<211> LENGTH: 16
<212> TYPE: DNA
<213> ORGANISM: Homo Sapiens

<400> SEQUENCE: 868
tatatactca caaata                                                     16

<210> SEQ ID NO 869
<211> LENGTH: 16
<212> TYPE: DNA
<213> ORGANISM: Homo Sapiens

<400> SEQUENCE: 869
atatactcac aaatat                                                     16

<210> SEQ ID NO 870
<211> LENGTH: 16
<212> TYPE: DNA
<213> ORGANISM: Homo Sapiens

<400> SEQUENCE: 870
tatactcaca aatatg                                                     16

<210> SEQ ID NO 871
<211> LENGTH: 16
<212> TYPE: DNA
<213> ORGANISM: Homo Sapiens

<400> SEQUENCE: 871
atactcacaa atatgg                                                     16

<210> SEQ ID NO 872
<211> LENGTH: 16
<212> TYPE: DNA
<213> ORGANISM: Homo Sapiens

<400> SEQUENCE: 872
tactcacaaa tatggc                                                     16

<210> SEQ ID NO 873
<211> LENGTH: 16
<212> TYPE: DNA
<213> ORGANISM: Homo Sapiens

<400> SEQUENCE: 873
actcacaaat atggct                                                     16

<210> SEQ ID NO 874
<211> LENGTH: 16
<212> TYPE: DNA
<213> ORGANISM: Homo Sapiens

<400> SEQUENCE: 874
ctcacaaata tggctc                                                     16

<210> SEQ ID NO 875
<211> LENGTH: 16
```

<212> TYPE: DNA
<213> ORGANISM: Homo Sapiens

<400> SEQUENCE: 875
tcacaaatat ggctcc                                              16

<210> SEQ ID NO 876
<211> LENGTH: 16
<212> TYPE: DNA
<213> ORGANISM: Homo Sapiens

<400> SEQUENCE: 876
cacaaatatg gctccc                                              16

<210> SEQ ID NO 877
<211> LENGTH: 16
<212> TYPE: DNA
<213> ORGANISM: Homo Sapiens

<400> SEQUENCE: 877
acaaatatgg ctcccc                                              16

<210> SEQ ID NO 878
<211> LENGTH: 16
<212> TYPE: DNA
<213> ORGANISM: Homo Sapiens

<400> SEQUENCE: 878
caaatatggc tccca                                               16

<210> SEQ ID NO 879
<211> LENGTH: 16
<212> TYPE: DNA
<213> ORGANISM: Homo Sapiens

<400> SEQUENCE: 879
aaatatggct ccccag                                              16

<210> SEQ ID NO 880
<211> LENGTH: 15
<212> TYPE: DNA
<213> ORGANISM: Homo Sapiens

<400> SEQUENCE: 880
tagatatata ctcac                                               15

<210> SEQ ID NO 881
<211> LENGTH: 15
<212> TYPE: DNA
<213> ORGANISM: Homo Sapiens

<400> SEQUENCE: 881
agatatatac tcaca                                               15

<210> SEQ ID NO 882
<211> LENGTH: 15
<212> TYPE: DNA
<213> ORGANISM: Homo Sapiens

<400> SEQUENCE: 882
gatatatact cacaa                                               15

<210> SEQ ID NO 883

```
<211> LENGTH: 15
<212> TYPE: DNA
<213> ORGANISM: Homo Sapiens

<400> SEQUENCE: 883
atatatactc acaaa                                                        15

<210> SEQ ID NO 884
<211> LENGTH: 15
<212> TYPE: DNA
<213> ORGANISM: Homo Sapiens

<400> SEQUENCE: 884
tatatactca caaat                                                        15

<210> SEQ ID NO 885
<211> LENGTH: 15
<212> TYPE: DNA
<213> ORGANISM: Homo Sapiens

<400> SEQUENCE: 885
atatactcac aaata                                                        15

<210> SEQ ID NO 886
<211> LENGTH: 15
<212> TYPE: DNA
<213> ORGANISM: Homo Sapiens

<400> SEQUENCE: 886
tatactcaca aatat                                                        15

<210> SEQ ID NO 887
<211> LENGTH: 15
<212> TYPE: DNA
<213> ORGANISM: Homo Sapiens

<400> SEQUENCE: 887
atactcacaa atatg                                                        15

<210> SEQ ID NO 888
<211> LENGTH: 15
<212> TYPE: DNA
<213> ORGANISM: Homo Sapiens

<400> SEQUENCE: 888
tactcacaaa tatgg                                                        15

<210> SEQ ID NO 889
<211> LENGTH: 15
<212> TYPE: DNA
<213> ORGANISM: Homo Sapiens

<400> SEQUENCE: 889
actcacaaat atggc                                                        15

<210> SEQ ID NO 890
<211> LENGTH: 15
<212> TYPE: DNA
<213> ORGANISM: Homo Sapiens

<400> SEQUENCE: 890
ctcacaaata tggct                                                        15
```

```
<210> SEQ ID NO 891
<211> LENGTH: 15
<212> TYPE: DNA
<213> ORGANISM: Homo Sapiens

<400> SEQUENCE: 891
tcacaaatat ggctc                                                          15

<210> SEQ ID NO 892
<211> LENGTH: 15
<212> TYPE: DNA
<213> ORGANISM: Homo Sapiens

<400> SEQUENCE: 892
cacaaatatg gctcc                                                          15

<210> SEQ ID NO 893
<211> LENGTH: 15
<212> TYPE: DNA
<213> ORGANISM: Homo Sapiens

<400> SEQUENCE: 893
acaaatatgg ctccc                                                          15

<210> SEQ ID NO 894
<211> LENGTH: 15
<212> TYPE: DNA
<213> ORGANISM: Homo Sapiens

<400> SEQUENCE: 894
caaatatggc tcccc                                                          15

<210> SEQ ID NO 895
<211> LENGTH: 15
<212> TYPE: DNA
<213> ORGANISM: Homo Sapiens

<400> SEQUENCE: 895
aaatatggct cccca                                                          15

<210> SEQ ID NO 896
<211> LENGTH: 25
<212> TYPE: DNA
<213> ORGANISM: Homo Sapiens

<400> SEQUENCE: 896
aaatatggct ccccagaatg gataa                                               25

<210> SEQ ID NO 897
<211> LENGTH: 25
<212> TYPE: DNA
<213> ORGANISM: Homo Sapiens

<400> SEQUENCE: 897
aatatggctc ccagaatgg ataac                                                25

<210> SEQ ID NO 898
<211> LENGTH: 25
<212> TYPE: DNA
<213> ORGANISM: Homo Sapiens

<400> SEQUENCE: 898
atatggctcc ccagaatgga taacc                                               25
```

```
<210> SEQ ID NO 899
<211> LENGTH: 25
<212> TYPE: DNA
<213> ORGANISM: Homo Sapiens

<400> SEQUENCE: 899
tatggctccc cagaatggat aacct                                          25

<210> SEQ ID NO 900
<211> LENGTH: 25
<212> TYPE: DNA
<213> ORGANISM: Homo Sapiens

<400> SEQUENCE: 900
atggctcccc agaatggata acctg                                          25

<210> SEQ ID NO 901
<211> LENGTH: 25
<212> TYPE: DNA
<213> ORGANISM: Homo Sapiens

<400> SEQUENCE: 901
tggctcccca gaatggataa cctgc                                          25

<210> SEQ ID NO 902
<211> LENGTH: 25
<212> TYPE: DNA
<213> ORGANISM: Homo Sapiens

<400> SEQUENCE: 902
ggctccccag aatggataac ctgct                                          25

<210> SEQ ID NO 903
<211> LENGTH: 25
<212> TYPE: DNA
<213> ORGANISM: Homo Sapiens

<400> SEQUENCE: 903
gctccccaga atggataacc tgctt                                          25

<210> SEQ ID NO 904
<211> LENGTH: 25
<212> TYPE: DNA
<213> ORGANISM: Homo Sapiens

<400> SEQUENCE: 904
ctccccagaa tggataacct gcttt                                          25

<210> SEQ ID NO 905
<211> LENGTH: 25
<212> TYPE: DNA
<213> ORGANISM: Homo Sapiens

<400> SEQUENCE: 905
tccccagaat ggataacctg cttta                                          25

<210> SEQ ID NO 906
<211> LENGTH: 25
<212> TYPE: DNA
<213> ORGANISM: Homo Sapiens

<400> SEQUENCE: 906
ccccagaatg gataacctgc tttaa                                          25
```

```
<210> SEQ ID NO 907
<211> LENGTH: 25
<212> TYPE: DNA
<213> ORGANISM: Homo Sapiens

<400> SEQUENCE: 907
cccagaatgg ataacctgct ttaaa                                              25

<210> SEQ ID NO 908
<211> LENGTH: 25
<212> TYPE: DNA
<213> ORGANISM: Homo Sapiens

<400> SEQUENCE: 908
ccagaatgga taacctgctt taaat                                              25

<210> SEQ ID NO 909
<211> LENGTH: 25
<212> TYPE: DNA
<213> ORGANISM: Homo Sapiens

<400> SEQUENCE: 909
cagaatggat aacctgcttt aaatg                                              25

<210> SEQ ID NO 910
<211> LENGTH: 25
<212> TYPE: DNA
<213> ORGANISM: Homo Sapiens

<400> SEQUENCE: 910
agaatggata acctgcttta aatga                                              25

<210> SEQ ID NO 911
<211> LENGTH: 25
<212> TYPE: DNA
<213> ORGANISM: Homo Sapiens

<400> SEQUENCE: 911
gaatggataa cctgctttaa atgat                                              25

<210> SEQ ID NO 912
<211> LENGTH: 25
<212> TYPE: DNA
<213> ORGANISM: Homo Sapiens

<400> SEQUENCE: 912
aatggataac ctgctttaaa tgatg                                              25

<210> SEQ ID NO 913
<211> LENGTH: 25
<212> TYPE: DNA
<213> ORGANISM: Homo Sapiens

<400> SEQUENCE: 913
atggataacc tgctttaaat gatga                                              25

<210> SEQ ID NO 914
<211> LENGTH: 25
<212> TYPE: DNA
<213> ORGANISM: Homo Sapiens

<400> SEQUENCE: 914
```
tggataacct gctttaaatg atgaa 25

<210> SEQ ID NO 915
<211> LENGTH: 25
<212> TYPE: DNA
<213> ORGANISM: Homo Sapiens

<400> SEQUENCE: 915
ggataacctg ctttaaatga tgaaa 25

<210> SEQ ID NO 916
<211> LENGTH: 25
<212> TYPE: DNA
<213> ORGANISM: Homo Sapiens

<400> SEQUENCE: 916
gataacctgc tttaaatgat gaaaa 25

<210> SEQ ID NO 917
<211> LENGTH: 25
<212> TYPE: DNA
<213> ORGANISM: Homo Sapiens

<400> SEQUENCE: 917
ataacctgct ttaaatgatg aaaaa 25

<210> SEQ ID NO 918
<211> LENGTH: 25
<212> TYPE: DNA
<213> ORGANISM: Homo Sapiens

<400> SEQUENCE: 918
taacctgctt taaatgatga aaaaa 25

<210> SEQ ID NO 919
<211> LENGTH: 25
<212> TYPE: DNA
<213> ORGANISM: Homo Sapiens

<400> SEQUENCE: 919
aacctgcttt aaatgatgaa aaaat 25

<210> SEQ ID NO 920
<211> LENGTH: 25
<212> TYPE: DNA
<213> ORGANISM: Homo Sapiens

<400> SEQUENCE: 920
acctgcttta aatgatgaaa aaatg 25

<210> SEQ ID NO 921
<211> LENGTH: 25
<212> TYPE: DNA
<213> ORGANISM: Homo Sapiens

<400> SEQUENCE: 921
cctgctttaa atgatgaaaa aatgt 25

<210> SEQ ID NO 922
<211> LENGTH: 25
<212> TYPE: DNA
<213> ORGANISM: Homo Sapiens

<400> SEQUENCE: 922
ctgctttaaa tgatgaaaaa atgtc                                             25

<210> SEQ ID NO 923
<211> LENGTH: 25
<212> TYPE: DNA
<213> ORGANISM: Homo Sapiens

<400> SEQUENCE: 923
tgctttaaat gatgaaaaaa tgtct                                             25

<210> SEQ ID NO 924
<211> LENGTH: 25
<212> TYPE: DNA
<213> ORGANISM: Homo Sapiens

<400> SEQUENCE: 924
gctttaaatg atgaaaaaat gtctc                                             25

<210> SEQ ID NO 925
<211> LENGTH: 25
<212> TYPE: DNA
<213> ORGANISM: Homo Sapiens

<400> SEQUENCE: 925
ctttaaatga tgaaaaatg tctcc                                              25

<210> SEQ ID NO 926
<211> LENGTH: 25
<212> TYPE: DNA
<213> ORGANISM: Homo Sapiens

<400> SEQUENCE: 926
tttaaatgat gaaaaatgt ctccc                                              25

<210> SEQ ID NO 927
<211> LENGTH: 25
<212> TYPE: DNA
<213> ORGANISM: Homo Sapiens

<400> SEQUENCE: 927
ttaaatgatg aaaaaatgtc tccct                                             25

<210> SEQ ID NO 928
<211> LENGTH: 25
<212> TYPE: DNA
<213> ORGANISM: Homo Sapiens

<400> SEQUENCE: 928
taaatgatga aaaatgtct ccctc                                              25

<210> SEQ ID NO 929
<211> LENGTH: 25
<212> TYPE: DNA
<213> ORGANISM: Homo Sapiens

<400> SEQUENCE: 929
aaatgatgaa aaatgtctc cctca                                              25

<210> SEQ ID NO 930
<211> LENGTH: 25
<212> TYPE: DNA
<213> ORGANISM: Homo Sapiens

```
<400> SEQUENCE: 930
aatgatgaaa aaatgtctcc ctcaa                                           25

<210> SEQ ID NO 931
<211> LENGTH: 25
<212> TYPE: DNA
<213> ORGANISM: Homo Sapiens

<400> SEQUENCE: 931
atgatgaaaa aatgtctccc tcaat                                           25

<210> SEQ ID NO 932
<211> LENGTH: 25
<212> TYPE: DNA
<213> ORGANISM: Homo Sapiens

<400> SEQUENCE: 932
tgatgaaaaa atgtctccct caatg                                           25

<210> SEQ ID NO 933
<211> LENGTH: 25
<212> TYPE: DNA
<213> ORGANISM: Homo Sapiens

<400> SEQUENCE: 933
gatgaaaaaa tgtctccctc aatgt                                           25

<210> SEQ ID NO 934
<211> LENGTH: 25
<212> TYPE: DNA
<213> ORGANISM: Homo Sapiens

<400> SEQUENCE: 934
atgaaaaaat gtctccctca atgtg                                           25

<210> SEQ ID NO 935
<211> LENGTH: 25
<212> TYPE: DNA
<213> ORGANISM: Homo Sapiens

<400> SEQUENCE: 935
tgaaaaaatg tctccctcaa tgtgt                                           25

<210> SEQ ID NO 936
<211> LENGTH: 25
<212> TYPE: DNA
<213> ORGANISM: Homo Sapiens

<400> SEQUENCE: 936
gaaaaaatgt ctccctcaat gtgtg                                           25

<210> SEQ ID NO 937
<211> LENGTH: 25
<212> TYPE: DNA
<213> ORGANISM: Homo Sapiens

<400> SEQUENCE: 937
aaaaaatgtc tccctcaatg tgtga                                           25

<210> SEQ ID NO 938
<211> LENGTH: 25
<212> TYPE: DNA
<213> ORGANISM: Homo Sapiens
```

```
<400> SEQUENCE: 938
aaaaatgtct ccctcaatgt gtgaa                                              25

<210> SEQ ID NO 939
<211> LENGTH: 25
<212> TYPE: DNA
<213> ORGANISM: Homo Sapiens

<400> SEQUENCE: 939
aaaatgtctc cctcaatgtg tgaaa                                              25

<210> SEQ ID NO 940
<211> LENGTH: 25
<212> TYPE: DNA
<213> ORGANISM: Homo Sapiens

<400> SEQUENCE: 940
aaatgtctcc ctcaatgtgt gaaat                                              25

<210> SEQ ID NO 941
<211> LENGTH: 25
<212> TYPE: DNA
<213> ORGANISM: Homo Sapiens

<400> SEQUENCE: 941
aatgtctccc tcaatgtgtg aaata                                              25

<210> SEQ ID NO 942
<211> LENGTH: 25
<212> TYPE: DNA
<213> ORGANISM: Homo Sapiens

<400> SEQUENCE: 942
atgtctccct caatgtgtga aatat                                              25

<210> SEQ ID NO 943
<211> LENGTH: 25
<212> TYPE: DNA
<213> ORGANISM: Homo Sapiens

<400> SEQUENCE: 943
tgtctccctc aatgtgtgaa atatc                                              25

<210> SEQ ID NO 944
<211> LENGTH: 25
<212> TYPE: DNA
<213> ORGANISM: Homo Sapiens

<400> SEQUENCE: 944
gtctccctca atgtgtgaaa tatca                                              25

<210> SEQ ID NO 945
<211> LENGTH: 25
<212> TYPE: DNA
<213> ORGANISM: Homo Sapiens

<400> SEQUENCE: 945
tctccctcaa tgtgtgaaat atcaa                                              25

<210> SEQ ID NO 946
<211> LENGTH: 25
<212> TYPE: DNA
```

<213> ORGANISM: Homo Sapiens

<400> SEQUENCE: 946
ctccctcaat gtgtgaaata tcaag 25

<210> SEQ ID NO 947
<211> LENGTH: 25
<212> TYPE: DNA
<213> ORGANISM: Homo Sapiens

<400> SEQUENCE: 947
tccctcaatg tgtgaaatat caagt 25

<210> SEQ ID NO 948
<211> LENGTH: 25
<212> TYPE: DNA
<213> ORGANISM: Homo Sapiens

<400> SEQUENCE: 948
ccctcaatgt gtgaaatatc aagta 25

<210> SEQ ID NO 949
<211> LENGTH: 25
<212> TYPE: DNA
<213> ORGANISM: Homo Sapiens

<400> SEQUENCE: 949
cctcaatgtg tgaaatatca agtac 25

<210> SEQ ID NO 950
<211> LENGTH: 25
<212> TYPE: DNA
<213> ORGANISM: Homo Sapiens

<400> SEQUENCE: 950
ctcaatgtgt gaaatatcaa gtaca 25

<210> SEQ ID NO 951
<211> LENGTH: 25
<212> TYPE: DNA
<213> ORGANISM: Homo Sapiens

<400> SEQUENCE: 951
tcaatgtgtg aaatatcaag tacag 25

<210> SEQ ID NO 952
<211> LENGTH: 25
<212> TYPE: DNA
<213> ORGANISM: Homo Sapiens

<400> SEQUENCE: 952
caatgtgtga aatatcaagt acaga 25

<210> SEQ ID NO 953
<211> LENGTH: 25
<212> TYPE: DNA
<213> ORGANISM: Homo Sapiens

<400> SEQUENCE: 953
aatgtgtgaa atatcaagta cagag 25

<210> SEQ ID NO 954
<211> LENGTH: 25

```
<212> TYPE: DNA
<213> ORGANISM: Homo Sapiens

<400> SEQUENCE: 954
atgtgtgaaa tatcaagtac agagc                                              25

<210> SEQ ID NO 955
<211> LENGTH: 25
<212> TYPE: DNA
<213> ORGANISM: Homo Sapiens

<400> SEQUENCE: 955
tgtgtgaaat atcaagtaca gagca                                              25

<210> SEQ ID NO 956
<211> LENGTH: 25
<212> TYPE: DNA
<213> ORGANISM: Homo Sapiens

<400> SEQUENCE: 956
gtgtgaaata tcaagtacag agcag                                              25

<210> SEQ ID NO 957
<211> LENGTH: 25
<212> TYPE: DNA
<213> ORGANISM: Homo Sapiens

<400> SEQUENCE: 957
tgtgaaatat caagtacaga gcaga                                              25

<210> SEQ ID NO 958
<211> LENGTH: 25
<212> TYPE: DNA
<213> ORGANISM: Homo Sapiens

<400> SEQUENCE: 958
gtgaaatatc aagtacagag cagac                                              25

<210> SEQ ID NO 959
<211> LENGTH: 25
<212> TYPE: DNA
<213> ORGANISM: Homo Sapiens

<400> SEQUENCE: 959
tgaaatatca agtacagagc agaca                                              25

<210> SEQ ID NO 960
<211> LENGTH: 25
<212> TYPE: DNA
<213> ORGANISM: Homo Sapiens

<400> SEQUENCE: 960
gaaatatcaa gtacagagca gacaa                                              25

<210> SEQ ID NO 961
<211> LENGTH: 25
<212> TYPE: DNA
<213> ORGANISM: Homo Sapiens

<400> SEQUENCE: 961
aaatatcaag tacagagcag acaac                                              25

<210> SEQ ID NO 962
```

```
<211> LENGTH: 25
<212> TYPE: DNA
<213> ORGANISM: Homo Sapiens

<400> SEQUENCE: 962
aatatcaagt acagagcaga caact                                    25

<210> SEQ ID NO 963
<211> LENGTH: 25
<212> TYPE: DNA
<213> ORGANISM: Homo Sapiens

<400> SEQUENCE: 963
atatcaagta cagagcagac aactg                                    25

<210> SEQ ID NO 964
<211> LENGTH: 25
<212> TYPE: DNA
<213> ORGANISM: Homo Sapiens

<400> SEQUENCE: 964
tatcaagtac agagcagaca actgt                                    25

<210> SEQ ID NO 965
<211> LENGTH: 25
<212> TYPE: DNA
<213> ORGANISM: Homo Sapiens

<400> SEQUENCE: 965
atcaagtaca gagcagacaa ctgtt                                    25

<210> SEQ ID NO 966
<211> LENGTH: 25
<212> TYPE: DNA
<213> ORGANISM: Homo Sapiens

<400> SEQUENCE: 966
tcaagtacag agcagacaac tgttc                                    25

<210> SEQ ID NO 967
<211> LENGTH: 25
<212> TYPE: DNA
<213> ORGANISM: Homo Sapiens

<400> SEQUENCE: 967
caagtacaga gcagacaact gttcc                                    25

<210> SEQ ID NO 968
<211> LENGTH: 25
<212> TYPE: DNA
<213> ORGANISM: Homo Sapiens

<400> SEQUENCE: 968
aagtacagag cagacaactg ttcca                                    25

<210> SEQ ID NO 969
<211> LENGTH: 25
<212> TYPE: DNA
<213> ORGANISM: Homo Sapiens

<400> SEQUENCE: 969
agtacagagc agacaactgt tccaa                                    25
```

```
<210> SEQ ID NO 970
<211> LENGTH: 25
<212> TYPE: DNA
<213> ORGANISM: Homo Sapiens

<400> SEQUENCE: 970
gtacagagca gacaactgtt ccaaa                                              25

<210> SEQ ID NO 971
<211> LENGTH: 25
<212> TYPE: DNA
<213> ORGANISM: Homo Sapiens

<400> SEQUENCE: 971
tacagagcag acaactgttc caaaa                                              25

<210> SEQ ID NO 972
<211> LENGTH: 25
<212> TYPE: DNA
<213> ORGANISM: Homo Sapiens

<400> SEQUENCE: 972
acagagcaga caactgttcc aaaac                                              25

<210> SEQ ID NO 973
<211> LENGTH: 25
<212> TYPE: DNA
<213> ORGANISM: Homo Sapiens

<400> SEQUENCE: 973
cagagcagac aactgttcca aaaca                                              25

<210> SEQ ID NO 974
<211> LENGTH: 25
<212> TYPE: DNA
<213> ORGANISM: Homo Sapiens

<400> SEQUENCE: 974
agagcagaca actgttccaa aacaa                                              25

<210> SEQ ID NO 975
<211> LENGTH: 25
<212> TYPE: DNA
<213> ORGANISM: Homo Sapiens

<400> SEQUENCE: 975
gagcagacaa ctgttccaaa acaaa                                              25

<210> SEQ ID NO 976
<211> LENGTH: 25
<212> TYPE: DNA
<213> ORGANISM: Homo Sapiens

<400> SEQUENCE: 976
agcagacaac tgttccaaaa caaag                                              25

<210> SEQ ID NO 977
<211> LENGTH: 25
<212> TYPE: DNA
<213> ORGANISM: Homo Sapiens

<400> SEQUENCE: 977
gcagacaact gttccaaaac aaagg                                              25
```

<210> SEQ ID NO 978
<211> LENGTH: 25
<212> TYPE: DNA
<213> ORGANISM: Homo Sapiens

<400> SEQUENCE: 978
cagacaactg ttccaaaaca aaggc                                  25

<210> SEQ ID NO 979
<211> LENGTH: 25
<212> TYPE: DNA
<213> ORGANISM: Homo Sapiens

<400> SEQUENCE: 979
agacaactgt tccaaaacaa aggca                                  25

<210> SEQ ID NO 980
<211> LENGTH: 25
<212> TYPE: DNA
<213> ORGANISM: Homo Sapiens

<400> SEQUENCE: 980
gacaactgtt ccaaaacaaa ggcat                                  25

<210> SEQ ID NO 981
<211> LENGTH: 25
<212> TYPE: DNA
<213> ORGANISM: Homo Sapiens

<400> SEQUENCE: 981
acaactgttc caaacaaag gcata                                   25

<210> SEQ ID NO 982
<211> LENGTH: 25
<212> TYPE: DNA
<213> ORGANISM: Homo Sapiens

<400> SEQUENCE: 982
caactgttcc aaacaaagg catat                                   25

<210> SEQ ID NO 983
<211> LENGTH: 25
<212> TYPE: DNA
<213> ORGANISM: Homo Sapiens

<400> SEQUENCE: 983
aactgttcca aacaaaggc atatc                                   25

<210> SEQ ID NO 984
<211> LENGTH: 25
<212> TYPE: DNA
<213> ORGANISM: Homo Sapiens

<400> SEQUENCE: 984
actgttccaa aacaaaggca tatca                                  25

<210> SEQ ID NO 985
<211> LENGTH: 25
<212> TYPE: DNA
<213> ORGANISM: Homo Sapiens

<400> SEQUENCE: 985
ctgttccaaa acaaaggcat atcat                                  25

<210> SEQ ID NO 986
<211> LENGTH: 25
<212> TYPE: DNA
<213> ORGANISM: Homo Sapiens

<400> SEQUENCE: 986
tgttccaaaa caaaggcata tcata                                              25

<210> SEQ ID NO 987
<211> LENGTH: 25
<212> TYPE: DNA
<213> ORGANISM: Homo Sapiens

<400> SEQUENCE: 987
gttccaaaac aaaggcatat catag                                              25

<210> SEQ ID NO 988
<211> LENGTH: 25
<212> TYPE: DNA
<213> ORGANISM: Homo Sapiens

<400> SEQUENCE: 988
ttccaaaaca aaggcatatc atagc                                              25

<210> SEQ ID NO 989
<211> LENGTH: 25
<212> TYPE: DNA
<213> ORGANISM: Homo Sapiens

<400> SEQUENCE: 989
tccaaaacaa aggcatatca tagca                                              25

<210> SEQ ID NO 990
<211> LENGTH: 25
<212> TYPE: DNA
<213> ORGANISM: Homo Sapiens

<400> SEQUENCE: 990
ccaaaacaaa ggcatatcat agcag                                              25

<210> SEQ ID NO 991
<211> LENGTH: 25
<212> TYPE: DNA
<213> ORGANISM: Homo Sapiens

<400> SEQUENCE: 991
caaaacaaag gcatatcata gcagt                                              25

<210> SEQ ID NO 992
<211> LENGTH: 25
<212> TYPE: DNA
<213> ORGANISM: Homo Sapiens

<400> SEQUENCE: 992
aaaacaaagg catatcatag cagtc                                              25

<210> SEQ ID NO 993
<211> LENGTH: 25
<212> TYPE: DNA
<213> ORGANISM: Homo Sapiens

<400> SEQUENCE: 993
aaacaaaggc atatcatagc agtca                                          25

<210> SEQ ID NO 994
<211> LENGTH: 25
<212> TYPE: DNA
<213> ORGANISM: Homo Sapiens

<400> SEQUENCE: 994
aacaaaggca tatcatagca gtcag                                          25

<210> SEQ ID NO 995
<211> LENGTH: 25
<212> TYPE: DNA
<213> ORGANISM: Homo Sapiens

<400> SEQUENCE: 995
acaaaggcat atcatagcag tcaga                                          25

<210> SEQ ID NO 996
<211> LENGTH: 25
<212> TYPE: DNA
<213> ORGANISM: Homo Sapiens

<400> SEQUENCE: 996
caaaggcata tcatagcagt cagaa                                          25

<210> SEQ ID NO 997
<211> LENGTH: 25
<212> TYPE: DNA
<213> ORGANISM: Homo Sapiens

<400> SEQUENCE: 997
aaaggcatat catagcagtc agaat                                          25

<210> SEQ ID NO 998
<211> LENGTH: 25
<212> TYPE: DNA
<213> ORGANISM: Homo Sapiens

<400> SEQUENCE: 998
aaggcatatc atagcagtca gaatt                                          25

<210> SEQ ID NO 999
<211> LENGTH: 25
<212> TYPE: DNA
<213> ORGANISM: Homo Sapiens

<400> SEQUENCE: 999
aggcatatca tagcagtcag aattt                                          25

<210> SEQ ID NO 1000
<211> LENGTH: 25
<212> TYPE: DNA
<213> ORGANISM: Homo Sapiens

<400> SEQUENCE: 1000
ggcatatcat agcagtcaga atttg                                          25

<210> SEQ ID NO 1001
<211> LENGTH: 25
<212> TYPE: DNA
<213> ORGANISM: Homo Sapiens

<400> SEQUENCE: 1001
gcatatcata gcagtcagaa tttgt 25

<210> SEQ ID NO 1002
<211> LENGTH: 25
<212> TYPE: DNA
<213> ORGANISM: Homo Sapiens

<400> SEQUENCE: 1002
catatcatag cagtcagaat ttgtg 25

<210> SEQ ID NO 1003
<211> LENGTH: 25
<212> TYPE: DNA
<213> ORGANISM: Homo Sapiens

<400> SEQUENCE: 1003
atatcatagc agtcagaatt tgtgt 25

<210> SEQ ID NO 1004
<211> LENGTH: 25
<212> TYPE: DNA
<213> ORGANISM: Homo Sapiens

<400> SEQUENCE: 1004
tatcatagca gtcagaattt gtgtt 25

<210> SEQ ID NO 1005
<211> LENGTH: 25
<212> TYPE: DNA
<213> ORGANISM: Homo Sapiens

<400> SEQUENCE: 1005
atcatagcag tcagaatttg tgtta 25

<210> SEQ ID NO 1006
<211> LENGTH: 25
<212> TYPE: DNA
<213> ORGANISM: Homo Sapiens

<400> SEQUENCE: 1006
tcatagcagt cagaatttgt gttac 25

<210> SEQ ID NO 1007
<211> LENGTH: 5
<212> TYPE: DNA
<213> ORGANISM: Homo Sapiens

<400> SEQUENCE: 1007 aacac 5

<210> SEQ ID NO 1008
<211> LENGTH: 6
<212> TYPE: DNA
<213> ORGANISM: Homo Sapiens

<400> SEQUENCE: 1008 gactgc 6

<210> SEQ ID NO 1009
<211> LENGTH: 6
<212> TYPE: DNA
<213> ORGANISM: Homo Sapiens

```
<400> SEQUENCE: 1009 tatgat                                                          6

<210> SEQ ID NO 1010
<211> LENGTH: 6
<212> TYPE: DNA
<213> ORGANISM: Homo Sapiens

<400> SEQUENCE: 1010 gaacag                                                          6

<210> SEQ ID NO 1011
<211> LENGTH: 5
<212> TYPE: DNA
<213> ORGANISM: Homo Sapiens

<400> SEQUENCE: 1011 aacag                                                           5

<210> SEQ ID NO 1012
<211> LENGTH: 6
<212> TYPE: DNA
<213> ORGANISM: Homo Sapiens

<400> SEQUENCE: 1012 gaggga                                                          6

<210> SEQ ID NO 1013
<211> LENGTH: 6
<212> TYPE: DNA
<213> ORGANISM: Homo Sapiens

<400> SEQUENCE: 1013 ggagac                                                          6

<210> SEQ ID NO 1014
<211> LENGTH: 6
<212> TYPE: DNA
<213> ORGANISM: Homo Sapiens

<400> SEQUENCE: 1014 ggggag                                                          6

<210> SEQ ID NO 1015
<211> LENGTH: 6
<212> TYPE: DNA
<213> ORGANISM: Homo Sapiens

<400> SEQUENCE: 1015 ggagcc                                                          6
```

COMPOUNDS FOR MODULATING FC-EPSILON-RI-BETA EXPRESSION AND USES THEREOF

CROSS REFERENCE TO RELATED APPLICATION

This application is a continuation of PCT International Patent Application Serial No. PCT/US2017/016042, filed Feb. 1, 2017, which itself claims the benefit of U.S. Provisional Patent Application Ser. No. 62/289,447, filed Feb. 1, 2016. The content of each of these applications is incorporated herein by reference in its entirety.

FIELD OF THE INVENTION

The present invention relates to the use of antisense oligonucleotides to modulate cell surface expression of FcεRIβ protein, thereby modulating IgE-mediated immune responses.

BACKGROUND

Asthma and related allergic diseases affect up to one in ten people in developed countries and about 10% of patients with asthma cannot be controlled with currently available approaches. Current therapies rely on damping the inflammatory response and relaxing the constricted airway smooth muscle cells with orally inhaled glucocorticosteroids and/or β adrenoreceptor agonists. But high doses of steroids are associated with undesirable side effects, and inhaled β-agonists increase the risk of death from asthma if not used in combination with glucocorticosteroids. Moreover, it has been suggested that β-agonists may promote the underlying inflammation that contributes to the airway remodeling observed in asthma patients. Other clinical approaches aimed at longer-term alleviation of symptoms include desensitization with incremental increases in the dose of allergen, or hypersensitization to induce immune tolerance. While such approaches have been beneficial for some patients, they have not been beneficial for all patients, and serious adverse side effects have been observed.

It is known that the FcεRIβ protein contributes to IgE-dependent mast cell signaling by trafficking the FcεRI receptor complex to the cell surface and amplifying FcεRI-induced signaling. The first transmembrane domain of FcεRIβ is required for trafficking the receptor complex, and the C-terminal immunoreceptor tyrosine-based activation motif (ITAM) amplifies signaling. While reports that polymorphisms in the MS4A2 gene were associated with the development of asthma raised interest in this area, studies into the functional consequences of mutations in the MS4A2 gene failed to affect the function of FcεRIβ.

There remains a need for new and effective treatments for treating allergic diseases. The invention utilizes new pathways and novel compounds for providing such treatments.

SUMMARY

Rather than the administration of β-agonists, glucocorticoids, or allergen to produce hypersensitization, the present invention relies on a different approach, namely altering cellular responses to IgE-directed antigens. This approach is based on the finding that the gene(s) at loci 11q12-q13 are strongly linked to allergy and asthma susceptibility, and the knowledge that the MS4A gene family is clustered around 11q12-q13. It is also known that the gene MS4A1, which encodes the protein CD20, and MS4A2, which encodes the FcεRIβ protein, are associated with activation and proliferation of B-cells and mast cells, respectively. Thus, these genes are considered candidates for the linkage of these genetic regions with allergy.

One aspect of this disclosure is an antisense oligomer comprising 10 to 50 linked nucleosides, wherein the antisense oligomer is targeted to a region of a pre-mRNA molecule encoding a FcεRIβ protein. The targeted region may comprise sequences involved in splicing of the FcεRIβ-encoding pre-mRNA such that hybridization of the antisense oligomer to the FcεRIβ-encoding pre-mRNA alters splicing of the pre-mRNA. Hybridization of the antisense oligomer to the FcεRIβ-encoding pre-mRNA may reduce cell surface expression of high affinity IgE receptor (FcεRI).

In one aspect, the targeted region comprises at least a portion of a polynucleotide sequence selected from the group consisting of an intron sequence, an exon sequence, a sequence comprising an intron/exon junction, a splice donor sequence, a slice acceptor sequence, a splice enhancer sequence, a splice branch point sequence, or a polypyrimidine tract. In this aspect, the targeted region of the pre-mRNA may comprise a polynucleotide sequence selected from an intron 2 sequence, an exon 3 sequence, a sequence comprising an intron 2/exon 3 junction, an exon 3 splice donor sequence, an exon 3 slice acceptor sequence, an exon 3 splice enhancer sequence, an exon 3 splice branch point sequence, or an exon 3 polypyrimidine tract.

These antisense oligomers may be targeted to regions of an FcεRIβ-encoding pre-mRNA transcribed from an MS4A2 gene (a "MS4A2 pre-mRNA"). The encoded FcεRIβ protein may be from any mammal, including a human, a mouse, a dog, a cat or a horse (e.g., the encoded FcεRIβ protein may be a human FcεRIβ protein, a murine FcεRIβ protein, a canine FcεRIβ protein, a feline FcεRIβ protein, and an equine FcεRIβ protein). In a preferred aspect, the MS4A2 pre-mRNA encodes a human FcεRIβ protein. The human FcεRIβ protein may comprise SEQ ID NO:2. The MS4A2 transcript comprises SEQ ID NO:1.

Hybridization of an antisense oligomer of this disclosure to an MS4A2 pre-mRNA may result in the production of a mature MS4A2 mRNA molecule lacking a portion, or all of exon 3, which encodes a transmembrane domain from an FcεRIβ protein. Hybridization of an antisense oligomer of this disclosure to an MS4A2 pre-mRNA results in production of an mRNA molecule encoding a truncated FcεRIβ protein. The truncated FcεRIβ protein may be t-FcεRIβ. One aspect of this disclosure is an antisense oligomer comprising 10 to 50 linked nucleosides, wherein the 10 to 50 linked nucleosides comprise a targeting nucleic acid sequence sufficiently complementary to a target nucleic acid sequence in an FcεRIβ-encoding pre-mRNA, such that the oligomer specifically hybridizes to the target sequence. Hybridization of the antisense oligomer to the FcεRIβ-encoding pre-mRNA alters splicing of the pre-mRNA. Hybridization of the antisense oligomer to the FcεRIβ-encoding pre-mRNA may reduce cell surface expression of high affinity IgE receptor (FcεRI).

In one aspect, the targeting sequence in the antisense oligomer comprises at least 6 contiguous nucleobases fully complementary to at least 6 contiguous nucleobases in the target sequence. The targeting sequence in the antisense oligomer may be at least 80% complementary over its entire length to an equal length of contiguous nucleobases in the target sequence. The targeting sequence may comprise at least a portion of a polynucleotide sequence selected from an intron sequence, an exon sequence, a sequence comprising an intron/exon junction, a splice donor sequence, a slice acceptor sequence, a splice enhancer sequence, a splice branch point sequence, or a polypyrimidine tract. In one aspect, the polynucleotide sequence is selected from an intron 2 sequence, an exon 3 sequence, a sequence comprising an intron 2/exon 3 junction, an exon 3 splice donor sequence, an exon 3 slice acceptor sequence, an exon 3 splice enhancer sequence, an exon 3 splice branch point sequence, or an exon 3 polypyrimidine tract.

The target nucleic acid sequences may be in an FcεRIβ-encoding pre-mRNA transcribed from an MS4A2 gene. The encoded FcεRIβ protein may be from any mammal, including a human, a mouse, a dog, a cat, or a horse. In a preferred aspect, the MS4A2 pre-mRNA encodes a human FcεRIβ protein.

One aspect of this disclosure is an antisense oligomer comprising 10 to 50 linked nucleosides, wherein the 10 to 50 linked nucleosides comprises a nucleic acid sequence at least partially complementary to a target nucleic acid sequence in a pre-mRNA molecule, which encodes a protein comprising SEQ ID NO:2 or SEQ ID NO:4. The protein may be encoded by an MS4A2 transcript comprising SEQ ID NO:1. Hybridization of the antisense oligomer to the pre-mRNA may alter splicing of the pre-mRNA. Hybridization of the antisense oligomer to the pre-mRNA may reduce cell surface expression of high affinity IgE receptor (FcεRI).

In these aspects, the target sequence may comprise at least a portion of a polynucleotide sequence selected from the group consisting of SEQ ID NOs:5-17, and an MSR4A2 sequence comprising any one of SEQ ID NOs:1007-1015. The portion may be at least 10 contiguous nucleotides. The target sequence may comprise a sequence at least 90% identical to a sequence selected from the group consisting of SEQ ID NOs:11-17, and an MSR4A2 sequence comprising any one of SEQ ID NOs:1007-1015. The target sequence may comprise a sequence selected from SEQ ID NOs:11-17, and an MSR4A2 sequence comprising any one of SEQ ID NOs:1007-1015.

In these aspects, the targeting sequence may comprise at least 10 contiguous nucleobases fully complementary in sequence to at least 10 contiguous nucleobases in a sequence selected from SEQ ID NOs:5-17, and an MSR4A2 sequence comprising any one of SEQ ID NOs:1007-1015. The targeting sequence may comprise a sequence at least 80% complimentary to at least a portion of a sequence selected from SEQ ID NO:5-17, and an MSR4A2 sequence comprising any one of SEQ ID NOs:1007-1015. The targeting sequence may be at least 80% identical over the full length of a sequence selected from the group consisting of SEQ ID NOs:22-1006. The targeting sequence may also be selected from any one of SEQ ID NOs:22-1006.

These antisense oligomers may be an antisense RNA molecule, which may further comprise a modification selected from a nucleoside modification, an internucleoside modification, a sugar modification, a sugar-internucleoside linkage modification, and combinations thereof. Such modifications may increase resistance to degradation by a ribonuclease. A morpholino oligomer is an exemplary modified antisense oligomer.

Another aspect provides an expression vector that expresses an antisense oligomer of this disclosure, while another aspect is a pharmaceutical composition comprising an antisense oligomer of this disclosure.

One aspect of this disclosure is a method of modulating splicing of FcεRIβ mRNA in a cell by contacting the cell with an antisense oligomer, an expression vector, or a composition of this disclosure, thereby modulating splicing of the FcεRIβ mRNA. The amount of full-length FcεRIβ-encoding mRNA produced by the cell may be reduced by at least 50%, at least 60%, at least 70%, at least 80%, at least 90%, at least 95%, at least 97%, or at least 99%, or completely eliminated.

One aspect of this disclosure is a method of reducing cell surface expression of FcεRI in a cell, comprising contacting the cell with an antisense oligomer, an expression vector, or a composition of this disclosure, thereby reducing expression of FcεRI on the surface of the cell. The amount of FcεRI expressed on the cell surface may be reduced by at least 50%, at least 60%, at least 70%, at least 80%, at least 90%, at least 95%, at least 97%, at least 99%, or completely eliminated.

One aspect of this disclosure is a method of modulating FcεRI receptor complex-dependent degranulation in a mast cell, comprising contacting the mast cell with an antisense oligomer, an expression vector, or a composition of this disclosure, thereby modulating FcεRI receptor complex-dependent degranulation in the mast cell. FcεRI receptor complex-dependent degranulation may be reduced by at least 50%, at least 60%, at least 70%, at least 80%, at least 90%, at least 95%, at least 97%, or at least 99%, or completely eliminated.

One aspect of this disclosure is a method of modulating FcεRI receptor complex-dependent mast-cell migration, comprising contacting the mast cell with an antisense oligomer, an expression vector, or a composition of this disclosure, thereby modulating FcεRI receptor complex-dependent mast cell migration. FcεRI receptor complex-dependent mast cell migration activity may be reduced by at least 50%, at least 60%, at least 70%, at least 80%, at least 90%, at least 95%, at least 97%, or at least 99%, or completely eliminated.

One aspect of this disclosure is a method of modulating cytokine release, comprising contacting a cytokine-producing cell with an antisense oligomer, an expression vector, or a composition of this disclosure, thereby modulating cytokine release. The cytokine may be a vasoactive amine, a proteoglycan, a protease, a growth factor, a chemokine, a pro-inflammatory lipid mediator, a histamine, a serotonin, heparin, tryptase, chymase, TNFα, IL-1, IL-6, IL-8, IL-10, TNFα, VEGF, TGFβ, CCL2-4, a prostaglandin, and/or a leukotriene. The amount of at least one cytokine released may be reduced by at least 50%, at least 60%, at least 70%, at least 80%, at least 90%, at least 95%, at least 97%, or at least 99%, or completely eliminated. These methods may be performed on a cell in culture or in the body of an individual.

One aspect of this disclosure is a method of inhibiting an anaphylactic reaction in an individual by administering to the individual an antisense oligomer, an expression vector, or a composition of this disclosure.

One aspect of this disclosure is a method of treating an allergic condition in an individual, by administering an antisense oligomer, an expression vector, or a composition of this disclosure, to an individual in need of such treatment. The allergic condition treated may be asthma, atopic dermatitis, chronic rhinitis, chronic sinusitis, and/or allergic conjunctivitis.

One aspect of this disclosure is a method of reducing the incidence or severity of an allergic reaction in an individual, by administering an antisense oligomer, an expression vector, or a composition of this disclosure, to an individual chronically experiencing allergic reactions or at risk of having an allergic reaction.

One aspect of this disclosure is a method of treating an individual at risk of developing an anaphylactic reaction, by administering an antisense oligomer, an expression vector, or a composition of this disclosure, to the individual at risk of developing an anaphylactic reaction.

One aspect of this disclosure is a method of treating a mast cell-related disease in an individual, comprising administering an antisense oligomer, an expression vector, or a composition of this disclosure, to an individual in need of such treatment. The mast cell-related disease may be mastocytosis, or a mast cell tumor, including mastocytoma.

In these methods, the individual to whom the antisense oligomer, expression vector, or composition of this disclosure is administered may be a human, mouse, dog, cat, or horse.

BRIEF DESCRIPTION OF THE DRAWINGS

FIG. 1A is density plots of FITC positivity (X axis) versus propridium iodide positivity (Y axis) of mock treated control cells (top panels) and FITC morpholino AON transfected cells (lower panels). FIG. 1B shows the data from the panels in FIG. 1A displayed as histograms.

FIG. 2A shows qualitative RT-PCR of FcεRIβ mRNA from the transfected cells. FL-FcεRIβ=full length FcεRIβ transcript; t-FcεRIβ=exon 3 truncation. FIG. 2B shows flow cytometric analysis of surface FcεRIα expression in mouse (left panel) and human (right panel) mast cells 48 hours after transfection with either the standard control AON (Std Con AON—rightmost peak) or FcεRIβ AONs (center peak). The leftmost peak represents the isotype control. Data are representative of five experiments. FIG. 2C shows FcεRIα surface expression in cells transfected with various amounts of AONs. The graphs show the results from five experiments using moue BMMCs (left panel) and three experiments for LAD-2 cells (right panel). FIG. 2D shows a comparison of the efficiency of MS4A2 exon skipping in mouse and human cells using various doses of AONs.

FIG. 3A shows antigen-induced degranulation in mast cells transfected with varying amounts of FcεRIβ antisense oligonucleotides. Data are the mean±SEM from five experiments. *p<0.05, **** p<0.0001. FIG. 3B shows the percent degranulation of BMMCs in response to either antigen (DNP—left panel) or thapsigargin (right panel). FIG. 3C shows ratiometric calcium signaling of the cells as in (FIG. 3B). The arrowhead denotes the time of the stimulant addition. Example plots are representative of four experiments. *p<0.05,  p<0.01, * p<0.001, **** p<0.0001.

FIG. 4A shows that IgE-dependent LAD-2 cell degranulation is significantly reduced with FcεRIβ exon skipping, but FIG. 4B shows that thapsigargin-induced degranulation is unaffected. Data are the mean±SEM from seven experiments. *P<0.05,  P<0.01, * P<0.001.

FIGS. 5A-5F show the effects of AONs on IgE-dependent cell signaling, cytokine production and migration. FIG. 5A shows immunoblots from mouse BMMCs transfected with either standard control AON (left four lanes) or FcεRIβ AON (right four lanes) and stimulated with the indicated molecules. FIGS. 5B-5D show combined quantification of phosphorylation data for standard control AON (left bars) or the FcεRIβ AON (right bars) transfected BMMCs. FIG. 5E is ELISA data for GM-CSF release after 6 h. FIG. 5F shows BMMC migration with FcεRIβ AON treatment. Data are the mean±SEM from three (FIGS. 5B-5E) or four (FIG. 5F) experiments. *p<0.05,  p<0.01, * p<0.001, **** p<0.0001

FIG. 6A shows a gating strategy for cell death and apoptosis flow cytometry. FIG. 6B shows that removal of IL-3 from BMMCs induces apoptosis and cell death. FcεRIα expression was eliminated with FcεRIβ AON (Bottom Left) compared with untreated cells (gray plots) and standard control AON (Top Left). Removal of IL-3-induced cell death in both standard control AON (Top Middle, light line compared with gray histogram) and FcεRIβ AON cells (Bottom Middle, light line compared with gray histogram). The addition of IgE to the cultures protected the standard control AON-treated BMMCs from cell death (Top Middle, dark line compared with gray histogram), but did not protect the FcεRIβ AON-treated BMMCs (Bottom Middle, dark line compared with gray histogram). Similar results were seen when examining apoptosis by gating out dead cells and plotting surface Annexin V staining (Right). Mast cells externalize Annexin V during exocytosis, and weakly Annexin V-positive cells likely represent constitutive exocytosis. Cumulative data from dead cells (FIG. 6C) or apoptotic cells (FIG. 6D) was assessed by flow cytometry. Data are the mean±SEM from three experiments. *P<0.05; ** P<0.01; n.s., not significant.

FIG. 7A shows CellTrace Violet dilution proliferation assays of mouse BMMCs, in the presence of IL-3, transfected with either standard control AON (blue lines) or FcεRIβ AON (light lines). CellTrace Violet was loaded into the BMMCs and cells were transfected with AONs at day 0. On day 5 (top panels) and day 7 (bottom panels) after CellTrace Violet loading BMMCs were immunostained for surface FcεRIα. Confirmation of loss of surface FcεRI with FcεRIβ AON treatment was performed on all experiments (left panels). No significant difference in proliferation was observed between the standard control AON (dark lines) and the FcεRIβ AON (light lines) at either 5 (top right panel) or 7 days (bottom right panel). Proliferation of cells results in dilution of the CellTrace Violet dye and a left shift in fluorescence in divided cells. Immunostaining for surface FcεRI confirmed that FcεRIβ AON treatment was effective 5 days after transfection (top left panel). However, by 7 days post-transfection, FcεRIβ AON efficacy began to decline with evidence of a population of cells that were re-expressing FcεRI (bottom, left panel). FIG. 7B shows flow cytometry histograms of FcεRIβ AON treated BMMCs from (FIG. 7A) gated on surface FcεRIα expression as either FcεRI+(light lines) or FcεRI−(black lines) populations demonstrate that the proliferating cells in the FcεRIβ AON treated condition are the FcεRI+cell population. Data are representative of three experiments. FIG. 7C shows aggregate data from three experiments for proliferation at days 5 and 7. Data are the mean±SEM.

FIG. 8A shows the measurement of Evan's blue extravasation into the ears of mice treated with either standard control Vivo-morpholino AON (left two bars) or Vivo-morpholino FcεRIβ AON (right two bars) after challenge with antigen. Data are the mean±SEM from 13 mice for standard control AON and 14 mice for FcεRIβ AON combined from three experiments. *p<0.05. FIG. 8B shows the qualitative RT-PCR of total RNA isolated from skin tissue near the site of AON administration from mice after the PCA reaction. Example RT-PCR reactions demonstrate exon skipping in vivo. Data are representative of 5 mice for each condition.

DETAILED DESCRIPTION

Figure 1A:
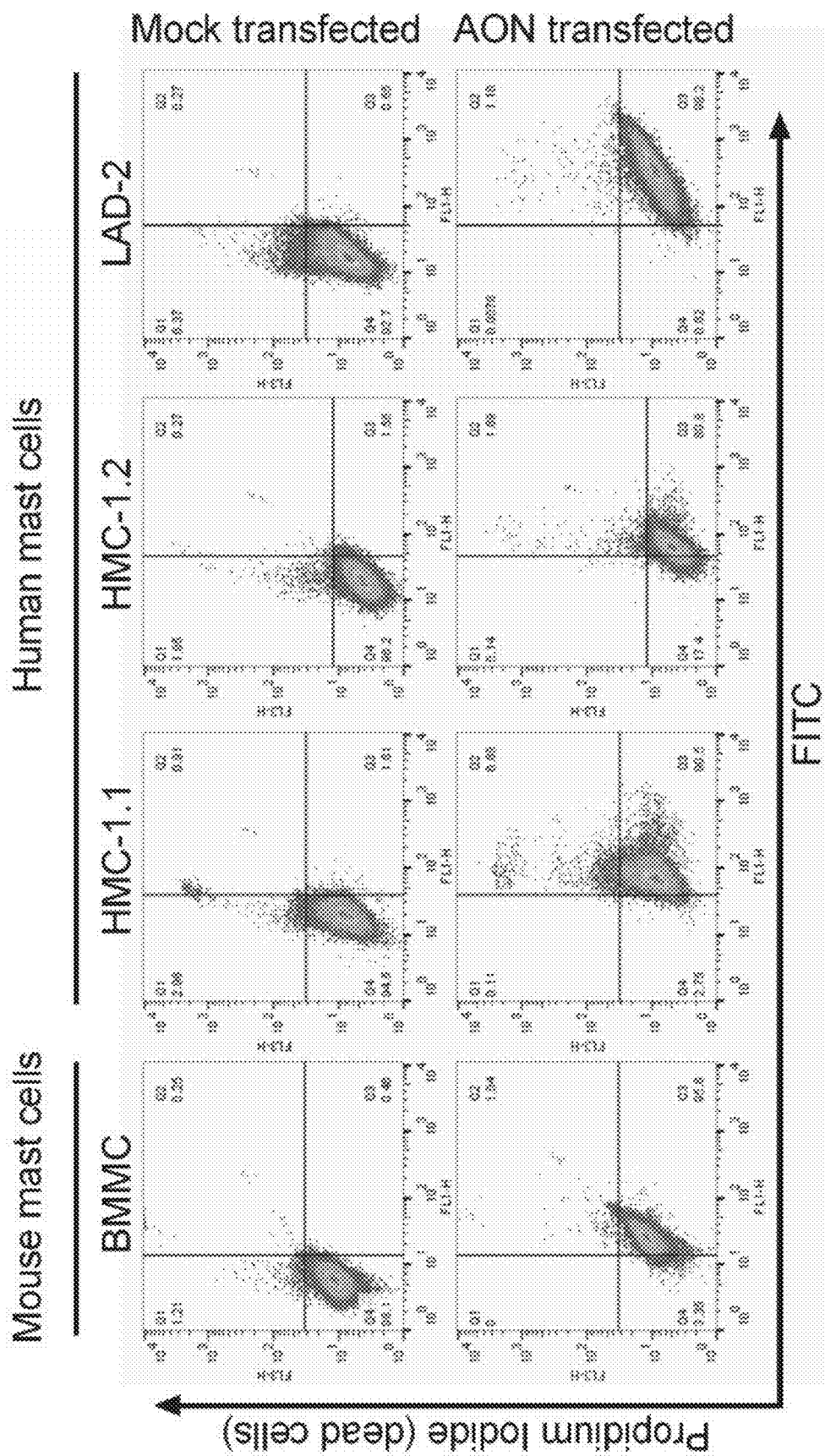
FIGS. 1A and 1B show the transfection efficiency and cytotoxicity of morpholino antisense oliogonucleotides (AONs).

Disclosed herein are novel methods for treating atopic diseases, including methods for treating diseases and syndromes mediated by the high-affinity Fc-epsilon receptor (FcεRI). The invention is based on the inventors' discovery of a novel, truncated isoform of the FcεRIβ protein (t-FcεRIβ), which lacks the first and second membrane-spanning regions, and the mRNA transcript for which is truncated in exon 3 (Cruse, et al., FASEB J., 2010 October; 24(10):4047-4057). This truncated FcεRIβ protein does not traffic to the plasma membrane, resulting in reduced expression of FcεRI on the plasma membrane. The finding of t-FcεRIβ, and its related effects, led to the discovery that selective editing of the FcεRIβ mRNA transcript, using antisense technology, to produce t-FcεRIβ, results in decreased cell-surface expression of the FcεRIβ protein. This in turn leads to a decrease in symptoms resulting from IgE-mediated diseases. Thus, methods and compounds of this disclosure are useful for treating FcεRI-mediated diseases by down-regulating cell-surface expression of FcεRI.

Antisense technology has been demonstrated to be an effective method of modifying the expression levels of gene products (see, for example, U.S. Pat. No. 8,765,703, U.S. Pat. No. 8,946,183, and U.S. Patent Publication No. 2015/0376615, which are incorporated herein by reference in their entirety). Antisense technology works by interfering with known steps in the normal processing of mRNA. Briefly, RNA molecules are transcribed from genomic DNA in the nucleus of the cell. These newly synthesized mRNA molecules, called primary mRNA or pre-mRNA, must be processed prior to transport to the cytoplasm for translation into protein at the ribosome. Such processing includes the addition of a 5' methylated cap and the addition of a poly(A) tail to the 3'end of the mRNA.

Maturation of 90-95% of mammalian mRNAs then occurs with splicing of the mRNA. Introns (or intervening sequences) are regions of a primary transcript (or the DNA encoding it) that are not included in the coding sequence of the mature mRNA. Exons (expressed sequences) are regions of a primary transcript (or the DNA encoding it) that remain in the mature mRNA when it reaches the cytoplasm. During the splicing process, exons in the pre-mRNA molecule are spliced together to form the mature mRNA sequence. Splice junctions, also referred to as splice sites, are utilized by cellular apparatus to determine which sequences are removed and where the ends to be joined start and stop. Sequences on the 5' side of the junction are called the 5' splice site, or splice donor site, whereas sequences on the 3' side the junction are referred to as the 3' splice site, or the splice acceptor site. In splicing, the 3' end of an upstream exon is joined to the 5' end of the downstream exon. Thus, the un-spliced RNA (or pre-mRNA) has an exon/intron junction at the 5' end of an intron and an intron/exon junction at the 3' end of an intron. After the intron is removed, the exons are contiguous at what is sometimes referred to as the exon/exon junction or boundary in the mature mRNA. Cryptic splice sites are those which are less often used but may be used when the usual splice site is blocked or unavailable. The use of different combinations of exons by the cell can result in multiple mRNA transcripts from a single gene.

In one application of antisense technology, an antisense oligonucleotide (AON) binds to a mRNA molecule transcribed from a gene of interest and inactivates ("turns off") the mRNA by increasing its degradation or by preventing translation or translocation of the mRNA by steric hindrance. The end result is that expression of the corresponding gene (i.e., final production of the protein encoded by the corresponding gene) is prevented.

Alternatively, antisense technology can be used to affect splicing of a gene transcript. In this application, the antisense oligonucleotide binds to a pre-spliced RNA molecule (pre-messenger RNA or pre-mRNA) and re-directs the cellular splicing apparatus, thereby resulting in modification of the exon content of the spliced mRNA molecule. Thus, the overall sequence of a protein encoded by the modified mRNA differs from a protein translated from mRNA, the splicing of which was not altered (i.e., the full length, wild-type protein). The protein that is translated from the altered mRNA may be truncated and/or it may be missing critical sequences required for proper function. Typically, the compounds used to affect splicing are, or contain, oligonucleotides having a base sequence complementary to the mRNA being targeted. Such oligonucleotides are referred to herein as "antisense oligonucleotides" (AONs).

This disclosure provides antisense technology to modulate splicing of mRNA encoding an FcεRIβ protein, thereby causing a decrease in the amount or "level" of FcεRI protein expressed on the surface of a cell. Accordingly, a method of this disclosure can generally be accomplished by contacting a cell expressing an MS4A2 transcript, with an antisense oligomer targeted to a region of the MS4A2 pre-mRNA. Such contact results in uptake of the antisense oligomer by the cell, hybridization of the oligomer to the MS4A2 mRNA, and subsequent modulation of splicing of the MS4A2 pre-mRNA. In preferred methods, such modulation of splicing of the MS4A2 mRNA decreases cell-surface expression of FcεRI.

This invention is not limited to the particular embodiments described herein, as such may vary. Additionally, the terminology used herein is for the purpose of describing particular embodiments only, and is not intended to be limiting on the finally claimed invention, since the scope of the invention will be limited only by the claims.

As used herein and in the appended claims, the singular forms "a," "an," and "the" include plural referents unless the context clearly dictates otherwise. For example, a nucleic acid molecule refers to one or more nucleic acid molecules. As such, the terms "a", "an", "one or more" and "at least one" can be used interchangeably. Similarly, the terms "comprising", "including" and "having" can be used interchangeably. It is further noted that the claims may be drafted to exclude any optional element. As such, this statement is intended to serve as antecedent basis for use of such exclusive terminology as "solely," "only" and the like, in connection with the recitation of claim elements, or use of a "negative" limitation.

As used herein, an MS4A2 gene, MS4A2, and the like, refer to a gene encoding an FcεRIβ protein from a mammal. Examples of MS4A2 genes include, but are not limited to, accession numbers NM_000139.4 (human) and NM_013516.2 (mouse). Similarly, an MS4A2 coding sequence refers to a nucleic acid sequence encoding at least a portion of an FcεRIβ protein. Such a portion can be a fragment of the protein (e.g., a 10, 20, 30, 40, 50, 60, 70, 80, 90 or 100 contiguous amino acid segment from any part of the whole protein), an exon, or a domain (e.g., a transmembrane domain), or it can refer to the entire protein, including any splicing variants. MS4A2 genes or coding sequences of this disclosure can be from any mammal having such gene or coding sequence. The MS4A2 gene or coding sequence may be from a human, mouse, canine, feline or equine.

As used herein, an MS4A2 transcript is an RNA molecule transcribed from an MS4A2 gene. Preferably, MS4A2 transcripts targeted by oligomers of this disclosure are primary transcripts or pre-mRNA molecules. As used herein, primary mRNA or pre-mRNA is an mRNA transcript that has not yet undergone splicing. Accordingly, a mature mRNA molecule is an mRNA molecule that has undergone splicing.

As used herein, the term antisense oligomer refers to a polymeric molecule comprising nucleobases, which is capable of hybridizing to a sequence in a nucleic acid molecule, such as an mRNA molecule. The term nucleobase, as used herein, refers to the heterocyclic base portion of a nucleoside. In general, a nucleobase is any group that contains one or more atoms, or groups of atoms, capable of hydrogen bonding to a base of another nucleoside. In addition to "unmodified" or "natural" nucleobases such as the purine nucleobases adenine (A) and guanine (G), and the pyrimidine nucleobases thymine (T), cytosine (C) and uracil (U), modified nucleobases or nucleobase mimetics known to those skilled in the art are also amenable to this disclosure. The term "modified nucleobase" refers to a nucleobase that is similar in structure to the parent nucleobase, such as for example, a 7-deaza purine, a 5-methyl cytosine, a G-clamp, or a tricyclic phenoxazine nucleobase mimetic. Methods for preparation of these modified nucleobases are known to those skilled in the art.

As is known in the art, a nucleoside is a base-sugar combination. The base portion of the nucleoside is normally a heterocyclic base (e.g., a nucleobase or simply a "base"). The two most common classes of such heterocyclic bases are purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. Within oligonucleotides, the phosphate groups are commonly referred to as forming the internucleoside backbone of the oligonucleotide. The normal linkage or backbone of RNA and DNA is a 3' to 5' phosphodiester linkage.

It is understood in the art that RNA molecules often have a short half-life, making their use as therapeutic agents problematic. Thus, it is often preferable to include chemical modifications in oligonucleotides to alter their activity. Chemical modifications can alter oligomer activity by, for example, increasing affinity of an antisense oligomer for its target RNA, increasing nuclease resistance (e.g., resistance to ribonucleases such as RNaseH), and/or altering the pharmacokinetics (e.g. half-life) of the oligomer. For example, it is possible to replace sugars, nucleobases and/or internucleoside linkages with a group that maintains the ability of the oligomer to hybridize to its target sequence, but which imparts a desirable characteristic to the oligomer (e.g., resistance to degradation, increased half-life, etc.). Such groups can be referred to as analogs (e.g., sugar analog, nucleobase analog, etc.). Generally, an analog is used in place of the sugar or sugar-internucleoside linkage combination, and the nucleobase is maintained for hybridization to a selected target. Representative examples of a sugar mimetic include, but are not limited to, cyclohexenyl or morpholino. Representative examples of a mimetic for a sugar-internucleoside linkage combination include, but are not limited to, peptide nucleic acids (PNA) and morpholino groups linked by uncharged, achiral linkages. In some instances, an analog is used in place of the nucleobase. Representative nucleobase mimetics are well known in the art and include, but are not limited to, tricyclic phenoxazine analogs and universal bases (Berger et al., Nuc. Acid Res. 2000, 28:2911-14, incorporated herein by reference). Examples of such sugar, nucleoside and nucleobase mimetics are disclosed in U.S. Pat. Nos. 8,765,703 and 8,946,183, which are incorporated herein by reference). Methods of synthesis of sugar, nucleoside and nucleobase mimetics, and the use of such mimetics to produce oligonucleotides are well known to those skilled in the art.

The term oligomer includes oligonucleotides, oligonucleosides, oligonucleotide analogs, oligonucleotide mimetics and chimeric combinations thereof. Such molecules are generally known to those skilled in the art. Oligomers of this disclosure include, but are not limited to, primers, probes, antisense compounds, antisense oligonucleotides, external guide sequence (EGS) oligonucleotides, alternate splicers, and siRNAs. As such, these compounds can be introduced in the form of single-stranded, double-stranded, circular, branched or hairpins and can contain structural elements such as internal or terminal bulges or loops.

Oligomers of this disclosure can be any length suitable for administering to a cell or individual in order to modulate splicing of an mRNA molecule. For example, antisense oligomers of this disclosure can comprise from about 10 to about 50 nucleobases (i.e. from about 10 to about 50 linked nucleosides). One having ordinary skill in the art will appreciate that this embodies antisense oligomers of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases. In one embodiment, antisense oligomers of this disclosure can comprise, or consist of, 10 to 30 nucleobases, or 10 to 25 nucleobases. Methods of determining the appropriate length for antisense oligomers of this disclosure are known to those skilled in the art.

As used herein, the terms "targeted to," "targeting," and the like, refer to a process of designing an antisense oligomer so that it specifically hybridizes with a desired nucleic acid molecule, such as a desired mRNA molecule. The terms "hybridizes," "hybridization," "hybridize to," and the like, are terms of art, and refer to the pairing of nucleobases in complementary strands of oligonucleotides (e.g., an antisense oligomer and a target sequence in a mRNA molecule). While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is complementary to the natural nucleobases thymidine and uracil, which pair through the formation of hydrogen bonds. Similarly, the natural base guanine is complementary to the natural bases cytosine and 5-methyl cytosine.

In the context of this disclosure, the phrase "specifically hybridizes" refers to the capacity of an antisense oligomer of this disclosure to preferentially bind an mRNA (e.g., pre-mRNA) encoding a FcεRIβ protein rather than binding an mRNA encoding a protein unrelated in structure to a FcεRIβ protein. Further, an antisense oligomer that preferentially binds a target sequence is one that hybridizes with an mRNA encoding a FcεRIβ protein (a FcεRIβ pre-mRNA), but which does not exhibit significant hybridization with mRNA molecules encoding proteins unrelated in structure to a FcεRIβ protein. In the context used herein, significant hybridization is, for example, binding of an oligomer of this disclosure to an mRNA encoding a protein unrelated in structure to a FcεRIβ protein, with an affinity or avidity sufficiently high enough to interfere with the ability of the antisense oligomer to achieve the desired effect. Examples of such desired effects include, but are not limited to, modulation of splicing of a MS4A2 pre-mRNA, reduction in the level of surface expression of FcεRI protein, and a reduction or inhibition in allergic symptoms in an individual. Thus, it will be understood by those skilled in the art that an antisense oligomer is considered specific for a target sequence (is specifically hybridizable, specifically hybridizes, etc.) when there is a sufficient degree of complementarity between the linear sequence of nucleobases in the antisense oligomer and a linear sequence of nucleobases in the target sequence, to avoid significant binding of the antisense oligomer to non-target nucleic acid sequences under conditions in which specific binding is desired (i.e., under physiological conditions in the case of in vivo assays or therapeutic treatment, and under conditions in which assays are performed in the case of in vitro assays).

A used herein, the terms "complement," "complementary," "complementarity," and the like, refer to the capacity for precise pairing between nucleobases in an oligomer and nucleobases in a target sequence. Thus, if a nucleobase (e.g., adenine) at a certain position of an oligomer is capable of hydrogen bonding with a nucleobase (e.g., uracil) at a certain position in a target sequence in a target nucleic acid, then the position of hydrogen bonding between the oligomer and the target nucleic acid is considered to be a complementary position. Usually, the terms complement, complementary, complementarity, and the like, are viewed in the context of a comparison between a defined number of contiguous nucleotides in a first nucleic acid molecule (e.g., an oligomer) and a similar number of contiguous nucleotides in a second nucleic acid molecule (e.g., a mRNA molecule), rather than in a single base to base manner. For example, if an antisense oligomer is 25 nucleotides in length, its complementarity with a target sequence is usually determined by comparing the sequence of the entire oligomer, or a defined portion thereof, with a number of contiguous nucleotides in a mRNA molecule. An oligomer and a target sequence are complementary to each other when a sufficient number of corresponding positions in each molecule are occupied by nucleobases which can hydrogen bond with each other. Positions are corresponding when the bases occupying the positions are spatially arranged such that, if complementary, the bases form hydrogen bonds. As an example, when comparing the sequence of an oligomer to a similarly sized sequence in a target sequence, the first nucleotide in the oligomer is compared with a chosen nucleotide at the start of the target sequence. The second nucleotide in the oligomer (3' to the first nucleotide) is then compared with the nucleotide directly 3' to the chosen start nucleotide. This process is then continued with each nucleotide along the length of the oligomer. Thus, the terms "specifically hybridizable" and "complementary" are terms which are used to indicate a sufficient degree of precise pairing or complementarity over a sufficient number of contiguous nucleobases such that stable and specific binding occurs between the antisense compound and a target nucleic acid.

Hybridization conditions under which a first nucleic acid molecule will specifically hybridize with a second nucleic acid molecule are commonly referred to in the art as stringent hybridization conditions. It is understood by those skilled in the art that stringent hybridization conditions are sequence-dependent and can be different in different circumstances. Thus, stringent conditions under which an oligomer of this disclosure specifically hybridizes to a target sequence are determined by the complementarity of the oligomer sequence and the target sequence and the nature of the assays in which they are being investigated. Persons skilled in the relevant art are capable of designing complementary sequences that specifically hybridize to a particular target sequence for a given assay or a given use.

The process of designing an antisense oligomer that is targeted to a nucleic acid molecule usually begins with identification of a target nucleic acid, the expression of which is to be modulated, and determining the sequence of the target nucleic acid molecule. As used herein, the terms "target nucleic acid," "nucleic acid encoding a FcεRIβ protein," and the like, encompass, for example, DNA encoding a FcεRIβ protein, RNA (including pre-mRNA and mRNA) transcribed from such DNA, and cDNA derived from such RNA. For example, the target nucleic acid can be a cellular gene (or pre-mRNA or mRNA transcribed therefrom), the expression of which is associated with a particular disorder or disease state. Thus, in one embodiment a useful target nucleic acid encodes an FcεRIβ protein. In one embodiment, the target nucleic acid is an MS4A2 transcript. In one embodiment, the target nucleic acid is a MS4A2 pre-mRNA.

Once a target nucleic acid has been identified, the targeting process includes determining at least one target region in which the antisense interaction will occur, thereby modulating splicing of the target nucleic acid. As used herein, a target region is defined as a portion of the target nucleic acid having at least one identifiable structure, function, or characteristic. Preferred target regions are those comprising sequences involved in splicing of pre-mRNA molecules. Examples of such identifiable structures, functions, or characteristics include, but are not limited to, at least a portion of an intron or exon, an intron/exon junction, a splice donor site, a splice acceptor site, a splice branch point or a splice enhancer site. Thus, in one embodiment, the target region comprises at least part of an intron or exon, a splice donor site, a splice acceptor site, a splice branch point, and/or a splice enhancer site. In one embodiment, the target region comprises at an intron or exon, a splice donor site, a splice acceptor site, a splice branch point, and/or a splice enhancer site.

Following identification of a target region, a target sequence within the target region can then be identified. As used herein, a target sequence is a nucleic acid sequence in a target region, to which an antisense oligomer of this disclosure specifically hybridizes. Preferred target sequences are those involved in splicing of pre-mRNA. Once a target sequence has been identified, the antisense oligomer is designed to include a nucleobase sequence sufficiently complementary to the target sequence so that the antisense oligomer specifically hybridizes to the target nucleic acid. More specifically, the nucleotide sequence of the antisense oligomer is designed so that it contains a region of contiguous nucleotides sufficiently complementary to the target sequence so that the antisense oligomer specifically hybridizes to the target nucleic acid. Such a region of contiguous, complementary nucleotides in the oligomer can be referred to as an "antisense sequence" or a "targeting sequence."

It is well known in the art that the greater the degree of complementarity between two nucleic acid sequences, the stronger and more specific is the hybridization interaction. It is also well understood that the strongest and most specific hybridization occurs between two nucleic acid molecules that are fully complementary. As used herein, the term fully complementary refers to a situation when each nucleobase in a nucleic acid sequence is capable of hydrogen binding with the nucleobase in the corresponding position in a second nucleic acid molecule. In one embodiment, the targeting sequence is fully complementary to the target sequence. In one embodiment, the targeting sequence comprises an at least 6 contiguous nucleobase region that is fully complementary to an at least 6 contiguous nucleobase region in the target sequence. In one embodiment, the targeting sequence comprises an at least 8 contiguous nucleobase sequence that is fully complementary to an at least 8 contiguous nucleobase sequence in the target sequence. In one embodiment, the targeting sequence comprises an at least 10 contiguous nucleobase sequence that is fully complementary to an at least 10 contiguous nucleobase sequence in the target sequence. In one embodiment, the targeting sequence comprises an at least 12 contiguous nucleobase sequence that is fully complementary to an at least 12 contiguous nucleobase sequence in the target sequence. In one embodiment, the targeting sequence comprises an at least 14 contiguous nucleobase sequence that is fully complementary to an at least 14 contiguous nucleobase sequence in the target sequence. In one embodiment, the targeting sequence comprises an at least 16 contiguous nucleobase sequence that is fully complementary to an at least 16 contiguous nucleobase sequence in the target sequence. In one embodiment, the targeting sequence comprises an at least 18 contiguous nucleobase sequence that is fully complementary to an at least 18 contiguous nucleobase sequence in the target sequence. In one embodiment, the targeting sequence comprises an at least 20 contiguous nucleobase sequence that is fully complementary to an at least 20 contiguous nucleobase sequence in the target sequence.

It will be understood by those skilled in the art that the targeting sequence may make up the entirety of an antisense oligomer of this disclosure, or it may make up just a portion of an antisense oligomer of this disclosure. For example, in an oligomer consisting of 30 nucleotides, all 30 nucleotides can be complementary to a 30 contiguous nucleotide target sequence. Alternatively, for example, only 20 contiguous nucleotides in the oligomer may be complementary to a 20-contiguous nucleotide target sequence, with the remaining 10 nucleotides in the oligomer being mismatched to nucleotides outside of the target sequence. In preferred embodiment, oligomers of this disclosure have a targeting sequence of at least 10 nucleobases, at least 11 nucleobases, at least 12 nucleobases, at least 13 nucleobases, at least 14 nucleobases, at least 15 nucleobases, at least 16 nucleobases, at least 17 nucleobases, at least 18 nucleobases, at least 19 nucleobases, at least 20 nucleobases, at least 21 nucleobases, at least 22 nucleobases, at least 23 nucleobases, at least 24 nucleobases, at least 25 nucleobases, at least 26 nucleobases, at least 27 nucleobases, at least 28 nucleobases, at least 29 nucleobases, or at least 30 nucleobases in length.

It will be understood by those skilled in the art that the inclusion of mismatches between a targeting sequence and a target sequence is possible without eliminating the activity of the oligomer (e.g., modulation of splicing). Moreover, such mismatches can occur anywhere within the antisense interaction between the targeting sequence and the target sequence, so long as the antisense oligomer is capable of specifically hybridizing to the targeted nucleic acid molecule. Thus, antisense oligomers of this disclosure may comprise up to about 20% nucleotides that are mismatched, thereby disrupting base pairing of the antisense oligomer to a target sequence, as long as the antisense oligomer specifically hybridizes to the target sequence. In preferred embodiments, antisense oligomers comprise no more than 20%, no more than about 15%, no more than about 10%, no more than about 5% or not more than about 3% of mismatches, or less. In a preferred embodiment, there are no mismatches between nucleotides in the antisense oligomer involved in pairing and a complementary target sequence. Preferably, mismatches do not occur at contiguous positions. For example, in an antisense oligomer containing 3 mismatch positions, it is preferred if the mismatched positions are separated by runs (e.g., 3, 4, 5, etc.) of contiguous nucleotides that are complementary with nucleotides in the target sequence The use of percent identity is a common way of defining the number of mismatches between two nucleic acid sequences. For example, two sequences having the same nucleobase pairing capacity would be considered 100% identical. Moreover, it should be understood that both uracil and thymidine will bind with adenine. Consequently, two molecules that are otherwise identical in sequence would be considered identical, even if one had uracil at position x and the other had a thymidine at corresponding position x. Percent identity may be calculated over the entire length of the oligomeric compound, or over just a portion of an oligomer. For example, the percent identity of a targeting sequence to a target sequence can be calculated to determine the capacity of an oligomer comprising the targeting sequence to bind to a nucleic acid molecule comprising the target sequence. In one embodiment, the targeting sequence is at least 80% identical, at least 85% identical, at least 90% identical, at least 95% identical, at least 97% identical, at least 98% identical or at least 99% identical over its entire length to a target sequence in a target nucleic acid molecule. In one embodiment, the targeting sequence is identical over its entire length to a target sequence in a target nucleic acid molecule.

It is understood by those skilled in the art that an antisense oligomer need not be identical to the oligomer sequences disclosed herein to function similarly to the antisense oligomers described herein. Shortened versions of antisense oligomers taught herein, or non-identical versions of the antisense oligomers taught herein, fall within the scope of this disclosure. Non-identical versions are those wherein each base does not have 100% identity with the antisense oligomers disclosed herein. Alternatively, a non-identical version can include at least one base replaced with a different base with different pairing activity (e.g., G can be replaced by C, A, or T). Percent identity is calculated according to the number of bases that have identical base pairing corresponding to the oligomer to which it is being compared. The non-identical bases may be adjacent to each other, dispersed throughout the oligomer, or both. For example, a 16-mer having the same sequence as nucleobases 2-17 of a 20-mer is 80% identical to the 20-mer. Alternatively, a 20-mer containing four nucleobases not identical to the 20-mer is also 80% identical to the 20-mer. A 14-mer having the same sequence as nucleobases 1-14 of an 18-mer is 78% identical to the 18-mer. Such calculations are well within the ability of those skilled in the art. Thus, antisense oligomers of this disclosure comprise oligonucleotide sequences at least 80% identical, at least 85% identical, at least 90% identical, at least 92% identical, at least 94% identical at least 96% identical or at least 98% identical to sequences disclosed herein, as long as the antisense oligomers are able to modulate splicing of a desired mRNA molecule.

Antisense oligomers of this disclosure are capable of modulating splicing of mRNA molecules. As used herein, "modulation" of splicing refers to the ability of an antisense oligomer to affect the processing of a pre-mRNA transcript such that the resulting spliced mRNA molecule contains a desired combination of exons as a result of exon skipping (or exon inclusion), a deletion in one or more exons, or additional sequence not normally found in the spliced mRNA (e.g., intronic sequences). For example, modulation of splicing can refer to affecting the splicing of a MS4A2 pre-mRNA such that the spliced mRNA (mature mRNA) is missing at least a portion, or the entirety, of one exon. In one embodiment, the spliced mRNA lacks at least a portion of exon 3.

It has previously been discussed that a truncated isoform of the FcεRIβ protein (t-FcεRIβ) is present in cells, and that such truncation is due to a truncation in exon 3 of the mRNA encoding the FcεRIβ protein. The inventors have also shown that the number or "level" of such truncated mRNA molecules is far less than the level of MS4A2 mRNA molecules including full-length exon 3. Thus, for the purposes of describing this disclosure, splicing of an MS4A2 pre-mRNA, due to the influence of an antisense oligomer, to produce a truncated mRNA encoding a truncated FcεRIβ protein, can be referred to as alternative splicing. Further, an MS4A2 mRNA transcript lacking at least a portion, or the entirety, of exon 3, due to the influence of an antisense oligomer, is a product of alternative splicing. Thus, in the context of this disclosure, modulation of splicing can refer to inducing alternative splicing of an MS4A2 pre-mRNA molecule, thereby reducing the level of mRNA molecules containing the entirely of exon 3, and increasing the level of mRNA molecules lacking at least a portion of exon 3.

One embodiment of this disclosure is an antisense oligomer comprising 10 to 50 linked nucleosides, wherein the oligomer is targeted to a region of an RNA molecule encoding an FcεRIβ protein. In a preferred embodiment, hybridization of the oligomer to the RNA molecule modulates splicing of the RNA molecule.

One embodiment of this disclosure is an antisense oligomer comprising a nucleic acid sequence sufficiently complementary to a target sequence in a target region of an MS4A2 mRNA molecule, such that the antisense oligomer specifically hybridizes to the target sequence, thereby modulating splicing of an MS4A2 mRNA transcript.

These antisense oligomers may consist of 10 to 50 linked nucleosides. These antisense oligomers may comprise 15 to 35 linked nucleotides. These antisense oligomers may consist of 15 to 35 linked nucleotides. These antisense oligomers may comprise or consist of 10 linked nucleosides, 11 linked nucleosides, 12 linked nucleosides, 13 linked nucleosides, 14 linked nucleosides, 15 linked nucleosides, 16 linked nucleosides, 17 linked nucleosides, 18 linked nucleosides, 19 linked nucleosides, 20 linked nucleosides, 21 linked nucleosides, 22 linked nucleosides, 23 linked nucleosides, 24 linked nucleosides, 25 linked nucleosides, 26 linked nucleosides, 27 linked nucleosides, 28 linked nucleosides, 29 linked nucleosides, 30 linked nucleosides, 31 linked nucleosides, 32 linked nucleosides, 33 linked nucleosides, 34 linked nucleosides, 34 linked nucleosides, 36 linked nucleosides, 37 linked nucleosides, 38 linked nucleosides, 39 linked nucleosides, 40 linked nucleosides, 41 linked nucleosides, 42 linked nucleosides, 43 linked nucleosides, 44 linked nucleosides, 45 linked nucleosides, 46 linked nucleosides, 47 linked nucleosides, 48 linked nucleosides, 49 linked nucleosides, or 50 linked nucleosides.

The mRNA molecule may encode an FcεRIβ protein from any mammal that produces an FcεRIβ protein. Examples of such mammals include, but are not limited to, a human, a mouse, a dog, a cat, and a horse. In one embodiment, the mRNA comprises a nucleotide sequence at least 80%, at least 85%, at least 90%, at least 95%, at least 97%, at least 99%, or 100% identical to SEQ ID NO:1 or SEQ ID NO:3. In one embodiment, the mRNA encodes a protein comprising an amino acid sequence at least 80%, at least 85%, at least 90%, at least 95%, at least 97%, at least 99% identical to SEQ ID NO:2 or SEQ ID NO:4. In one embodiment, the mRNA encodes a protein comprising SEQ ID NO:2 or SEQ ID NO:4.

The RNA molecule may be an MS4A2 transcript. In one embodiment, the RNA molecule is an MS4A2 mRNA molecule. In preferred embodiments, the RNA molecule is an MS4A2 pre-mRNA.

The target region targeted by the antisense oligomer can be any region of the RNA molecule that is functionally involved in splicing of the RNA molecule. By "functionally involved in splicing" is meant the sequences in the target region are utilized by the cellular splicing apparatus (e.g., the spliceosome or components thereof) to effect splicing of the mRNA molecule. Examples of such regions include, but are not limited to, regions comprising intron sequences, regions comprising exon sequences, regions comprising intron/exon junctions, regions comprising splice donor site sequences, regions comprising splice acceptor site sequences, regions comprising splice enhancer site sequences, regions comprising branch point sequences, and regions comprising polypyrimidine tracts. Such sequences are known to those skilled in the art. Such sequences are also disclosed herein.

Thus in one embodiment, the target region comprises at least a portion of a sequence selected from the group consisting of an exon sequence, an intron sequence, a sequence comprising an exon/intron junction, a splice donor site sequence, a splice acceptor site sequence, a splice enhancer site sequence, a branch point sequence, and a polypyrimidine tract. In the context of this disclosure, "at least a portion" refers to at least 5 nucleosides, at least 6 nucleosides, at least 7 nucleosides, at least 8 nucleosides, at least 9 nucleosides, at least 10 nucleosides, at least 11 nucleotides, at least 12 nucleosides, at least 13 nucleotides, at least 14 nucleosides, at least 15 nucleosides, at least 16 nucleosides, at least 17 nucleosides, at least 18 nucleosides, at least 19 nucleosides, or at least 20 nucleosides in length. In one embodiment, the at least a portion comprises at least 10%, at least 25%, at least 50%, at least 75%, at least 90%, at least 90%, at least 95% or at least 97% of a known splice donor site sequence, splice acceptor site sequence, splice enhancer site sequence, branch point sequence or polypyrimidine sequence. The splice donor site sequence, splice acceptor site sequence, splice enhancer site sequence, branch point sequence or polypyrimidine sequence may be from an MS4A2 pre-MRNA.

In one embodiment, the target region comprises at least a portion of an MS4A2 sequence of this disclosure, which may be any one of SEQ ID Nos: 1-1015, including SEQ ID NOs:22-1006. In one embodiment, the at least a portion comprises at least 10%, at least 25%, at least 50%, at least 75%, at least 80%, at least 90% at least 95% or at least 97% of an MS4A2 sequence of this disclosure. In one embodiment, the at least a portion comprises a polynucleotide sequence at least 80%, at least 90% at least 95% or at least 97% identical to a portion of an MS4A2 sequence of this disclosure.

In one embodiment, the target region comprises a nucleotide sequence at least 80%, at least 90%, at least 95%, at least 97%, at least 99%, or 100% identical to at least a portion of a sequence selected from the group consisting of SEQ ID NO:1, SEQ ID NO:3, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and an MSR4A2 sequence comprising any one of SEQ ID NOs:1007-1015. In one embodiment, the target region comprises at least a portion of a sequence selected from the group consisting of SEQ ID NOs:5-17, and an MSR4A2 sequence comprising any one of SEQ ID NOs:1007-1015. In one embodiment, the target region comprises a nucleotide sequence selected from the group consisting of SEQ ID NOs:5-17, and an MSR4A2 sequence comprising any one of SEQ ID NOs:1007-1015.

In one embodiment, the antisense oligomer is targeted to a region or sequence involved in splicing of an MS4A2 pre-mRNA. In one embodiment, the antisense oligomer is target to an MS4A2 intron sequence, an MS4A2 exon sequence, an MS4A2 splice donor site sequence, an MS4A2 splice acceptor site sequence, an MS4A2 splice enhancer site sequence, an MS4A2 branch point sequence, or an MS4A2 polypyrimidine tract. In one embodiment, the antisense oligomer is targeted to exon 3 of an MS4A2 pre-mRNA. In one embodiment, the antisense oligomer is targeted to an MS4A2 exon 3 splice donor sequence, an exon 3 splice acceptor sequence, or an exon 3 spice enhancer sequence.

In one embodiment, the antisense oligomer is targeted to a target molecule comprising a sequence at least 80%, at least 90%, at least 95%, at least 97%, at least 99%, or 100% identical to a sequence selected from the group consisting of SEQ ID NO:1, SEQ ID NO:3, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and an MSR4A2 sequence comprising any one of SEQ ID NOs:1007-1015. In one embodiment, the antisense oligomer is targeted to a target molecule comprising a sequence selected from the group consisting of SEQ ID NO:1, SEQ ID NO:3, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and an MSR4A2 sequence comprising any one of SEQ ID NOs:1007-1015.

In one embodiment, the antisense oligomer is targeted to a sequence at least 80%, at least 90%, at least 95%, at least 97%, at least 99%, or 100% identical to a sequence selected from the group consisting of SEQ ID NOs:5-17, and an MSR4A2 sequence comprising any one of SEQ ID NOs:1007-1015. In one embodiment, the antisense oligomer is targeted to a sequence selected from the group consisting of SEQ ID NOs:5-17, and an MSR4A2 sequence comprising any one of SEQ ID NOs:1007-1015.

In one embodiment, the antisense oligonucleotide is targeted to a sequence at least 80%, at least 90%, at least 95%, at least 97%, at least 99%, or 100% identical to a sequence selected from the group consisting of SEQ ID NOs:11-17. In one embodiment, the antisense oligonucleotide is targeted to a sequence selected from the group consisting of SEQ ID NOs:11-17.

In one embodiment, the antisense oligomer comprises a targeting sequence at least 80%, at least 90%, at least 95%, at least 97%, or at least 99% identical to a sequence fully complementary to at least a portion of a splice donor site sequence, a splice acceptor site sequence, a splice enhancer site sequence, a branch point sequence or a polypyrimidine sequence from an MS4A2 mRNA. In one embodiment, the antisense oligomer comprises a targeting sequence fully complementary to at least a portion of a splice donor site sequence, a splice acceptor site sequence, a splice enhancer site sequence, a branch point sequence, or a polypyrimidine sequence from an MS4A2 mRNA. In one embodiment, the antisense oligomer comprises a targeting sequence at least 80%, at least 90%, at least 95%, at least 97%, at least 99%, or 100% identical to a sequence fully complementary to at least a portion of a sequence selected from the group consisting of SEQ ID NO:1, SEQ ID NO:3, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and an MSR4A2 sequence comprising any one of SEQ ID NOs:1007-1015. In one embodiment, the antisense oligomer comprises a targeting sequence at least 80%, at least 90%, at least 95%, at least 97%, at least 99%, or 100% identical to a sequence fully complementary to at least a portion of a sequence selected from the group consisting of SEQ ID NOs:11-17. The portion is preferably least 10 nucleotides in length. The antisense oligomer may modulate splicing of an MS4A2 pre-mRNA molecule.

In one embodiment, the targeting sequence comprises a sequence at least 80%, at least 90%, at least 95%, at least 97%, or at least 99% identical to a sequence selected from the group consisting of SEQ ID NOs:22-1006. In one embodiment, the targeting sequence consists of a sequence at least 80%, at least 90%, at least 95%, at least 97%, or at least 99% identical to a sequence selected from the group consisting of SEQ ID NOs:22-1006.

In one embodiment, the targeting sequence comprises a sequence selected from the group consisting of SEQ ID NOs:22-1006. In one embodiment, the targeting sequence consists of a sequence selected from the group consisting of SEQ ID NOs:22-SEQ ID NO:1006. The portion is preferably at least 10 nucleotides in length. The antisense oligomer may modulate splicing of an MS4A2 pre-mRNA molecule.

In one embodiment, the target region comprises at least a portion of a sequence selected from an MS4A2 splice donor site sequence, an MS4A2 splice acceptor site sequence, an MS4A2 splice enhancer site sequence, an MS4A2 branch point sequence and an MS4A2 polypyrimidine sequence. In one embodiment, the at least a portion comprises at least 10%, at least 25%, at least 50%, at least 75%, at least 90% or at least 90% of an MS4A2 splice donor site sequence, an MS4A2 splice acceptor site sequence, an MS4A2 splice enhancer site sequence, an MS4A2 branch point sequence or an MS4A2 polypyrimidine sequence. The MS4A2 splice donor site sequence, the MS4A2 splice acceptor site sequence, the MS4A2 splice enhancer site sequence, the MS4A2 branch point sequence, or the MS4A2 polypyrimidine sequence, may be from exon 3 of an MS4A2 pre-mRNA. The portion may be at least 10 nucleotides in length. The antisense oligomer may modulate splicing of an MS4A2 pre-mRNA molecule.

In one embodiment, the complementary nucleic acid sequence comprised by the antisense oligomer (i.e., the "targeting sequence") is at least 80%, at least 90%, at least 95%, at least 97%, or at least 99% identical to a sequence fully complementary to at least a portion of a splice donor site sequence, splice acceptor site sequence, splice enhancer site sequence, branch point sequence or polypyrimidine sequence from an MS4A2 mRNA. In one embodiment, the complementary nucleic acid sequence comprised by the antisense oligomer comprises a sequence at least 80%, at least 90%, at least 95%, at least 97%, at least 99%, or 100% identical to a sequence fully complementary to a portion of a sequence selected from the group consisting of SEQ ID NO:1, SEQ ID NO:3, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and an MSR4A2 sequence comprising any one of SEQ ID NOs: 1007-1015. In one embodiment, the complementary nucleic acid sequence comprised by the antisense oligomer comprises a sequence at least 80%, at least 90%, at least 95%, at least 97%, at least 99%, or 100% identical to a sequence fully complementary to a portion of a sequence selected from the group consisting of SEQ ID NOs:11-17. The portion may be at least 10 nucleotides in length. The antisense oligomer may modulate splicing of an MS4A2 pre-mRNA molecule.

In one embodiment, the complementary nucleic acid sequence of the antisense oligomer comprises a sequence at least 80%, at least 90%, at least 95%, at least 97%, or at least 99% identical to a sequence selected from the group consisting of SEQ ID NOs:22-1006. In one embodiment, the complementary nucleic acid sequence comprised by the antisense oligomer consists of a sequence at least 80%, at least 90%, at least 95%, at least 97%, or at least 99% identical to a sequence selected from the group consisting of SEQ ID NOs:22-1006. In one embodiment, the complementary nucleic acid sequence comprised by the antisense oligomer comprises a sequence selected from the group consisting of SEQ ID NOs:22-1006. In one embodiment, the complementary nucleic acid sequence comprised by the antisense oligomer consists of a sequence selected from the group consisting of SEQ ID NOs:22-1006.

In one embodiment, an antisense oligomer comprises a sequence at least 80% identical, at least 85% identical, at least 90% identical, at least 95% identical, at least 97% identical, or at least 99% identical to a sequence selected from the group consisting of SEQ ID NOs:22-1006. In one embodiment, an antisense oligomer comprises a sequence selected from the group consisting of SEQ ID NO:22-1006.

One embodiment of this disclosure is an expression vector that expresses an antisense oligomer of this disclosure. As used herein, an "expression vector" is a nucleic acid molecule comprising a polynucleotide sequence functionally linked to a promoter, such that transcription of the polynucleotide sequence by a polymerase results in production of an antisense oligomer of this disclosure. Exemplary expression vectors include polynucleotide molecules, preferably DNA molecules, that are derived, for example, from a plasmid, bacteriophage, yeast or virus (e.g., adenovirus, adeno-associated virus, lentivirus, retrovirus, etc.), into which a polynucleotide can be inserted or cloned. Suitable expression vectors are known to those skilled in the art.

One embodiment of this disclosure is a pharmaceutical composition comprising an antisense oligomer or expression vector of this disclosure. Such compositions are suitable for the therapeutic delivery of antisense oligomers, or expression vectors, described herein. Hence, this disclosure provides pharmaceutical compositions that comprise a therapeutically-effective amount of one or more of the antisense oligomers or expression vectors described herein, formulated together with one or more pharmaceutically-acceptable carriers (additives) and/or diluents. While it is possible for an antisense oligomer or expression vector of this disclosure to be administered alone, it is preferable to administer the compound as a pharmaceutical composition.

Pharmaceutical compositions of this disclosure may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) inhaled into the lungs, for example, by nebulizer or aerosol inhaler; or (9) nasally. Examples of suitable carriers, additives and diluents are described in U.S. Patent Publication No. 2015/0361428, which is incorporated herein by reference in its entirety.

As has been described above, antisense oligomers of this disclosure are capable of reducing cell-surface expression of FcRI. Such reduction is achieved by modulating splicing of an mRNA molecule encoding a FcεRIβ protein. More specifically, antisense oligomers of this disclosure decrease the production of FcεRIβ-encoding mRNA molecules comprising exon 3, and increase the production of FcεRIβ-encoding mRNA molecules lacking exon 3. Because these latter FcεRIβ-encoding mRNA molecules lack exon 3, the encoded FcεRIβ proteins lack the first transmembrane domain, which is required for trafficking of the FcεRI complex to the cell membrane.

Thus, one embodiment of this disclosure is a method of modulating splicing of an FcεRIβ mRNA in a cell, the method comprising contacting the cell with an antisense oligomer of this disclosure. The cell may be any cell expressing an FcεRIβ mRNA molecule. Accordingly, the cell can be a cell in culture, or a cell in the body of an individual. In one embodiment, the cell is an epidermal Langerhans cell, an eosinophil, a mast cell, or a basophil. In a specific embodiment, the cell is a mast cell.

The mRNA may comprise a nucleotide sequence at least 80%, at least 85%, at least 90%, at least 95%, at least 97%, at least 99%, or 100% identical to SEQ ID NO:1 or SEQ ID NO:3. In one embodiment, the mRNA encodes a protein comprising an amino acid sequence at least 80%, at least 85%, at least 90%, at least 95%, at least 97%, or at least 99% identical to SEQ ID NO:2 or SEQ ID NO:4. In one embodiment, the mRNA encodes a protein comprising SEQ ID NO:2 or SEQ ID NO:4.

In one embodiment, the antisense oligomer hybridizes to a target region that is involved in splicing of MS4A2 pre-mRNA. In one embodiment, the antisense oligomer hybridizes to a target region in the mRNA comprising at least a portion of a sequence selected from the group consisting of an MS4A2 splice donor site sequence, an MS4A2 splice acceptor site sequence, an MS4A2 splice enhancer site sequence, an MS4A2 branch point sequence and an MS4A2 polypyrimidine sequence. The MS4A2 splice donor site sequence, the MS4A2 splice acceptor site sequence, the MS4A2 splice enhancer site sequence, the MS4A2 branch point sequence, or the MS4A2 polypyrimidine sequence may be from exon 3 of an MS4A2 pre-mRNA.

Modulation of splicing of FcεRIβ pre-mRNA by antisense oligomers of this disclosure can result in production of a truncated mRNA (t-FcεRIβ mRNA), which produces a truncated form of the FcεRIβ protein. t-FcεRIβ mRNA differs from full-length FcεRIβ mRNA (FL-FcεRIβ mRNA) in that it is truncated in exon 3, thereby producing an FcεRIβ protein lacking the first and second membrane-spanning regions. Normally, the amount of FL-FcεRIβ mRNA in mast cells is greater than the amount of t-FcεRIβ mRNA. Thus, one embodiment of this disclosure is a method of altering the ratio of FL-FcεRIβ mRNA to t-FcεRIβ mRNA in a mast cell, the method comprising contacting the mast cell with an antisense oligomer of this disclosure. Contact of a mast cell with an antisense oligomer of this disclosure may cause a decrease in the amount of FL-FcεRIβ mRNA and an increase in the amount of t-FcεRIβ mRNA. Contact of a mast cell with an antisense oligomer of this disclosure may result in a decreased FL-FcεRIβ mRNA/t-FcεRIβ mRNA ratio. In one embodiment, the amount of FL-FcεRIβ produced by the cell is decreased by at least 50%, at least 60%, at least 70%, at least 80%, at least 90%, at least 95%, least 97%, or at least 99%.

One embodiment of this disclosure is a method of reducing cell surface expression of FcεRI protein in a cell, the method comprising contacting the cell with an antisense oligomer of this disclosure. In embodiments of this disclosure, the cell can be any cell expressing an FcεRI protein on its surface. Accordingly, the cell can be a cell in culture (e.g., tissue culture) or a cell in the body of an individual. In one embodiment, the cell is an epidermal Langerhans cell, an eosinophil, a mast cell or a basophil. In a specific embodiment, the cell is a mast cell.

In one embodiment, the amount of FcεRI expressed on the surface of the cell is decreased by at least 50%, at least 60%, at least 70%, at least 80%, at least 90%, at least 95%, at least 97%, or at least 99%.

Mast cells are tissue-bound cells of the innate immune system which are well known for immunoglobulin (Ig)E-triggered degranulation in allergic reactions. Consequently, mast cells express large quantities of FcεRI receptor on their surface. As the binding of IgE to FcεRI is essentially irreversible, mast cells are largely covered with IgE. The main function of mast cells is considered to be degranulation, with immunoglobulin (Ig)E as the main trigger. Once an IgE molecule encounters a specific antigen or allergen, IgE:FcεRI-crosslinking and calcium influx leads to degranulation of the mast cells. As a result, histamine is released and causes the well-known symptoms such as bronchoconstriction or pruritus. Thus, one embodiment of this disclosure is a method of modulating FcεRI-dependent mast-cell degranulation, the method comprising contacting a mast cell with an antisense oligomer of this disclosure. In accordance with this disclosure, the cell can be a cell in culture (e.g., tissue culture) or a cell in the body of an individual.

Upon activation, mast cells rapidly release pre-formed mediators from cytoplasmic granules, such as vasoactive amines (e.g., histamine and serotonin), proteoglycans (e.g., heparin), proteases (e.g., tryptases and chymases), and some pre-stored cytokines (e.g., TNFα). They also release a plethora of mediators, including growth factors, cytokines, and chemokines, such as IL-1, IL-6, IL-8, IL-10, TNFα, VEGF, TGFβ, CCL2-4, as well as pro-inflammatory lipid mediators, such as prostaglandins and leukotrienes. Thus, one embodiment of this disclosure is a method of modulating the release of one or more mediators from a mast cell, the method comprising contacting a mast cell with an antisense oligomer of this disclosure, where the one or more mediators is selected from the group consisting of a mast cell-produced vasoactive amine, a mast cell-produced proteoglycan, a mast cell-produced protease, a cytokine, a growth factor, a chemokine, and a pro-inflammatory lipid mediator. The one or more mediator may be any one of histamine, serotonin, heparin, tryptase, chymase, TNFα, IL-1, IL-6, IL-8, IL-10, TNFα, VEGF, TGFβ, CCL2-4, a prostaglandin, and a leukotriene. In specific embodiments, the mast cell can be a cell in culture, or a cell in the body of an individual.

As players in innate immunity, mast cells have the capacity to initiate and amplify immune responses (see, Bulfone-Paus and Rahri, *Front. Immunol.* 2015; 6:394). Several lines of evidence have demonstrated that mast cells participate in the sensitization phase of acquired immune responses via the secretion of mediators, which sustain dendritic cell (DC) maturation, function, and recruitment to the tissue or their migration to local draining lymph nodes. However, mast cells also exert important effector functions, since mast cells and T cells of different origin and subsets establish tight cell-cell interactions and modulate their respective effector functions in a bidirectional manner; this has been shown in a variety of models. Thus, one embodiment of this disclosure is a method of reducing an immune response in an individual, the method comprising administering an antisense oligomer of this disclosure to the individual. Such immune response can, but need not be, IgE-mediated immune responses.

An antisense oligomer of this disclosure may be administered to any individual expressing an FcεRIβ protein. As used herein, the terms individual, subject, patient, and the like, are meant to encompass any mammal that expresses an FcεRIβ protein, with a preferred mammal being a human. The terms individual, subject, and patient by themselves do not denote a particular age, sex, race, and the like. Thus, individuals of any age, whether male or female, are intended to be covered by this disclosure. Likewise, the methods of this disclosure can be applied to any race of human, including, for example, Caucasian (white), African-American (black), Native American, Native Hawaiian, Hispanic, Latino, Asian, and European. In some embodiments of this disclosure, such characteristics may be significant. In such cases, the significant characteristic(s) (e.g., age, sex, race, etc.) will be indicated. Additionally, the term "individual" encompasses both human and non-human animals. Suitable non-human animals to which antisense oligomers of this disclosure may be administered include, but are not limited to companion animals (i.e. pets), food animals, work animals, or zoo animals. Preferred animals include, but are not limited to, cats, dogs, horses, ferrets and other Mustelids, cattle, sheep, swine, and rodents.

Antisense oligomers of this disclosure can be administered to an individual by any suitable route of administration. Examples of such routes include, but are not limited to, oral and parenteral routes, (e.g., intravenous (IV), subcutaneous, intraperitoneal (IP), and intramuscular), inhalation (e.g., nebulization and inhalation) and transdermal delivery (e.g., topical). Any methods effective to deliver an antisense oligomer of this disclosure into the bloodstream of an individual are also contemplated in these methods. For example, transdermal delivery of antisense oligomers may be accomplished by use of a pharmaceutically acceptable carrier adapted for topical administration. Antisense oligomers can be administered in the absence of other molecules, such as proteins or lipids, or they be administered in a complex with other molecules, such as proteins or lipids. For example, the use of cationic lipids to encapsulate antisense oligomers is disclosed in U.S. Pat. No. 8,569,256, and U.S.

Pat. No. 6,806,084, which are incorporated herein by reference in their entirety. Similarly, the use of peptide-linked morpholino antisense oligonucleotides is disclosed in U.S. Patent Publication No. 2015/0238627, which is incorporated herein by reference. IgE and IgE-mediated immune responses are known to be involved in numerous allergic conditions. Because antisense oligomers of this disclosure can reduce FcεRI-mediated responses, such antisense oligomers can be used to treat allergic conditions. Thus, one embodiment of this disclosure is a method of treating an allergic condition in an individual, by administering to an individual in need of such treatment an antisense oligomer of this disclosure. Allergic conditions being treated can be any condition mediated by a pathway comprising FcεRI. Such conditions include, but are not limited to, asthma, food allergies allergic conjunctivitis, and atopic dermatitis.

In an allergic person, whose tissue mast cells and other cell types already have antigen-specific IgE bound to FcεRI, re-exposure to the original or a cross-reactive bivalent or multivalent antigen results in the cross-linking of adjacent FcεRI-bound IgE and the consequent aggregation of surface FcεRI. When the FcεRI aggregation is of sufficient strength and duration, it triggers mast cells and basophils to initiate complex signaling events that ultimately result in the secretion of a diverse group of biologically active products. In aggregate, mediators released shortly after antigen- and IgE-induced mast cell degranulation induce a response termed an immediate hypersensitivity (or early phase) reaction within minutes of their release. If localized to the airways, this response is characterized by increased vascular permeability, contraction of the airway smooth muscle and enhanced secretion of mucus, resulting in acutely reduced airflow and wheezing. If the response is systemic, it can result in anaphylaxis, a catastrophic immune response that can rapidly result in death if not properly treated (for a review, see Galli and Tsai, Nature Medicine. 2012 May 4; 18(5):693-704). Thus, one embodiment of this disclosure is a method for preventing or treating an anaphylactic reaction in an individual, the method comprising administering to an individual in need of such treatment an antisense oligomer of this disclosure. The antisense oligomer of this disclosure may be administered in advance of an anaphylactic reaction or anticipated anaphylactic reaction in the individual. The antisense oligomer of this disclosure is preferably administered at regular intervals to prevent or reduce the incidence and/or severity of any anaphylactic reaction in an individual at risk of having an anaphylactic reaction or developing anaphylactic shock. The individual being treated may or may not be at immediate risk for having an anaphylactic reaction. One embodiment of this disclosure is a method of modulating an anaphylactic reaction in an individual, the method comprising administering to an individual in need of such treatment an antisense oligomer of this disclosure.

Mastocytosis is a rare mast cell activation disorder caused by an individual having too many mast cells and mast cell precursors. Because mast cells are involved in atopic responses, individuals suffering from mastocytosis are susceptible to hives, itching and anaphylactic shock. Thus, one method of this disclosure is a method of treating an individual suffering from mastocytosis, the method comprising administering to an individual in need of such treatment an antisense oligomer of this disclosure. The individual may or may not already be exhibiting symptoms of mastocytosis, such as itching, hives and anaphylaxis. In one embodiment, an antisense oligomer is administered to an individual at risk for developing symptoms of mastocytosis.

Mast cells are produced in the bone marrow and are found throughout the connective tissue of the body. In some individuals, mast cells accumulate the skin, forming clusters that appear as a bump. Such clusters of mast cells are referred to as mastocytomas. A common symptom resulting from a mastocytoma is itching, although afflicted individuals can also experience urticarial, pigmentosa, flushing, nausea, vomiting, diarrhea and abdominal pain. One method of this disclosure is a method of treating an individual diagnosed with a mastocytoma or suspected of having a mastocytoma, by administering to the individual an antisense oligomer of this disclosure. In one embodiment, administration of an antisense oligomer eliminates one or more symptom(s) resulting from a mastocytoma.

This disclosure also provides kits for modulating splicing of an FcεRIβ mRNA, reducing cell surface expression of an FcεRI protein, modulating an anaphylactic reaction in an individual, and/or treating an individual for an allergic condition, the kit comprising at least one antisense oligomer of this disclosure. The kit may also comprise instructions for using the kit, and various reagents, such as buffers, necessary to practice the methods of this disclosure. These reagents or buffers may be useful for administering an antisense oligomer of this disclosure to a cell or an individual. The kit may also comprise any material necessary to practice the methods of this disclosure, such as syringes, tubes, swabs, and the like.

EXAMPLES

Example 1

Design of Antisense Oligonucleotides (AONs)

Antisense technology was utilized to demonstrate that manipulation of MS4A2 mRNA splicing to favor t-FcεRIβ formation would disrupt FcεRI expression and signaling, thereby rendering cells unresponsive to IgE-mediated antigen challenge. To achieve this, AONs were designed to target exon 3 of MS4A2 mRNA for the human (NM_000139.4) or mouse (NM_013516.2) genes. Specifically, AONs were designed to hybridize to the MS4A2 exon 3 splice donor site, the MS4A2 splice acceptor site and a potential MS4A2 splice enhancer site. AON constructs were then purchased from Gene-Tools (Philomath, Oreg.), and contained proprietary morpholino chemistry. For the mouse AON, a region within the splicing acceptor region was targeted with the sequence (SEQ ID NO: 22)
5'-GTGTTGCCTGTGGAAAACATGAATT-3'.

For the human AON, an open sequence within exon was targeted with the AON sequence:

(SEQ ID NO: 14)
5'-AGTACAGAGCAGACAACTGTTCA-3'.

The standard control AON, provided by Gene-Tools, had sequence:

(SEQ ID NO: 23)
5'-CCTCTTACCTCAGTTACAATTTATA-3'.

For in vivo studies, Vivo-Morpholino Chemistry (Gene-Tools) was used.

Example 2

Transfection Efficiency and Cytotoxicity of AONs

The inventors examined the ability of AONs of this disclosure to efficiently transfect mast cells using a FITC-conjugated morpholino AON in primary mouse bone marrow-derived mast cells (BMMC), and in the transformed human mast cell lines HMC-1.1, HMC-1.2, and LAD-2 cells. Human mast cell lines were cultured in StemPro-34 medium containing StemPro-34 Nutrient Supplement, L-glutamine (2 mM), Penicillin (100 U/ml)/Streptomycin (100 μg/ml) (GIBCO) with 100 ng/ml recombinant human SCF added (Peprotech). Half of the medium supplemented with SCF was changed every 7 days. $2 \times 10^6$ mast cells were used for each transfection. To determine transfection efficiency, 10 μM of FITC-conjugated standard control 25 mer AON was used (purchased from Gene-Tools). All other AONs were not conjugated. Transfection was achieved using the Nucleofector II and Cell Line Kit V (Lonza). Program U-025 (aortic smooth muscle program) was used for LAD-2 human mast cells and program X-001 was used for mouse BMMCs.

Figure 1B:
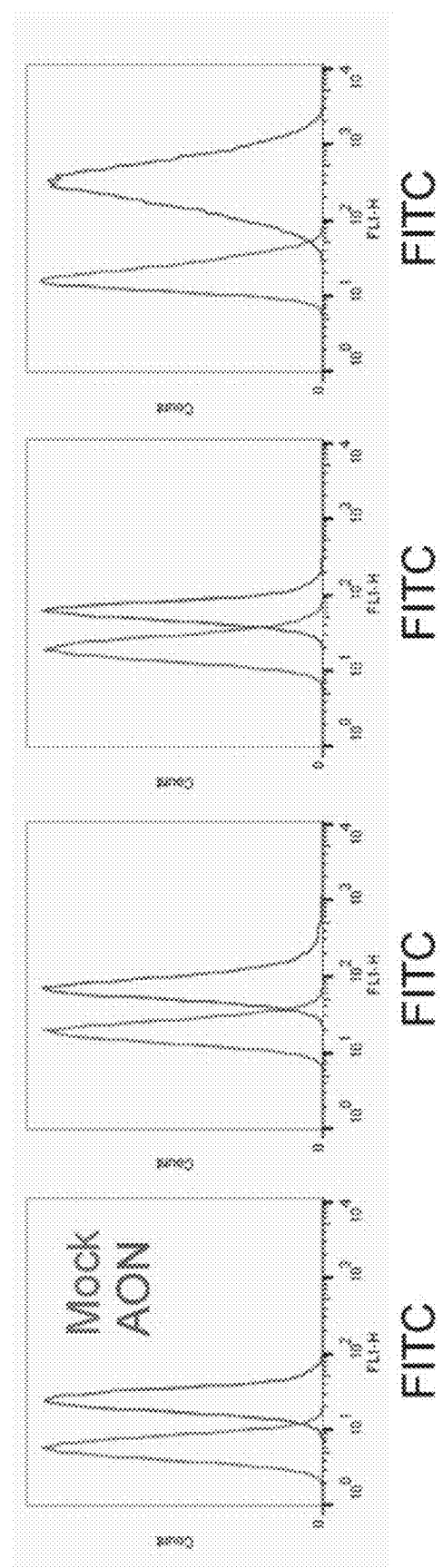

Greater than 80% transfection efficiency was achieved in all cells tested, as determined using FITC-conjugated AON (FIG. 1A). Greater than 95% efficiency was observed in mouse BMMC and human LAD-2 cells at 24 h (FIGS. 1A and 1B) and 48 h. There was no further increase in transfection efficiency at 48 h when compared to 24 h. Cell viability was determined by propridium iodide staining. No evidence of cytotoxicity with AON transfection in either human LAD-2 cells or mouse BMMCs was observed.

Example 3

Induction of Exon-Skipping in Mast Cells

AONs targeted to either mouse MS4A2 or human MS4A2 exon 3 were measured for their ability to induce exon-skipping in human and mouse mast cells. Murine mast cells were transfected with either 10 μM of standard control AON (non-matching 25-mer morpholino AON; SEQ ID NO:15) or 10 μM of 25-mer morpholino AON targeted against a region within the splicing acceptor site at the intron-exon boundary (SEQ ID NO:13). Human mast cells were transfected with either 10 μM of standard control AON (non-matching 25-mer morpholino AON) or 10 μM of 25-mer morpholino AON targeted against an exposed exonic splicing enhancer site within MS4A2 exon 3 (SEQ ID NO:14). AONs were transfected as described in Example 2 and the resulting effect on splicing determined by PCR. Briefly, 24 h after transfection, mast cells were washed twice in ice cold PBS and total RNA was isolated using the RNAeasy plus mini-kit (QIAGEN™) according to the manufacturer's instructions with inclusion of the QIAShredder step. RT-PCR was carried out using the QIAGEN™ One-Step RT-PCR kit with 2 μg of total RNA and 1 μM of each primer. Reverse transcription and PCR was carried out in the same tube in one step with 1 cycle at 50° C. for 30 min, 1 cycle at 95° C. for 15 min, 35 cycles of 94° C. for 45 sec-55° C. for 45 sec-72° C. for 1 min, followed by a final 1 cycle at 72° C. for 10 min. The primers used were designed to amplify the open reading frames. For mouse FcεRIβ mRNA the following primers were used:

```
Forward-
                                          (SEQ ID NO: 18)
5'-ATGGACACAGAAAATAGGAGCA-3'

Reverse-
                                          (SEQ ID NO: 19)
5'-TGAATCAACTGGAGAAGATGTTT-3'.
```

For human FcεRIβ mRNA the following primers were used:

```
Forward-
                                          (SEQ ID NO: 20)
5'-ATGGACACAGAAAGTAATAGGAG-3'

Reverse-
                                          (SEQ ID NO: 21)
5'-TTATAAATCAATGGGAGGAGAC-3'.
```

Figure 2A:
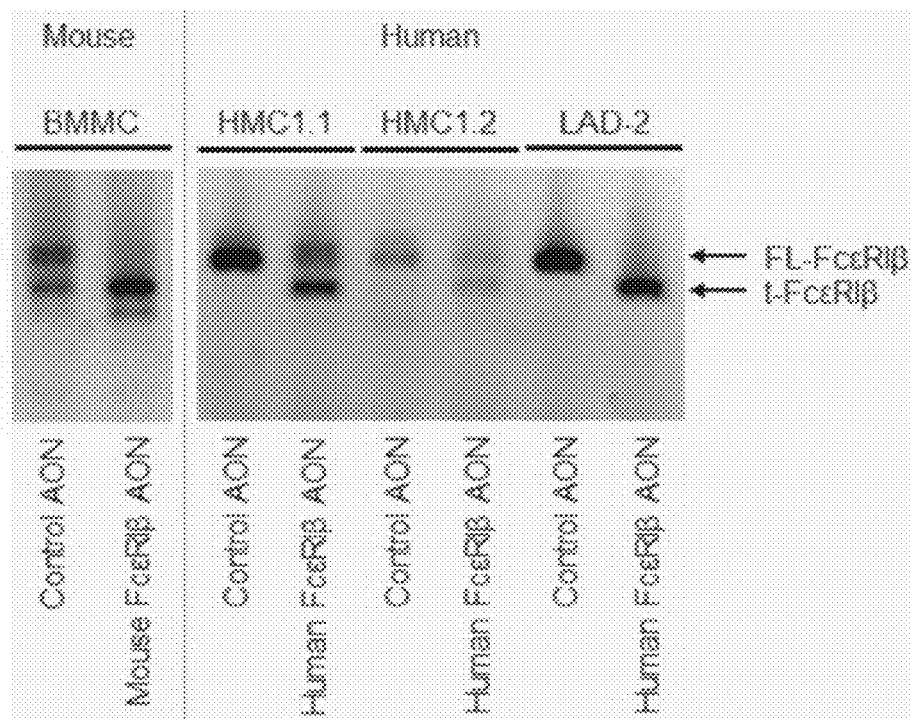
FIGS. 2A-2D show the effects of transfecting mouse and human mast cells with antisense oligonucleotides targeting exon 3 of the MS4A2 gene. Mouse BMMC and human mast cell lines were transfected with either 10 µM of standard control AON (non-matching 25 mer morpholino AON) or 10 µM of 25 mer morpholino AONs targeting FcεRIβ pre-mRNA.
Figure 2B:
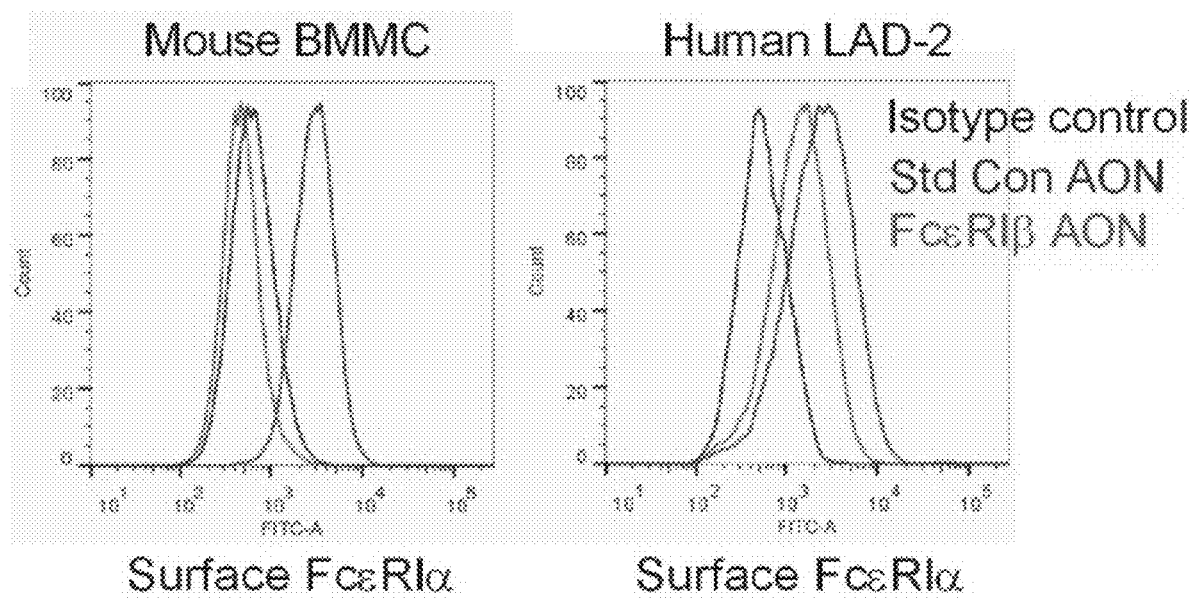
Figure 2C:
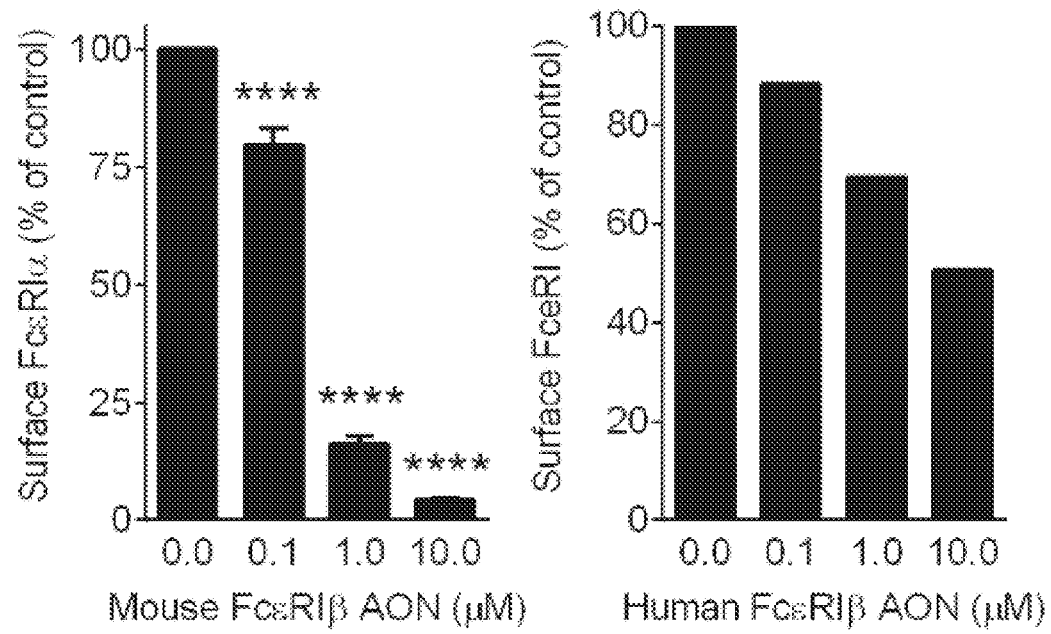
Figure 2D:
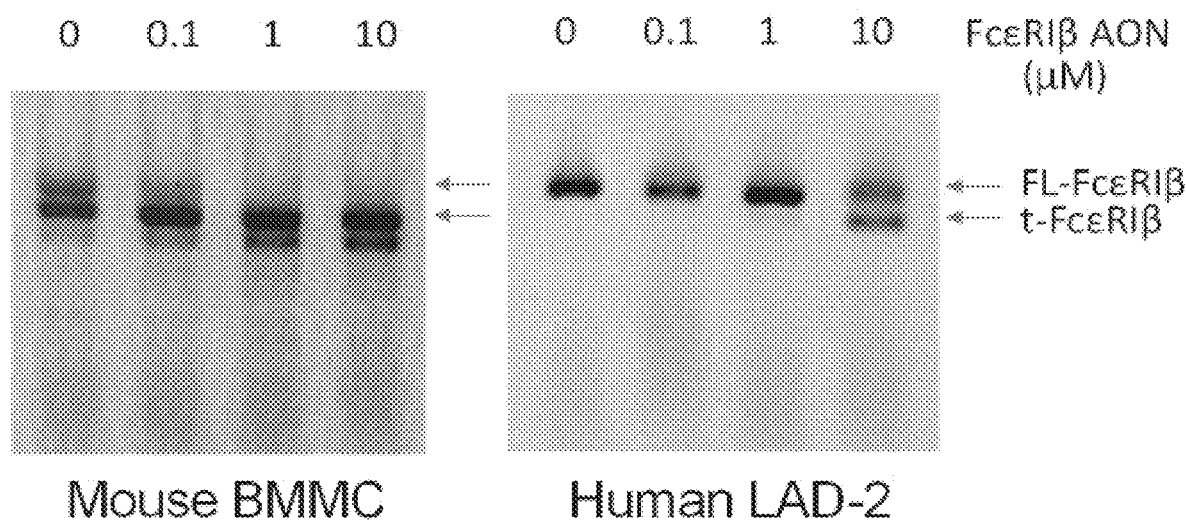

The results of this analysis, which are shown in FIGS. 2A and 2D, demonstrate that both the mouse and human FcεRIβ AONs induced exon-skipping of FcεRIβ mRNA in mouse and human mast cells, respectively, when compared to cells transfected with an equivalent amount of 25-mer standard control AON.

Example 4

Effect of AONs on FcεRI Surface Expression in Mast Cells

The first transmembrane domain of FcεRIβ is required for trafficking of the receptor complex, whilst the C-terminal immunoreceptor tyrosine-based activation motif (ITAM) amplifies signaling. A truncation of MS4A2 exon 3 (t-FcεRIβ) leads to loss of the first two transmembrane domains of FcεRIβ resulting in the expression of t-FcεRIβ that does not traffic to the plasma membrane nor associate with FcεRI. Therefore, AON-induced skipping of exon 3 should result in preferential production of t-FcεRIβ instead of FL FcεRIβ with subsequent loss of expression of surface FcεRI, which is dependent on FL FcεRIβ. Thus, surface expression of FcεRI in the mast cells of Example 3 were measured by flow cytometry. The results of this analysis, which are shown in FIGS. 2A, 2B and 2C, demonstrate that surface FcεRI expression in mouse BMMCs was reduced by 95.6±0.4% (n=5, p<0.001) (FIG. 2B), thus virtually eliminating FcεRI expression (FIG. 2A). In human LAD-2 mast cells, surface FcεRIα expression was reduced by 48.7±2.8% (n=5, p<0.001) (FIG. 2C). Thus, both the mouse and human AONs reduced surface FcεRI expression and induced exon-skipping (FIG. 2D) in a dose-dependent manner Loss of surface FcεRI expression was evident as soon as 4 h and maximal by 24 h with no evidence of loss of efficacy over the 5-day time-course tested in both human and mouse cells.

Example 5

Effect of AONs on Mast Cell Ig-E Responsiveness

In view of the loss of surface FcεRI expression with FcεRIβ AON transfection, transfected mast cells were analyzed for a corresponding reduction in responses to antigen in BMMCs. To measure degranulation, mast cells transfected as described above were cultured for 32 h to allow for loss of surface FcεRI expression. The cells were then sensitized with 100 ng/ml of biotinylated IgE for human cells, or anti-DNP IgE (SPE7 clone) (Sigma) for mouse cells, and incubated overnight (16 h). Degranulation was assayed by β-hexosaminidase release as described by Kuehn et al. (Measuring Mast Cell Mediator Release. *Current protocols in immunology*/edited by John E. Coligan, et al. CHAPTER (2010): Unit7.38). Briefly, cells were washed twice in HEPES buffer (10 mM HEPES, 137 mM NaCl, 2.7 mM KCl, 0.4 mM $Na_2HPO_4 \cdot 7H_2O$, 5.6 mM glucose, 1.8 mM $CaCl_2 \cdot 2H_2O$, and 1.3 mM $MgSO_4 \cdot 7H_2O$ with 0.04% BSA) and $1 \times 10^4$ (LAD-2 cells) or $2.5 \times 10^4$ (BMMCs) were plated into a 96 well plate in 100 µl HEPES buffer. Cells were stimulated with indicated stimuli and incubated for 30 min at 37° C. before centrifugation at 250×g for 5 min at 4° C. Supernatants were removed and the pellets were lysed with 0.1% triton-X 100 for calculation of released β-hexosaminidase.

Figure 3A:
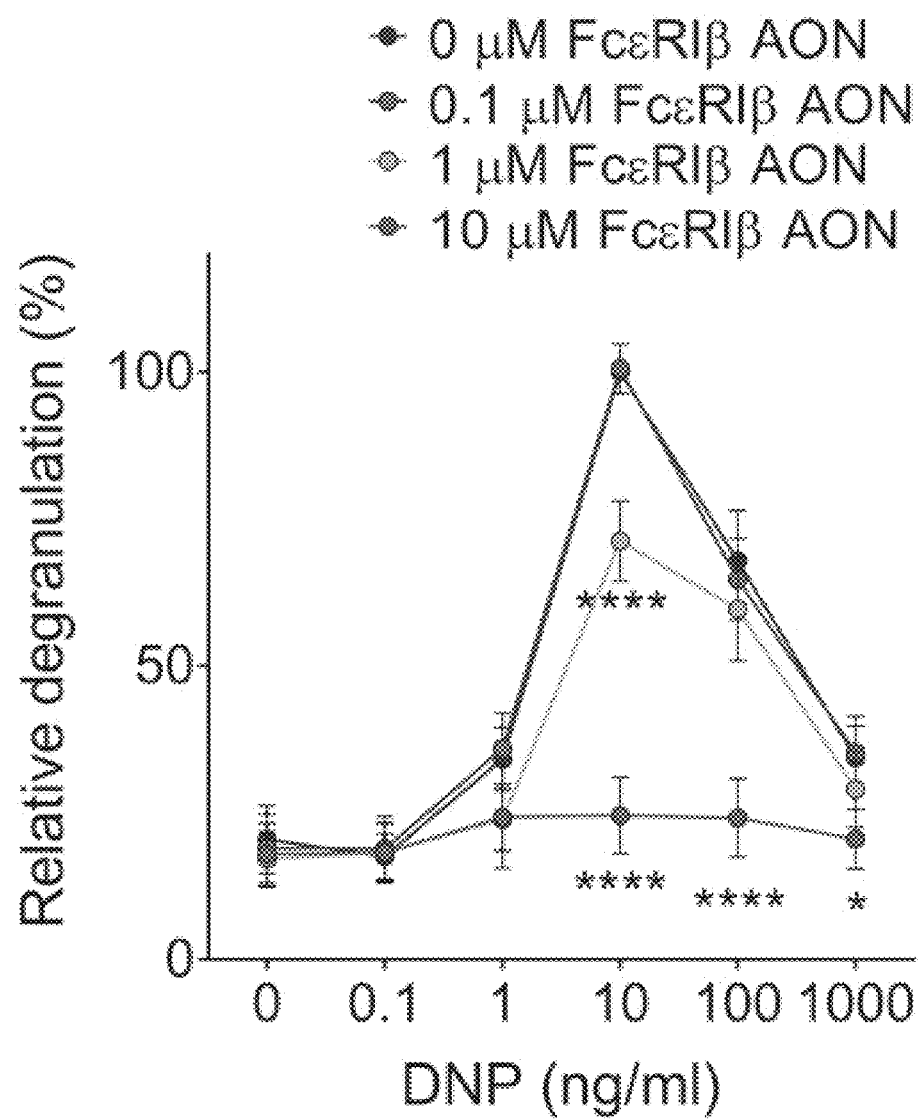
FIGS. 3A-3C show the effect of FcεRIβ antisense oligonucleotides on degranulation on mast cells.
Figure 3B:
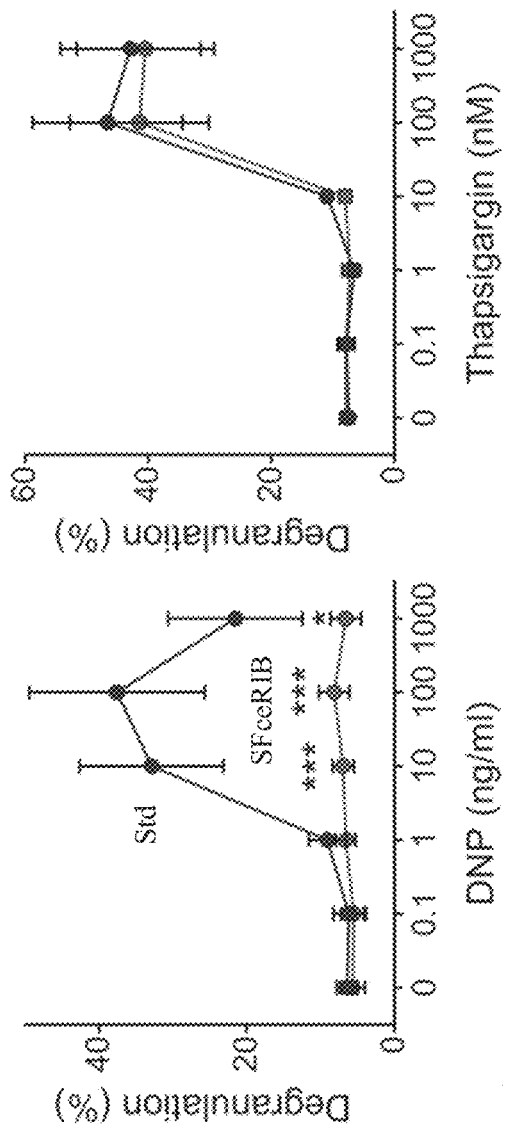

The results of this analysis, which are shown in FIGS. 3A and 3B, show a dose-dependent decrease in degranulation in response to DNP with increasing concentrations of FcεRIβ AON (FIG. 3A). They also show that degranulation was eliminated with 10 µM FcεRIβ AON (FIG. 3A). However, 1 µM FcεRIβ AON resulted in 80% reduction in surface FcεRI expression (FIG. 2C) while the reduction in degranulation, though significant, was lower (25%) (FIG. 3A). A possible explanation for this disparity is that the number of FcεRI receptors and signaling capacity may far exceed the requirements for degranulation. It is estimated that RBL-2H3 mast cells have five-fold more receptors and capacity to generate inositol phosphate and calcium signals than is required for maximal secretory responses. FcεRI numbers vary during the cell cycle and among different mast cell types, with estimates ranging from 130,000 in human lung mast cells to ~290,000/cell in RBL-2H3 cells and 120,000 to 380,000 in human cord blood-derived mast cell/basophil cultures. It is likely that mast cells in general harbor surplus FcεRI as significant degranulation is observed with aggregation of a few hundred receptors (Maeyama, K., et al, *J. Biol. Chem.* 261:2583-92 (1986)).

The specificity of FcεRIβ AON treatment was next determined by its effect on thapsigargin-induced degranulation. The results of these studies, which are shown in FIG. 3B, demonstrate that while FcεRI-dependent degranulation was eliminated in BMMCs (FIG. 3B, left panel), thapsigargin-induced degranulation was unaffected by FcεRIβ exon-skipping (FIG. 3B, right panel)).

Figure 3C:
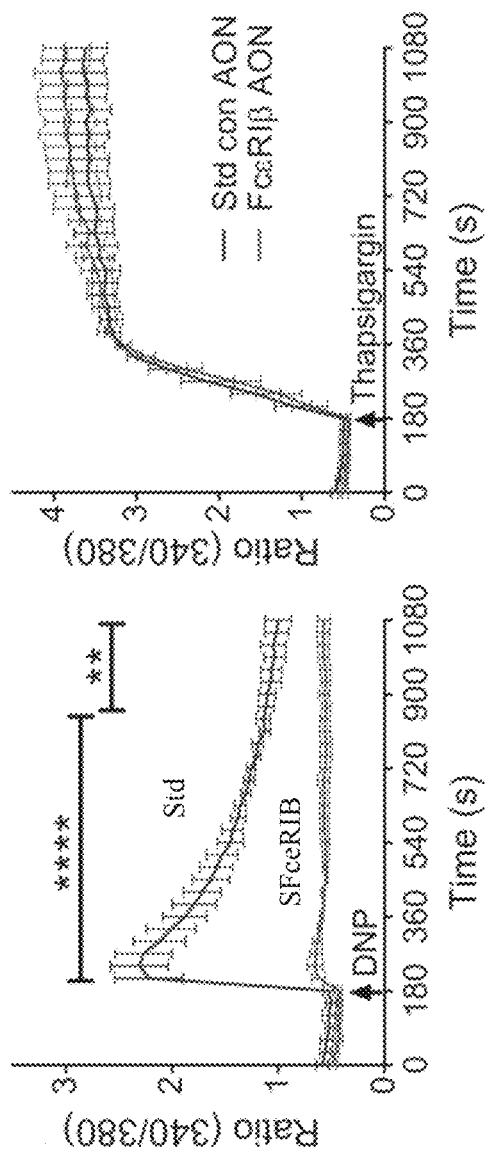
Figure 4A:
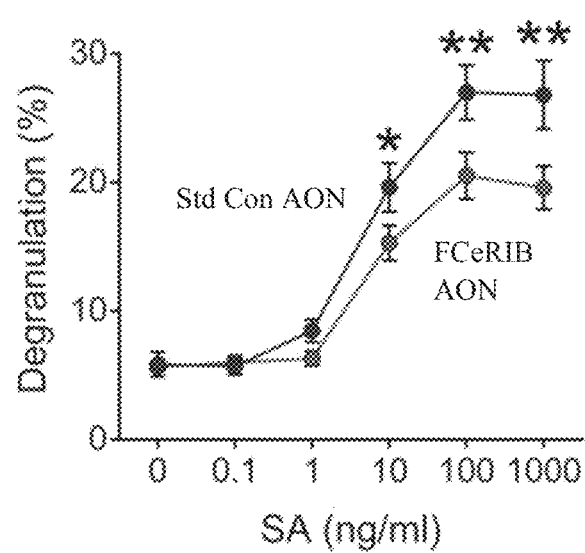
FIGS. 4A and 4B show the effects of FcεRIβ antisense oligonucleotides on IgE-dependent degranulation in human mast cells.
Figure 4B:
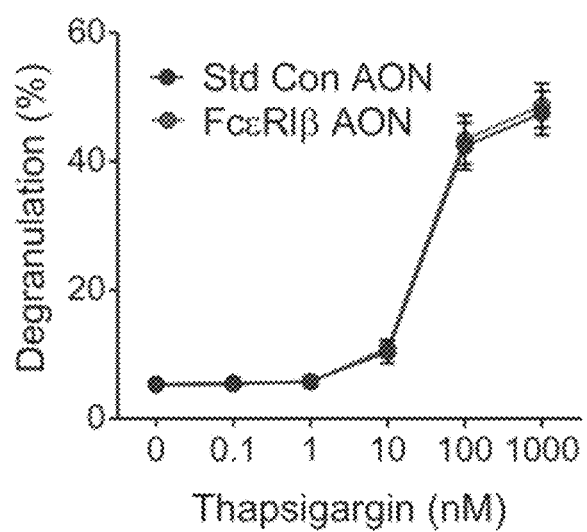

In addition to measuring degranulation, changes in cytosolic $Ca^{2+}$ levels were determined following loading of the cells with Fura-2 AM ester (Molecular Probes) as described by Tkaczyk, C., et al. (*J. Biol. Chem.*, 278:48474-84). BMMCs were transfected as described above. Cells were cultured for 32 h and then sensitized with 100 ng/ml anti-DNP IgE (SPE7 clone) for 16 h. Fluorescence was measured at two excitation wavelengths (340 and 380 nm) and an emission wavelength of 510 nm. The ratio of the fluorescence readings was calculated following subtraction of the fluorescence of the cells that had not been loaded with Fura-2 AM. The results of this analysis, which are shown in FIG. 3C, demonstrate transfection with an AON causes a robust inhibition of the calcium signal in response to FcεRI aggregation (FIG. 3C, left panel). In contrast, the response to thapsigargin was unaffected (FIG. 3C, right panel). As with thapsigargin, IgE-mediated calcium influx is dependent upon store-operated calcium entry. Thus, FcεRIβ exon-skipping appears to selectively target IgE-dependent activation without disrupting cell responses to other stimuli. A similar trend was observed in human LAD-2 cells with a reduction in IgE-dependent degranulation (FIG. 4A) and no reduction in thapsigargin-induced degranulation (FIG. 4B), or compound 48:80-induced degranulation.

Example 6

Modulation of Cytokine Production by AONs

The effects of FcεRIβ exon-skipping on cell signaling events that regulate both degranulation and de novo cytokine synthesis were examined Specifically, studies were conducted to determine whether residual weak signals that fail to stimulate degranulation were sufficient to induce synthesis of cytokines. Briefly, BMMCs were transfected as described above. Cells were cultured for 32 h and then BMMCs were sensitized with 100 ng/ml anti-DNP IgE (SPE7 clone) for 16 h (DNP stimulated cells only) and some cells were not sensitized with IgE (all other conditions). Cytokine release was assayed at a cell concentration of $1\times10^6$ BMMCs per ml. Mouse GM-CSF cytokines was measured using Duo-Set ELISAs (R & D Systems) according to the manufacturer's instructions.

Figure 5A:
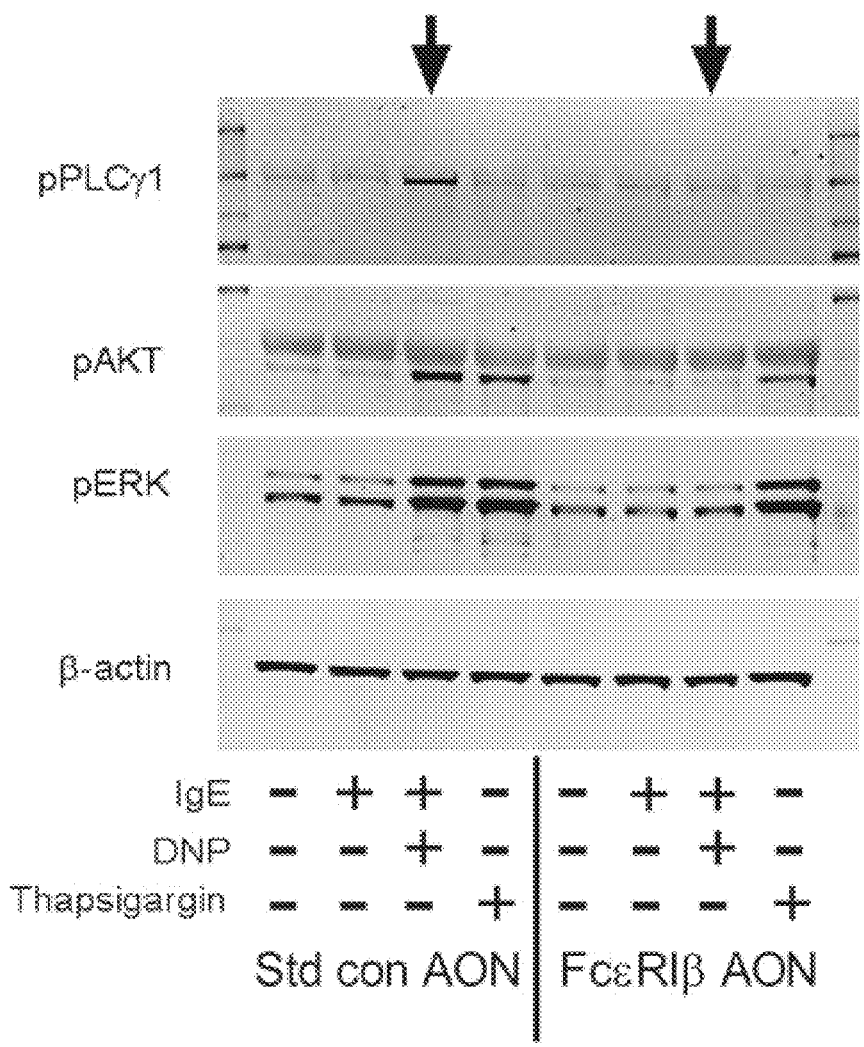

No significant FcεRI-mediated phosphorylation of PLCγ1 was observed following FcεRIβ AON transfection. However, unlike FcεRI-mediated activation, thapsigargin did not induce phosphorylation since it acts independently of PLCγ (FIGS. 5A and 5B). While phosphorylation of AKT and ERK are more distal signals than PLCγ1 phosphorylation, the phosphorylation of both of AKT and ERK were also markedly reduced by FcεRIβ exon-skipping (FIGS. 5A, 5C and 5D). In contrast to PLCγ1, the AKT and ERK pathways are activated by thapsigargin, but neither AKT nor ERK phosphorylation was affected by FcεRIβ exon-skipping (FIGS. 5A, 5C and 5D). Low level activation of mast cells can result in the production of cytokines without evidence of acute signaling events. One such example is IgE alone, which did not elicit rapid phosphorylation of PLCγ1, AKT or ERK (FIG. 5A-5D), but did cause robust release of the cytokine GM-CSF after 6 h (FIG. 5E). Furthermore, this release, as well as that induced by IgE plus antigen to induce FcεRI aggregation, was blocked by FcεRIβ exon-skipping without affecting thapsigargin-induced GM-CSF release in BMMCs (FIG. 5E).

Example 7

Effect of AONs on Cell Migration

It has been reported that antigen induces IgE-dependent BMMC migration. Thus, the effects of exon-skipping on antigen-mediated BMMC migration were examined Briefly, BMMCs were transfected as described above. Cells were cultured for 32 h and then some cells were sensitized with 100 ng/ml anti-DNP IgE (SPE7 clone) for 16 h (to measure migration towards DNP) while some cells were not sensitized with IgE (to measure migration towards SCF). Migration was assayed using transwell chambers as described by Cruse, G. et al. (*J. Allergy and Clin. Immun.* 128:1303-09; and *Thorax* 61:880-85) with the exception that transwells with 5 µm pores were used for BMMCs instead of 8 µm pores for human cells. $2\times10^5$ BMMCs were loaded into the top chamber and the percentage of cells that migrated to the bottom chamber was calculated.

The results show that standard control AON treated BMMCs sensitized with IgE migrated towards antigen (DNP-BSA); however, FcεRIβ AON treated BMMCs did not (FIG. 5F). However, BMMC migration mediated through KIT, the receptor for stem cell factor (SCF) was not reduced and if anything, it was enhanced by FcεRIβ exon-skipping, although not to a statistically significant extent (FIG. 5F). Collectively, these data indicated that FcεRIβ exon-skipping selectively and completely abrogated FcεRI-dependent responses in BMMCs.

Example 8

Survival

Figure 6A:
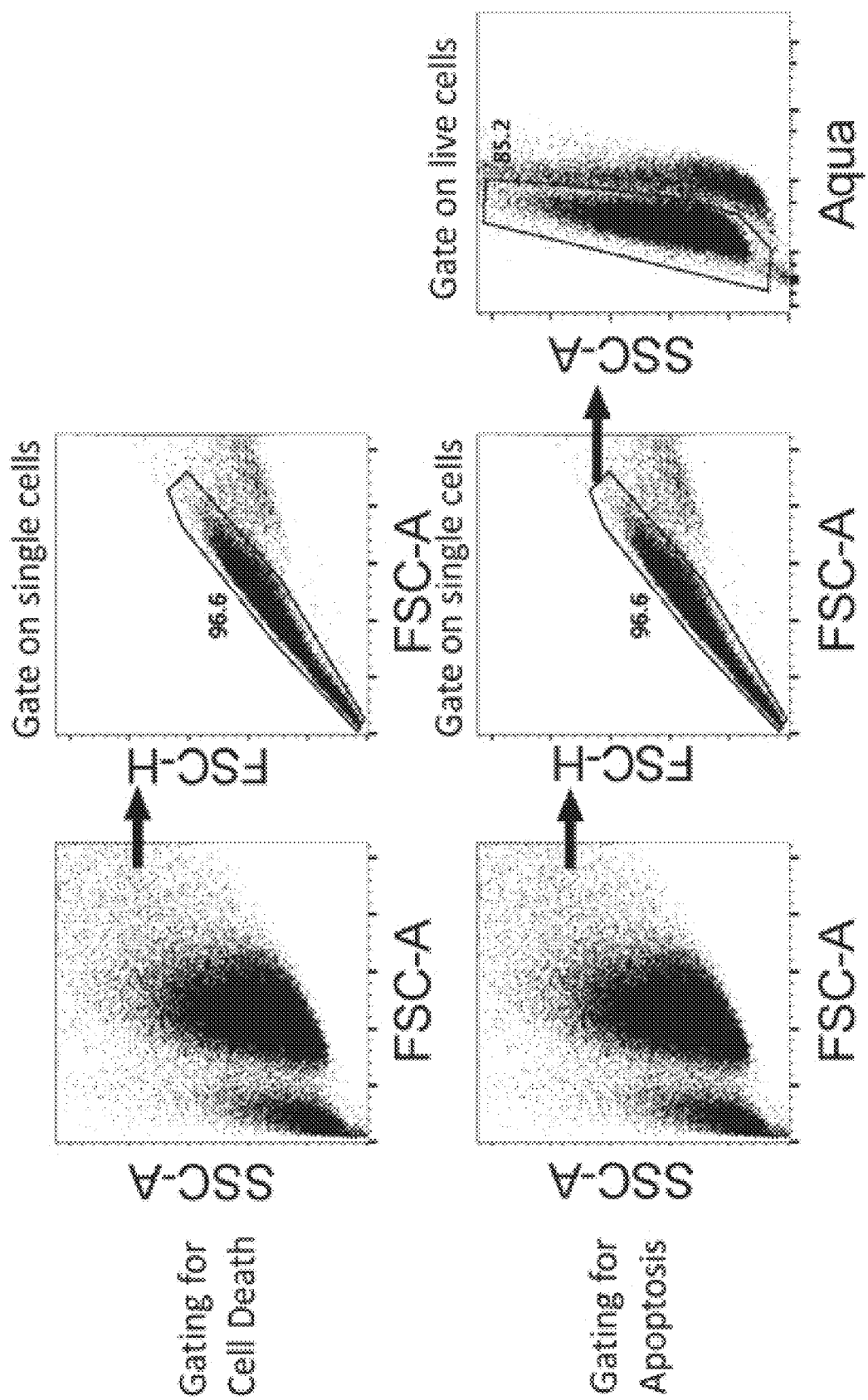
FIGS. 6A-6D show that transfection of FcεRIβ antisense oligonucleotides (AONs) eliminate the pro-survival effect of IgE.
Figure 6B:
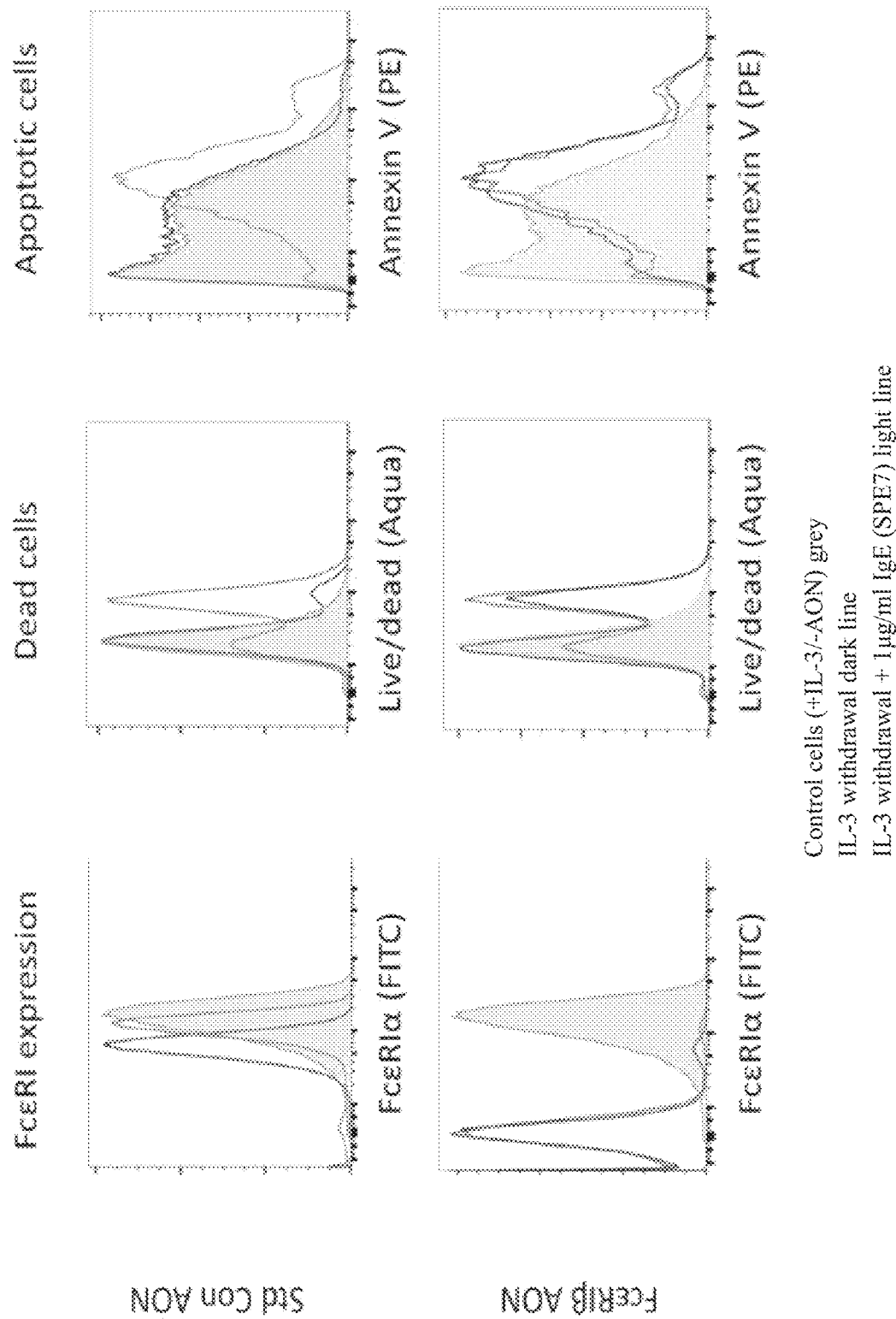
Figure 6C:
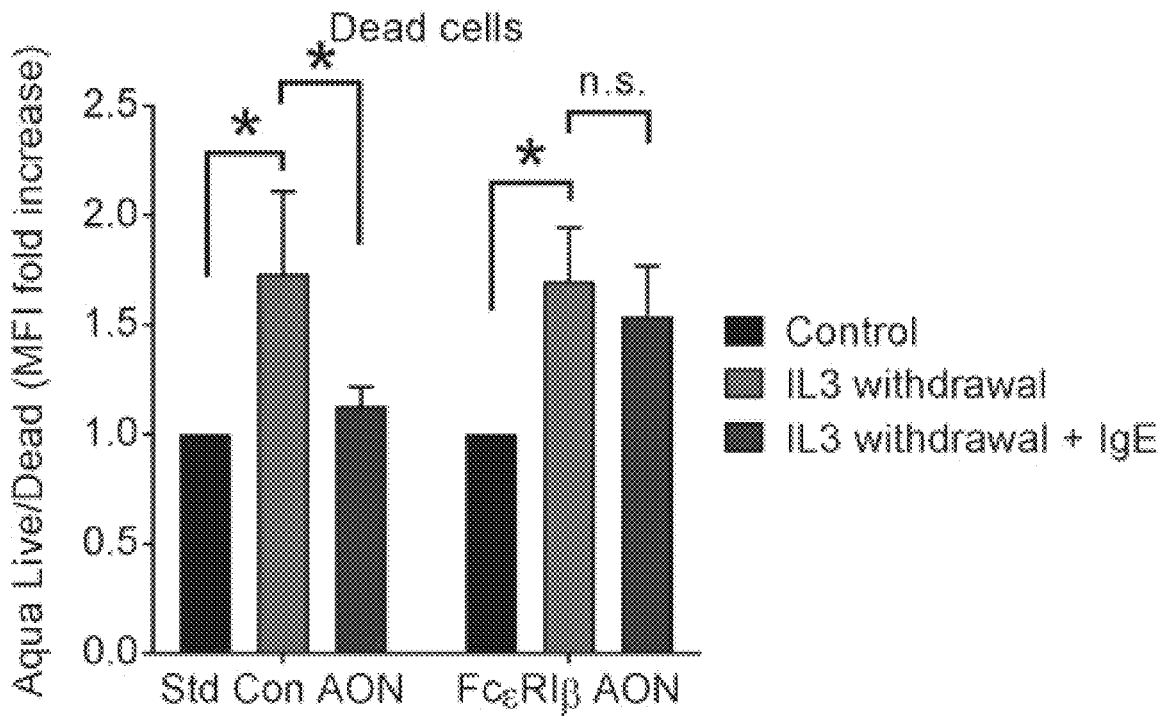
Figure 6D:
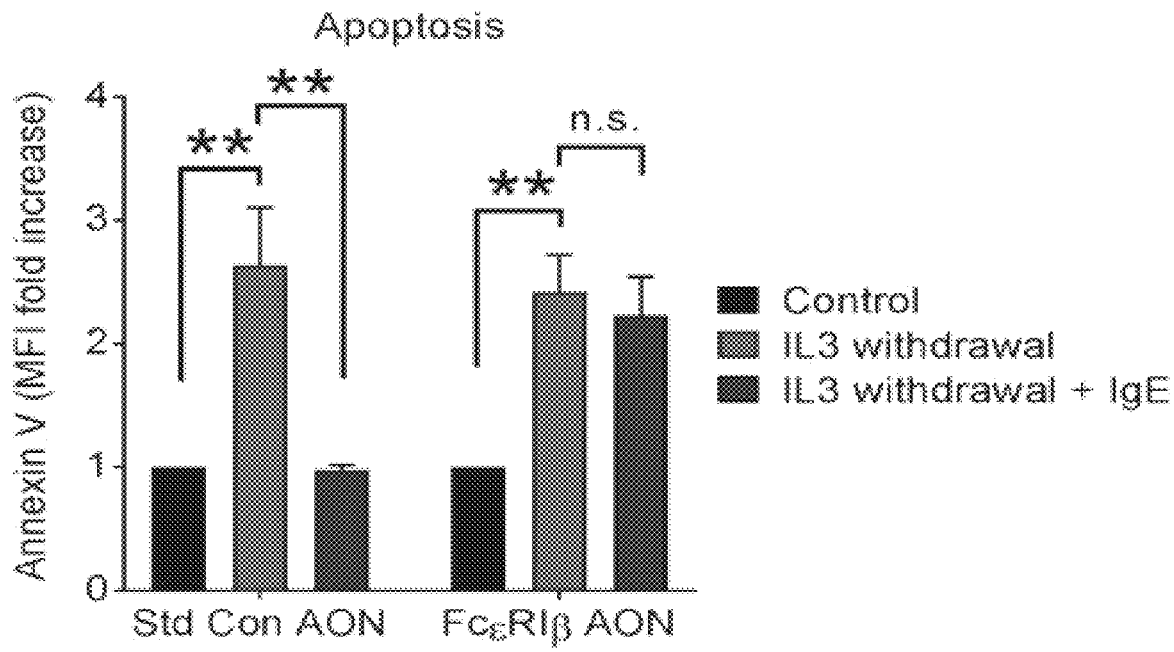

In addition to the classical view that IgE binding to FcεRI on mast cells primes mast cells for activation by bi/multivalent antigens, it is now recognized that IgE binding to FcεRI can, by itself, lead to activation of mast cells to release pro-survival cytokines that maintain viability of the cells. In the absence of external supporting cytokines, mast cells rapidly undergo apoptosis, which is suppressed by the addition of IgE. Therefore, elevation of tissue IgE during allergic diseases, such as the lung in asthma, could contribute to increased mast cell numbers by promoting cytokine release and mast cell survival. Thus, studies were conducted to determine whether FcεRIβ exon-skipping would also eliminate the pro-survival effect of IgE on mast cells. BMMCs were deprived of the culture growth-promoting cytokine, IL-3, for 24 h after transfection with AONs. The results showed that over the course of 72 h, IgE almost completely protected mast cells from cell death and apoptosis after withdrawal of IL-3 in control AON-treated BMMCs (FIG. 6A and FIG. 6B, top panels). However, treatment of BMMCs with FcεRIβ AON, which resulted in loss of surface FcεRI expression (FIG. 6B, left panels) eliminated the protective effect of IgE after IL-3 withdrawal (FIG. 6B, bottom panels, FIGS. 6C and 6D). Therefore, FcεRIβ exon-skipping could suppress the pro-survival effect of elevated IgE in vivo and thus the increase in mast cell population, as well as reduce IgE-dependent degranulation in allergic disease.

Example 9

Proliferation

Figure 7A:
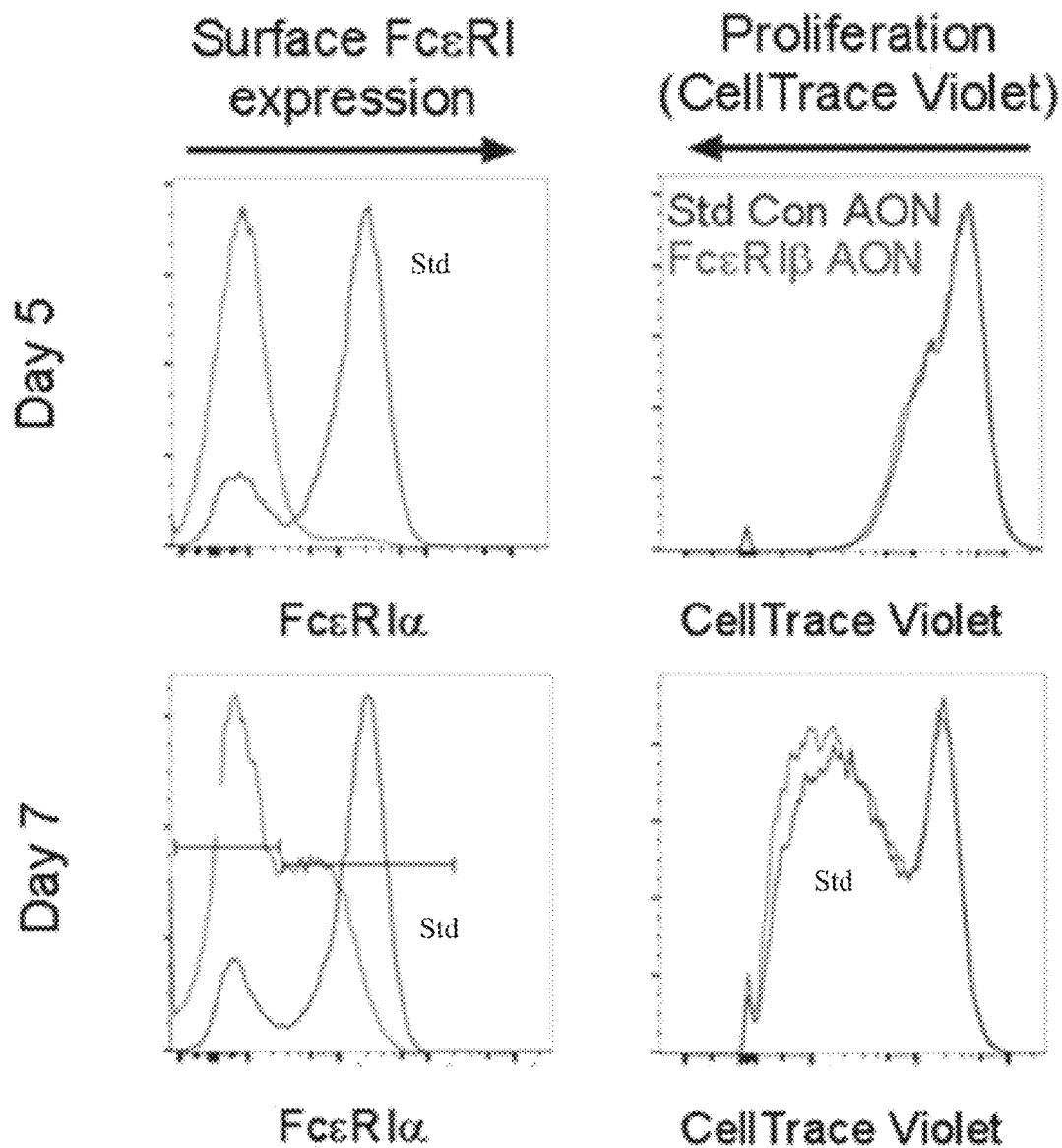
FIGS. 7A-7C show the effect of transfection with FcεRIβ antisense oligonucleotides on BMM cell proliferation.
Figure 7B:
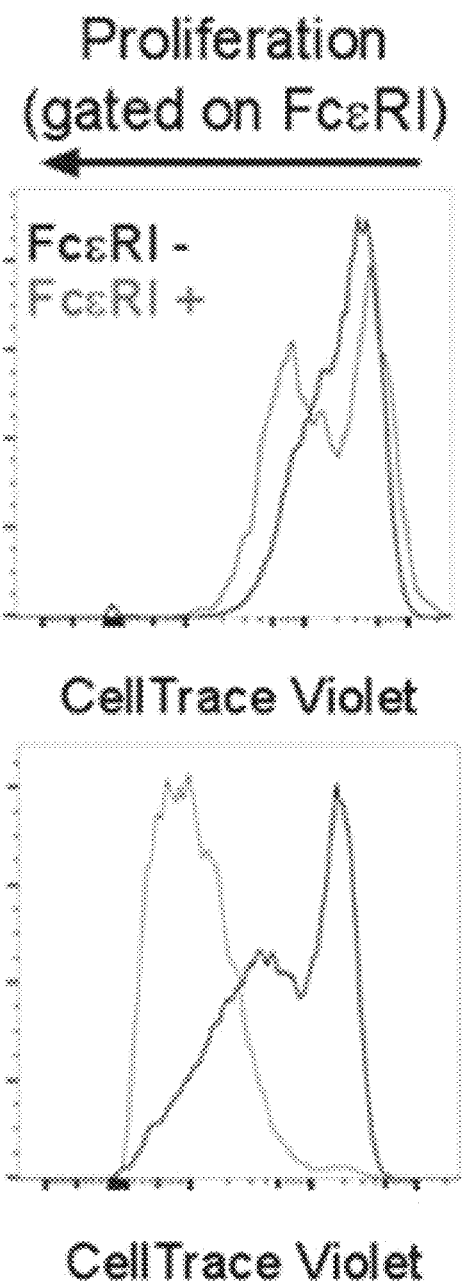
Figure 7C:
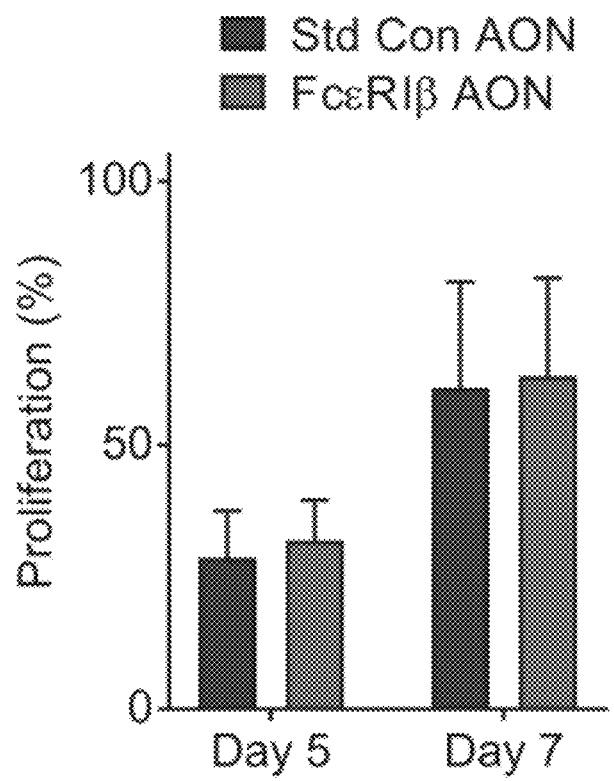

Studies were conducted to examine the effects of FcεRIβ exon-skipping (day 0) on mast cell proliferation while monitoring both surface FcεRI expression (FIG. 7A) and proliferation using a CellTrace Violet dilution assay (FIG. 7B). Briefly, BMMCs were washed once with PBS. 2×10$^6$ BMMCs were stained with CellTrace Violet (INVITROGEN™) according to the manufacturer's instructions. Cells were then stained for 15 min, followed by addition of 5× volume of complete RPMI 1640 medium with 10% FBS at 37° C. BMMCs were pelleted and transfected as described above. BMMCs were cultured in complete RPMI 1640 supplemented with 30 ng/ml recombinant mouse IL-3 at 37° C. for 5-7 days and stained with Aqua live/dead (INVITROGEN™) and FITC-FcεRIα (EBIOSCIENCE™). Flow cytometry was performed on an LSRII flow cytometer. Dead cells were gated out using the Aqua live/dead stain with an additional gate set for the single cell population The results showed that the majority of the proliferation occurred between day 5 and day 7, with a population of cells appearing with diluted CellTrace dye at day 7 (FIG. 7B). There was no difference in proliferation with FcεRIβ exon-skipping at either 5 or 7 days. There was a population of BMMCs treated with FcεRIβ AON that began to express FcεRI on the surface at day 7, despite all of the cells at day 5 being negative for surface FcεRI (FIG. 7C) suggesting that these cells were regaining FcεRI expression. Gating the populations of cells based on surface FcεRI expression and plotting CellTrace Violet fluorescence demonstrated that the cells expressing surface FcεRI were the cells that had proliferated (FIG. 7B). These data indicate that while overall proliferation is not affected by FcεRIβ AON treatment, BMMCs that do proliferate dilute FcεRIβ AONs between daughter cells, reducing exon-skipping efficacy.

Example 10

Treatment of Cutaneous Anaphylaxis Using AONs

This example demonstrates the therapeutic utility of AONs of this disclosure for treating affected tissues in allergic diseases such as allergic rhinitis, asthma, or allergic dermatitis. The example utilizes the well-established model of passive cutaneous anaphylaxis (PCA) to test the efficacy of localized delivery of the AONs by means of the Vivo-Morpholino AONs. The experiments described below use morpholino AONs linked through the terminal 3'-N to an octaguanidinium dendrimer (Vivo-Morpholino), which were purchased from Gene-Tools. 20 μl of 0.5 mM standard control AON or FcεRIβ AON (approximately 100 μg of AON) was injected intradermally into one ear of each mouse at day 0. 20 μl of PBS was injected into the other control ear. 24 h later, the AON or PBS injections were repeated. 24 h later, 75 ng of anti-DNP-HSA IgE (in 20 μl of PBS) was injected into the AON treated ears and 20 μl of PBS was injected into the control ears. 24 h later, 200 μg of DNP-HSA in 200 μl of PBS containing 0.5% Evan's blue dye was administered by intravenous injection to all mice. After 30 min, mice were euthanized with $CO_2$ gas and AON treated and control ears were removed. Ears were minced and 700 μl of formamide was added to the tubes containing ear tissue and incubated for 2 h at 55° C. to extract the Evan's blue dye. Evan's blue dye extracted into the filtered formamide extract was measured by absorbance in a plate reader set at 620 nm and calculated as induction of inflammation in the AON treated ear compared to the internal control ear.

For a subset of mice, skin tissue was retrieved from the side of the head near the base of the ear after the ears had been removed. The skin tissue retrieved was within 10 mm of the AON injection site. Removed skin was immediately placed in RNA later and stored at 4° C. overnight. The following day, the tissue was removed from RNA later and submerged in lysis buffer from the RNAeasy plus mini kit (QIAGEN™). Skin tissue was then lysed and homogenized using a mechanical homogenizer. RNA was isolated from the homogenized lysate using the RNAeasy plus mini kit with added QIAShredder step according to the manufacturer's instructions. RT-PCR was carried out as described above.

Figure 8B:
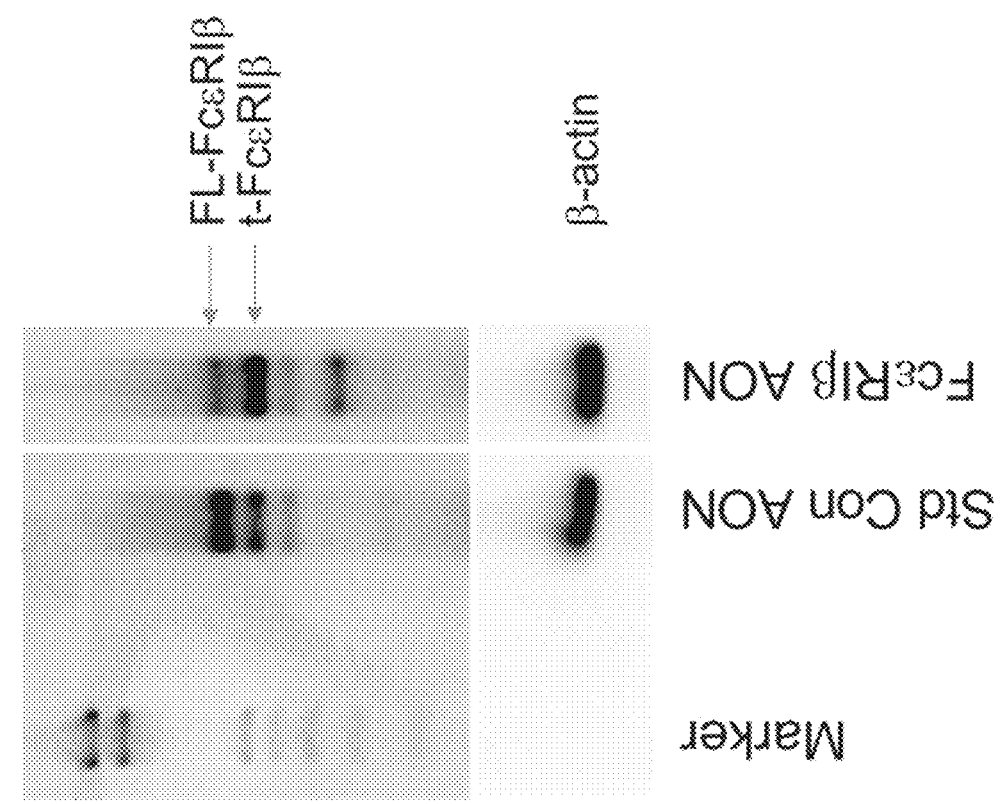
FIGS. 8A and 8B show the effect of FcεRIβ antisense oligonucleotides on an anaphylactic allergic response.
Figure 8A:
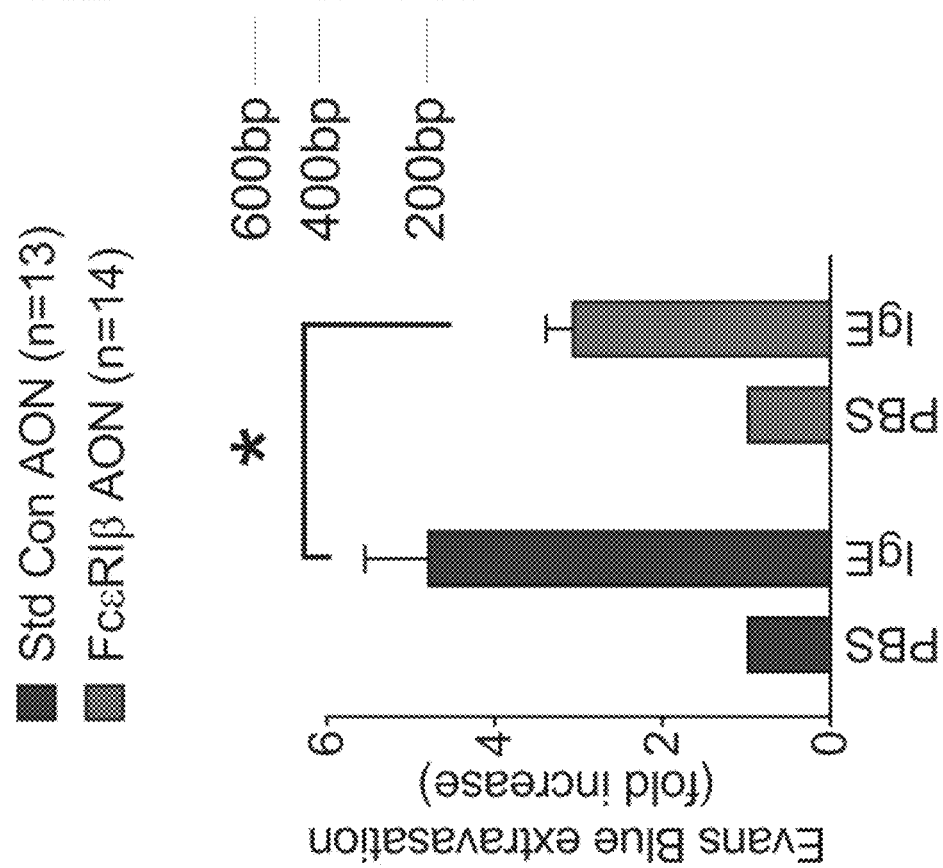

The results of this study, shown in FIGS. 8A and 8B, revealed a substantial reduction in PCA reaction with administration of FcεRIβ AON when compared to control AON (FIG. 8A). Examination of total RNA isolated from skin adjacent to the injected ears by qualitative RT-PCR revealed that the administration of FcεRIβ AON had resulted in exon-skipping in vivo (FIG. 8B). However, the efficiency of exon-skipping in vivo was less than that observed in BMMC cultures, which is consistent with the partial reduction in the PCA reaction (FIG. 8A) as compared to near complete block of degranulation in BMMCs (FIG. 3B). In this PCA model, as in cell culture, FcεRI receptors are saturated with DNP-specific IgE whereas in an allergic disease, only a minor fraction of receptors may be occupied by an allergen-specific IgE and thus more susceptible to FcεRIβ exon-skipping therapy.

The foregoing examples of this disclosure have been presented for purposes of illustration and description. These examples are not intended to limit the disclosure to the form disclosed herein, as variations and modifications commensurate with the teachings of the description of the disclosure, and the skill or knowledge of the relevant art, are within the scope of this disclosure. It is intended that the appended claims be construed to include alternative embodiments to the extent permitted by the prior art.

What is claimed is:

1. A method for modulating splicing of a pre-mRNA encoding a human FcεRIβ protein that comprises an amino acid sequence as set forth in SEQ ID NO: 2 in cells or tissues, comprising contacting the cells or tissues with an antisense oligomer of from 15 to 50 linked nucleosides that comprises one of SEQ ID NOs: 460-615, wherein the antisense oligomer is targeted to a region of the pre-mRNA encoding the human FcεRIβ protein, and further wherein the targeted region comprises sequences involved in splicing of the pre-mRNA encoding the human FcεRIβ protein, whereby the contacting results in the antisense oligomer modulating splicing of the human FcεRIβ mRNA in the cells or tissues.

2. A method of reducing cell surface expression of a human FcεRI protein in a cell, comprising contacting the cell with an antisense oligomer 15 to 50 linked nucleosides that comprises one of SEQ ID NOs: 460-615 and is targeted to a region of a pre-mRNA encoding a human FcεRIβ protein comprising SEQ ID NO: 2, and wherein the targeted region comprises sequences involved in splicing of the pre-mRNA encoding the human FcεRIβ protein, whereby the contacting results in the antisense oligomer reducing cell surface expression of FcεRIβ protein in the cell.

3. The method of claim 1, wherein the targeted region is selected from the group consisting of an exon 3 sequence, an exon 3 slice acceptor sequence, an exon 3 splice enhancer sequence, and an exon 3 splice branch point sequence, or an exon 3 polypyrimidine tract of the pre-mRNA encoding the FcεRIβ protein.

4. The method of claim 3, wherein hybridization of the antisense oligomer to the pre-mRNA encoding the FcεRIβ protein results in production of a mature MS4A2 mRNA molecule that lacks at least a portion of exon 3.

5. The method of claim 1, wherein the target sequence comprises at least a portion of a polynucleotide sequence comprising SEQ ID NO: 13.

6. The method of claim 1, wherein the antisense oligomer comprises a nucleotide sequence that is identical over its full length to a sequence selected from the group consisting of SEQ ID NOs: 460-615.

7. The method of claim 1, wherein the antisense oligomer is an antisense RNA molecule.

8. The method of claim 7, wherein the antisense RNA molecule comprises a modification selected from the group consisting of a nucleoside modification, an internucleoside modification, a sugar modification, a sugar-internucleoside linkage modification, and combinations thereof.

9. The method of claim 8, wherein the modification increases degradation of a target sequence by a ribonuclease when the antisense RNA molecule hybridizes to the target sequence in the presence of the ribonuclease.

10. The method of claim 8, wherein the antisense RNA molecule is a morpholino oligomer.

11. The method of claim 6, wherein the antisense RNA molecule is a morpholino oligomer comprising a nucleotide sequence comprising SEQ ID NO: 602.

12. The method of claim 2, wherein the targeted region is selected from the group consisting of an exon 3 sequence, an exon 3 slice acceptor sequence, an exon 3 splice enhancer sequence, an exon 3 splice branch point sequence, and an exon 3 polypyrimidine tract of the pre-mRNA encoding the FcεRIβ protein.

13. The method of claim 12, wherein hybridization of the antisense oligomer to the pre-mRNA encoding the FcεRIβ protein results in production of a mature MS4A2 mRNA molecule that lacks at least a portion of exon 3.

14. The method of claim 2, wherein the target sequence comprises at least a portion of a polynucleotide sequence comprising SEQ ID NO: 13.

15. The method of claim 2, wherein the antisense oligomer comprises a nucleotide sequence that is identical over its full length to a sequence comprising SEQ ID NO: 13.

16. The method of claim 2, wherein the antisense oligomer is an antisense RNA molecule.

17. The method of claim 16, wherein the antisense RNA molecule comprises a modification selected from the group consisting of a nucleoside modification, an internucleoside modification, a sugar modification, a sugar-internucleoside linkage modification, and combinations thereof.

18. The method of claim 17, wherein the modification increases degradation of a target sequence by a ribonuclease when the antisense RNA molecule hybridizes to the target sequence in the presence of the ribonuclease.

19. The method of claim 17, wherein the antisense RNA molecule is a morpholino oligomer.

20. The method of claim 15, wherein the antisense RNA molecule is a morpholino oligomer comprising a nucleotide sequence comprising SEQ ID NO: 602.

* * * * *